US009856512B2

(12) United States Patent
Bonetta et al.

(10) Patent No.: US 9,856,512 B2
(45) Date of Patent: Jan. 2, 2018

(54) COMPOSITIONS, METHODS, AND PLANT GENES FOR THE IMPROVED PRODUCTION OF FERMENTABLE SUGARS FOR BIOFUEL PRODUCTION

(71) Applicant: The Governing Council of the University of Toronto, Toronto (CA)

(72) Inventors: Dario Torquato Bonetta, Toronto (CA); Peter John McCourt, Toronto (CA); Danielle Vidaurre, Toronto (CA); George Stamatiou, Toronto (CA)

(73) Assignee: THE GOVERNING COUNCIL OF THE UNIVERSITY OF TORONTO, Toronto (CA)

( * ) Notice: Subject to any disclaimer, the term of this patent is extended or adjusted under 35 U.S.C. 154(b) by 20 days.

(21) Appl. No.: 14/388,089

(22) PCT Filed: Mar. 26, 2013

(86) PCT No.: PCT/CA2013/000289
§ 371 (c)(1),
(2) Date: Sep. 25, 2014

(87) PCT Pub. No.: WO2013/142968
PCT Pub. Date: Oct. 3, 2013

(65) Prior Publication Data
US 2015/0044678 A1  Feb. 12, 2015

Related U.S. Application Data

(60) Provisional application No. 61/615,530, filed on Mar. 26, 2012.

(51) Int. Cl.
| | |
|---|---|
| *C12N 15/82* | (2006.01) |
| *C12N 15/29* | (2006.01) |
| *C12N 15/52* | (2006.01) |
| *C12Q 1/54* | (2006.01) |
| *A01N 37/30* | (2006.01) |
| *A01N 47/34* | (2006.01) |
| *G01N 33/50* | (2006.01) |
| *C12Q 1/68* | (2006.01) |
| *C07K 14/415* | (2006.01) |

(52) U.S. Cl.
CPC ............. *C12Q 1/54* (2013.01); *A01N 37/30* (2013.01); *A01N 47/34* (2013.01); *C12N 15/8245* (2013.01); *C12Q 1/6895* (2013.01); *G01N 33/5097* (2013.01); *C07K 14/415* (2013.01); *C12N 15/8274* (2013.01); *C12Q 2600/13* (2013.01); *C12Q 2600/156* (2013.01); *G01N 2333/91114* (2013.01); *Y02E 50/17* (2013.01)

(58) Field of Classification Search
None
See application file for complete search history.

(56) References Cited

U.S. PATENT DOCUMENTS 7,154,026 B2 * 12/2006 Arioli .................. C12N 9/1059
435/183

OTHER PUBLICATIONS

Koonin, E. Annual Review of Genetics 39: 309-338 (2005).*
Oomen et al., "Modulation of the cellulose content of tuber cell walls by antisense expression of different potato (*Solanum tuberosum* L.) Ces A clones", Phytochemistry, 65(5):535-546 (2004).
Himmel, et al., Science 315:804-807 (2007). "Biomass Recalcitrance: Engineering plants and enzymes for biofuels production.".
Carroll et al., Annu Rev Plant Biol. 60:165-82 (2009). "Cellulosic biofuels.".
Pauly et al., Curr. Opin. Plant Sci. 13:305-312 (2010). "Plant cell wall polymers as precursors for biofuels.".
Pingali et al., Biomacromolecules 11:2329-2335 (2010). "Breakdown of cell wall nanostructure in dilute acid pretreated biomass.".
Kumar et al., Ind. Eng. Chem. Res., 48:3713-3729 (2009). "Methods for pretreatment of lignocellulosic biomass for efficient hydrolysis and biofuel production.".
Vanholme et al., Trends in Biotech. 28:543-547 (2010). "Potential of Arabidopsis systems biology to advance the biofuel field.".
Austin et al. Next-Generation Mapping of Arabidopsis Genes. Plant J. 67:715-725 (2011). "Next-generation mapping of Arabidopsis genes.".
Reiter et al., Plant J. 12:335-45 (1997). "Mutants of Arabidopsis thaliana with altered cell wall polysaccharide composition.".
Williams et al., Plant Phys. 138:686-800 (2005). "Mutations in the Arabidopsis phosphoinositide phosphatase gene SAC9 lead to overaccumulation of PtdIns(4,5)P2 and constitutive expression of the stressresponse pathway.".
Reiter et al., Science 261:1032-1035 (1993). "Altered growth and cell walls in a fucose-deficient mutant of Arabidopsis.".
Chia et al., Plant J. 37:853-863 (2004). "A cytosolic glucosyltransferase is required for conversion of starch to sucrose in Arabidopsis leaves at night.".
Kotting et al., Plant Cell 21:334-46 (2009). "Starch-EXCESS4 is a laforin-like phophoglucan phophatase required for starch degradation in Arabidopsis thaliana.".
Caspar et al., Plant Phys. 95:1181-1188 (1991). "Mutants of Arabidopsis with altered regulation of starch degradation.".
Wattebled, F. et al., Plant Phys 138:184-195 (2005). "Mutants of Arabidopsis lacking a chloroplastic isoamylase accumulate phytoglycogen and an abnormal for anylopectin.".

(Continued)

*Primary Examiner* — David T Fox
(74) *Attorney, Agent, or Firm* — Nixon Peabody LLP; David S. Resnick; Nicole D. Kling

(57) ABSTRACT

Described herein are compositions comprising at least one auxin transport inhibitor for pre-treating a plant or seed to increase saccharification, or saccharide release by hydrolysis, the at least one auxin transport inhibitor being in an amount effective to increase sugar release from a plant tissue by hydrolysis. Also described are plant mutations, and methods to screen for such plant mutations, having an improved sugar release phenotype. The described compositions, methods and plant mutations are particularly useful for producing biofuel crops, such as maize, to improve sugar extractability from lignocellulosic biomass and hence, the efficiency of bioethanol production overall.

15 Claims, 9 Drawing Sheets
(4 of 9 Drawing Sheet(s) Filed in Color)

(56) References Cited

OTHER PUBLICATIONS

Fulton et al., Plant Cell 20:1040-1058 (2008). "b-AMYLASE4, a noncatalytic protein required for starch breakdown, acts upstream of three active b-amylases in Arabidopsis chloroplasts.".
Okada et al., Plant Cell 3:677-684 (1991). "Requirement of the auxin polar transport system in early stages of Arabidopsis floral bud formation.".
Christensen et al., Cell 100:469-78 (2000). "Regulation of auxin response by the protein kinase PINOID.".
Przemeck et al. Planta 200:229-237 (1996). "Studies on the role of the Arabidopsis gene MONOPTEROS in vascular development and plant cell axialization.".
Wu et al., Am. J. Bot. 11:1745-1755 (2007). "The role of auxin transport during inflorescence development in maize (*Zea mays*, Poaceae).".
Skirpan et al., Plant J. 55, 787-797 (2008). "Genetic and physical interactions suggest that Barren STALK1 is a target of Barren INFLORESCENCE2 in maize inflorescence development.".
Reinhardt et al., Plant Cell 12:507-518 (2000). "Auxin regulates the initiation and radial position of plant lateral organs.".
Reinhardt et al. Nature 426, 255-260 (2003). "Regulation of phyllotaxis by polar auxin transport.".
Fu et al. Proc. Natl. Acad. Sci. USA 108, 3803-8 (2011). "Genetic manipulation of lignin reduces recalcitrance and improves ethanol production from switchgrass.".
Chen et al., Nat Biotech. 25, 759-61 (2007). "Lignin modification improves fermentable sugar yields for biofuel production.".
Li et al., Proc. Natl. Acad. Sci. 100, 4939-44 (2003). "Combinatorial modification of multiple lignin traits in trees through multigene cotransformation.".
Somerville et al. Science 306, 2206-2211 (2004). "Toward a Systems Approach to Understanding Plant Cell Walls. ".
Sánchez-Rodriguez et al., Trends Plant Sci. 15:291-301 (2010). "Phytohormones and the cell wall in Arabidopsis during seedling growth.".
Feraru et al. Curr. Biol. 4:33-43 (2011). "PIN polarity maintenance by the cell wall in Arabidopsis.".
McCourt et al., New Phytol. 185:15-26 (2010). "Plant chemical genetics.".
Scheible et al., Proc Natl Acad Sci U S A. 98(18):10079-84 (2001). "Modifications of cellulose synthase confer resistance to isoxaben and thiazolidinone herbicides in Arabidopsis Ixr1 mutants.".
Harris et al., GCB Bioenergy, 1:51-61(2009). "Genetic modification in cellulose-synthase reduces crystallinity and improves biochemical conversion to fermentable sugar.".
Scanlon. M.J. (2003) Plant Physiol. 133:597-605.
Pressoir et al. (2009) Plant J. 58:618-628.
Besseau. S. et al. (2007) Plant Cell 19:1-l-8-162.
Stamatiou. G. et al. (2013) PLOS One 8. eiSSN: 1932-6203.
Li et al. (2010) Plant Cell 22:1620-1632.
Weng et al. (2008) Curr. Opin. Bioteclznol. 19:166-172.
Gardner et al., "Screening of Arabidopsis thaliana stems for variation in cell wall polysaccharides", Phytochemistry, 60(3)241-254 (2002).
Gomez et al., "Analysis of saccharification in Brachypodium distachyon stems under mild conditions of hydolysis", Biotechnology for Biofuels, 1(1):12 (2008).
Gomez et al., "Automated saccharification assay for determination of digestibility in plant materials", Biotechnology for Biofuels, 3:23 (2010).
Gomez et al., "High-throughput Saccharification Assay for Lignocellulosic Materials", Journal of Visualized Experiments, (53):3240 (2011).
Harris, "Molecular and Chemical Dissection of Cellulose Biosynthesis in Plants", Theses and Dissertations—Plant and Soil Sciences, 193 (2011).
Daras et al., "The thanatos mutation in Arabidopsis thaliana cellulose synthase 3 (AtCesA3) has a dominant-negative effect on cellulose synthesis and plant growth." New Phytologist 184(1):114-126 (2009).
Desprez et al., "Resistance against herbicide isoxaben and cellulose deficiency caused by distinct mutations in same cellulose synthase isoform CESA6." Plant Physiology 128(2):482-490 (2002).
Harris et al., "Cellulose microfibril crystallinity is reduced by mutating C-terminal transmembrane region residues CESA1A903V and CESA3T942I of cellulose synthase." PNAS 109(11):4098-4103 (2012).
Lu et al., "The role of amylomaltase in maltose metabolism in the cytosol of photosynthetic cells." Planta 218 (3):466-473 (2004).

\* cited by examiner

COMPOSITIONS, METHODS, AND PLANT GENES FOR THE IMPROVED PRODUCTION OF FERMENTABLE SUGARS FOR BIOFUEL PRODUCTION

CROSS-REFERENCE TO RELATED APPLICATIONS

This application is a 35 U.S.C. §371 National Phase Entry Application of International Application No. PCT/CA13/00289 filed Mar. 26, 2013, and which claims benefit under 35 U.S.C. §119(e) of U.S. Provisional Application Ser. No.: 61/615,530 filed Mar. 26, 2012 the contents of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on September 22, 2014, is named 924270WO_ST25.txt and is 257,246 bytes in size.

FIELD OF THE INVENTION

The present invention is directed to compositions and methods for improving saccharide extraction from biomass, as well as to methods for identifying mutations that affect saccharide extraction. More particularly, the invention relates to compositions comprising auxin transport inhibitors, methods relating thereto, mutant plant varieties, and methods of genetic screening for such mutations that affect saccharification in plant tissue.

BACKGROUND OF THE INVENTION

Plant biomass and in particular cellulosic ethanol has gained considerable interest as a stable, environmentally benign source of energy that could partially offset fossil fuels. However, the encapsulation of cellulose and branched polysaccharides collectively known as hemicellulose lignin, together with the crystalline nature of cellulose, make the biochemical conversion of lignocellulosic biomass to biofuels a costly and energy inefficient process. The recalcitrance of lignocellulose has led to the development of a variety of technologies that usually involve the deconstruction of plant cell walls through acid, thermochemical, or enzymatic hydrolysis. For example, hemicellulose can be hydrolyzed by dilute acid treatments, but these conditions are not severe enough for cellulose hydrolysis. Increasing acid concentrations or carrying out acid treatments at high temperature and pressure improves sugar yields from cellulose, but both processes are corrosive and increase costs. Unfortunately, enzymatic approaches of digesting lignocellulose are still in their infancy. Moreover, the protective nature of the cell wall to cellulases means digestion is slow and inefficient. As a consequence, acid hydrolysis pretreatments are often used to depolymerize and solubilize hemicelluloses.

The lack of energy efficient and environmentally friendly conversion of lignocellulosic polymers into fermentable sugars, or saccharification, has spurred interest in using genetic and genomic approaches that modify the cell wall for industrial processing. Often these approaches have involved manipulating known cell wall synthesis or degradation enzymes. Although these rational approaches are promising they depend on a prior molecular knowledge of the genes of interest, usually followed by reverse genetics to test functionality.

Most approaches to genetically improving conversion of lignocellulosic biomass into a fermentable sugar source take advantage of our understanding of cell wall polymer synthesis. This usually involves manipulating glycosyltransferases and glycan synthases that are involved in polymerizing polysaccharides or modulating levels of lignin. However, the rudimentary knowledge about the regulation of this complex matrix limits this approach. For example, estimates of over 1000 cell wall proteins in *Arabidopsis* alone make it difficult to know which ones will functionally influence saccharification. Furthermore, over 700 genes are annotated as encoding putative glycosyltransferases or glycosyl hydrolases.

By contrast, forward genetic screens, which inherently have no mechanistic bias have the potential to uncover novel processes that could improve saccharification. The limitation of forward screens, however, is designing specific high throughput assays, followed by efficient molecular identification of the genes involved. In this latter case, however, the recent development of next generation sequencing technologies to identify mutant alleles has greatly reduced this bottleneck.

SUMMARY OF THE INVENTION

The invention is directed to a use of an auxin transport inhibitor in the pretreatment of a plant tissue to increase the sugar released from the plant tissue through hydrolysis.

The invention is further directed to the use of a genetically modified plant that has disrupted auxin transport to increase the sugar released from the plant through hydrolysis.

The invention is further directed to the use of a genetically modified plant that contains cell wall defects to increase the sugar released from the plant through hydrolysis.

The invention is further directed to the use of genetically modified plant tissue with increased starch accumulation to increase the sugar released from the plant through hydrolysis.

The invention is further directed to the use of any of the forgoing in production of bioplastic, biofoam, biorubber, biocomposite, forestry biofibre, agricultural textile, chemical, biocosmetic, and feed stock production.

The invention is further directed to a method of identifying plant genotypes that show an improved sugar release under mild acid treatment comprising the following steps:
a) providing a plurality of mutated plant seeds;
b) germinating the mutated plant seeds;
c) retrieving samples from each mutated plant seed;
d) submerging the samples in a weak acid;
e) incubating the samples with a colorimetric reagent in a concentrated acid; and
f) measuring the colour absorbance to determine the relative concentration of the sugar release.

The invention is further directed to a screening method to identify new plant cellulose synthase (CESA) alleles wherein mutagenized plants are screened with a cellulose biosynthetic inhibitor (CBI).

The invention is further directed to the use of an X-ray diffractometer to measure the proportion of crystalline cellulose relative to the proportion of amorphous cellulose in plant stem tissue.

The invention is further directed to the use of forward genetic screens for identifying mutants with improved saccharification from plant tissues.

The invention is further directed to the use of a forward genetic screen for identifying mutations that show increased sugar release from plant biomass as compared with wild types, under mild acid hydrolysis conditions.

The invention is further directed to a method of identifying genes involved with saccharification by means of a genetic screen.

According to an aspect of the invention, there is provided a composition for pre-treating a plant tissue to increase saccharide, or sugar, release from said plant tissue by hydrolysis, the composition comprising at least one auxin transport inhibitor in an amount effective to increase sugar release from said plant tissue by hydrolysis.

In a further aspect of the invention, there is also provided a method of pre-treating a plant tissue to increase saccharide release the said plant tissue by hydrolysis, the method comprising administering a composition as defined herein in an amount effective to increase sugar release from the plant, or tissues thereof, by hydrolysis.

Also provided is a method of screening for plants having an increased saccharide release phenotype, a reduced cellulose crystallinity phenotype, or both. The method comprises:
  treating at least one plant or plant seed with at least one cellulose biosynthetic inhibitor (CBI) in an amount effective to select for CBI-resistance in the plant or plant seed;
  germinating the plant seeds and/or incubating the plant and selecting for CBI-resistant mutant plants, or seeds thereof; and
  measuring saccharide release, cellulose crystallinity, or both, in the CBI-resistant mutant plants to identify an increased saccharide release phenotype, a reduced cellulose crystallinity phenotype, or both.

Other details and aspects of the invention will be apparent from the following description of these compositions, uses and methods, as well as the mutant plants and genes described in detail throughout this application.

BRIEF DESCRIPTION OF THE FIGURES

This patent or application file contains at least one drawing executed in color. Copies of this patent or patent application publication with color drawing(s) will be provided by the Office upon request and payment of the necessary fee.

These and other features of the invention will become more apparent from the description, in which reference is made to the following drawings wherein.

DETAILED DESCRIPTION

Figure 1A:
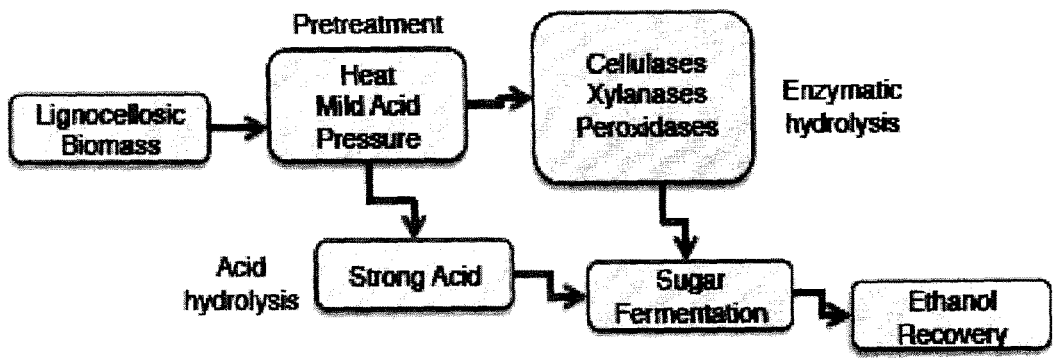
FIG. 1 illustrates methodology and results of screening for wall hydrolysis sensitive (whs) mutants. (A)(PRIOR ART) is a schematic of the production of ethanol from cellulosic biomass. For biomass pretreatment, dilute sulphuric acid is used to solubilize the hemicellulosic fraction and to disrupt the crystalline structure of cellulose so that hydrolyzing enzymes can easily access and convert cellulose to fermentable sugars. (B) illustrates the results of measuring hexose content in known cell wall mutants subjected to acid hydrolysis using 1M $H_2SO_4$ at 21 days after germination (DAG). Of the 30 cell wall mutants tested, only mur11-1 showed a significant difference in cell wall accessibility relative to wild type. All experiments were repeated at least three times with similar results. Dotted line denotes wild type levels (Results are averages±s.d. (n=4). *, P<0.05 using Student's t-test.) (C) shows the results of measuring hexose content in mur11-1 and sac9-3 (SALK_058870) relative to wild type. Leaf discs were assayed for increased saccharification using 1M $H_2SO_4$ at 21 days. (Results are averages±s.d. (n=8-10).)

Described herein are compositions, methods, mutant genes, cells, plants and other materials which are useful to increase carbohydrate availability for saccharification, in particular, through pre-treatment of a plant with an auxin transport inhibitor.

Saccharification is generally known as the process of breaking a complex carbohydrate (such as starch or cellulose) into its monosaccharide components. By increasing carbohydrate availability for saccharification, the compositions, methods, mutant genes, cells, plants and other materials described in this application can be used for a variety of industrial processes. For instance, they may be used to pretreat feedstock typically used in the biofuels industry for production of bioethanol. They may be employed in the production of biomass which is, for example, useful in producing biofuels, bioplastic, biofoam, biorubber, biocomposite, forestry biofibre, agricultural textile, chemical, biocosmetics, and in other feed stock production.

The compositions and methods described herein are applicable in a variety of plant species. Of interest are the monocotyledonous plants, e.g. corn (*Zea mays*), sugar cane (*Saccharum* sp.), switchgrass (*Panicum virgatum*) and other grass species (*Miscanthus*), and other species used in bioethanol production. However, the present invention is also applicable in dicotyledonous plants, e.g. *Arabidopsis*, . . . .

In certain embodiments of the invention, the auxin transport inhibitor may include at least one of the following: 1-N-Naphthylphthalmaic acid (NPA), 2-{(E)-1-[4-(3,5-difluorophenyl)semicarbazono]ethyl}nicotinic acid (diflufenzopyr), 2,3,5-triiodobenzoic acid (TIBA), 9-hydroxyfluorene-9-carboxylic acid (HFCA), p-chlorophenoxyisobutyric acid (PCIB), 2-carboxyphenyl-3-phenylpropane-1,2-dione (CPD), chlorflurenol, quimerac, tricyclopyr, CPIB, quercetin, genistein, including agriculturally acceptable salts, esters, or derivatives thereof.

Chemical structures for some of the above-listed compounds, and certain additional examples of auxin transport inhibitors, include the following:

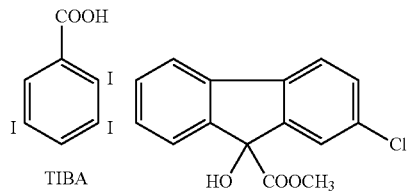

TIBA

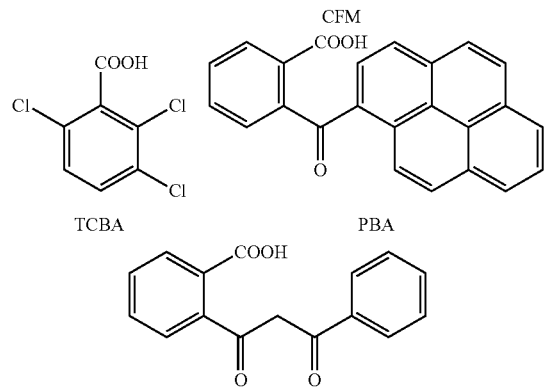

TCBA

CFM

PBA

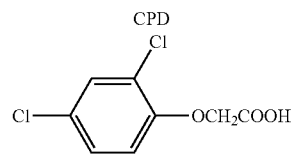

CPD

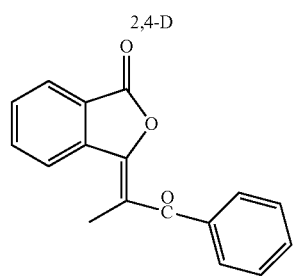

2,4-D

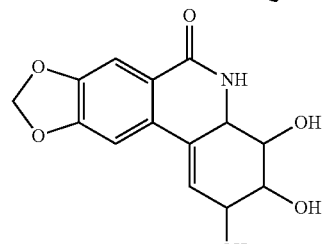

Lycoricidinol

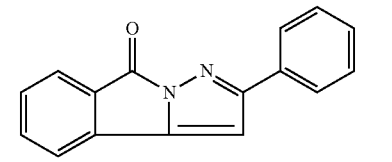

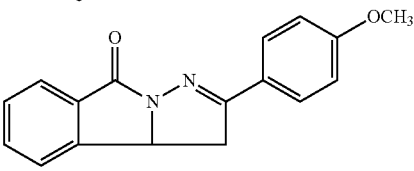

DPX1840

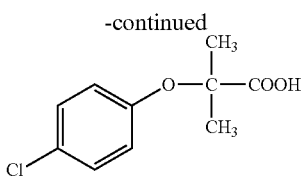

PCIB

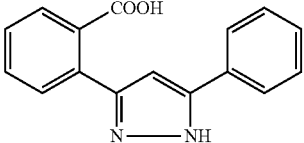

CPP

In certain preferred embodiments of the invention, the auxin transport inhibitor may be of a phthalamate (e.g. 1-N-naphthylphthalmaic acid (NPA)) or semicarbazone (2-{(E)-1-[4-(3,5-difluorophenyl)semicarbazono]ethyl}nicotinic acid (diflufenzopyr)) class of auxin transport inhibitor.

In certain other embodiments of the invention, which are non-limiting, the auxin transport inhibitor may be of the following molecular class of auxin transport inhibitors:

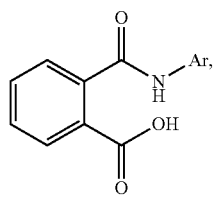

including agriculturally acceptable salts, esters, or derivatives thereof. The term "Ar" represents "aryl", and refers to a monovalent unsaturated aromatic carbocyclic group having a single ring (e.g. phenyl) or multiple condensed rings (e.g. naphthyl or anthryl), which can optionally be unsubstituted or substituted with, e.g., halogen (for instance F, Cl, Br, or I), alkyl (for instance, a lower alkyl group), alkoxy, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, or other functionality.

The term "alkyl" refers to a cyclic, branched, or straight chain alkyl group containing only carbon and hydrogen, and unless otherwise mentioned contains one to twelve carbon atoms. This term is further exemplified by groups such as methyl, ethyl, n-propyl, isobutyl, t-butyl, pentyl, pivalyl, heptyl, adamantyl, and cyclopentyl. Alkyl groups can either be unsubstituted or substituted with one or more substituents, e.g. halogen, alkyl, alkoxy, alkylthio, trifluoromethyl, acyloxy, hydroxy, mercapto, carboxy, aryloxy, aryloxy, aryl, arylalkyl, heteroaryl, amino, alkylamino, dialkylamino, morpholino, piperidino, pyrrolidin-1-yl, piperazin-1-yl, or other functionality.

The term "lower alkyl" refers to a cyclic, branched or straight chain monovalent alkyl radical of one to seven carbon atoms. This term is further exemplified by such radicals as methyl, ethyl, n-propyl, i-propyl, n-butyl, t-butyl, i-butyl (or 2-methylpropyl), cyclopropylmethyl, i-amyl, n-amyl, hexyl and heptyl. Lower alkyl groups can also be unsubstituted or substituted, where a specific example of a substituted alkyl is 1,1-dimethyl heptyl.

The auxin transport inhibitor may, in certain embodiments of the invention, be Naptalam, which is also known as N-1-naphthylphthalamic acid of the chemical formula:

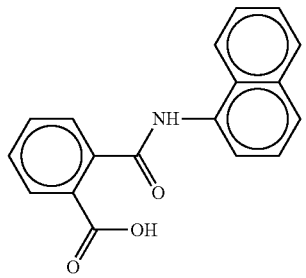

including agriculturally acceptable salts, esters, or derivatives thereof.

Certain auxin transport inhibitors, including NPA and diflufenzopyr, may have functional groups which can be ionized, and accordingly can also be used in the form of an agriculturally acceptable salt. In general, an "agriculturally acceptable" salt will be a salt form whose cation has no adverse effect on the action of the active compound. For example, agriculturally acceptable cations may include ions of the alkali metals, such as lithium, sodium and potassium; of the alkaline earth metals, such as calcium and magnesium; of the transition metals, such as manganese, copper, zinc and iron; ammonium; substituted ammonium (organoammonium) ions in which one to four hydrogen atoms are replaced by $C_1$-$C_8$-alkyl, $C_1$-$C_4$-alkyl, hydroxy-$C_1$-$C_4$-alkyl, in particular hydroxy-$C_2$-$C_4$-alkyl, $C_1$-$C_4$-alkoxy-$C_1$-$C_4$-alkyl, in particular $C_1$-$C_4$-alkoxy-$C_2$-$C_4$-alkyl, hydroxy-$C_1$-$C_4$-alkoxy-$C_1$-$C_4$-alkyl, in particular hydroxy-$C_2$-$C_4$-alkoxy-$C_2$-$C_4$-alkyl, phenyl or benzyl, preferably ammonium, methylammonium, isopropylammonium, dimethylammonium, diisopropylammonium, trimethylammonium, tetramethylammonium, tetraethylammonium, tetrabutylammonium, pentylammonium, hexylammonium, heptylammonium, 2-hydroxyethylammonium (olamine salt), 2-(2-hydroxyethoxy)eth-1-ylammonium (diglycolamine salt), di(2-hydroxyeth-1-yl)ammonium (=diethanolammonium salt or diolamine salt), tri(2-hydroxyethyl)ammonium (=triethanolammonium salt or trolamine salt), mono-, di- and tri(hydroxypropyl)ammonium (=mono-, di- and tripropanolammonium), benzyltrimethylammonium, benzyltriethylammonium; phosphonium ions; or sulfonium ions, preferably tri($C_1$-$C_4$-alkyl)sulfonium such as trimethylsulfonium, and sulfoxonium ions, preferably tri ($C_1$-$C_4$-alkyl)sulfoxonium.

Auxin transport inhibitors, including N-1-naphthylphthalamic acid, may also carry a carboxyl group that can also be employed in the form of agriculturally acceptable derivatives, for example as amides such as mono- or di-$C_1$-$C_6$-alkylamides or arylamides, as esters, for example as allyl esters, propargyl esters, $C_1$-$C_{10}$-alkyl esters or alkoxyalkyl esters, and also as thioesters, for example as $C_1$-$C_{10}$-alkyl thioesters. Preferred mono- and di-$C_1$-$C_6$-alkylamides are the methyl- and the dimethylamides. Preferred arylamides are, for example, the anilidines and the 2-chloroanilides. Preferred alkyl esters are, for example, the methyl, ethyl, propyl, isopropyl, butyl, isobutyl, pentyl, mexyl (1-methylhexyl) or isooctyl (2-ethylhexyl) esters. Preferred $C_1$-$C_4$-alkoxy-$C_1$-$C_4$-alkyl esters are the straight-chain or branched $C_1$-$C_4$-alkoxyethyl esters, for example the methoxyethyl, ethoxyethyl or butoxyethyl (butoyl) esters. An example of the straight-chain or branched $C_1$-$C_{10}$-alkyl thioesters is the ethyl thioester. Preferred derivatives are the esters.

The compositions of the invention preferably comprise N-1-naphthylphthalamic acid, or a salt or ester thereof. Suitable salts of N-1-naphthylphthalamic acid include those salts where the counterion is an agriculturally acceptable cation. In certain non-limiting embodiments, suitable salts of N-1-naphthylphthalamic acid may include the alkali metal salts, in particular the sodium and the potassium salts, and the ammonium or substituted ammonium salts, in particular the ammonium salt, the diethanolammonium salt, the diglycolammonion salt, the isopropylammonium salt, the dimethylammonium salt or the triethanolammonium salt.

The above-described compositions may be applied using any number of techniques as would be customary to one of skill in the art. Without wishing to be limiting in any way, the compositions may be applied e.g. by spraying or foliar application. A variety of spray application techniques are known and would be apparent to those of skill in the art. For example, the composition may be applied with water as a carrier, and applied to the soil and/or the plants at desired spray rates. In other embodiments of the invention, the composition may be applied by foliar application using an appropriate spray mixture.

It is also envisioned that the auxin transport inhibitor described herein may be used in combination with other compounds or agents, for instance, herbicidal agents, compound synergistic, fertilizers and the like. Such combinations may be formulated into a single composition, or applied separately.

Also provided herein is a method of pre-treating a plant to increase saccharide release from a plant tissue by hydrolysis, the method comprising administering an auxin transport inhibitor, or a composition as described herein, in an amount effective to increase sugar release from the plant tissue by hydrolysis.

In an embodiment of the above method, the auxin transport inhibitor or composition is administered in an amount effective to increase saccharide release from cellulose, starch, or both, in said plant tissue.

In addition, the method may further comprise a step of hydrolyzing cellulose, starch, or both, from the plant tissue, to produce monosaccharides, disaccharides, polysaccharides, or a combination thereof.

In a further non-limiting embodiment, the auxin transport inhibitor or composition may be applied by spraying, foliar application, or a combination thereof.

Also provided herein is a method of screening for plants having an increased saccharide release phenotype, a reduced cellulose crystallinity phenotype, or both, the method comprising:
  treating at least one plant or plant seed with at least one cellulose biosynthetic inhibitor (CBI) in an amount effective to select for CBI-resistance in said plant or plant seed;
  germinating the plant seeds and/or incubating the plant and selecting for CBI-resistant mutant plants, or seeds thereof; and
  measuring saccharide release, cellulose crystallinity, or both, in the CBI-resistant mutant plants to identify an increased saccharide release phenotype, a reduced cellulose crystallinity phenotype, or both.

In a non-limiting embodiment of the method, the cellulose crystallinity may be measured using an X-ray diffractometer, for example, to determine a proportion of crystalline cellulose relative to a proportion of amorphous cellulose in a tissue of said CBI-mutagenized plant.

In a further non-limiting embodiment of the method, the tissue may be a stem and/or leaf tissue.

Without wishing to be limiting, the cellulose biosynthetic inhibitor may be of a nitrile, benzamide, triazolocarboxamide, or quinoline carboxylic acid class of cellulose biosynthetic inhibitor. For example, the cellulose biosynthetic inhibitor may be one or more of dichlobenil, chlorthiamid, isoxaben, flupoxam, quinclorac, or a salt, ester, or derivative thereof. In particular embodiments, the cellulose biosynthetic inhibitor may preferably comprise isoxaben or flupoxam.

Also described are uses of the compositions described herein for pre-treating a plant or plant tissue to increase saccharide release from the plant tissue by hydrolysis. For example, the plant or plant tissue may comprise biomass, e.g. for production of biofuel (such as bioethanol), bioplastic, biofoam, biorubber, biocomposite, forestry biofibre, agricultural textiles, monosaccharides, disaccharides, polysaccharides, other chemicals, as well as biocosmetics.

Also described herein are plant mutations which result in improved saccharide release upon hydrolysis treatment. Without limitation, the mutations may include one or more of the following mutations in maize or *Arabidopsis* genes, or equivalent genes having corresponding gene products in other plant species:
  barren inflorescence2 (bif2), comprising a mutation in the bif2 sequence corresponding to SEQ ID NO: 1 reducing or substantially inhibiting bif2 function;
  barren stalk1 (BA1), comprising a mutation in the BA1 sequence corresponding to SEQ ID NO: 3, reducing or substantially inhibiting BA1 function;
  mur11-1 comprising a mutation corresponding to R278H in SEQ ID NO: 5, including polypeptides, polypeptide fragments, and nucleotides encoding the mutant mur11-1 polypeptide or fragment thereof;
  pid-100 comprising a mutation corresponding to D223N in SEQ ID NO: 7, including polypeptides, polypeptide fragments, and nucleotides encoding the mutant pid-100 polypeptide or fragment thereof;
  dpe2-100, comprising a mutation in the dpe2-100 sequence which reduces or substantially inhibits dpe2-100 function, such as but not limited to the W323Stop mutation in SEQ ID NO: 9, including nucleotides encoding the mutant dpe2-100 sequence;
  dpe2-101 comprising a mutation corresponding to R561K in SEQ ID NO: 11, including polypeptides, polypeptide fragments, and nucleotides encoding the mutant dpe2-101 polypeptide or fragment thereof;
  sex4-100, comprising a mutation in the sex4-100 sequence which reduces or substantially inhibits sex4-100 function, such as but not limited to the sex4-100 splice junction mutant corresponding to SEQ ID NO: 13, or a fragment thereof containing a mutation corresponding to G2194A in SEQ ID NO: 13, including nucleic acid sequences that are 80% identical (or 85%, more particularly 90%, even more particularly 99% identical) thereto;
  fpx 2-1 comprising a mutation corresponding to G1013R in SEQ ID NO: 15, including polypeptides, polypeptide fragments, and nucleotides encoding the mutant fpx 2-1 polypeptide or fragment thereof;
  fpx 2-2 comprising a mutation corresponding to P1010L in SEQ ID NO: 17, including polypeptides, polypeptide fragments, and nucleotides encoding the mutant fpx 2-2 polypeptide or fragment thereof;

fpx 2-3 comprising a mutation corresponding to G1009D in SEQ ID NO: 19, including polypeptides, polypeptide fragments, and nucleotides encoding the mutant fpx 2-3 polypeptide or fragment thereof;

fpx 1-1 comprising a mutation corresponding to S1040L in SEQ ID NO: 21, including polypeptides, polypeptide fragments, and nucleotides encoding the mutant fpx 1-1 polypeptide or fragment thereof;

fpx 1-2 comprising a mutation corresponding to S1037F in SEQ ID NO: 23, including polypeptides, polypeptide fragments, and nucleotides encoding the mutant fpx 1-2 polypeptide or fragment thereof;

fpx 1-3 comprising a mutation corresponding to S983F in SEQ ID NO: 25, including polypeptides, polypeptide fragments, and nucleotides encoding the mutant fpx 1-3 polypeptide or fragment thereof;

ixr1-3 comprising a mutation corresponding to G998S in SEQ ID NO: 27, including polypeptides, polypeptide fragments, and nucleotides encoding the mutant ixr1-3 polypeptide or fragment thereof;

ixr1-4 comprising a mutation corresponding to R806K in SEQ ID NO: 29, including polypeptides, polypeptide fragments, and nucleotides encoding the mutant ixr1-4 polypeptide or fragment thereof;

ixr1-5 comprising a mutation corresponding to L797F in SEQ ID NO: 31, including polypeptides, polypeptide fragments, and nucleotides encoding the mutant ixr1-5 polypeptide or fragment thereof;

ixr1-6 comprising a mutation corresponding to S377F in SEQ ID NO: 33, including polypeptides, polypeptide fragments, and nucleotides encoding the mutant ixr1-6 polypeptide or fragment thereof;

ixr1-7 comprising a mutation corresponding to R276H in SEQ ID NO: 35, including polypeptides, polypeptide fragments, and nucleotides encoding the mutant ixr1-7 polypeptide or fragment thereof; and ixr2-2 polypeptide comprising a mutation corresponding to S1002F in SEQ ID NO: 37, including polypeptides, polypeptide fragments, and nucleotides encoding the mutant ixr2-2 polypeptide or fragment thereof.

The above listed mutant nucleotide and polypeptide sequences may, in certain embodiments, be provided in isolated form, and may have 80% identity to their respective sequences listed, whereas in other embodiments the sequence identity may be higher, including 85%, 90%, or even 99% identical, including identity ranges intervening these integers. In addition, these same mutations may be made in corresponding sequences from other species, including both monocot and dicot species such as but not limited to corn (*Zea mays*), sugar cane (*Saccharum* sp.), switchgrass (*Panicum virgatum*) and other grass species (*Miscanthus*), other species used in bioethanol production, as well as *Arabidopsis* and other dicotyledonous plant species.

Each of the above-listed mutants may also be provided in the form, for example, of a plant or seed thereof having a phenotype characterized by increased saccharide release from plant tissue by hydrolysis. In one non-limiting example, which can be applied throughout the above list of mutations, the plant or seed thereof may comprise a mutant barren inflorescence2 (bif2) gene comprising a mutation in the bif2 sequence corresponding to SEQ ID NO: 1 which reduces or substantially inhibits bif2 function. The plant or seed thereof may accordingly be used to produce biomass for production of bioethanol, bioplastic, biofoam, biorubber, biocomposite, forestry biofibre, agricultural textiles, monosaccharides, disaccharides, polysaccharides, or biocosmetics, preferably for production of bioethanol. The plant or seed thereof may also be provided, in non-limiting embodiments, in a commercial package comprising the plant or seed thereof, wherein the commercial package is for producing biomass for production of bioethanol, bioplastic, biofoam, biorubber, biocomposite, forestry biofibre, agricultural textiles, monosaccharides, disaccharides, polysaccharides, or biocosmetics.

Also provided herein are vectors, such as but not limited to plasmids, which include a nucleic acid or encoding a polypeptide sequence of one or more of the mutants described herein. Host cells comprising such vectors, or a nucleic acid encoding a polypeptide sequence of one or more of the mutants described herein are also provided. Similarly, seeds and plants may be provided which comprise such vectors and/or nucleic acids.

The seeds or plants containing these mutant sequences, or which express the mutant polypeptides described herein, have a phenotype which is characterized by an increased saccharide release from the plant tissue by hydrolysis.

Thus, the nucleic acids or polypeptides, the vectors, the host cells, the seeds and plants described herein can be used to produce plant tissues with a phenotype characterized by increased saccharide release by hydrolysis. These nucleic acids, polypeptides, vectors, host cells, seeds and plants are especially useful in producing biomass for production of biofuels (such as bioethanol), as well as bioplastic, biofoam, biorubber, biocomposite, forestry biofibre, agricultural textiles, monosaccharides, disaccharides, polysaccharides, and biocosmetics.

EXPERIMENTS

A high-throughput strategy, using the model plant *Arabidopsis*, was used to identify mutants with improved sugar release from plant biomass. Molecular analysis showed a variety of processes, including starch degradation, cell wall composition and polar transport of the plant hormone auxin, can contribute to this improved saccharification. Genetic or chemical inhibition of polar auxin transport in maize is also shown to result in increased sugar release from plant tissues. This information not only uncovers new functions that contribute to cell wall integrity but also demonstrates that information gleaned from genetic approaches involving *Arabidopsis* can be directly translated to monocotyledonous biofuel crops, such as but not limited to maize, to improve sugar extractability from lignocellulosic biomass.

The high throughput strategy involved a forward genetic screen to identify genotypes that showed an improved sugar release under mild acid treatment, and identified a large collection of lines. The frequency of mutant identification (0.3%) and lack of many alleles within the collection suggested the screen was not saturated, and that more genetic variation remains to be discovered.

The identification of mutants that over-accumulate starch in vegetative tissues presents an unforeseen approach with respect to the improvement of fermentable sugars for biofuel production. Because starch is a simple easily accessible glycopolymer compared to lignocellulose, it is efficiently converted to sugar for ethanol production. However, unlike reproductive tissues such as corn kernels, starch levels in stems and leaves are limited, and therefore these vegetative tissues have not previously been considered a useful starch based feedstock.

The inventors have shown that genetically increasing vegetative starch levels can contribute to the overall fermentable sugar yields during acid pretreatment. Because this sugar source is not lignocellulosic, in principle its genetic manipulation should be a stackable trait with other lignocellulosic feedstock technologies. The observation that only some starch excess mutants were identified in the screens, however, suggests that the relationship between starch and acid-dependent sugar release is complex. Without wishing to be bound by theory, it is possible that certain mutants accumulate starch as a secondary consequence of a mutation. For example, not all sugar release from mur11 mutants is explained through starch accumulation, which is consistent with this mutant also having a defective cell wall. It is also possible that various starch accumulating mutants accumulate slightly different forms of starch, and that these forms may not be equally accessible to mild acid hydrolysis.

An association between cell walls and auxin has existed for some time with respect to the role of this hormone in cell expansion. More recently, the demonstration that mutating the cellulose synthase gene CESA results in mislocalization of PIN1 efflux carriers further suggests a close linkage between auxin transport and cell wall synthesis. As shown in the experiments below, pinoid and additional pin-shaped inflorescence mutants have increased cell wall accessibility, which reveals an important role for auxin in maintaining the integrity of the cell wall. Interestingly, this association is limited to auxin mutants that display a pin-shaped inflorescence phenotype, which may mean that altering cell wall integrity contributes to aberrant inflorescence development.

The acid hydrolysis screen only identified pinoid loss-of-function mutants. Presumably, additional *Arabidopsis* mutants that form pin-shaped inflorescences such as pin1 or mp were not found because, unlike pinoid, these mutants are completely penetrant and therefore infertile. Although this makes propagation of these lines problematic, the pin-shaped phenotype may have advantages with respect to preventing gene flow among commercially grown transgenic crops.

The inventors also show that treatment of wild type *Arabidopsis* and maize plants with the polar auxin transport inhibitor, 1-N-Naphthylphthalamic acid (NPA), also results in increased saccharification. In contrast to making transgenic plants, which can be costly, time-consuming and often involve constitutive phenotypes, chemically-induced phenotypes using compounds such as NPA allows for more tailored temporal and spatial control of the cell wall composition. Moreover, NPA, which is already an approved pre-emergence herbicide, can be applied broadly, for example, to bio-energy crops that have rudimentary genetics, or that are difficult to transform.

Finally, the ability to increase saccharification using NPA suggests chemical genetic screening using *Arabidopsis* can be applied to develop further chemical leads that may be useful in pretreatment lignocellulosic processing. The experiments presented here show that the results obtained in *Arabidopsis* can be successfully translated to maize, and thus other monocot species, such as but not limited to sugarcane (*Saccharum* sp.), *Miscanthus* or switchgrass, are expected to show similar results.

Example 1

Screening for Wall Hydrolysis Sensitive Mutants

A colorimetric assay was developed that allowed for the visualization of saccharification from plant tissue incubated in dilute acid at room temperature for one hour.

Figure 1B:
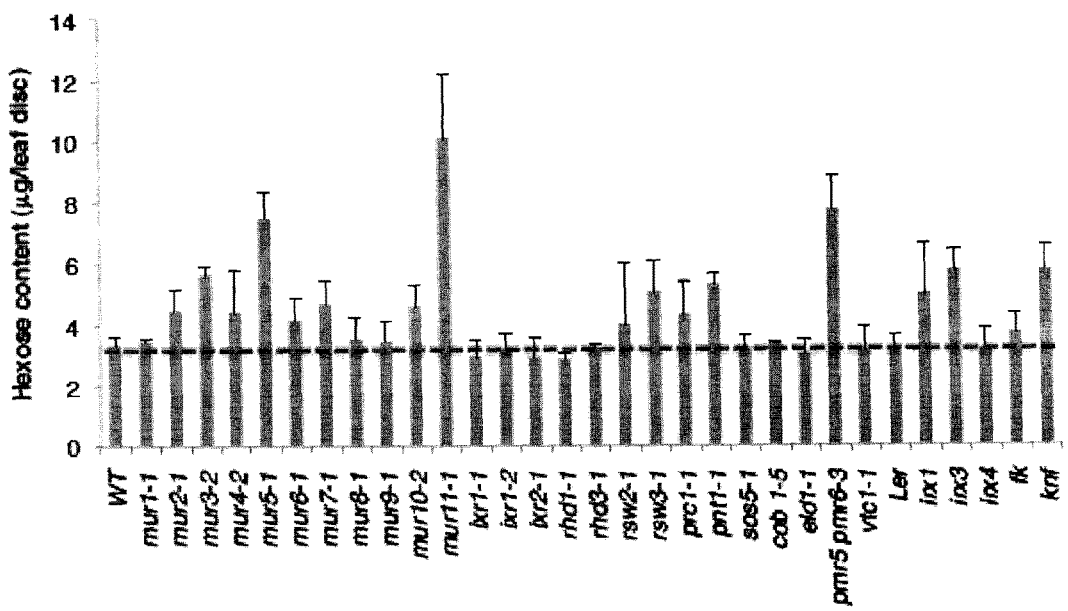
Figure 5:
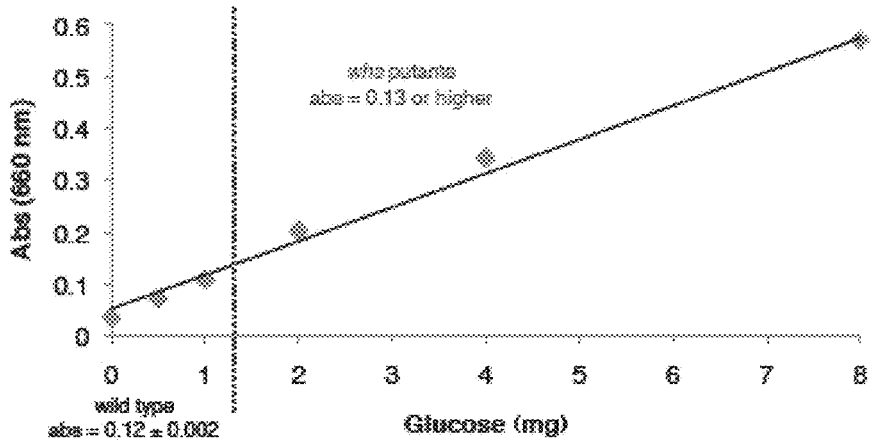
FIG. 5 shows absorbance readings from anthrone acid hydrolysis as quantified against a glucose curve. Candidate whs mutants are considered as releasing a significant amount of sugars when readings measure 2 or more standard deviations above wild type ($Abs_{660nm}$ 0.12±0.002).

Using an anthrone reagent, which turns blue or green in the presence of sugars, (in this example, hexoses,) an average sugar release (4.1±0.1 µg sugar/leaf disc) from 100 wild type leaf samples was determined (FIG. 5). With this baseline, the assay was applied against a collection of 30 known cell wall mutants as indexed by the Plant Cell Wall Biosynthesis Research Network (WallBioNet) (FIG. 1(b)).

Table 1 shows known cell wall mutants and their gene products. MUR11 was molecularly identified in this study and is shown in the table in bold.

TABLE 1

| Mutant | AGI | GENE |
|---|---|---|
| csld3-1 | At3g03050 | CELLULOSE SYNTHASE-LIKE 3 |
| eld1-1 | At3g08550 | ELONGATION DEFECTIVE 1 |
| fk | At3g52940 | FACKEL |
| irx1 | At4g18780 | IRREGULAR XYLEM 1/CESA8 |
| irx3 | At5g17420 | IRREGULAR XYLEM 3/CESA7/MUR10 |
| irx4 | At1g15950 | IRREGULAR XYLEM 4/CINNAMOYL COA REDUCTASE 1 |
| ixr1-1 | At5g05170 | ISOXABEN RESISTANT 1/CESA3 |
| lxr1-2 | At5g05170 | ISOXABEN RESISTANT 1/CESA3 |
| lxr2-1 | At5g64740 | ISOXABEN RESISTANT 2/PROCUSTE1/CESA6 |
| knf | At1g67490 | KNOPF |
| mur1-1 | At3g51160 | GDP-D-MANNOSE-4,6-DEHYDRATASE |
| mur2-1 | At2g03220 | FUCOSYLTRANSFERASE 1 |
| mur3-2 | At2g20370 | XYLOGLUCAN GALACTOSYLTRANSFERASE |
| mur4-2 | At1g30620 | UDP-D-XYLOSE 4-EPIMERASE |
| mur5-1 | | MURUS 5 |
| mur6-1 | | MURUS 6 |
| mur7-1 | | MURUS 7 |
| mur8-1 | | MURUS 8 |
| mur9-1 | | MURUS 9 |
| mur10-2 | At5g17420 | CESA7/IRX3 |
| mur11-1 | At3g59770 | SUPPRESSOR OF ACTIN 9 |
| pmr4-1 | At4g03550 | POWDERY MILDEW RESISTANT 4 |
| pmr5 pmr6-3 | At5g58600; At3g54920 | POWDERY MILDEW RESISTANT 5; POWDERY MILDEW RESISTANT 6 |
| pnt1-1 | At5g22130 | PEANUT 1 |
| prc1-1 | At5g64740 | PROCUSTE1/CESA6/IXR2 |
| rhd1-1 | At1g64440 | ROOT HAIR DEFECTIVE 1/UDP0GLUCOSE 4-EPIMERASE |
| rhd3-1 | At3g13870 | ROOT HAIR DEFECTIVE 3 |
| rsw2-1 | At5g49720 | RADIAL SWELLING 2/IXR2 |
| rsw3-1 | At5g63840 | RADIAL SWELLING 3 |
| sos5-1 | At3g46550 | SALT OVERLY SENSITIVE 5 |
| vtc1-1 | At2g39770 | VITAMIN C DEFECTIVE 1/GDP-MANNOSE PYROPHOSPHORYLASE |

Figure 6:
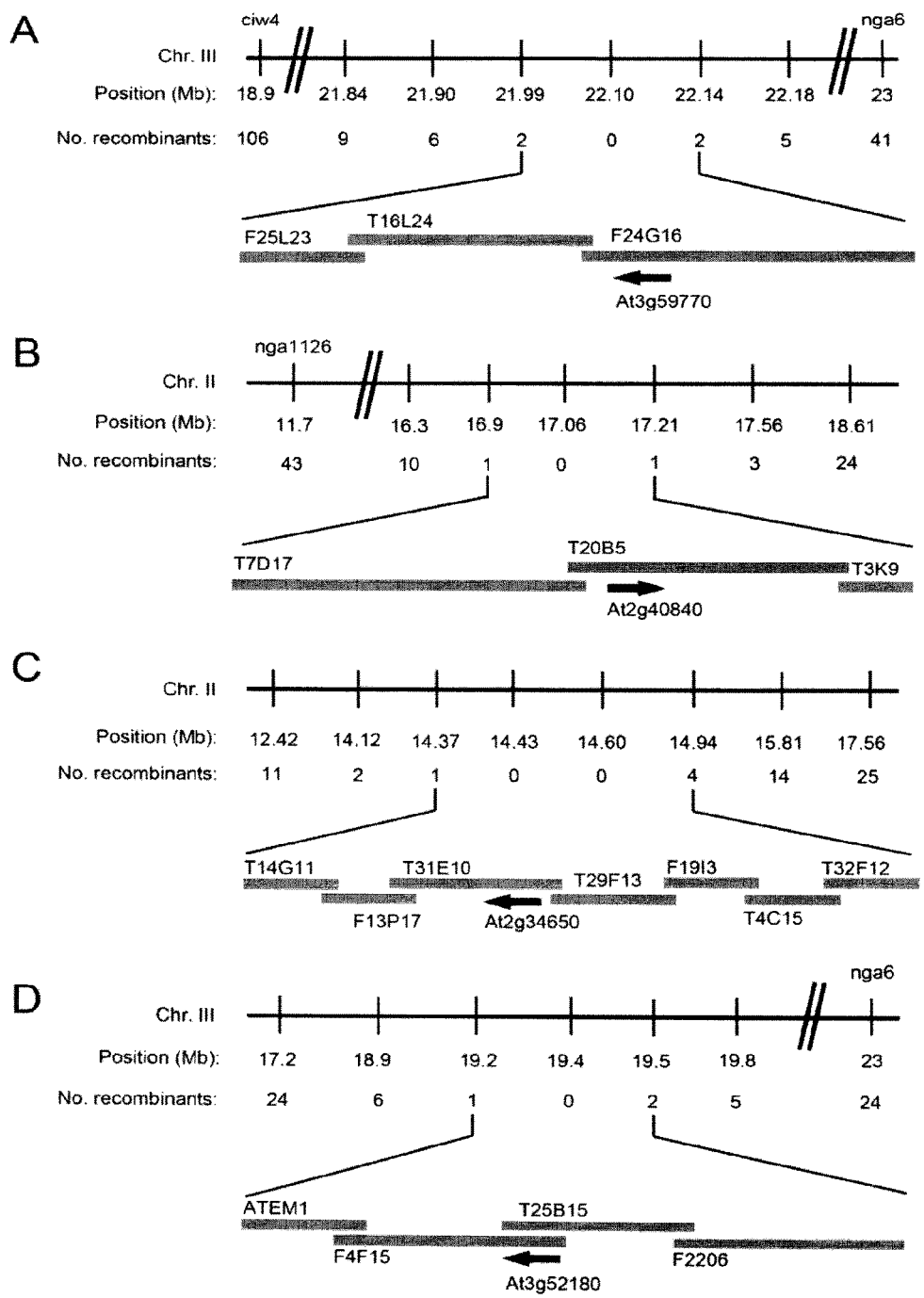
FIG. 6 shows the map based cloning of cell wall accessible genes.

Of the 30 mutants tested, only mur11-1 consistently showed increased saccharification relative to wild type. Map-based cloning of the mur11-1 allele identified a transition mutation (G→A) in a conserved domain of the previously characterized gene, SUPPRESSOR OF ACTIN9 (SAC9), which encodes a phosphoinositide phosphatase (FIG. 6). Table 2 shows the genotypes used in the study.

TABLE 2

| Allele | Lesion[a] | Genomic position[b] | Amino acid |
|---|---|---|---|
| mur11-1 | G → A (SEQ ID NO: 6) | 1157 bp | $R^{278}$→ H (SEQ ID NO: 5) |
| sac9-3 | SALK_058870 | | |
| pid-100 | G → A (SEQ ID NO: 8) | 974 bp | $D^{223}$→ N (SEQ ID NO: 7) |
| pid-14 | SALK_049736 | | |
| pid-2 | CS8063 | | |
| pin1-1; ttg-1 | CS8065 | | |
| pin1 | SALK_047613 | | |
| arf5-2 | SALK_021319 | | |
| dpe2-100 | G → A (SEQ ID NO: 10) | 1457 bp | $W^{323}$→ Stop (SEQ ID NO: 9) |

TABLE 2-continued

| Allele | Lesion[a] | Genomic position[b] | Amino acid |
|---|---|---|---|
| dpe2-101 | G → A (SEQ ID NO: 12) | 3201 bp | R[561] → K (SEQ ID NO: 11) |
| dpe2-5 | SALK_073273 | | |
| sex4-100 | G → A (SEQ ID NO: 13) | 2194 bp | Splice junction |
| sex4-5 | SALK_126784 | | |
| sex1-100 | SALK_077211 | | |
| isa3-3 | CS88929 | | |
| bam1 | SALK_039895 | | |
| bam2 | SALK_020838 | | |
| bam3 | SALK_041214 | | |
| bam4 | SALK_037355 | | |

[a]Type of lesion due to EMS mutagenesis or T-DNA insertion.
[b]Position of base pair change is given from the start codon of genes isolated from the whs primary screen.

Figure 1C:
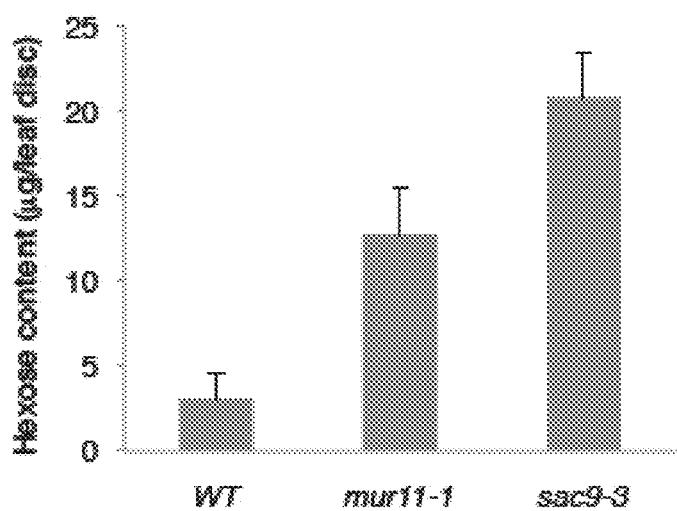
Figure 7:
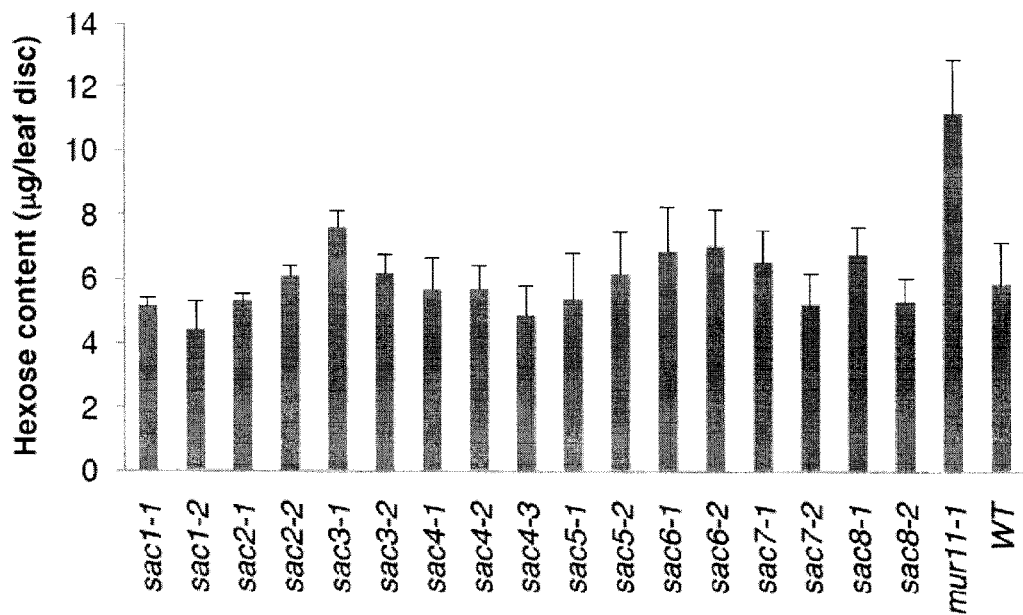
FIG. 7 shows the wall hydrolysis sensitivity of the SAC domain family in *Arabidopsis* using the following T-DNA insertions: sac1-1 (SALK_070875), sac1-2 (SALK_020109), sac2-1 (SALK_099031), sac2-2 (SALK_091926), sac3-1 (SALK_023548), sac3-2 (SALK_049623), sac4-1 (SALK_119184), sac4-2 (SALK_005871), sac4-3 (SALK_056500), sac5-1 (SALK_012372), sac5-2 (SALK_125856), sac6-1 (SALK_021488), sac6-2 (SALK_136049), sac7-1 (SALK_000558), sac7-2 (SALK_092575), sac8-1 (SALK_062145) and sac8-2 (SALK_115643). Leaf disc tissue from 21 day-old plants was assayed using 1 M $H_2SO_4$. (Results are averages±s.d. (n=3-4).)

This result was verified by demonstrating that other mur11 alleles also showed improved saccharification by acid hydrolysis (FIG. 1(c)). Because previous biochemical analysis of sac9 mutants suggests this phosphatase modulates phosphoinositide signaling during stress, the original MUR11 cell wall defects may be a secondary consequence of the mutation. With the finding that mutations in SAC9 gave increased sugar release it was decided to assay loss-of-function alleles of the complete SAC family of genes in *Arabidopsis* (sac1-sac9). However, no other SAC genes were found that contributed to lignocellulose sugar release, which is perhaps not surprising since SAC9 is only distantly related to the other SAC members of this family (FIG. 7)

Figure 2A:
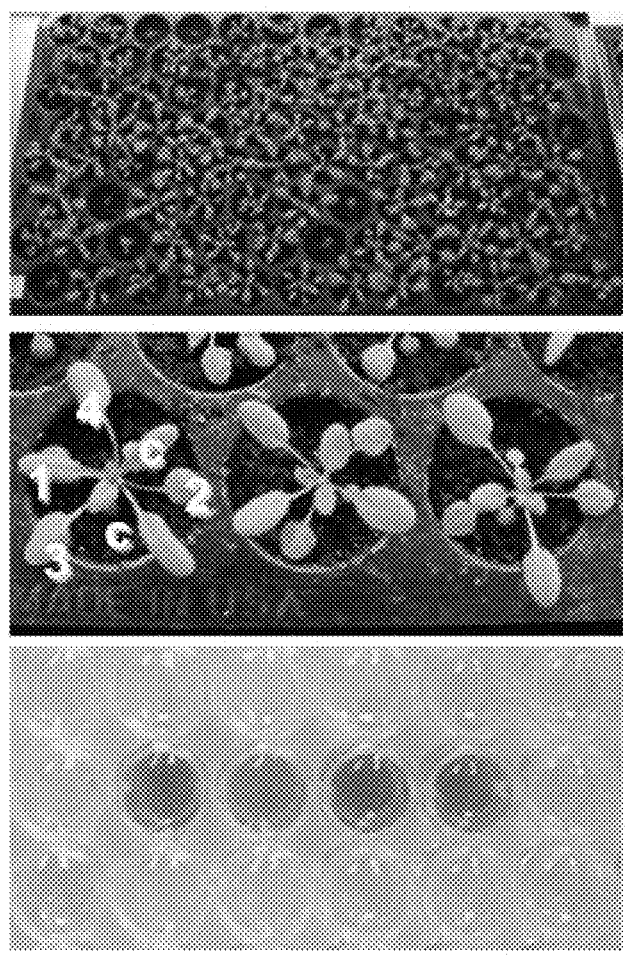
FIG. 2 illustrates the results of characterizing whs mutants. (A) shows three-week old *Arabidopsis* plants grown in 96-well flats at 22° C. under a 16 h/8 h light/dark cycle (top panel). Leaf 3 or 4 was excised from 21 day-old plants using a hole punch and subjected to acid hydrolysis using 1 M $H_2SO_4$. c; cotyledon, leaf numbers indicated (middle panel). Results of colorimetric anthrone assay illustrating that whs mutants release more sugars and turn a blue/green colour. Yellow indicates baseline levels of sugar release (bottom panel). (B) shows the hierarchical cluster analysis of monosaccharide composition analysis by gas chromatography of whs mutants in 21 day-old seedlings. Values are shown as a percentage relative to wild type. Yellow indicates high expression and blue indicates low expression. (C) shows a clustered heatmap of hexose content from 63 whs mutants subjected to acid hydrolysis of fresh leaf tissue using 1M $H_2SO_4$, acid hydrolysis of senesced whole plant tissues using 0.2 M $H_2SO_4$, enzymatic assays using cellulase, cellulase+xylanase and cellulase+peroxidase and starch staining of 14 day-old seedlings. Values are shown as a percentage relative to wild type. Yellow indicates high expression and black indicates low expression.

The scarcity of improved sugar release from the cell wall mutant collection underscored the limited utility of a reverse genetic approach to identify increased saccharification mutants using weak acid hydrolysis. The mutational space was therefore expanded by applying the acid screen to a population of EMS-mutagenized *Arabidopsis* seedlings (FIG. 2(a)).

The screen was limited to plants that showed no obvious growth or developmental defects, since such defects would compromise the application value of the genes identified. From approximately 23,000 M2 plants representing 32 M1 parental groups, 63 mutants were identified that showed increased saccharification (Table 3). Designated wall hydrolysis sensitive (whs), the mutant lines were sub-categorized into four groups based on the amount of sugar they released per fresh leaf disc.

TABLE 3

| Amount of hexonea released (ug/fresh leaf disc.) | | | |
|---|---|---|---|
| 4.5-9 | 9.1-13 | 13.1-17 | 17.1-21 |
| # of mutants 30 | 21 | 10 | 3 |
| whs34 | whs49 | whs14 | whs29 | whs4 | whs1 |
| whs35 | whs50 | whs15 | whs30 | whs5 | whs2 |
| whs36 | whs51 | whs16 | whs31 | whs6 | whs3 |
| whs37 | whs52 | whs17 | whs32 | whs7 | |
| whs38 | whs53 | whs18 | whs33 | whs8 | |
| whs39 | whs54 | whs19 | whs11-1 | whs9 | |
| whs40 | whs55 | whs20 | | whs10 | |
| whs41 | whs56 | whs21 | | whs11 | |
| whs42 | whs57 | whs22 | | whs12 | |
| whs43 | whs58 | whs23 | | whs13 | |
| whs44 | whs59 | whs24 | | | |
| whs45 | whs60 | whs25 | | | |
| whs46 | whs61 | whs26 | | | |
| whs47 | whs62 | whs27 | | | |
| whs48 | whs63 | whs28 | | | |

Figure 2B:
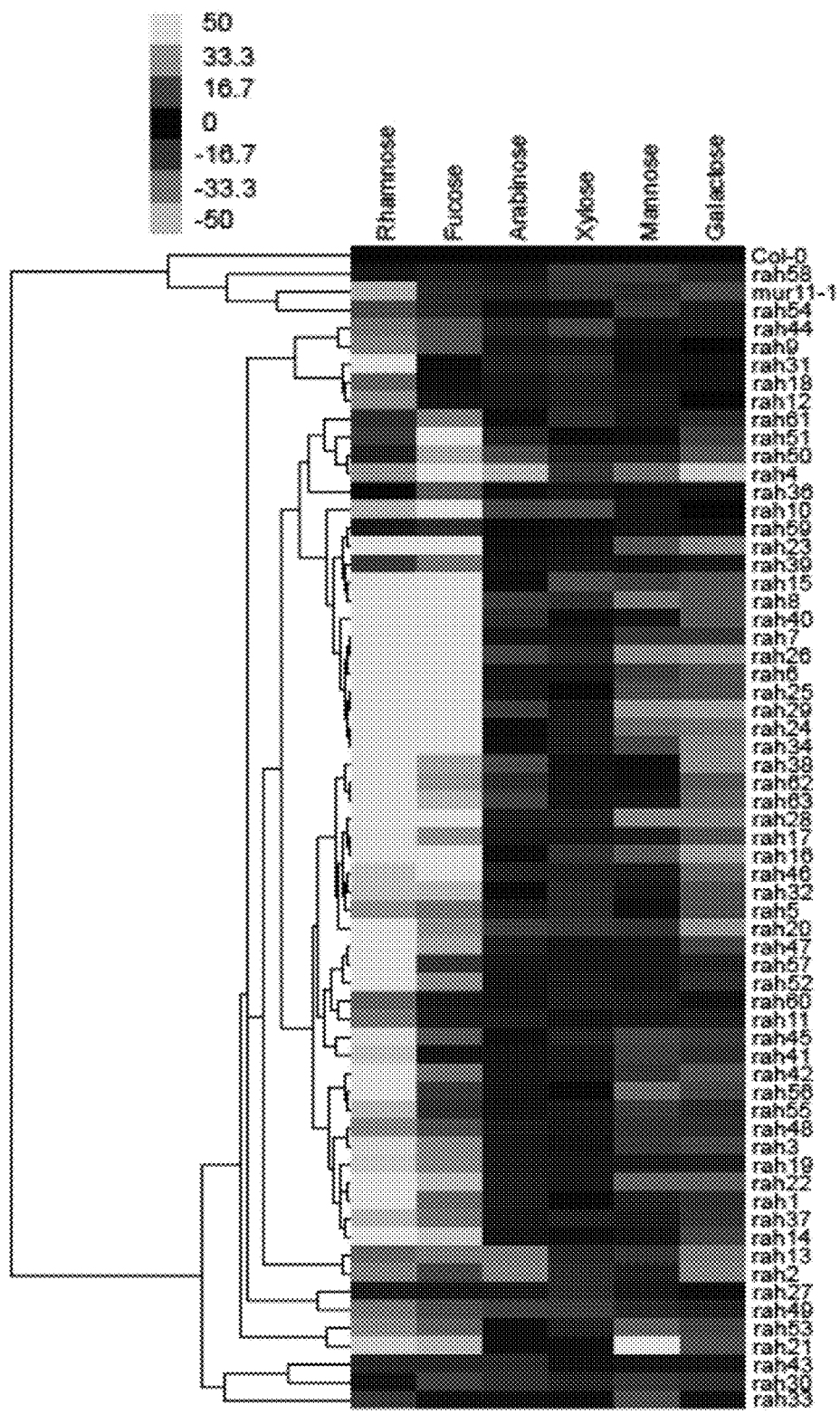

To determine if any of these mutants showed defects in cell wall sugars, gas chromatographic analysis of alditol acetates was performed to identify changes in monosaccharide composition of the cell wall (FIG. 2(b)). Interestingly many of the whs lines showed increases in rhamnose and fucose compared to wild type samples, which indicated that many of the mutations did perturb cell wall composition. Next, the mutant collection was further studied by enzymatic hydrolysis assays using cellulase and cellobiase, to assay cellulose hydrolysis, cellulase, cellobiase and xylanase, to monitor hemicellulose break down, and a cocktail of cellulase, cellobiase, xylanase and peroxidase which, in addition to cellulose and hemicellulose, degrades lignin (FIG. 2(c)). The presence of starch in the samples was also assayed, as this source of carbon could potentially contribute to an increased sugar release phenotype in these assays. Finally, in addition to the fresh leaf material, an assay was carried out on senesced whole plant tissue hydrolyzed with 0.2 M sulphuric acid, biomass that is more akin to field grown plant material and acid concentrations that are more similar to industrial standards.

Hierarchical clustering of the various assays broadly identified three subcategories. One category consisted of five mutant lines (whs27, whs6, whs4, whs20, whs36) that showed good sugar release in both fresh and senesced tissue acid hydrolysis. A second category consisted of twelve lines (mur11-1, whs1, whs43, whs53, whs14, whs2, whs5, whs21, whs3, whs60, whs9, whs22) which hyper-accumulated starch. Within this grouping, two lines (whs9 and whs22) were of particular interest as they also showed excess sugar release in all enzymatic assays. The remaining mutant lines did not show good saccharification in senesced tissues or in any enzymatic assay and therefore were not further studied.

Example 2

Specific Genes Involved in Starch Metabolism Improve Saccharification

To understand the molecular nature of the mutant category that showed both a high saccharification and increased starch accumulation, map-based cloning of the mutant alleles was performed on three lines (whs1, whs22 and whs9). The whs1 and whs22 lines contained allelic mutations in the DISPROPORTIONATING ENZYME 2 (DPE2) gene, which encodes a glucosyltransferase required for starch degradation, and these lines were subsequently re-designated dpe2-100 and dpe2-101 respectively (FIG. 6, Table 2). Subsequent molecular analysis of lines whs3, whs5, whs14, whs21 showed they were siblings of whs1. The whs9 line contained a new allele of STARCH EXCESS 4 (sex4-100), which encodes a glycan phosphatase involved in starch degradation (FIG. 6, Table 2).

Figure 3:
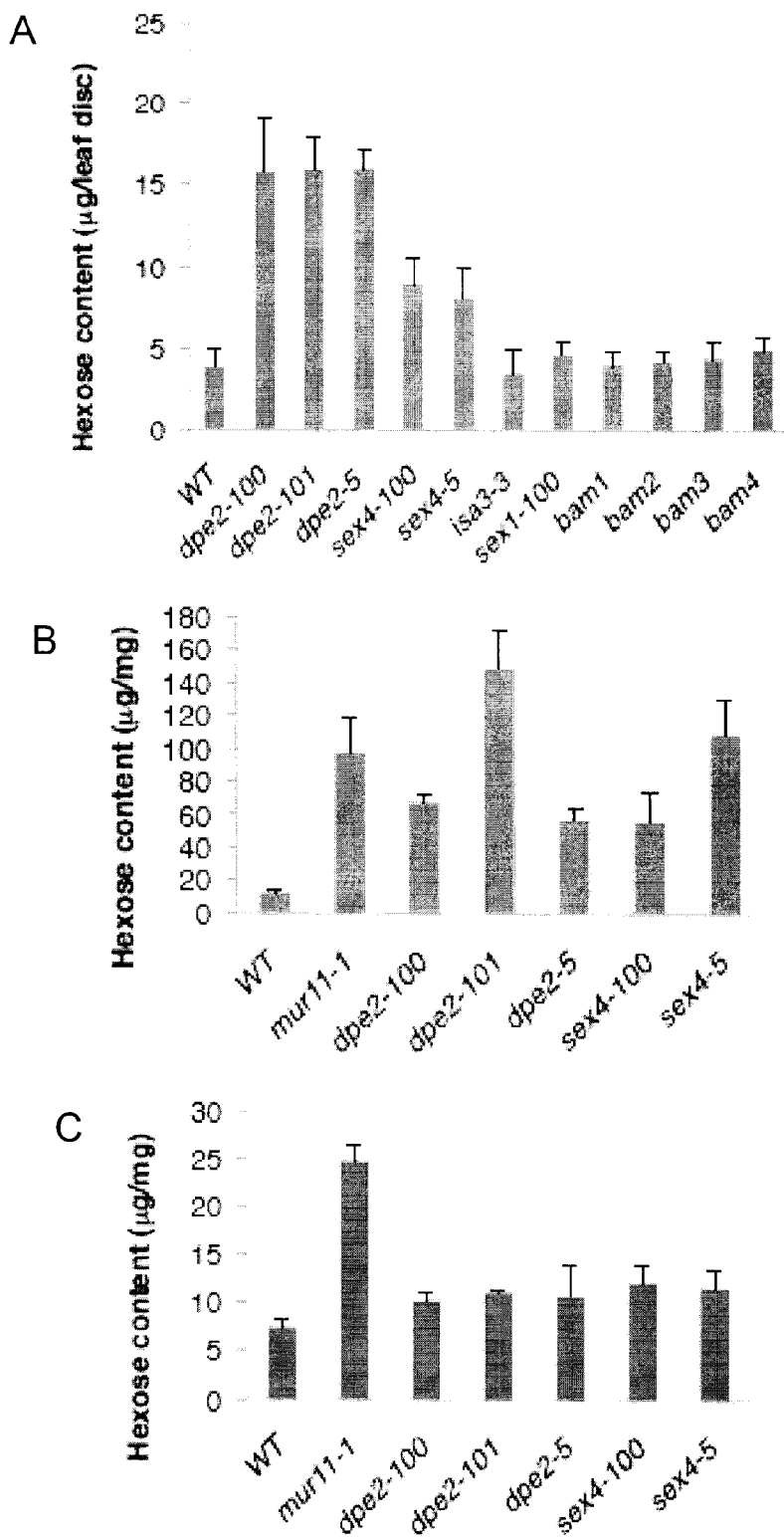
FIG. 3 illustrates the starch analysis of whs mutants mur11, dpe2 and sex4. (A) shows the acid hydrolysis of fresh leaf disc tissue from known starch mutants using 1 M $H_2SO_4$. (Results are averages±s.d. (n=4); all experiments were repeated at least three times with similar results.) (B) shows the treatment of senesced material from starch mutants with α-amylase and the quantification of the amount of starch released using the anthrone method. (Results are averages±s.d. (n=4); all experiments were repeated two times with similar results.) (C) shows the assay of the tissue by acid hydrolysis for residual hexose release using 1 M $H_2SO_4$, post-amylase treatment. (Results are averages±s.d. (n=3).)

The identification of these genes was validated by showing that T-DNA knockout insertion alleles in both DPE2 and SEX4 also showed improved sugar release by acid hydrolysis (FIG. 3(a)).

The identification of dpe2 and sex4 in the screens suggested that starch could be a source of acid-dependent sugar release. The contribution of starch to saccharification was determined by treating senesced whole plant tissue with α-amylase, which specifically converts starch to glucose and maltose (FIG. 3(b)). Once tissue was devoid of starch, it was subjected to acid hydrolysis to determine the residual hexose release (FIG. 3(b)). This analysis clearly showed that the improved sugar release observed in both dpe2 and sex4 mutants can be accounted for by their increased starch content. By contrast, the mur11-1 samples showed a higher sugar release than wild type even after a-amylase treatment, suggesting some of the increased saccharification is due to polymers other than starch.

The connection of starch over-accumulation and increased saccharification by acid hydrolysis was further explored by subjecting a collection of well characterized *Arabidopsis* starch mutants to the acid hydrolysis assay. The analysis included starch-excess 1 (sex1), which is defective in the regulation of starch degradation, isoamylase 3 (isa3), which is defective in a starch debranching enzyme 15, and b-amylase (bam) mutants, which are defective in the breakdown of starch (bam1 through 4) (FIG. 3(a)). Surprisingly, only alleles of mur11, dpe2 and sex4 mutants showed increased sugar release.

Example 3

Inhibiting Polar Auxin Transport Improves Saccharification

Figure 4:
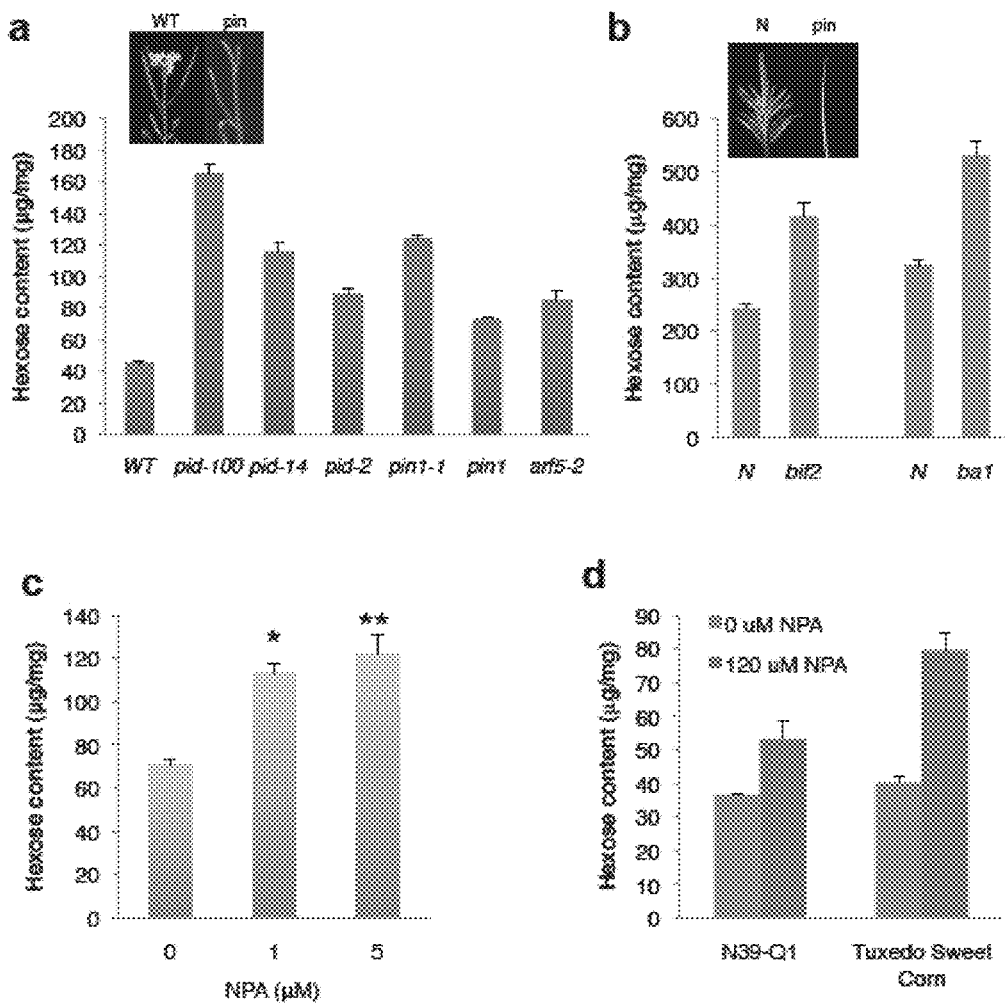
FIG. 4 illustrates the analysis of pin-shaped inflorescence mutants and NPA treatment, resulting in increased saccharification in *Arabidopsis* and maize. (A) shows senesced tissue from *Arabidopsis* pin-shaped inflorescence mutants subjected to 0.2 M acid hydrolysis. (Results are averages±s.d. (n=3); all experiments were repeated three times with similar results.) Inset shows representative pin-shaped inflorescence in *Arabidopsis*. (B) shows maize inflorescence mutants bif2 and ba1 subjected to 0.2 M $H_2SO_4$ acid hydrolysis. (Results are averages±s.d. (n=3-4). N, phenotypically normal siblings.) Inset shows representative maize inflorescence mutant. (C) shows wild type (Col-0) *Arabidopsis* 28 day-old seedlings grown on MS media supplemented with 0, 1 or 5 µM NPA and subjected to 0.2 M $H_2SO_4$ acid hydrolysis. (Results are averages±s.d. (n=4). *, P<0.001 and **, P<0.005 using Student's t-test; all experiments were repeated two times with similar results.) (D) shows two maize cultivars treated with 120 µM NPA for 2 weeks and subjected to 0.2 M $H_2SO_4$ acid hydrolysis. (Results are averages±s.d. (n=6-9).)
Figure 8:
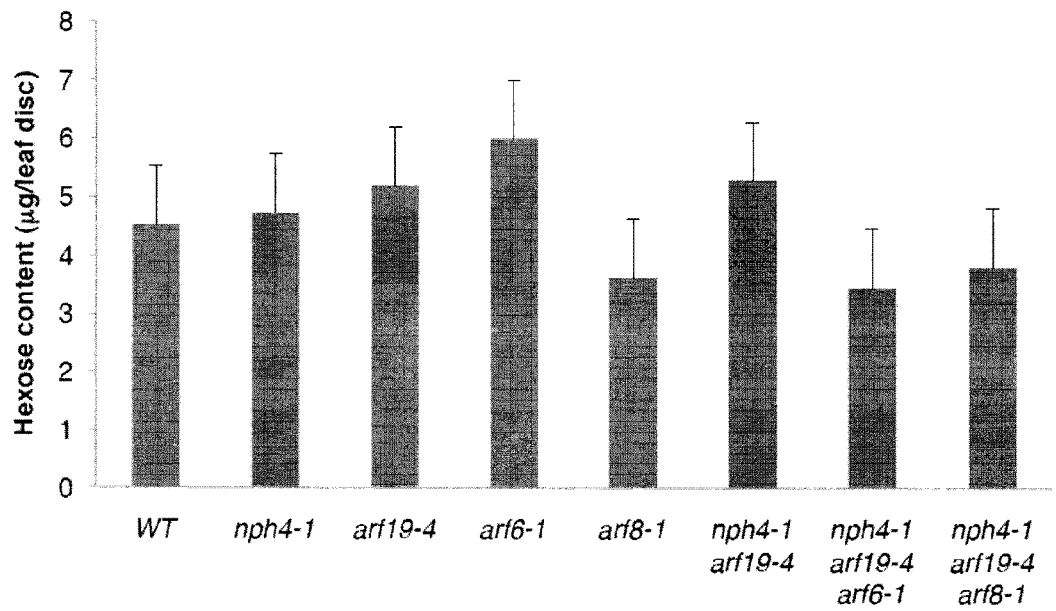
FIG. 8 shows the wall hydrolysis sensitivity of auxin response factor mutants. Leaf disc tissue from 21 day-old plants was assayed using 1 M $H_2SO_4$. (Results are averages±s.d. (n=4-8).)

Among those lines which showed good sugar release in both fresh and senesced tissue, one line (whs20) in particular stood out because it showed an incompletely penetrant pin-shaped inflorescence phenotype that was reminiscent of mutations that perturb the polar transport of the plant hormone auxin. Subsequent molecular analysis of this line identified a mutation in the PINOID (PID) gene (FIG. 6; Table 2). PID encodes a serine threonine protein kinase that is thought to play a role in the cellular localization of the PIN efflux auxin carrier. Mutations in other genes that result in a pin-shaped phenotype, such as pin1 and mp (also known as arf5), also show an improved saccharification phenotype (FIG. 4(a)). By contrast, other auxin response factor mutants defective in auxin signalling (arf6, 7, 8 and 19), did not show increase sugar release, however, these mutants also do not have the pin inflorescence phenotype. Furthermore, none of the single, double or triple combination of arf mutants tested displayed an increase in cell wall accessibility (FIG. 8).

Finally, maize mutants with barren inflorescence phenotypes were tested. Barren inflorescence2 (bif2) is a co-ortholog of PID in *Arabidopsis* 20 and barren stalk1 (ba1), a basic helix-loop-helix transcription factor, has been shown to be a downstream target of BIF2 in maize. Consistent with the results from *Arabidopsis*, both bif2 (SEQ ID NOS: 1 and 2) and ba1 (SEQ ID NOS: 3 and 4) maize inflorescence mutants show an improved saccharification phenotype (FIG. 4(b)).

The connection between auxin transport and increased sugar release was further probed using a specific inhibitor of auxin transport N-1-naphthylphthalamic acid (NPA). Application of varying concentrations of NPA to wild type *Arabidopsis* seedlings resulted in a 1.5 to 2 fold increase in the release of sugars relative to untreated plants (FIG. 4(c)). More importantly, the ability to chemically perturb auxin transport allowed the expansion of the analysis to *Zea mays* (maize). Application of NPA to two different cultivars of maize also resulted in a significant increase in cell wall accessibility (FIG. 4(d)). Together, these results provide strong support that genetic or chemical manipulation of auxin transport increases sugar release. Moreover, it appears that genes and processes identified using *Arabidopsis* can be transferred to maize and potentially other monocot species dedicated to biofuel production.

Example 4

Screening for Novel Cellulose Synthase (CESA) Alleles

Further genetic screens aimed at identifying resistance to cellulose biosynthetic inhibitors (CBIs) were also conducted. The aim of conducting resistance screens can be to identify potential inhibitor targets. In the case of some CBIs, like isoxaben, resistance screens have been carried out using high concentrations of the inhibitor with the aim of identifying the target protein. Indeed, high resistance to isoxaben is only possible if certain CELLULOSE SYNTHASE (CESA) genes are altered by mutation. An unforeseen consequence of some of the resistance alleles has been to reduce overall cellulose crystallinity, which ultimately leads to overall improved saccharification of starting cell wall material. With this information as a starting point, the inventors sought to identify novel CESA alleles by conducting additional resistance screens, but utilizing much lower CBI concentrations than in the original screens.

EMS mutagenized plants (M2) were screened on 20 nM of two different CBIs, isoxaben or flupoxam. Those plants that showed resistance at this concentration of either CBI were then retested in the M3 generation. In total, 2 million M2 seeds were screened and 12 new CESA alleles were isolated, 3 in CESA1, 8 in CESA3 and 1 in CESA6. All of the new mutant alleles led to single amino acid substitutions, which could not have been predicted a priori. Interestingly, one of these alleles led to an amino acid substitution in the proposed catalytic site of the enzyme (ixr1-4). Table 4 shows a summary of the identified mutant alleles.

TABLE 4

| Allele | Genetic Background | Gene | Mutation | Concentration at which root length is 50% of wt |
|---|---|---|---|---|
| wild-type | Ler | — | — | 5 nM |
| wild-type | Col-o | — | — | 5 nM |
| Isoxaben Resistant | | | | |
| ixr1-1 (published) | Col-0 | CesA3 | G(998)D | >1 μM |
| ixr1-2 (published) | Col-0 | CesA3 | T(942)I | 500 nM |
| ixr1-3 | Ler | CesA3 | G(998)S (SEQ ID NOS: 26 and 27) | 100 nM |
| ixr1-4 | Ler | CesA3 | R(806)K (SEQ ID NOS: 28 and 29) | 50 nM |
| ixr1-5 | Ler | CesA3 | L(797)F (SEQ ID NOS: 30 and 31) | 10 nM |
| ixr1-6 | Ler | CesA3 | S(377)F (SEQ ID NOS: 32 and 33) | 50 nM |
| ixr1-7 | Ler | CesA3 | R(276)H (SEQ ID NOS: 34 and 35) | 50 nM |
| ixr2-1 (published) | Col-0 | CesA6 | R(1064)W | 50 nM |
| ixr2-2 | Ler | CesA6 | S(1002)F (SEQ ID NOS: 36 and 37) | 10 nM |
| Flupoxam resistant (Described in http://www.jstor.org/stable/4046145 with recent work in DOI: 10.1111/j.1365-313X.2011.04619.x) | | | | |
| fpx 1-1 | Col-o | CesA3 | S(1040)L (SEQ ID NOS: 20 and 21) | 500 nM |

TABLE 4-continued

| Allele | Genetic Background | Gene | Mutation | Concentration at which root length is 50% of wt |
|---|---|---|---|---|
| fpx 1-2 | Ler | CesA3 | S(1037)F (SEQ ID NOS: 22 and 23) | >1 µM |
| fpx 1-3 | Ler | CesA3 | S(983)F (SEQ ID NOS: 24 and 25) | 100 nM |
| fpx 2-1 | Ler | CesA1 | G(1013)R (SEQ ID NOS: 14 and 15) | >1 µM |
| fpx 2-2 | Ler | CesA1 | P(1010)L (SEQ ID NOS: 16 and 17) | 100-500 nM |
| fpx 2-3 | Ler | CesA1 | G(1009)D (SEQ ID NOS: 18 and 19) | 1 µM |

Figure 9:
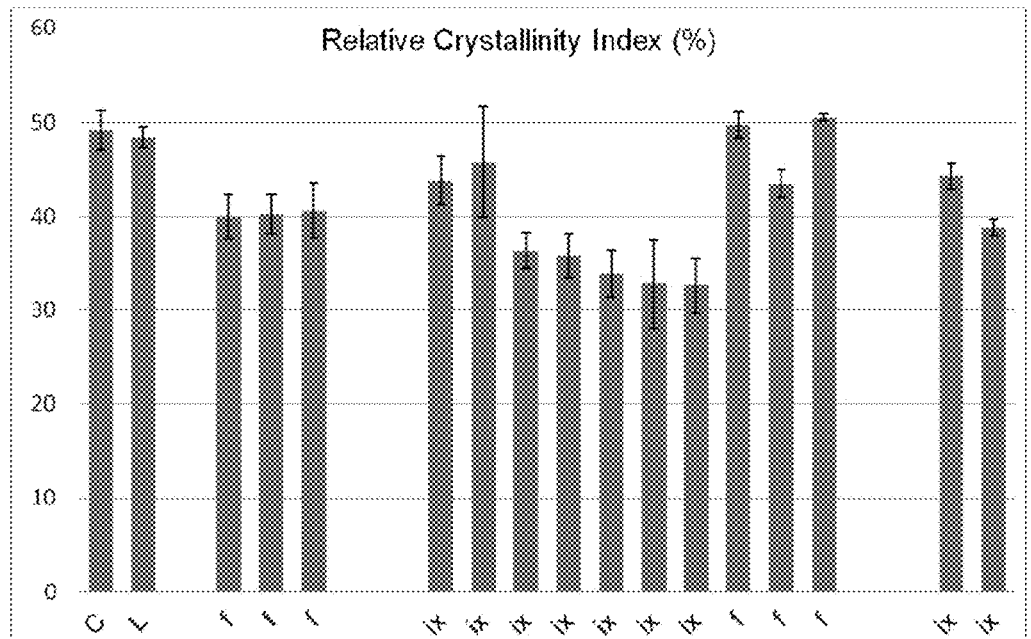
FIG. 9 shows the relative cellulose crystallinity of wt (Col, Ler) and mutant lines. "C" refers to Col-0; "L" refers to Ler; each instance of "f" denotes a fxr mutant line; and each instance of "ix" denotes an ixr mutant line.
Figure 10:
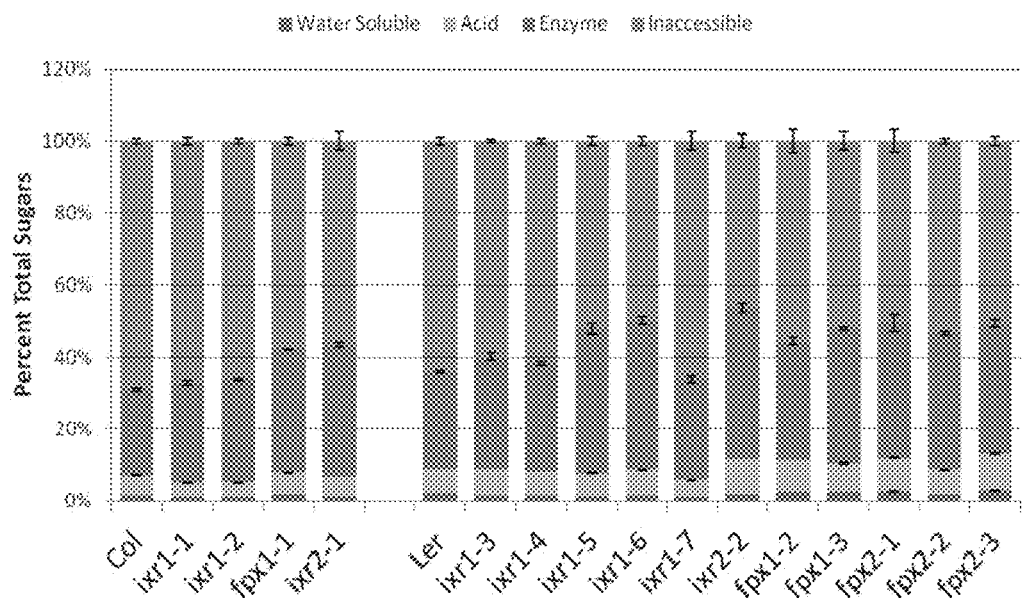
FIG. 10 shows the percent total sugar releases following hydrolysis of wt (Col, Ler) and mutant stem tissue using different treatments.

The mutants were further characterized by determining their relative cellulose crystallinity, as well as their saccharification profiles. This was accomplished by using an X-ray diffractometer to measure the proportion of crystalline cellulose relative to the proportion of amorphous cellulose in stem tissue (FIG. 9). To determine the saccharification properties of the mutant lines, commercial enzyme cocktails were used to digest cell wall preparations and determine the amount of sugar released (FIG. 10). It is significant that many of these alleles, to a greater or lesser extent, showed reduced cellulose crystallinity and in addition were also more amenable to enzyme hydrolysis (FIG. 9 and FIG. 10). However, some lines with apparently unaltered cellulose crystallinity did show improved hydrolysis (e.g. fpx1-1, fpx1-2, fpx 1-3) or some lines with reduced crystallinity did not show improved hydrolysis (e.g. ixr1-7). This indicates that there isn't a tight correlation between cellulose crystallinity and hydrolysis properties.

The value of screening for CESA alleles using this methodology is twofold. Novel CESA alleles can be easily identified, many of which cause cellulose hydrolysis to improve, in a high-throughput manner. The fact that no a priori assumptions about CESA function and structure are required makes this approach particularly useful. In addition, it should be possible to conduct similar screens on target plants to create modified biomass feedstocks directly without the need for generating transgenic plants. One potential limitation is that the CBI that is used may need to specifically target the CESA complex in that plant. For example, the sensitivity to isoxaben is lower in grasses than it is in broadleaf species, which might indicate that alternative CBIs would be required for conducting resistance screens in grasses.

Examples 1-5

Materials and Methods

Plant Materials and Growth Conditions

*Arabidopsis thaliana* M2 ecotype Columbia seeds mutagenized by ethyl methane sulfonate (EMS) were purchased from Lehle Seeds (Round Rock, Tex.). EMS mutant alleles and T-DNA insertions were provided by the *Arabidopsis* Biological Resource Centre (Ohio State University, Columbus, USA). Seeds were surface sterilized in 50% bleach, 0.01% Tween™–20 for 5 min, rinsed 5 times with sterile water and stored in the dark at 4° C. for 4 days to synchronize germination. Seeds were plated on 0.5× strength Murashige and Skoog (MS) agar plates and sealed with surgical tape under continuous light at room temperature. The maize mutants, bif2-N2354 (stock #108A) and bal (stock #318B) in the W23/M14 genetic background, were obtained from the Maize Genetics Cooperation Stock Center.

Anthrone Mutant Screen

The M2 generation of EMS-mutagenized *Arabidopsis* (Col-0) seeds were chilled for 4 days and sowed onto 0.5×MS plates placed vertically under continuous light conditions at room temperature. After 7 days, the seedlings were transferred to soil in 96-well flats. Leaf 3 or 4 was excised from 21 day-old plants using a hole punch and placed abaxial side up in a 96-well plate corresponding to the same coordinates as the flat. Samples were submerged in 200 µl of 1M $H_2SO_4$ and incubated at room temperature for 1 hour. A 50 µl aliquot was removed and incubated with 100 µl of 0.2% anthrone in concentrated $H_2SO_4$. The samples were incubated at 100° C. for 5 minutes, cooled and the absorbance was read at 660 nm. Approximately 22,000 seedlings from 32 pools were screened from which 63 wall hydrolysis sensitive (whs) mutants were identified as having an absorbance reading greater than 2 standard deviations from wild type (FIG. 5). whs mutants were retested in the M3 generation.

Enzymatic Digestion

Approximately 0.1-0.2 g of senesced tissue was washed twice with water for 30 min at 80° C. and washed with 70% ethanol at 80° C. for 1 hour. The tissue was rinsed with acetone and oven dried at 60° C. for 2 days. Cellulase from *Trichoderma reesi* ATCC 26921 and the Cellobiase (Novozyme 188) activities were empirically determined to be 111 FPU/mL and 500 U/mL, respectively. Glucose levels were determined via anthrone assay and cellobiase activity was determined by measuring p-nitro phenol (PNP) absorbance levels at 400 nm. 15 FPU/g of tissue of cellulase and 80 U/g of cellobiase were used on 5 mg of tissue/tube with a total volume of 200 µL in triplicates. The samples were incubated with a final 10× dilution of cellulase and cellobiase at 50° C. for 24 hours and heat inactivated at 100° C. for 5 min. Once cooled on ice, the samples were centrifuged and the supernatant was analyzed for its glucose concentration by the Glucose (HK) Assay Kit (GAHK20-1KT) (Sigma) according to the manufacturer's instructions.

Gas-liquid Chromatography

Hydrolysis of leaf material and quantification of monosaccharides by gas-liquid chromatography of alditol acetates was carried out as previously described by Reiter et al., 1993. At least 5-20 mg of fresh tissue from 5 plant lines were pooled and extracted three times with chloroform:methanol (1:1) for 30 min. Three technical replicates were performed for each whs mutant. The tissue was washed with 70% ethanol at 70° C. for 1 hour, rinsed with acetone and left to air dry overnight and hydrolyzed in 1M $H_2SO_4$ at 120° C. for 1 hour. The released monosaccharides were converted into alditol acetates and quantified by gas chromatography. Relative sugar composition values were calculated as a mol percentage.

Clustering and Heatmap Analysis

Figure 2C:
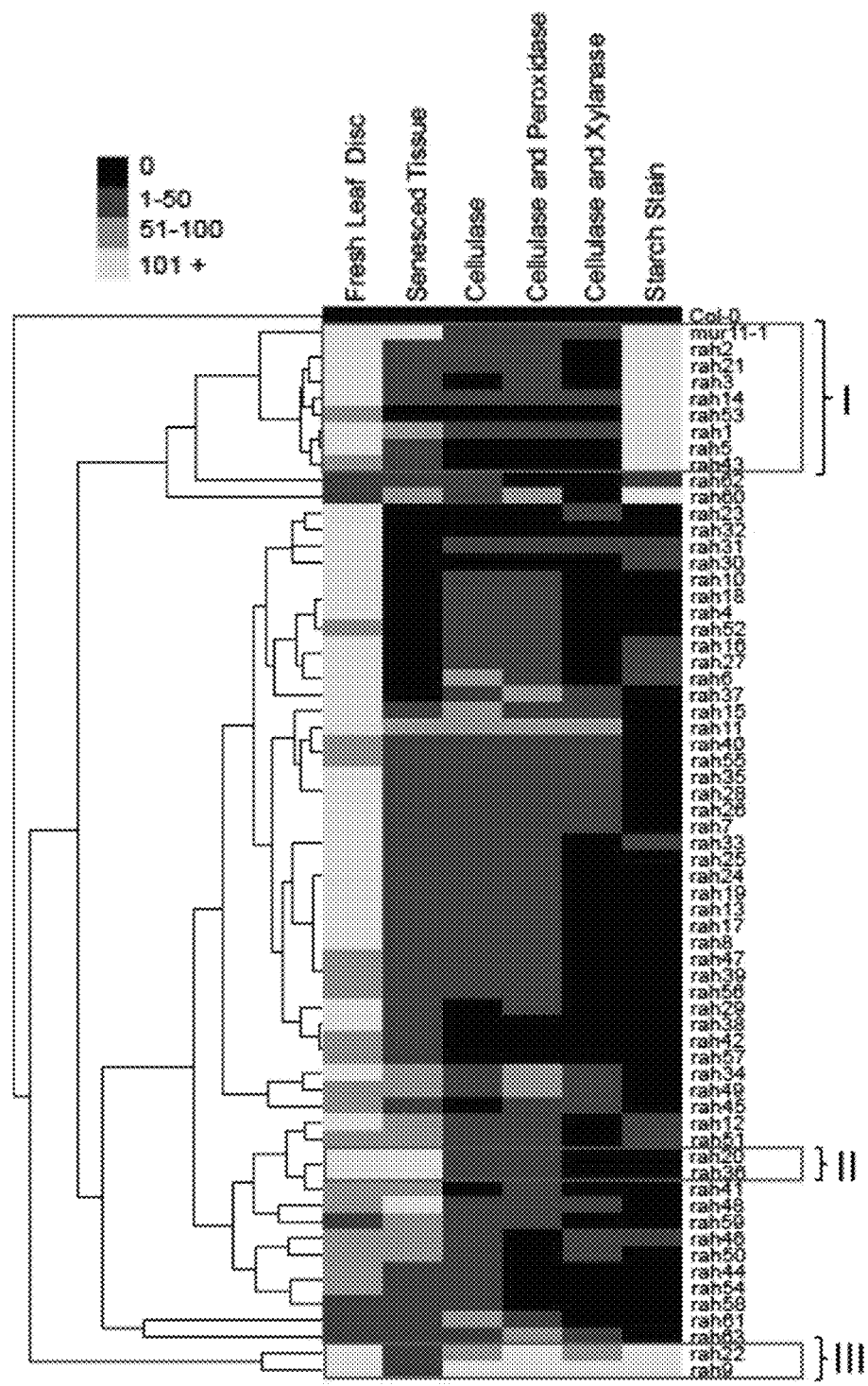

Monosaccharide composition of 62 whs mutants (whs35 not determined) and mur11-1 was determined by liquid gas chromatography and calculated as a percent difference relative to wild type (FIG. 2(c)). Cluster 3.0 using the C Clustering Library version 1.49 was used to cluster the values by Average Linkage and centered correlation. Java TreeView 1.1.5r2 was then used to display the data and colour-coded yellow (more than wild type) or blue (less than wild type). Glucose values quantified from the acid hydrolysis and enzymatic assays performed on the 63 whs mutants, excluding the starch staining, were calculated as a percent difference relative to wild type. Mutants with values equal to wild type were given color coded black and mutants with hexose values greater than wild type were color coded yellow. For starch staining, 14 day-old seedlings were stained with IKI and were visually analyzed for the presence of starch in their cotyledons and determined qualitatively.

Amylase Digestion

Five milligrams of tissue was weighed out in triplicate and re-suspended in 0.1 M sodium acetate, pH 5, and incubated at 80° C. for 30 min to gelatinize the starch. The tubes were cooled on ice then 30 µL of 0.1×α-amylase (Sigma A7595, activity: 250 U/mL for 1×) from *Bacillus amyloliquefaciens* was added. In addition, 15 µL of pullulanase M1 from *Klebsiella planticola* (Megazyme 42 U/mg) and 15 µL of pullulanase M2 from *Bacillus licheniformis* (Megazyme 26 U/mg) were added to bring the total liquid volume to 1 mL. The samples were vortexed then placed in an incubator at 37° C. for 16 hours. The samples were spun down at 12,000 g for 10 min and the reducing sugar equivalents were quantified using 0.2% anthrone. It should be noted that the HK Assay did not detect the products of the amylase digestion.

NPA Treatment of Monocot Plants

Polar auxin transport inhibition was carried out as described by Wu & McSteen, 2007. The two maize cultivars, Syngenta hybrid N39-Q1 and Tuxedo Sweet Corn, were grown in a greenhouse at 24° C. with a 12 hour day/night cycle. The plants were grown four weeks before NPA treatment followed by a two week watering regime using 120 µM NPA (ChemService, West Chester, Pa., USA) or DMSO alone (solvent) applied every two days in a volume of 150 mL for each pot. Plants were fertilized once a week with 20-20-20 fertilizer. After 2 weeks of treatment, whole plants were collected and de-stained in chloroform:methanol (1:1 v/v). Acid hydrolysis was performed as described previously.

Genetic and Physical Mapping of Mutants

Genetic mapping was accomplished using an F2 population derived from a cross between the whs mutants (Columbia genotype, Col-0) and Landsberg erecta (Ler). F2 seedlings were scored for wall hydrolysis sensitivity by anthrone screening. Genomic DNA was isolated from individual F2 plants from a mapping population showing the mutant phenotype and assigned to a chromosome using published simple sequence length polymorphism (SSLP) markers. New molecular markers were developed using the Monsanto Col-0 and Ler polymorphism database. The cloned WHS genes were amplified by PCR using X-Taq DNA polymerase with proofreading activity (Takara). Sequencing reactions were performed by The Centre for the Analysis of Genome Evolution and Function (CAGEF) at the University of Toronto. F2 mutants from two independent crosses were used for sequencing and verifying lesions.

The compositions, methods, mutant genes, cells, plants and other materials described in this application may be employed in the production of biomass useful, for example, in production of biofuels such as bioethanol, as well as other materials such as bioplastic, biofoam, biorubber, biocomposite, forestry biofibre, agricultural textile, chemical, monosaccharide, disaccharide, polysaccharide, biocosmetics, and in other feed stock production.

The scope of the claims should not be limited by the preferred embodiments set forth in the examples, but should be given the broadest interpretation consistent with the description as a whole.

REFERENCES

1. Himmel, M. E. et al. Biomass Recalcitrance: Engineering plants and enzymes for biofuels production. *Science* 315, 804-807 (2007).
2. Carroll A. & Somerville C. Cellulosic biofuels. *Annu Rev Plant Biol.* 60, 165-82 (2009).
3. Pauly, M. & Keegstra, K. Plant cell wall polymers as precursors for biofuels. *Curr. Opin. Plant Sci.* 13, 305-312 (2010).
4. Pingali, S. V. et al. Breakdown of cell wall nanostructure in dilute acid pretreated biomass. *Biomacromolecules* 11, 2329-2335 (2010).
5. Kumar, P. et al. Methods for pretreatment of lignocellulosic biomass for efficient hydrolysis and biofuel production. *Ind. Eng. Chem. Res.* 48, 3713-3729 (2009).
6. Vanholme, R., Van Acker, R. & Boerjan, W. Potential of *Arabidopsis* systems biology to advance the biofuel field. *Trends in Biotech.* 28, 543-547 (2010).
7. Austin et al. Next-Generation Mapping of *Arabidopsis* Genes. Plant J. April 23. doi: 10.1111/j.1365–313x.2011.04619.x. [Epub ahead of print] (2011).
8. Fry, S. C. *The Growing Plant Cell Wall: Chemical and Metabolic Analysis.* (The Blackburn Press, Caldwell, N.J., USA, 1988).
9. Reiter, W.-D., Chapple, C. & Somerville, C. R. Mutants of *Arabidopsis thaliana* with altered cell wall polysaccharide composition. *Plant J.* 12, 335-45 (1997).
10. Williams, M. E. et al. Mutations in the *Arabidopsis* phosphoinositide phosphatase gene SAC9 lead to overaccumulation of PtdIns(4,5)P2 and constitutive expression of the stressresponse pathway. *Plant Phys.* 138, 686-800 (2005).
11. Reiter, W.-D., Chapple, C. C. S. & Somerville, C. R. Altered growth and cell walls in a fucose-deficient mutant of *Arabidopsis. Science* 261, 1032-1035 (1993).
12. Chia, T. et al. A cytosolic glucosyltransferase is required for conversion of starch to sucrose in *Arabidopsis* leaves at night. *Plant J.* 37, 853-863 (2004).
13. Kotting, O. et al. STARCH-EXCESS4 is a laforin-like phophoglucan phophatase required for starch degradation in *Arabidopsis thaliana. Plant Cell* 21, 334-46 (2009).
14. Caspar, T. et al. Mutants of *Arabidopsis* with altered regulation of starch degradation. *Plant Phys.* 95, 1181-1188 (1991).
15. Wattebled, F. et al. Mutants of *Arabidopsis* lacking a chloroplastic isoamylase accumulate phytoglycogen and an abnormal for anylopectin. *Plant Phys.* 138, 184-195 (2005).
16. Fulton, D. C. et al., b-AMYLASE4, a noncatalytic protein required for starch breakdown, acts upstream of three active b-amylases in *Arabidopsis* chloroplasts. *Plant Cell* 20, 1040-1058 (2008).
17. Okada, K. et al. Requirement of the auxin polar transport system in early stages of *Arabidopsis* floral bud formation. *Plant Cell* 3, 677-684 (1991).
18. Christensen, S. K., Dagenais, N., Chory, J. & Weigel, D. Regulation of auxin response by the protein kinase PINOID. Cell 100, 469-78 (2000).

19. Przemeck, G. K. H. et al. Studies on the role of the *Arabidopsis* gene MONOPTEROS in vascular development and plant cell axialization. *Planta* 200, 229-237 (1996).
20. Wu, X. & McSteen, P. The role of auxin transport during inflorescence development in maize (*Zea mays, Poaceae*). *Am. J. Bot.* 11, 1745-1755 (2007).
21. Skirpan, A., Wu, X. & McSteen, P. Genetic and physical interactions suggest that BARREN STALK1 is a target of BARREN INFLORESCENCE2 in maize inflorescence development. *Plant J.* 55, 787-797 (2008).
22. Reinhardt, D., Madel, T. & Kuhlemeier, C. Auxin regulates the initiation and radial position of plant lateral organs. *Plant Cell* 12, 507-518 (2000).
23. Reinhardt, D. et al. Regulation of phyllotaxis by polar auxin transport. *Nature* 426, 255-260 (2003).
24. Fu, C. et al. Genetic manipulation of lignin reduces recalcitrance and improves ethanol production from switchgrass. *Proc. Natl. Acad. Sci. USA* 108, 3803-8 (2011).
25. Chen F, Dixon R A. Lignin modification improves fermentable sugar yields for biofuel production. *Nat. Biotech.* 25, 759-61 (2007).
26. Li, L et al. Combinatorial modification of multiple lignin traits in trees through multigene cotransformation. *Proc. Natl. Acad. Sci.* 100, 4939-44 (2003).
27. Somerville C. R. et al. Toward a Systems Approach to Understanding Plant Cell Walls. *Science* 306, 2206-2211 (2004).
28. Sánchez-Rodriguez C., Rubio-Somoza I., Sibout R., & Persson S. Phytohormones and the cell wall in *Arabidopsis* during seedling growth. *Trends Plant Sci.* 15, 291-301 (2010).
29. Feraru, E. et al. PIN polarity maintenance by the cell wall in *Arabidopsis. Curr. Biol.* 4, 33-43 (2011).
30. McCourt P. & Desveaux D. Plant chemical genetics. *New Phytol.* 185, 15-26 (2010).
31. Scheible W R, Eshed R, Richmond T, Delmer D, Somerville C. Modifications of cellulose synthase confer resistance to isoxaben and thiazolidinone herbicides in *Arabidopsis* Ixr1 mutants. Proc Natl Acad Sci USA. 98(18):10079-84 (2001).
32. Harris, D., Stork, J. and Debolt, S. Genetic modification in cellulose-synthase reduces crystallinity and improves biochemical conversion to fermentable sugar. GCB Bioenergy, 1: 51-61 (2009).

The invention claimed is:

1. An isolated nucleic acid which encodes:

a mutant fpx 1-2 polypeptide comprising a mutation corresponding to S1037F in SEQ ID NO: 23, or fragment thereof encoding said mutant fpx 1-2 polypeptide wherein said fragment comprises said S1037F mutation and is at least 80% identical to SEQ ID NO: 23.

2. The isolated nucleic acid of claim 1, comprising:

a nucleic acid sequence 80% identical to SEQ ID NO: 22 or encoding a polypeptide which is at least 80% identical to SEQ ID NO: 23.

3. A vector comprising a nucleic acid as defined in claim 1.

4. A host cell comprising a nucleic acid as defined in claim 1.

5. A seed or plant comprising a nucleic acid as defined in claim 1.

6. The isolated nucleic acid of claim 1, comprising a nucleic acid sequence 85% identical to SEQ ID NO: 22 or encoding a polypeptide which is 85% identical to SEQ ID NO: 23.

7. The isolated nucleic acid of claim 1, comprising a nucleic acid sequence 90% identical to SEQ ID NO: 22 or encoding a polypeptide which is 90% identical to SEQ ID NO: 23.

8. The isolated nucleic acid of claim 1, comprising a nucleic acid sequence 99% identical to SEQ ID NO: 22 or encoding a polypeptide which is 99% identical to SEQ ID NO: 23.

9. The isolated nucleic acid of claim 1, having the nucleic acid sequence of SEQ ID NO: 22 or encoding a polypeptide having the sequence of SEQ ID NO: 23.

10. A vector comprising a nucleic acid as defined in claim 7.

11. A host cell comprising a nucleic acid as defined in claim 7.

12. A seed or plant comprising a nucleic acid as defined in claim 7.

13. A vector comprising a nucleic acid as defined in claim 9.

14. A host cell comprising a nucleic acid as defined in claim 9.

15. A seed or plant comprising a nucleic acid as defined in claim 9.

* * * * *

SEQUENCE LISTING

<160> NUMBER OF SEQ ID NOS: 37

<210> SEQ ID NO 1
<211> LENGTH: 1651
<212> TYPE: DNA
<213> ORGANISM: Zea mays

<400> SEQUENCE: 1

```
tcgtcctcgc tcggagacac ggcaagcgag tcctcctcac tcacgcaaac acacgccgtg      60
ccgcgagcgc acgagacaac cgagcggagc tgccgcctgc ccgccagtgc cagccatgga     120
cgccgcggtg cgcgtccccc cggcgctcgg gaacaagacg gtgaccgagg tgacgccgcc     180
gccgccacca ccggcggggg aggagcggct gtcggacgcc gacacgacgg cgtcgtcgac     240
ggcggcgccc aactcgagcc tcagctcggc cagcagcgcc gccagcctgc cgcgctgctc     300
cagcctgtcc cgcctctcct tcgactgctc tccgtccgcg gccctgtcct cttcctcggc     360
ggcggcggcg gccgcggccg cgtcatcgcc ggcgccagcg ccggcgcggc cgcaccgggc     420
aggggacgcg gcgtgggcgg cgatccgcgc ggcgtcggcg tcggccgcgg cgccgctggg     480
gccgcgggac ttcaggctgc tgcgccgcgt gggcggcggc gacgtcggca ccgtgtacct     540
gtgccgcctc agggcgccac ccgcgcccgc gcccgtctgc tgcctgtacg cgatgaaggt     600
ggtggaccgg cgcgtggcgg ccgcgaagaa gaagctggag cacgcggcgg cggagcggcg     660
gatcctgcgg gcgctggacc atccgttcct gcccacgctc ttcgccgact tcgacgccgc     720
gccgcacttc tcctgcgtcg tcacggagtt ctgccccggc ggggacctcc actcgctccg     780
ccaccgcatg cccaaccgcc gcttcccgct cccgtcagct cggttctacg cggcggaggt     840
gttgctggcg ctggagtacc tgcacatgat gggcatcgtg taccgcgacc tcaagccgga     900
gaacgtgctg atccgcgcgg acggccacat catgctcacg gacttcgacc tgtcgctgca     960
gtgcacgtcg acgccgtcgc tcgagccgtg cgccgccccc gaggcggcgg cggcgtcctg    1020
cttcccggac cacctgttcc gccgccgcg cgcgcgactc cgccgtgccg cctcggcgcg    1080
gcggccgcca acgaccctgg tggcggagcc ggtggaggcg cggtcgtgct cgttcgtggg    1140
cacgcacgag tacgtggcgc ccgaggtggc ccgcggcggg cccacggcg cggccgtcga    1200
```

```
ctggtgggcg ctcggcgtgt tcctgtacga gctcctgcac gggcgcaccc cgttcgcggg    1260
cgccgacaac gaggccacgc tccgcaacat cgcgcgccgc ccgctgtcct tccccgctgc    1320
cggcgccggt gatgccgacg cgcgcgacct catcgcccgc ctcctcgcca aggacccgcg    1380
ccaccggttg gggtcccggc gcggcgccgc cgacgtgaag gcgcaccgt tcttccgcgg     1440 gctcaacttc gcgctgctcc ggtcctcccg cccgcccgtc gtccccgccg cgtcgcgctc    1500
cccgctgcac cgctcgcagt cctgcagcgc ggcgcgcacg agagcgtcga agccgaagcc    1560
gccgccggac acccggttcg aactgttctg acacgaccgt tgccggcgtc acgcacgtgc    1620
gtgttgacct agttgcatca ctcgccattg t                                   1651
```

<210> SEQ ID NO 2
<211> LENGTH: 491
<212> TYPE: PRT
<213> ORGANISM: Zea mays

<400> SEQUENCE: 2

```
Met Asp Ala Ala Val Arg Val Pro Pro Ala Leu Gly Asn Lys Thr Val
1               5                   10                  15

Thr Glu Val Thr Pro Pro Pro Pro Ala Gly Glu Glu Arg Leu
            20                  25                  30

Ser Asp Ala Asp Thr Thr Ala Ser Ser Thr Ala Ala Pro Asn Ser Ser
        35                  40                  45

Leu Ser Ser Ala Ser Ser Ala Ala Ser Leu Pro Arg Cys Ser Ser Leu
    50                  55                  60

Ser Arg Leu Ser Phe Asp Cys Ser Pro Ser Ala Ala Leu Ser Ser Ser
65                  70                  75                  80

Ser Ala Ala Ala Ala Ala Ala Ala Ser Ser Pro Ala Pro Ala Pro
                85                  90                  95

Ala Arg Pro His Arg Ala Gly Asp Ala Ala Trp Ala Ala Ile Arg Ala
            100                 105                 110

Ala Ser Ala Ser Ala Ala Ala Pro Leu Gly Pro Arg Asp Phe Arg Leu
        115                 120                 125

Leu Arg Arg Val Gly Gly Gly Asp Val Gly Thr Val Tyr Leu Cys Arg
    130                 135                 140

Leu Arg Ala Pro Pro Ala Pro Ala Pro Val Cys Cys Leu Tyr Ala Met
145                 150                 155                 160

Lys Val Val Asp Arg Arg Val Ala Ala Ala Lys Lys Lys Leu Glu His
                165                 170                 175

Ala Ala Ala Glu Arg Arg Ile Leu Arg Ala Leu Asp His Pro Phe Leu
            180                 185                 190

Pro Thr Leu Phe Ala Asp Phe Asp Ala Ala Pro His Phe Ser Cys Val
        195                 200                 205

Val Thr Glu Phe Cys Pro Gly Gly Asp Leu His Ser Leu Arg His Arg
    210                 215                 220

Met Pro Asn Arg Arg Phe Pro Leu Pro Ser Ala Arg Phe Tyr Ala Ala
225                 230                 235                 240

Glu Val Leu Leu Ala Leu Glu Tyr Leu His Met Met Gly Ile Val Tyr
                245                 250                 255

Arg Asp Leu Lys Pro Glu Asn Val Leu Ile Arg Ala Asp Gly His Ile
            260                 265                 270

Met Leu Thr Asp Phe Asp Leu Ser Leu Gln Cys Thr Ser Thr Pro Ser
        275                 280                 285
```

Leu Glu Pro Cys Ala Ala Pro Glu Ala Ala Ala Ser Cys Phe Pro
    290                 295                 300

Asp His Leu Phe Arg Arg Arg Ala Arg Leu Arg Arg Ala Ala Ser
305                 310                 315                 320

Ala Arg Arg Pro Pro Thr Thr Leu Val Ala Glu Pro Val Glu Ala Arg
                325                 330                 335

Ser Cys Ser Phe Val Gly Thr His Glu Tyr Val Ala Pro Glu Val Ala
                340                 345                 350

Arg Gly Gly Pro His Gly Ala Ala Val Asp Trp Trp Ala Leu Gly Val
                355                 360                 365

Phe Leu Tyr Glu Leu Leu His Gly Arg Thr Pro Phe Ala Gly Ala Asp
    370                 375                 380

Asn Glu Ala Thr Leu Arg Asn Ile Ala Arg Arg Pro Leu Ser Phe Pro
385                 390                 395                 400

Ala Ala Gly Ala Gly Asp Ala Asp Ala Arg Asp Leu Ile Ala Arg Leu
                405                 410                 415

Leu Ala Lys Asp Pro Arg His Arg Leu Gly Ser Arg Arg Gly Ala Ala
                420                 425                 430

Asp Val Lys Ala His Pro Phe Phe Arg Gly Leu Asn Phe Ala Leu Leu
                435                 440                 445

Arg Ser Ser Arg Pro Pro Val Val Pro Ala Ala Ser Arg Ser Pro Leu
    450                 455                 460

His Arg Ser Gln Ser Cys Ser Ala Ala Arg Thr Arg Ala Ser Lys Pro
465                 470                 475                 480

Lys Pro Pro Pro Asp Thr Arg Phe Asp Leu Phe
                485                 490

<210> SEQ ID NO 3
<211> LENGTH: 958
<212> TYPE: DNA
<213> ORGANISM: Zea mays

<400> SEQUENCE: 3
caaagccaac agaactgcac agtgtagtag ttgcacatag gcgtccgcgc gtcgtcctag      60
ctatggatcc atatcactac caaaccatgt atgacccacg cggcttcccc atcatccacc    120
cgcagcctta cctccagcac ccggtggccg gcgccctcgg tgacagcagg gtgcgcggcg    180
gcggcagtgg cgcgcggcgg cgtcctggcg ccaagctctc cacggacccg cagagcgttg    240
cggcgcgcga gcggcggcac cgcatcagcg accgcttccg cgtgctccgc agcctcgtcc    300
ccggcggcag caagatggac actgtgtcca tgctcgagca ggccatccac tacgtcaagt    360
tcctcaagac gcagatcagc ctgcatcagg ccgcgctgat gcagcacgag gaaggatgcc    420
atgctgagct cgccgcctat ccgcggtgg cggtggttgg tgacaacgag gtgacactcg     480
cgtcccatgg tcgtaccggc gcatgcgacg agatgatgca gctccaggtg gcggcggagg    540
aagctttgag ttatggtgtt gatgcccatc agccgtacgg gctcgatccc aggcagctga    600
gtggtgggca cgagctgcca ccgctgcctg cttcttgcat cttcctcgag gagcctgcag    660
acgcatgcta ctctgtgtgt gacctcgacg acggggacac cggtctgccc ggctcttact    720
agagtagtag tagaagtttc ttaaggtagc atcccgtgtg tgttggtgtc tgctagacgc    780
tagtacgtct aattagcaaa gtttagctag tactcgatca attgtctgtc tagttcgctc    840
agagttaaag tatatgatga tgcatctgca tatatgggct ctgtaattct gttatccgct    900
gatcgcagat gatacaccgt atgtaatcac atgtatgtat gttgcctaaa aaaaaaaa     958

<210> SEQ ID NO 4
<211> LENGTH: 219
<212> TYPE: PRT
<213> ORGANISM: Zea mays

<400> SEQUENCE: 4

Met Asp Pro Tyr His Tyr Gln Thr Met Tyr Asp Pro Arg Gly Phe Pro
1               5                   10                  15

Ile Ile His Pro Gln Pro Tyr Leu Gln His Pro Val Ala Gly Ala Leu
            20                  25                  30

Gly Asp Ser Arg Val Arg Gly Gly Ser Gly Ala Arg Arg Arg Arg Pro
        35                  40                  45

Gly Ala Lys Leu Ser Thr Asp Pro Gln Ser Val Ala Ala Arg Glu Arg
    50                  55                  60

Arg His Arg Ile Ser Asp Arg Phe Arg Val Leu Arg Ser Leu Val Pro
65                  70                  75                  80

Gly Gly Ser Lys Met Asp Thr Val Ser Met Leu Glu Gln Ala Ile His
                85                  90                  95

Tyr Val Lys Phe Leu Lys Thr Gln Ile Ser Leu His Gln Ala Ala Leu
            100                 105                 110

Met Gln His Glu Glu Gly Cys His Ala Glu Leu Ala Ala Tyr Ser Ala
        115                 120                 125

Val Ala Val Val Gly Asp Asn Glu Val Thr Leu Ala Ser His Gly Arg
    130                 135                 140

Thr Gly Ala Cys Asp Glu Met Met Gln Leu Gln Val Ala Ala Glu Glu
145                 150                 155                 160

Ala Leu Ser Tyr Gly Val Asp Ala His Gln Pro Tyr Gly Leu Asp Pro
                165                 170                 175

Arg Gln Leu Ser Gly Gly His Glu Leu Pro Pro Leu Pro Ala Ser Cys
            180                 185                 190

Ile Phe Leu Glu Glu Pro Ala Asp Ala Cys Tyr Ser Val Cys Asp Leu
        195                 200                 205

Asp Asp Gly Asp Thr Gly Leu Pro Gly Ser Tyr
    210                 215

<210> SEQ ID NO 5
<211> LENGTH: 1646
<212> TYPE: PRT
<213> ORGANISM: Arabidopsis thaliana

<400> SEQUENCE: 5

Met Asp Leu His Pro Pro Gly Gly Ser Lys Lys Thr Ser Val Val Val
1               5                   10                  15

Val Thr Leu Asp Thr Gly Glu Val Tyr Val Ile Ala Ser Leu Leu Ser
            20                  25                  30

Lys Ala Asp Thr Gln Val Ile Tyr Ile Asp Pro Thr Thr Gly Ile Leu
        35                  40                  45

Arg Tyr Asn Gly Lys Pro Gly Leu Asp Asn Phe Lys Ser Glu Arg Glu
    50                  55                  60

Ala Leu Asp Tyr Ile Thr Asn Gly Ser Arg Gly Gly Val Arg Ser Ser
65                  70                  75                  80

Val Tyr Ala Arg Ala Ile Leu Gly Tyr Ala Val Leu Gly Ser Phe Gly
                85                  90                  95

Met Leu Leu Val Ala Thr Arg Leu Asn Pro Ser Ile Pro Asp Leu Pro
            100                 105                 110

-continued

Gly Gly Gly Cys Val Tyr Thr Val Ala Glu Ser Gln Trp Val Lys Ile
            115                 120                 125

Pro Leu Tyr Asn Pro Gln Pro Gln Gly Lys Gly Glu Thr Lys Asn Ile
130                 135                 140

Gln Glu Leu Thr Glu Leu Asp Ile Asp Gly Lys His Tyr Phe Cys Asp
145                 150                 155                 160

Thr Arg Asp Ile Thr Arg Pro Phe Pro Ser Arg Met Pro Leu Gln Ser
                165                 170                 175

Pro Asp Asp Glu Phe Val Trp Asn Arg Trp Leu Ser Val Pro Phe Lys
            180                 185                 190

Asn Ile Gly Leu Pro Glu His Cys Val Ile Leu Leu Gln Gly Phe Ala
            195                 200                 205

Glu Tyr Arg Pro Phe Gly Ser Ser Gly Gln Leu Glu Gly Ile Val Ala
            210                 215                 220

Leu Met Ala Arg Arg Ser Arg Leu His Pro Gly Thr Arg Tyr Leu Ala
225                 230                 235                 240

Arg Gly Ile Asn Ser Cys Ser Gly Thr Gly Asn Glu Val Glu Cys Glu
                245                 250                 255

Gln Leu Val Trp Ile Pro Lys Arg Asn Gly Gln Ser Ile Ala Phe Asn
            260                 265                 270

Ser Tyr Ile Trp Arg His Gly Thr Ile Pro Ile Trp Trp Gly Ala Glu
            275                 280                 285

Leu Lys Met Thr Ala Ala Glu Ala Glu Ile Tyr Val Ala Asp Arg Asp
            290                 295                 300

Pro Tyr Lys Gly Ser Thr Glu Tyr Tyr Gln Arg Leu Ser Lys Arg Tyr
305                 310                 315                 320

Asp Thr Arg Asn Leu Asp Ala Pro Val Gly Glu Asn Gln Lys Lys Lys
                325                 330                 335

Ala Phe Val Pro Ile Val Cys Val Asn Leu Leu Arg Ser Gly Glu Gly
            340                 345                 350

Lys Ser Glu Cys Ile Leu Val Gln His Phe Glu Glu Ser Met Asn Phe
            355                 360                 365

Ile Lys Ser Ser Gly Lys Leu Pro Tyr Thr Arg Val His Leu Ile Asn
            370                 375                 380

Tyr Asp Trp His Ala Ser Val Lys Leu Lys Gly Glu Gln Gln Thr Ile
385                 390                 395                 400

Glu Gly Leu Trp Met Tyr Leu Lys Ser Pro Thr Met Ala Ile Gly Ile
                405                 410                 415

Ser Glu Gly Asp Tyr Leu Pro Ser Arg Gln Arg Leu Lys Asp Cys Arg
            420                 425                 430

Gly Glu Val Ile Cys Ile Asp Asp Ile Glu Gly Ala Phe Cys Leu Arg
            435                 440                 445

Ser His Gln Asn Gly Val Ile Arg Phe Asn Cys Ala Asp Ser Leu Asp
450                 455                 460

Arg Thr Asn Ala Ala Ser Phe Phe Gly Leu Gln Val Phe Val Glu
465                 470                 475                 480

Gln Cys Arg Arg Leu Gly Ile Ser Leu Asp Thr Asp Leu Gly Tyr Gly
                485                 490                 495

His Asn Ser Val Asn Asn Gln Gly Gly Tyr Asn Ala Pro Leu Pro Pro
            500                 505                 510

Gly Trp Glu Lys Arg Ala Asp Ala Val Thr Gly Lys Ser Tyr Tyr Ile
            515                 520                 525

Asp His Asn Thr Lys Thr Thr Thr Trp Ser His Pro Cys Pro Asp Lys

```
                530             535             540
Pro Trp Lys Arg Leu Asp Met Arg Phe Glu Glu Phe Lys Arg Ser Thr
545                 550                 555                 560

Ile Leu Ser Pro Val Ser Glu Leu Ala Asp Leu Phe Leu Gln Gln Gly
                565                 570                 575

Asp Ile His Ala Thr Leu Tyr Thr Gly Ser Lys Ala Met His Ser Gln
                580                 585                 590

Ile Leu Asn Ile Phe Ser Glu Glu Ser Gly Ala Phe Lys Gln Phe Ser
                595                 600                 605

Ala Ala Gln Lys Asn Met Lys Ile Thr Leu Gln Arg Arg Tyr Lys Asn
610                 615                 620

Ala Met Val Asp Ser Ser Arg Gln Lys Gln Leu Glu Met Phe Leu Gly
625                 630                 635                 640

Met Arg Leu Phe Lys His Leu Pro Ser Ile Pro Val Gln Pro Leu His
                645                 650                 655

Val Leu Ser Arg Pro Ser Gly Phe Phe Leu Lys Pro Val Pro Asn Met
                660                 665                 670

Ser Glu Ser Ser Asn Asp Gly Ser Ser Leu Leu Ser Ile Lys Arg Lys
                675                 680                 685

Asp Ile Thr Trp Leu Cys Pro Gln Ala Ala Asp Ile Val Glu Leu Phe
690                 695                 700

Ile Tyr Leu Ser Glu Pro Cys His Val Cys Gln Leu Leu Leu Thr Ile
705                 710                 715                 720

Ser His Gly Ala Asp Asp Leu Thr Cys Pro Ser Thr Val Asp Val Arg
                725                 730                 735

Thr Gly Arg His Ile Glu Asp Leu Lys Leu Val Val Glu Leu Val Gln
                740                 745                 750

Leu Asp Tyr Arg Leu Pro Val Ile Met Phe Ser Gly Gln Gly Ala Ser
                755                 760                 765

Ile Pro Arg Cys Ala Asn Gly Thr Asn Leu Leu Val Pro Leu Pro Gly
                770                 775                 780

Pro Ile Ser Ser Glu Asp Met Ala Val Thr Gly Ala Gly Ala Arg Leu
785                 790                 795                 800

His Glu Lys Asp Thr Ser Ser Leu Ser Leu Leu Tyr Asp Phe Glu Glu
                805                 810                 815

Leu Glu Gly Gln Leu Asp Phe Leu Thr Arg Val Val Ala Val Thr Phe
                820                 825                 830

Tyr Pro Ala Gly Ala Val Arg Ile Pro Met Thr Leu Gly Gln Ile Glu
                835                 840                 845

Val Leu Gly Ile Ser Leu Pro Trp Lys Gly Met Phe Thr Cys Glu Arg
850                 855                 860

Thr Gly Gly Arg Leu Ala Glu Leu Ala Arg Lys Pro Asp Glu Asp Gly
865                 870                 875                 880

Ser Pro Phe Ser Ser Cys Ser Asp Leu Asn Pro Phe Ala Ala Thr Thr
                885                 890                 895

Ser Leu Gln Ala Glu Thr Val Ser Thr Pro Val Gln Gln Lys Asp Pro
                900                 905                 910

Phe Pro Ser Asn Leu Leu Asp Leu Leu Thr Gly Glu Asp Ser Ser Ser
                915                 920                 925

Asp Pro Phe Pro Gln Pro Val Val Glu Cys Ile Ala Ser Gly Gly Asn
                930                 935                 940

Asp Met Leu Asp Phe Leu Asp Glu Ala Val Val Glu Tyr Arg Gly Ser
945                 950                 955                 960
```

```
Asp Thr Val Pro Asp Gly Ser Val Pro Gln Asn Lys Arg Pro Lys Asp
            965                 970                 975

Ser Gly Ala His Leu Tyr Leu Asn Cys Leu Lys Ser Leu Ala Gly Pro
            980                 985                 990

Asn Met Ala Lys Lys Leu Glu Phe Val Glu Ala Met Lys Leu Glu Ile
            995                 1000                1005

Glu Arg Leu Arg Leu Asn Ile Ser Ala Ala Glu Arg Asp Arg Ala
        1010                1015                1020

Leu Leu Ser Ile Gly Ile Asp Pro Ala Thr Ile Asn Pro Asn Ser
        1025                1030                1035

Ser Tyr Asp Glu Leu Tyr Ile Gly Arg Leu Cys Lys Ile Ala Asn
        1040                1045                1050

Ala Leu Ala Val Met Gly Gln Ala Ser Leu Glu Asp Lys Ile Ile
        1055                1060                1065

Ala Ser Ile Gly Leu Glu Lys Leu Glu Asn Asn Val Ile Asp Phe
        1070                1075                1080

Trp Asn Ile Thr Arg Ile Gly Glu Gly Cys Asp Gly Gly Met Cys
        1085                1090                1095

Gln Val Arg Ala Glu Val Asn Lys Ser Pro Val Gly Ser Ser Thr
        1100                1105                1110

Lys Ser Ser Arg Gly Glu Ser Gly Ser Val Phe Leu Cys Phe Gln
        1115                1120                1125

Cys Met Lys Lys Ala Cys Lys Phe Cys Ala Gly Lys Gly Ala
        1130                1135                1140

Leu Leu Leu Ser Lys Ser Tyr Ser Arg Asp Thr Ala Asn Gly Gly
        1145                1150                1155

Gly Ser Leu Ala Asp Val Ser Ala Thr Ser Ile Gly Ser Asp His
        1160                1165                1170

Tyr Ile Cys Lys Lys Cys Cys Ser Ser Ile Val Leu Glu Ala Leu
        1175                1180                1185

Ile Val Asp Tyr Val Arg Val Met Val Ser Leu Arg Arg Ser Gly
        1190                1195                1200

Arg Val Asp Asn Ala Gly Arg Glu Ala Leu Asn Glu Val Phe Gly
        1205                1210                1215

Ser Asn Ile Thr Asn His Leu Ala Val Arg Gly Gln Pro Ser Pro
        1220                1225                1230

Asn Arg Glu Asp Phe Asn Phe Leu Arg Gln Ile Leu Gly Lys Glu
        1235                1240                1245

Glu Ser Leu Ser Glu Phe Pro Phe Ala Ser Phe Leu His Lys Val
        1250                1255                1260

Glu Thr Ala Thr Asp Ser Ala Pro Phe Phe Ser Leu Leu Thr Pro
        1265                1270                1275

Leu Asn Leu Ala Ser Ser Asn Ala Tyr Trp Lys Ala Pro Pro Ser
        1280                1285                1290

Ala Asp Ser Val Glu Ala Ala Ile Val Leu Asn Thr Leu Ser Asp
        1295                1300                1305

Val Ser Ser Val Ile Leu Leu Val Ser Pro Cys Gly Tyr Ser Asp
        1310                1315                1320

Ala Asp Ala Pro Thr Val Gln Ile Trp Ala Ser Ser Asp Ile Asn
        1325                1330                1335

Lys Glu Ala Arg Thr Leu Met Gly Lys Trp Asp Val Gln Ser Phe
        1340                1345                1350
```

| Ile | Arg | Ser | Ser | Pro | Glu | Leu | Ser | Gly | Ser | Glu | Lys | Ser | Gly | Arg |
|---|---|---|---|---|---|---|---|---|---|---|---|---|---|---|
| 1355 | | | | | 1360 | | | | | 1365 | | | | |

Ala Pro Arg His Ile Lys Phe Ala Phe Lys Asn Pro Val Arg Cys
1370                1375                1380

Arg Ile Ile Trp Ile Thr Leu Arg Leu Pro Arg Leu Gly Ser Ser
1385                1390                1395

Ser Ser Val Ser Leu Asp Lys Asn Ile Asn Leu Leu Ser Leu Asp
1400                1405                1410

Glu Asn Pro Phe Ala Pro Ile Pro Arg Arg Ala Ser Phe Gly Ala
1415                1420                1425

Thr Ile Glu Asn Asp Pro Cys Ile His Ala Lys His Ile Leu Val
1430                1435                1440

Thr Gly Asn Thr Val Arg Asp Lys Thr Leu Gln Ser Val Glu Ser
1445                1450                1455

Met Ser Val Arg Asn Trp Leu Asp Arg Ala Pro Arg Leu Asn Arg
1460                1465                1470

Phe Leu Ile Pro Leu Glu Thr Glu Arg Pro Met Glu Asn Asp Leu
1475                1480                1485

Val Leu Glu Leu Tyr Leu Gln Pro Ala Ser Pro Leu Ala Ala Gly
1490                1495                1500

Phe Arg Leu Asp Ala Phe Ser Ala Ile Lys Pro Arg Val Thr His
1505                1510                1515

Ser Pro Ser Ser Asp Val Val Asp Ile Trp Asp Pro Thr Ser Val
1520                1525                1530

Ile Met Glu Asp Arg His Val Ser Pro Ala Ile Leu Tyr Ile Gln
1535                1540                1545

Val Ser Val Leu Gln Glu Gln Tyr Lys Met Val Thr Ile Ala Glu
1550                1555                1560

Tyr Arg Leu Pro Glu Ala Arg Asp Gly Thr Lys Leu Tyr Phe Asp
1565                1570                1575

Phe Pro Lys Gln Ile Gln Ala Gln Arg Val Ser Phe Lys Leu Leu
1580                1585                1590

Gly Asp Val Ala Ala Phe Thr Asp Glu Pro Ala Glu Ala Val Asp
1595                1600                1605

Leu Ser Ser Arg Ala Ser Pro Phe Ala Ala Gly Leu Ser Leu Ala
1610                1615                1620

Asn Arg Ile Lys Leu Tyr Tyr Tyr Ala Asp Pro Tyr Glu Val Gly
1625                1630                1635

Lys Trp Thr Ser Leu Ser Ser Val
1640                1645

<210> SEQ ID NO 6
<211> LENGTH: 6394
<212> TYPE: DNA
<213> ORGANISM: Arabidopsis thaliana

<400> SEQUENCE: 6
atggatctgc atccaccagg ttagtttctt tttgaagatt caagtgtttt ttttttttcac    60 tctagctgtt ttcatcattt ggttggctaa ttttcttatc ttcttggtgt aggtggttca   120
aaaaagacat ctgtagttgt tgtcaccttc gacactggtg aagtctatgt cattgcaagt   180
ttgttatcta aggctgatac tcaagttatc tatatcgatc ctacgactgg tatcctgcgg   240
tacaatggga agcctggcct tgataatttt aagtcagagc gtgaagcctt agattatatt   300
acgaatggat caagaggagg tgttagaagc tctgtttatg ccagggcaat actcggttat   360

-continued

```
gctgtcttgg ggagctttgg gatgctttta gttgcgacca ggctaaatcc aagtattcca    420
gatttgcctg gtggtggatg tgtatataca gtggctgaga gtcaatgggt caaaatacca    480
ctctacaatc cacagcctca agggaaaggt gaaaccaaga atattcagga gttgactgag    540
cttgacatcg acgggaagca ctatttctgt gatactagag acatcactcg gcccttccca    600
agccgtatgc cacttcaaag ccctgatgat gaatttgttt ggaatagatg gttgtccgtg    660
cctttttaaga atattgggct acctgaacac tgtgtcattc ttctgcaggt tcgtcctcca    720
ttaatgaatt gatgaaggtt gatctaccta tccgatttcg gttttgtgtg aagattcaaa    780
agcatataaa ttgatatgac atcatcttct tatttgatgt taattatagg ggtttgcaga    840
atatcgacct tttgggagct caggccagct agaagggatt gttgctctaa tggcccgtcg    900
tagcagactg catccaggga ctcgttacct agctaggggc attaattcat gttctggcac    960
aggtgacatg ccccctaaa atgctcctct ctcttaattt ctttgttgtt ctcttaaaaa   1020
gtgtggctct ggattgacta gggcctaatt tagaagtata tgtgtagtgc aggtaacgaa   1080
gttgagtgtg agcagcttgt atggatacct aaaagaaatg gtcaaagcat tgctttcaac   1140
tcgtacattt ggcgacatgg caccatacca atatggtggg gtgcagaatt aaagatgact   1200
gcggcagaag cagaaattta tgtggcagat agggatcctt ataaaggcag tacagagtat   1260
taccaaaggt taagcaagcg atatgatact aggaatctag atgcacctgt tggagaaaac   1320
cagaagaaaa aggcttttgt tcctattgtg tgcgttaatt tactaagaag tggagaaggg   1380
aaatcagaat gtatcttagt acaacatttt gaagaatcga tgaactttat caaatccagt   1440
ggaaagcttc cttatactcg tgttcacctg ataaattatg attggcatgc cagcgtgaaa   1500
ctaaaagggg aacagcaaac tattgaagga ttgtggatgt atctaaaatc tcccactatg   1560
gcaataggaa tttctgaagg tgactatttg ccttcacgtc aaagactgaa agattgcaga   1620
ggtgaggtaa tctgtattga tgacattgaa ggtgccttct gtttgagatc acatcaaaat   1680
ggggtgatac gttttaactg cgctgattcc ttggatcgaa caaatgcggc tagtttcttt   1740
ggtggtcttc aagtgtttgt agagcaatgt agaaggctgg gaatatcact tgatactgat   1800
cttggatatg gtcataattc tgttaataat caggggggat ataacgctcc ccttccaccg   1860
ggatgggaaa aaagagctga tgccgtaact ggaaaatcat attatataga tcacaataca   1920
aagacaacaa catggagtca tccatgtcct gataaaccat ggaagagact tgacatgagg   1980
tttgaggaat ttaagagatc aactatctta tctcctgtgt cagaacttgc cgatcttttt   2040
ctgcaacaag gtgatatcca tgcaaccctc tatactggct cgaaagctat gcacagccaa   2100
attctcaaca tcttcagtga agaatcagga gcatttaaac agttttctgc agcacagaaa   2160
aacatgaaga ttacactaca gagaagatat aaaaatgcta tggttgatag ttcacggcaa   2220
aaacagctcg agatgtttct gggaatgagg cttttcaagc atcttccatc aattcctgtc   2280
cagcctttac atgtaagcac attgacacga ttccagtaaa aaattcccag ctctcagctc   2340
tccttttttc catgtatatt aactgctcta agtatgaat cacgtttttt tgcgtgtatg   2400
tagattttgt ttcatattgg accgatacac tttgtttatt gtgtgtagat ataaattcc    2460
taagagcata acagattcgt tgatttgtag actctactat ttgttgcttt ctatattctc   2520
tgtctacttc tcactgcaaa atattcatg tcaggtactt tctcgaccat ctggtttctt    2580
tctgaaacct gtacctaaca tgtccgaaag ttccaatgat gggtccagtc tgctgagtat   2640
caagaggaag gacataactt gggtacctca acttagatat aagattaccct cttagttctc   2700
```

```
attacttgaa tacttgagct aaaaaaattc catgctttt gttactttg cagctatgtc      2760 cacaagctgc agatattgtt gaattattta tctatctcag tgagccttgc catgtatgtc      2820
aacttctact gaccatatca cacggtgcgg atgatttgac atgtccatcc actgtggacg      2880
tgagaactgg acgccacata gaggacctta aattagttgt tgaggttgac tctcttttag      2940
gtcttgtccc ttctgtttta ttgtttgtag gagatctgta gacttacatg caagttagtt      3000
caactggatt accgattacc tgtaattatg ttttctggac agggtgcttc aataccacgc      3060
tgtgcaaatg gtacaaatct tctggtaccc ttaccagggc aattagttc tgaggatatg      3120 gctgttactg gagctggtgc acgtcttcat gaaaaagata cgtcaagtct ttcactgcta      3180
tatgattttg aagaactaga aggacagttg gatttcttaa cccgtgtagt tgctgttaca      3240
ttttatccag ctggtgctgt tagaattcct atgactcttg gtcaggtact tactagtttc      3300
caaactatga attgatgaat atctattagc ttcatcatgc tctgaactcg ttaaagttta      3360
tgattagcta tcatcaaaag aagaaaaaac aaacacttttt tctgcattgt gtctatgccg      3420
cagatagaag tccttggaat ttctcttcca tggaaaggaa tgtttacttg tgaacgtact      3480
ggaggaagat tagctgaact tgcaaggaaa ccagatgaag atggaagtcc ttttcatct      3540 tgttctgact tgaatccgtt tgctgcaaca acatctttac aggctgaaac tgtttccaca      3600
ccagtacaac agaaggatcc cttttcccagt aatctgcttg accttttgac aggagaggac      3660
tcttcttctg acccttccc acaaccagtg gtggaatgta ttgcaagtgg aggcaatgac      3720
atgcttgatt tcttagacga agcagttgtt gaatatcgcg gctctgacac tgttcctgac      3780
gggtctgtcc cacaaaataa aaggcccaag gacagtggtg ctcatctgta cttaaattgc      3840
ctaaagtccc ttgcgggtcc aaacatggtg agatgcaatt acgtctttcc agttgccaca      3900
aactgtagtt ctgattgtat gaatctttca ttggtttaac tattcttctc atatgttatc      3960
tttcttcgta aaattccatt ttctatggta aatttaattt ctgcatgtct ggcataatac      4020
aggcaaagaa gcttgagttt gtagaagcta tgaagcttga aattgaacgt ctacgtctca      4080
atatttctgc agcagaaaga gatagggcac tgttatcgat tggaattgat ccagctacca      4140
ttaatccaaa ctcttcatac gacgagttat atattggaag attatgcaaa atagcaaatg      4200
cacttgcagt tatgggccag gcttctcttg aagataaaat tatagcttct attggtctag      4260
agaagctgga aaataatgtg atagatttct ggaacataac cagaattggt gagggttgtg      4320
atggcggaat gtgtcaagtc cgagccgagg tcaataaaag tccagttgga tcttctacca      4380
agagttcaag aggagagtcg ggctcagtgt tcttgtgctt ccaatgtatg aaaaaagctt      4440
gcaagttttg ttgtgctgga aaaggagctc ttctgctttc aaaatcctac tccagggaca      4500
ctgcgaatgg aggtggaagt cttgcagatg tctctgctac ttcgataggt tcagatcatt      4560
acatttgtaa aaaatgctgc agctcgatag tgcttgaagc cctgattgta gattatgtaa      4620
gggtcatggt cagcttgcga agaagtggcc gtgttgataa tgctggtcgg aagctttga      4680 atgaggtatt tggatctaac attacaaatc accttgctgt tagaggtcaa ccttctccta      4740
atcgagaaga cttcaattc cttcgtcaaa ttttgggtaa agaggagtcg ctttctgagt      4800
tcccatttgc aagcttctta cataaggtaa tatgcttctt atgtgtttta aaattactat      4860
gatcacttca ttgtctttgg aaagagctgt tatgtaatac ctaatcctcc tttctctctt      4920
ttggatgttt gcataatgca atttaggtcg aaactgcgac tgattcagca ccattttct      4980 cattgctcac ccctctgaat cttgcttcaa gtaatgccta ctggaaagct cctccgtctg      5040
cagactctgt tgaagccgcc attgttctca acaccctttc agatgtcagc agtgtgattc      5100
```

```
tactcgttag tccatgtggt tactctgatg ctgatgctcc taccgtaagt ttgacttttc    5160
tatcttcagt tgaattcttg ttaacccatg ccattactta cgtgataatg ctgccactca    5220
tttcaacatt ttatgtatct tcattgcagg tccaaatttg ggcgagcagc gacataaaca    5280
aggaagcacg gactttgatg ggaaagtggg atgtacagtc ctttattaga tcttcgcctg    5340
agctttctgg ttcagaaaag tctggtagag cacctaggca tataaaattt gctttcaaga    5400
atcctgtccg ttgccgcatt atatggataa cactgcgtct tcctaggctt ggatctagta    5460
gctcagttag tttggacaaa acatcaatc tcttatcttt ggatgagaac ccatttgctc     5520
caattcctcg acgtgcctct tttggagcaa ccattgagaa tgatccatgt attcatgcaa    5580
aacacatctt ggtcactgga aacaccgtga gggataaaac gctacaaagt gttgagagca    5640
tgagcgtaag aaactggctg acagagccc cacgtttgaa tagattcctg gttagtgcct     5700
tagagaactg ctcgttcctt ttcaccttt tctgtggtat ttcgtttatt gtcactaata     5760
tttgtttttt tcaccttcca gataccatta gagactgaga gaccaatgga gaatgatcta    5820
gtcttggaac tttatctgca acctgcttca cctttagctg ctggattccg tttagatgct    5880
tttagtgcga taaagcctcg tgtaacccac tcgccttctt cagatgtagt tgacatttgg    5940 gaccccgacga gtgtcataat ggaagataga cacgtctctc cggccatctt gtatatacaa    6000
gtatctgttc tacaggtatc tatctctcct cctcccggtt tattatatat cctcagaaac    6060
caaaatgttg taataacttt ttcatgttga tctgaaaaat gttaatctac aggagcaata    6120
caaaatggtg acaatcgcgg aatacagatt gcctgaggcg agagatggaa caaagttgta    6180
ttttgacttc cctaaacaga tacaagcaca gagagtatcg tttaaactgc taggagatgt    6240
agcagctttt acagatgagc ccgcagaggc tgttgatttg agcagccggg cttctccttt    6300
tgctgcagga ctgtctttag caaacaggat caagctatat tactatgcgg atccttacga    6360
agtaggcaaa tggactagcc tttcaagtgt ctga                                 6394
```

<210> SEQ ID NO 7
<211> LENGTH: 438
<212> TYPE: PRT
<213> ORGANISM: Arabidopsis thaliana

<400> SEQUENCE: 7

```
Met Leu Arg Glu Ser Asp Gly Glu Met Ser Leu Gly Thr Thr Asn Ser
1               5                   10                  15

Pro Ile Ser Ser Gly Thr Glu Ser Cys Ser Ser Phe Ser Arg Leu Ser
                20                  25                  30

Phe Asp Ala Pro Pro Ser Thr Ile Pro Glu Glu Glu Ser Phe Leu Ser
            35                  40                  45

Leu Lys Pro His Arg Ser Ser Asp Phe Ala Tyr Ala Glu Ile Arg Arg
        50                  55                  60

Arg Lys Lys Gln Gly Leu Thr Phe Arg Asp Phe Arg Leu Met Arg Arg
65                  70                  75                  80

Ile Gly Ala Gly Asp Ile Gly Thr Val Tyr Leu Cys Arg Leu Ala Gly
                85                  90                  95

Asp Glu Glu Glu Ser Arg Ser Ser Tyr Phe Ala Met Lys Val Val Asp
                100                 105                 110

Lys Glu Ala Leu Ala Leu Lys Lys Lys Met His Arg Ala Glu Met Glu
            115                 120                 125

Lys Thr Ile Leu Lys Met Leu Asp His Pro Phe Leu Pro Thr Leu Tyr
        130                 135                 140
```

```
Ala Glu Phe Glu Ala Ser His Phe Ser Cys Ile Val Met Glu Tyr Cys
145                 150                 155                 160

Ser Gly Gly Asp Leu His Ser Leu Arg His Arg Gln Pro His Arg Arg
            165                 170                 175

Phe Ser Leu Ser Ser Ala Arg Phe Tyr Ala Ala Glu Val Leu Val Ala
        180                 185                 190

Leu Glu Tyr Leu His Met Leu Gly Ile Ile Tyr Arg Asp Leu Lys Pro
    195                 200                 205

Glu Asn Ile Leu Val Arg Ser Asp Gly His Ile Met Leu Ser Asn Phe
210                 215                 220

Asp Leu Ser Leu Cys Ser Asp Ser Ile Ala Ala Val Glu Ser Ser Ser
225                 230                 235                 240

Ser Ser Pro Glu Asn Gln Gln Leu Arg Ser Pro Arg Arg Phe Thr Arg
            245                 250                 255

Leu Ala Arg Leu Phe Gln Arg Val Leu Arg Ser Lys Lys Val Gln Thr
        260                 265                 270

Leu Glu Pro Thr Arg Leu Phe Val Ala Glu Pro Val Thr Ala Arg Ser
    275                 280                 285

Gly Ser Phe Val Gly Thr His Glu Tyr Val Ala Pro Glu Val Ala Ser
290                 295                 300

Gly Gly Ser His Gly Asn Ala Val Asp Trp Trp Ala Phe Gly Val Phe
305                 310                 315                 320

Leu Tyr Glu Met Ile Tyr Gly Lys Thr Pro Phe Val Ala Pro Thr Asn
            325                 330                 335

Asp Val Ile Leu Arg Asn Ile Val Lys Arg Gln Leu Ser Phe Pro Thr
        340                 345                 350

Asp Ser Pro Ala Thr Met Phe Glu Leu His Ala Arg Asn Leu Ile Ser
    355                 360                 365

Gly Leu Leu Asn Lys Asp Pro Thr Lys Arg Leu Gly Ser Arg Arg Gly
370                 375                 380

Ala Ala Glu Val Lys Val His Pro Phe Phe Lys Gly Leu Asn Phe Ala
385                 390                 395                 400

Leu Ile Arg Thr Leu Thr Pro Pro Glu Ile Pro Ser Val Val Lys
            405                 410                 415

Lys Pro Met Lys Ser Ala Thr Phe Ser Gly Arg Ser Ser Asn Lys Pro
        420                 425                 430

Ala Ala Phe Asp Tyr Phe
        435
```

<210> SEQ ID NO 8
<211> LENGTH: 1624
<212> TYPE: DNA
<213> ORGANISM: Arabidopsis thaliana

<400> SEQUENCE: 8

```
atgttacgag aatcagacgg tgagatgagt ttaggaacaa caaactcacc gataagcagc      60
ggaacagaga gttgcagcag tttcagccgg ttatcattcg acgcgccgcc gtcaactatc     120
cccgaagaag aaagcttcct ttctctcaaa cctcaccgat cctcagattt cgcttacgca     180
gagatccgaa gacgaaaaaa acaaggccta accttccgag attttcgcct catgcgtcgt     240
atcggcgccg cgacatcgga acagtttac ttatgccgtc tagccggaga cgaagaagag     300
agccggagct cgtattttgc gatgaaagtt gtggataaag aagctcttgc gttgaagaag     360
aagatgcata gagcagagat ggagaaaacg attttgaaaa tgcttgacca tccattttg      420
```

-continued

```
ccgactcttt acgctgagtt tgaagcctca catttctctt gcatcgttat ggaatattgc    480
tccggtggtg atttacactc tctccgtcat agacaacctc accggcgatt ctccctctct    540
tccgccaggt aaaaaatatc aaattttatt gaataattta atattatgga caaagtcaga    600
ttttttttca aaaaaaaaa attgtgaaaa aagattcatc atcatcaatg tatatatata    660
ttttatagtt acatgcattg actctgttca catttgttat cttgttctgc aagaacagac    720
ctgttcttat catgtcggtc ttttccagtt ctttgaattg ttatcaaaga gtcttttca    780
gcccatcaca atttataaac gtcaataatt atgattttat tagctaatga gtatttattt    840
tgtttttggt tacagatttt atgccgccga agttctagtg gcgttagaat atctacacat    900
gttgggtatc atctacagag atctgaagcc tgaaaatatc ttagttagat ccgacggtca    960
cattatgctc tctaactttg acctctctct atgctccgac tcaatcgcag ccgttgaatc   1020
ttcctcgtct tcgccggaga atcaacaact ccgttcaccg cgacgattca ctcgtctcgc   1080
tagactttc caacgagtct tgcggtctaa aaaggttcag actttagaac caacccgtct   1140
ctttgttgct gaaccggtta ctgcccggtc cggttcgttc gttggtacgc atgaatacgt   1200
ggcaccagaa gttgcttcag gtggatcaca tggtaatgcc gttgactggt gggcctttgg   1260
agtgtttctc tacgagatga tatatggcaa gactccgttc gttgcgccga ctaatgacgt   1320
cattctccgt aacattgtga aaagacagtt gagtttcccg actgattcgc cggcgactat   1380
gtttgagctt catgcgcgga atttgatttc cgggttgctt aacaaagatc cgactaaaag   1440
acttgggtca cggcgaggtg cggcggaggt taaagtgcat cctttttca aaggtctaaa   1500
ctttgcgctc attcgtacgc ttactccgcc ggagattcct tcttccgtcg tcaagaagcc   1560
gatgaaatcg gcgacgttta gtggtagaag tagtaacaaa ccagcggcgt tcgattactt   1620
ttga                                                                1624
```

<210> SEQ ID NO 9
<211> LENGTH: 322
<212> TYPE: PRT
<213> ORGANISM: Arabidopsis thaliana

<400> SEQUENCE: 9

```
Met Met Asn Leu Gly Ser Leu Ser Leu Ser Thr Ser Lys Ser Lys
1               5                   10                  15

Pro Met Val Ser Ile Ser Phe Trp Ile Pro Tyr Phe Thr His Trp Gly
                20                  25                  30

Glu Ser Leu Leu Val Cys Gly Ser Ala Pro Gly Leu Gly Ser Gly Asn
            35                  40                  45

Val Lys Lys Gly Leu Leu Leu Lys Pro Ser Gln Gln Asp Asp Gln Leu
        50                  55                  60

Ile Trp Ser Gly Ser Val Ser Val Pro Pro Gly Phe Ser Ser Asp Tyr
65                  70                  75                  80

Cys Tyr Tyr Val Val Asp Asp Ser Lys Ser Val Leu Arg Ser Glu Phe
                85                  90                  95

Gly Met Lys Arg Lys Leu Val Val Pro Glu Thr Leu Thr Gly Gly Glu
            100                 105                 110

Ser Val His Leu Arg Asp Leu Trp Gln Ser Gly Asp Gln Ala Leu Pro
        115                 120                 125

Phe Arg Ser Ala Phe Lys Asp Val Ile Phe His His Ser Phe Asp Val
    130                 135                 140

Lys Val Glu Lys Pro Leu Gly Val Phe Met Asn Lys Ser Asp Gln Asp
```

```
                145                 150                 155                 160
Asp Ser Val Val Gln Phe Lys Ile Cys Cys Pro Asp Ile Gly Glu
                    165                 170                 175
Gly Thr Ser Val Tyr Val Leu Gly Thr Pro Glu Lys Leu Gly Asn Trp
                    180                 185                 190
Lys Val Glu Asn Gly Leu Arg Leu Asn Tyr Val Asp Asp Ser Ile Trp
                195                 200                 205
Glu Ala Asp Cys Leu Ile Pro Lys Ala Asp Phe Pro Ile Lys Tyr Arg
        210                 215                 220
Tyr Cys Lys Val Gln Lys Glu Asp Ser Ile Gly Phe Glu Ser Gly Gly
225                 230                 235                 240
Asn Arg Glu Leu Ser Leu His Ser Ile Gly Ser Lys Gln Glu Tyr Ile
                    245                 250                 255
Val Met Ser Asp Gly Leu Phe Arg Ala Met Pro Trp Arg Gly Ala Gly
                260                 265                 270
Val Ala Val Pro Met Phe Ser Val Arg Ser Glu Asp Val Gly Val
            275                 280                 285
Gly Glu Phe Leu Asp Leu Lys Leu Leu Val Asp Trp Ala Val Asp Ser
        290                 295                 300
Gly Leu His Leu Val Gln Leu Leu Pro Val Asn Asp Thr Ser Val His
305                 310                 315                 320
Lys Met
```

<210> SEQ ID NO 10
<211> LENGTH: 5412
<212> TYPE: DNA
<213> ORGANISM: Arabidopsis thaliana

<400> SEQUENCE: 10

```
atgatgaatc taggatctct ttcgttgagt acgagcaagt cgagtaagcc aatggttagc     60
atcagctttt ggataccgta tttcactcac tggggagaga gcctgctggt ctgtggctcg    120
gctcctggac ttggttccgg aatgtgaaaa aaggtttgc tgctaaagcc atcccagcaa    180
gatgatcagc tcatctggag tggctctgtc tcggttccac tgggtttag ctctgactat    240
tgttactatg tggtggatga ctcgaagagt gtgttaaggt cggagtttgg gatgaaacga    300
aaacttgtgg tgcctgagac attgaccggt ggagagtctg ttcatcttcg tgatctctgg    360
caggtttgag ttcttgtcc ttttcgagtg tattatacaa attttgtaat ctgattttgt    420
agtgttgtga ttgatgttct gttccttta ttagagtg gggatcaagc tcttccattt    480
agaagtgcat ttaaagatgt catcttccac cacagtttcg atgtgaaagt agaaaaacct    540
ctaggggtct ttatgaataa gtcagatcaa gatggtattc attttttat ctaatcctat    600
cacaccattg tctctgagat tctctagttt gtgattgatc tctttgctaa ctgttgtggc    660
cttatgactt taccatgtaa acagattcag ttgttgtcca attcaaaatc tgttgtccag    720
acattggaga gggaacatct gtaagccttt ctctatgatc tttggttttc tttcttttca    780
tgtttgagcc tgatgtggtg ttgtggccat cattcttacc cttgattatg acatgtacag    840
gtgtatgttc taggcacccc agaaaagttg gggaattgga agttgaaaaa tggacttaga    900
ctcaactatg tcgatgattc catatgggaa gcagattgct tgatccctaa agcagacttt    960
cctatcaaat atcctttctt tttactttct tccagactaa ttagttgaac atagttgaca   1020
cttcacttct catatgcttt ctgcatgttg ggttcttaac gattctttca catatagata   1080
ctgtaaagtt cagaaggaag atagcatagg gtttgaatct ggtggtaatc gggagctgtc   1140
```

```
tcttcactcc atcggtagta aacaggaata cattgtcatg tcagatggct tgtttcgagt      1200
aagtaacaga gacaagctat gaactagctc taatgtgaca gaatcaatgt tgtcttacta      1260
ttatttaatt ttacttgtag gcaatgccat ggaggggtgc tggtgtagca gttcccatgt      1320
tctctgtaag gtcagaagat gatgttggtg tgggagagtt tctcgatctg aagttgcttg      1380
ttgattgggc tgtagattcc gggttgcatc tagtacaact tttaccagta aatgacacat      1440
ccgttcataa gatgtgatgg gactcgtatc cctacaggta tgatgattac atttatgtta      1500
gttttgcagg agttcaataa aggacttctg tcacttactt aacggatgga aacaaatatc      1560
cagaattttt gttattattc tttcttgact actgaattca taaatagttc attttttgct      1620
tcaatttggt tttcgagacc ttgggttcca tatactttgg ttgatgatta gtgactgagc      1680
ctgaggctct gctgaatatt agtctctact ctctacttag taaaatttct atatcaactc      1740
attgaactgt gtgattcatt cttattgttc ctttcctcat ttggattgct tctcttgcag      1800
ctcgttatct gtgtttgcat tgcatccatt atatcttaga gtgcaggctc tctctgaacg      1860
tctgccagaa gatatcaagg taagtttcta cacttattgt atcctggaag agactcctaa      1920
gcaatatatt ggctgacctt tttcgttctc tttcaggaag aaattcagaa ggcgaagaat      1980
caactggaca agaatgtaat gagtcccttg ttagacgttt catagatttt cttacttta       2040 cgtccttgaa aaagatagca tcagataaac gggatatagt atttttaaat ggtttgtgtc      2100
tgtatcagca tgatgtgttt aaacgcctgc aagcaattgg ttcatatgtt agttcgtcac      2160
aatcagagtt tgagtgttgt aacctaatcc tttaaagatt gttacgtgta ggatgttgat      2220
tatgaggcta ccatggaaac taagctttca attgccaaga aaatctttga catagagaaa      2280
gaccagactt tgaactcaag caccttccag aaattcttct ctgaaaacga ggtatgcttc      2340
aaaatctgat attgtttcct tgatatctct tgagaattgt ctgcatagaa cttatgcctc      2400
caaaggccac gtcagcgttc cattggctta cggattttg ttatctttga aagggctggt       2460
tgaaaccata tgcagctttc tgcttccttc gtgactttt tgagacttca gatcatagtc       2520
agtgggggac ttttctgac tatacagacg acaaggtata atttgctttt atgttgttca       2580
agtttaagtt gtgatcgaat tagttcaagc tttccagatg tatttcatat agtttcagta      2640
atttctcaca tctccaaata acatttgcca cagcttgaaa aattgatatc caaggacaac      2700
ttgcactata acactatatg cttccactac tacattcagt accatttaca tgtacaagta      2760
agtatgttct gatttatcta gttatattcc attcttgtaa gtgaagtcgg ttactggatg      2820
tttcatctaa agtgtgttct ggttccattt tcaaaagttg tcagcagcag cagaatatgc      2880
aaggaagaaa ggagttgtgc tgaaaggaga cctacctatt ggcgttgaca gaaacagtgt      2940
tgatacgtgg gttacagga atctgtttcg catgaatacg tcaactggag cacctccaga       3000
ctattttgac aaaaatggtc agaactgggg atttcctact tataactggg aggaaatgtc      3060
aaaagacaac tatgcctggt ggcgtgctcg cctaacacag gttggaatta ttgtccttac      3120
cagccacatc ctttgtagat ctgaaggctg accacattgc atacttgctt tgcagatggg      3180
gaaatatttc acagcataca ggattgatca tatattggga ttcttcagaa tctgggagct      3240
tccagctcat gctatgactg gtttagtggg gaagttccgt ccatctattc ctttaagtca      3300
ggtacacaag ctacatgctt acagttaaaa aaaacttggc tttgagagtt acttgatgat      3360
aaaactgctg ctgatgcagg aagagttgga aaaggaggga atatgggatt ttgaccgctt      3420
aagcaagccc tatatccaga agaagtttct tgaggttagt tttccatcac atttattatg      3480
```

```
atctgcctct gtcacagctt agttagtttg tgagttttca atctcattac ctatttgttg     3540
ataatatgtc attgttctgt tccttcagga gaaatttgga gattttttggc cttttattgc    3600 atcaaacttt cttaatgaaa ctcagaagga catgtatgag gttagtaaaa atcctcattt     3660
agagatcgtt ttcctttgga gaaccaagtc ttacctttt ctgtccaaaa ctctgtggtg     3720
ttttttgcta agtggatgta ttaaatcttt cttaattggt ttcctttaat tgtactctag     3780
ttcaaggagg actgcaacac agagaagaag attgtagcaa agctgaagtc attggctgag    3840
aagtctttgt tgctagaaaa tgaggacaaa gttcgacgtg atgtctttga cattttacgg    3900
gtaaactttc atgcatcaca agggctttcc agatttcttc tccttgttat ataaagtgac    3960
tctgtccact tcacgtctct ctcaagtcca ctgtcccaat tgtttatttc tgttgaactt    4020
gtgtccctag aatgttgttc tgatcaaaga tccagaggat gcaagaaaat tctatcctcg    4080
ctttaatatt gaggatactt caagcttcca ggatttggat gatcacaggt acattcaaaa    4140
ccttttccca gtcacttccc aaatagagta gtctgctctt gttcctttga ttttatatcg    4200
cccatgaaca tttacacaga tcctctcttg ctattgtatc gtgctgtatt tttctacttt    4260
tcatcaatat gggaaaatct gattaaggtt ttctcataca gcaaaaatgt tctgaagagg    4320
ctatactatg actactattt ccaacgccaa gaggatctat ggagaaaaaa tgctttgaaa    4380
accttgcctg ctctgttgaa ttcatctaat atgctggcat gtggggagga tctgggtctc    4440
attccatctt gtgtacatcc tgtatgtgct ctgttttctt tctcttggtt catccaactt    4500
ctttataaaa cttgtgtaga agcatatgct aaaattaata gttactcagg ttatgcaaga    4560
actgggattg gttggccttc gcatccagcg catgccaagt gagtccgatg tgaagtttgg    4620
gattccgtct aattatgact atatgacggt tagatatttt tcctcagact tctgtctttc    4680
ttacttatag cttcctaccg ttcatttttct gagaattttg taatgggtga gtgattcact    4740
gcataattca aactatcgtc ttaatatttt aggtgtgtgc tccttcatgc cacgactgct    4800
ctaccctgcg agcttggtgg gaagaggacg aagagagaag acagcagtac ttcaaggaag    4860
tgattggtgt agatggaatc cctccaagtc agtgtattcc agagataact catttcattc    4920
tgaggcaaca tgttgaagct ccatcaatgt gggctatttt cccgcttcag gtaatcatca    4980
ccactgtccg acttctcaga tttattagaa cttttttatga ggctcaataa cagtatgtgt    5040
tgtttgtttt tttcctctgg aacaatttag gatatgatgg ctctgaaaga agagtacact    5100
actcgtcctg caacagagga gacaatcaat gatccaacaa accccaaaca ctactggaga    5160
taccgtaagt atttactact aactaacaca caaccctaag aactatacca gttttaactt    5220
agactgtttt ttgtgcatat aggcgtacac gtgactttgg actcgcttct aaaggacact    5280
gacctgaagt caaccatcaa gaacctcgtt tccagcagtg aagatctgt tcctgctaat     5340 gtttctggtg aagacatcaa caaaagccga ggagaagtta tagccaatgg ctcgactaag    5400
ccaaacccat aa                                                         5412
```

<210> SEQ ID NO 11
<211> LENGTH: 955
<212> TYPE: PRT
<213> ORGANISM: Arabidopsis thaliana

<400> SEQUENCE: 11

```
Met Met Asn Leu Gly Ser Leu Ser Leu Ser Thr Ser Lys Ser Ser Lys
 1               5                  10                  15

Pro Met Val Ser Ile Ser Phe Trp Ile Pro Tyr Phe Thr His Trp Gly
            20                  25                  30
```

```
Glu Ser Leu Leu Val Cys Gly Ser Ala Pro Gly Leu Gly Ser Gly Asn
            35                  40                  45

Val Lys Lys Gly Leu Leu Lys Pro Ser Gln Gln Asp Asp Gln Leu
 50                  55                  60

Ile Trp Ser Gly Ser Val Ser Val Pro Gly Phe Ser Ser Asp Tyr
 65                  70                  75                  80

Cys Tyr Tyr Val Val Asp Asp Ser Lys Ser Val Leu Arg Ser Glu Phe
                    85                  90                  95

Gly Met Lys Arg Lys Leu Val Val Pro Glu Thr Leu Thr Gly Gly Glu
                100                 105                 110

Ser Val His Leu Arg Asp Leu Trp Gln Ser Gly Asp Gln Ala Leu Pro
                115                 120                 125

Phe Arg Ser Ala Phe Lys Asp Val Ile Phe His His Ser Phe Asp Val
    130                 135                 140

Lys Val Glu Lys Pro Leu Gly Val Phe Met Asn Lys Ser Asp Gln Asp
145                 150                 155                 160

Asp Ser Val Val Val Gln Phe Lys Ile Cys Cys Pro Asp Ile Gly Glu
                    165                 170                 175

Gly Thr Ser Val Tyr Val Leu Gly Thr Pro Glu Lys Leu Gly Asn Trp
                180                 185                 190

Lys Val Glu Asn Gly Leu Arg Leu Asn Tyr Val Asp Asp Ser Ile Trp
                195                 200                 205

Glu Ala Asp Cys Leu Ile Pro Lys Ala Asp Phe Pro Ile Lys Tyr Arg
    210                 215                 220

Tyr Cys Lys Val Gln Lys Glu Asp Ser Ile Gly Phe Glu Ser Gly Gly
225                 230                 235                 240

Asn Arg Glu Leu Ser Leu His Ser Ile Gly Ser Lys Gln Glu Tyr Ile
                245                 250                 255

Val Met Ser Asp Gly Leu Phe Arg Ala Met Pro Trp Arg Gly Ala Gly
                260                 265                 270

Val Ala Val Pro Met Phe Ser Val Arg Ser Glu Asp Asp Val Gly Val
    275                 280                 285

Gly Glu Phe Leu Asp Leu Lys Leu Leu Val Asp Trp Ala Val Asp Ser
    290                 295                 300

Gly Leu His Leu Val Gln Leu Leu Pro Val Asn Asp Thr Ser Val His
305                 310                 315                 320

Lys Met Trp Trp Asp Ser Tyr Pro Tyr Ser Ser Leu Ser Val Phe Ala
                325                 330                 335

Leu His Pro Leu Tyr Leu Arg Val Gln Ala Leu Ser Glu Arg Leu Pro
                340                 345                 350

Glu Asp Ile Lys Glu Glu Ile Gln Lys Ala Lys Asn Gln Leu Asp Lys
                355                 360                 365

Asn Asp Val Asp Tyr Glu Ala Thr Met Glu Thr Lys Leu Ser Ile Ala
    370                 375                 380

Lys Lys Ile Phe Asp Ile Glu Lys Asp Gln Thr Leu Asn Ser Ser Thr
385                 390                 395                 400

Phe Gln Lys Phe Phe Ser Glu Asn Glu Gly Trp Leu Lys Pro Tyr Ala
                405                 410                 415

Ala Phe Cys Phe Leu Arg Asp Phe Phe Glu Thr Ser Asp His Ser Gln
                420                 425                 430

Trp Gly Thr Phe Ser Asp Tyr Thr Asp Asp Lys Leu Glu Lys Leu Ile
                435                 440                 445
```

```
Ser Lys Asp Asn Leu His Tyr Asn Thr Ile Cys Phe His Tyr Tyr Ile
450                 455                 460

Gln Tyr His Leu His Val Gln Leu Ser Ala Ala Ala Glu Tyr Ala Arg
465                 470                 475                 480

Lys Lys Gly Val Val Leu Lys Gly Asp Leu Pro Ile Gly Val Asp Arg
            485                 490                 495

Asn Ser Val Asp Thr Trp Val Tyr Arg Asn Leu Phe Arg Met Asn Thr
            500                 505                 510

Ser Thr Gly Ala Pro Pro Asp Tyr Phe Asp Lys Asn Gly Gln Asn Trp
            515                 520                 525

Gly Phe Pro Thr Tyr Asn Trp Glu Glu Met Ser Lys Asp Asn Tyr Ala
530                 535                 540

Trp Trp Arg Ala Arg Leu Thr Gln Met Gly Lys Tyr Phe Thr Ala Tyr
545                 550                 555                 560

Lys Ile Asp His Ile Leu Gly Phe Phe Arg Ile Trp Glu Leu Pro Ala
                565                 570                 575

His Ala Met Thr Gly Leu Val Gly Lys Phe Arg Pro Ser Ile Pro Leu
            580                 585                 590

Ser Gln Glu Glu Leu Glu Lys Glu Gly Ile Trp Asp Phe Asp Arg Leu
            595                 600                 605

Ser Lys Pro Tyr Ile Gln Lys Lys Phe Leu Glu Lys Phe Gly Asp
610                 615                 620

Phe Trp Pro Phe Ile Ala Ser Asn Phe Leu Asn Glu Thr Gln Lys Asp
625                 630                 635                 640

Met Tyr Glu Phe Lys Glu Asp Cys Asn Thr Glu Lys Lys Ile Val Ala
                645                 650                 655

Lys Leu Lys Ser Leu Ala Glu Lys Ser Leu Leu Glu Asn Glu Asp
            660                 665                 670

Lys Val Arg Arg Asp Val Phe Asp Ile Leu Arg Asn Val Val Leu Ile
            675                 680                 685

Lys Asp Pro Glu Asp Ala Arg Lys Phe Tyr Pro Arg Phe Asn Ile Glu
690                 695                 700

Asp Thr Ser Ser Phe Gln Asp Leu Asp Asp His Ser Lys Asn Val Leu
705                 710                 715                 720

Lys Arg Leu Tyr Tyr Asp Tyr Phe Gln Arg Gln Glu Asp Leu Trp
                725                 730                 735

Arg Lys Asn Ala Leu Lys Thr Leu Pro Ala Leu Leu Asn Ser Ser Asn
            740                 745                 750

Met Leu Ala Cys Gly Glu Asp Leu Gly Leu Ile Pro Ser Cys Val His
            755                 760                 765

Pro Val Met Gln Glu Leu Gly Leu Val Gly Leu Arg Ile Gln Arg Met
770                 775                 780

Pro Ser Glu Ser Asp Val Lys Phe Gly Ile Pro Ser Asn Tyr Asp Tyr
785                 790                 795                 800

Met Thr Val Cys Ala Pro Ser Cys His Asp Cys Ser Thr Leu Arg Ala
                805                 810                 815

Trp Trp Glu Glu Asp Glu Glu Arg Arg Gln Gln Tyr Phe Lys Glu Val
            820                 825                 830

Ile Gly Val Asp Gly Ile Pro Ser Gln Cys Ile Pro Glu Ile Thr
            835                 840                 845

His Phe Ile Leu Arg Gln His Val Glu Ala Pro Ser Met Trp Ala Ile
850                 855                 860

Phe Pro Leu Gln Asp Met Met Ala Leu Lys Glu Glu Tyr Thr Thr Arg
```

```
                    865                 870                 875                 880
Pro Ala Thr Glu Glu Thr Ile Asn Asp Pro Thr Asn Pro Lys His Tyr
                885                 890                 895
Trp Arg Tyr Arg Val His Val Thr Leu Asp Ser Leu Leu Lys Asp Thr
                900                 905                 910
Asp Leu Lys Ser Thr Ile Lys Asn Leu Val Ser Ser Gly Arg Ser
                915                 920                 925
Val Pro Ala Asn Val Ser Gly Glu Asp Ile Asn Lys Ser Arg Gly Glu
            930                 935                 940
Val Ile Ala Asn Gly Ser Thr Lys Pro Asn Pro
945                 950                 955

<210> SEQ ID NO 12
<211> LENGTH: 5412
<212> TYPE: DNA
<213> ORGANISM: Arabidopsis thaliana

<400> SEQUENCE: 12
atgatgaatc taggatctct ttcgttgagt acgagcaagt cgagtaagcc aatggttagc      60
atcagctttt ggataccgta tttcactcac tggggagaga gcctgctggt ctgtggctcg     120
gctcctggac ttggttccgg aatgtgaaaa aaggtttgc tgctaaagcc atcccagcaa      180
gatgatcagc tcatctggag tggctctgtc tcggttccac tgggtttag ctctgactat      240 tgttactatg tggtggatga ctcgaagagt gtgttaaggt cggagtttgg gatgaaacga     300
aaacttgtgg tgcctgagac attgaccggt ggagagtctg ttcatcttcg tgatctctgg     360
caggtttgag ttcttttgtcc ttttcgagtg tattatacaa attttgtaat ctgattttgt    420
agtgttgtga ttgatgttct gttcctttaa ttttagagtg gggatcaagc tcttccattt     480
agaagtgcat ttaaagatgt catcttccac cacagtttcg atgtgaaagt agaaaaacct    540
ctaggggtct ttatgaataa gtcagatcaa gatggtattc attttttat ctaatccat      600 cacaccattg tctctgagat tctctagttt gtgattgatc tctttgctaa ctgttgtggc     660
cttatgactt taccatgtaa acagattcag ttgttgtcca attcaaaatc tgttgtccag     720
acattggaga gggaacatct gtaagccttt ctctatgatc tttggttttc tttcttttca    780
tgtttgagcc tgatgtggtg ttgtggccat cattcttacc cttgattatg acatgtacag    840
gtgtatgttc taggcacccc agaaaagttg gggaattgga agttgaaaaa tggacttaga    900
ctcaactatg tcgatgattc catatgggaa gcagattgct tgatccctaa agcagacttt    960
cctatcaaat atcctttctt tttacttct tccagactaa ttagttgaac atagttgaca     1020
cttcacttct catatgcttt ctgcatgttg ggttcttaac gattctttca catatagata    1080
ctgtaaagtt cagaaggaag atagcatagg gtttgaatct ggtggtaatc gggagctgtc    1140
tcttcactcc atcggtagta acaggaata cattgtcatg tcagatggct tgtttcgagt    1200
aagtaacaga gacaagctat gaactagctc taatgtgaca gaatcaatgt tgtcttacta    1260
ttatttaatt ttacttgtag gcaatgccat ggaggggtgc tggtgtagca gttcccatgt    1320
tctctgtaag gtcagaagat gatgttggtg tgggagagtt tctcgatctg aagttgcttg    1380
ttgattgggc tgtagattcc gggttgcatc tagtacaact tttaccagta aatgacacat    1440
ccgttcataa gatgtggtgg gactcgtatc cctacaggta tgatgattac atttatgtta    1500
gttttgcagg agttcaataa aggacttctg tcacttactt aacggatgga aacaaatatc    1560
cagaattttt gttattattc tttcttgact actgaattca taaatagttc attttttgct    1620
```

```
tcaatttggt tttcgagacc ttgggttcca tatactttgg ttgatgatta gtgactgagc    1680
ctgaggctct gctgaatatt agtctctact ctctacttag taaaatttct atatcaactc    1740
attgaactgt gtgattcatt cttattgttc ctttcctcat ttggattgct tctcttgcag    1800
ctcgttatct gtgtttgcat tgcatccatt atatcttaga gtgcaggctc tctctgaacg    1860
tctgccagaa gatatcaagg taagtttcta cacttattgt atcctggaag agactcctaa    1920
gcaatatatt ggctgacctt tttcgttctc tttcaggaag aaattcagaa ggcgaagaat    1980
caactggaca agaatgtaat gagtcccttg ttagacgttt catagatttt cttactttta    2040
cgtccttgaa aaagatagca tcagataaac gggatatagt attttttaaat ggtttgtgtc    2100 tgtatcagca tgatgtgttt aaacgcctgc aagcaattgg ttcatatgtt agttcgtcac    2160
aatcagagtt tgagtgttgt aacctaatcc tttaaagatt gttacgtgta ggatgttgat    2220
tatgaggcta ccatggaaac taagctttca attgccaaga aaatctttga catagagaaa    2280
gaccagactt tgaactcaag caccttccag aaattcttct ctgaaaacga ggtatgcttc    2340
aaaatctgat attgtttcct tgatatctct tgagaattgt ctgcatagaa cttatgcctc    2400
caaaggccac gtcagcgttc cattggctta cggattttttg ttatctttga aagggctggt    2460
tgaaaccata tgcagctttc tgcttccttc gtgactttt tgagacttca gatcatagtc    2520
agtgggggac ctttttctgac tatacagacg acaaggtata atttgctttt atgttgttca    2580
agtttaagtt gtgatcgaat tagttcaagc tttccagatg tatttcatat agtttcagta    2640
atttctcaca tctccaaata acatttgcca cagcttgaaa aattgatatc caaggacaac    2700
ttgcactata acactatatg cttccactac tacattcagt accatttaca tgtacaagta    2760
agtatgttct gatttatcta gttatattcc attcttgtaa gtgaagtcgg ttactggatg    2820
tttcatctaa agtgtgttct ggttccattt tcaaaagttg tcagcagcag cagaatatgc    2880
aaggaagaaa ggagttgtgc tgaaaggaga cctacctatt ggcgttgaca gaaacagtgt    2940
tgatacgtgg gttacagga atctgtttcg catgaatacg tcaactggag cacctccaga    3000
ctattttgac aaaaatggtc agaactgggg atttcctact tataactggg aggaaatgtc    3060
aaaagacaac tatgcctggt ggcgtgctcg cctaacacag gttggaatta ttgtccttac    3120
cagccacatc ctttgtagat ctgaaggctg accacattgc atacttgctt tgcagatggg    3180
gaaatatttc acagcataca agattgatca tatattggga ttcttcagaa tctgggagct    3240
tccagctcat gctatgactg gtttagtggg gaagttccgt ccatctattc ctttaagtca    3300
ggtacacaag ctacatgctt acagttaaaa aaaacttggc tttgagagtt acttgatgat    3360
aaaactgctg ctgatgcagg aagagttgga aaaggaggga atatgggatt ttgaccgctt    3420
aagcaagccc tatatccaga agaagttttct tgaggttagt tttccatcac atttattatg    3480
atctgcctct gtcacagctt agttagtttg tgagttttca atctcattac ctatttgttg    3540
ataatatgtc attgttctgt tccttcagga gaaatttgga gatttttggc cttttattgc    3600
atcaaacttt cttaatgaaa ctcagaagga catgtatgag gttagtaaaa atcctcattt    3660
agagatcgtt ttcctttgga gaaccaagtc ttaccttttt ctgtccaaaa ctctgtggtg    3720
ttttttgcta agtggatgta ttaaatcttt cttaattggt ttcctttaat tgtactctag    3780
ttcaaggagg actgcaacac agagaagaag attgtagcaa agctgaagtc attggctgag    3840
aagtctttgt tgctagaaaa tgaggacaaa gttcgacgtg atgtctttga cattttacgg    3900
gtaaactttc atgcatcaca agggcttcc agatttcttc tccttgttat ataaagtgac    3960
tctgtccact tcacgtctct ctcaagtcca ctgtcccaat tgtttatttc tgttgaactt    4020
```

```
gtgtccctag aatgttgttc tgatcaaaga tccagaggat gcaagaaaat tctatcctcg    4080 cttaatatt gaggatactt caagcttcca ggatttggat gatcacaggt acattcaaaa    4140
ccttttccca gtcacttccc aaatagagta gtctgctctt gttcctttga ttttatatcg    4200
cccatgaaca tttacacaga tcctctcttg ctattgtatc gtgctgtatt tttctacttt    4260
tcatcaatat gggaaaatct gattaaggtt ttctcataca gcaaaatgt tctgaagagg    4320 ctatactatg actactattt ccaacgccaa gaggatctat ggagaaaaaa tgctttgaaa    4380
accttgcctg ctctgttgaa ttcatctaat atgctggcat gtggggagga tctgggtctc    4440
attccatctt gtgtacatcc tgtatgtgct ctgttttctt tctcttggtt catccaactt    4500
ctttataaaa cttgtgtaga agcatatgct aaaattaata gttactcagg ttatgcaaga    4560
actgggattg gttggccttc gcatccagcg catgccaagt gagtccgatg tgaagtttgg    4620
gattccgtct aattatgact atatgacggt tagatatttt tcctcagact tctgtctttc    4680
ttacttatag cttcctaccg ttcatttct gagaattttg taatgggtga gtgattcact    4740
gcataattca aactatcgtc ttaatatttt aggtgtgtgc tccttcatgc cacgactgct    4800
ctaccctgcg agcttggtgg gaagaggacg aagagagaag acagcagtac ttcaaggaag    4860
tgattggtgt agatggaatc cctccaagtc agtgtattcc agagataact catttcattc    4920
tgaggcaaca tgttgaagct ccatcaatgt gggctatttt cccgcttcag gtaatcatca    4980
ccactgtccg acttctcaga tttattagaa ctttttatga ggctcaataa cagtatgtgt    5040
tgtttgtttt tttcctctgg aacaatttag gatatgatgg ctctgaaaga agagtacact    5100
actcgtcctg caacagagga gacaatcaat gatccaacaa accccaaaca ctactggaga    5160
taccgtaagt atttactact aactaacaca caaccctaag aactataccca gttttaactt    5220 agactgtttt ttgtgcatat aggcgtacac gtgactttgg actcgcttct aaaggacact    5280
gacctgaagt caaccatcaa gaacctcgtt ccagcagtg gaagatctgt tcctgctaat    5340
gtttctggtg aagacatcaa caaaagccga ggagaagtta tagccaatgg ctcgactaag    5400
ccaaacccat aa                                                        5412
```

<210> SEQ ID NO 13
<211> LENGTH: 3576
<212> TYPE: DNA
<213> ORGANISM: Arabidopsis thaliana

<400> SEQUENCE: 13

```
atgaattgtc ttcagaatct tcccaggtat cttcttgctt tccgaaatta gcaaatgttg      60
ttgatttgtg tggttctttg attcgatatg aatttgtgtg ttgttgatgt ctttgatcgt     120
catttatttc agatgttcag tctcacctct gctgggattc gggtgcattc aaagagatca     180
ttcttcttct tcttcttctt tgaagatgct aatatcgcct ccgatcaaag ccaatgatcc     240
aaaatctcga cttgttttac atgtatacac ctcttttaag atatattgtt atatcagttt     300
ttttcttcta acttttattg acacttttgt aaatgctttg agtgtaggca gtatcagagt     360
caaaatccag ctcagagatg agtggtgttg caaggatga agagaaatct gatgaatata     420
gccaagacat gactcaagct atgggtgctg gtaaattgtt ttcatcatac ctatacatgt     480
ccttagattg gaaactctaa tgatgtccac catttttgt ctcatattgg aaatattgat     540
ttagctcatt ggattgtatt ctactcttgt ttttcatctt tcatcttgat tagttttgtt     600
catctgtcta ccaaggaatc ttatatcttt tgcttgttta ttgacaaact tatcttcttg     660
```

```
ttctccttaa ttatgtattt cagtcactga ttcattctca tgtgtctttc atttcagttc    720
taacttacag gcacgagtta ggaatgaact acaactttat tcgtccagat ctaattgttg    780
gatcctgctt acaggttcac ttttatatcc ttctctcaaa tgatgatttt gttttggata    840
tgtggtactt tcctcgtgtt cttactgtat gctctccttt attgctagac ccctgaagat    900
gttgacaagc ttcgtaaaat tggagttaaa accatatttt gcttgcaaca agatccagac    960
ctggagtatc cttccaaagc cctctttttc tgttcatgat tatgattttg ttttcacttt   1020
ccttcgcatt gagtgaggaa gaatgatctg cagtgcagaa tgccttgacc aatccttcca   1080
gatattttgg agtagacata agcagcatcc aagcctatgc taagaaatat agtgatattc   1140
agcatattcg ctgtgaaatt aggtaaggca acgatctagc tgtgactttt taatatattg   1200
gtattcaaag ctgatgcgta atgaatcgaa ggagagatca tgagttgatt tttagtttcc   1260
tttccaatat ttttcttatt gcttgacttt ataagaagca tatgaggtag ttttttttcc   1320
agaattatct gaataggcga gggaacaaag gtatatacac tgttggaggg tagtctcaga   1380
tatcttttag gcacgcaatc tttaaattct tattgttttg tcagtgaagt gttatacttt   1440
cttttctttt gggctcttta cttttatcac gtttcctaag ctaatgggaa atcagcacac   1500
ttttgtgtaa gcaataactg gtttatgacg aattgtgagt gatagttttt ttttaccggg   1560
tgtgaaatca ctgctatcaa ctaactttt tgttcgtcca cctttgtctg tttacaaact   1620
agagtaactg tagaagttag tcatcatccc attctcacta aatttcttta ctgctaaaga   1680
cttggaacca tcatcatccc ttttggcata tatgagactg ttcacgagca catgcataga   1740
aaaattcacc atggacgtac ccactcacaa cgtaggggat tgacatatta tatatcattg   1800
atgtaacaga gactttgatg catttgattt gagaatgcgt cttccagccg tggttggtac   1860
tctttacaaa gctgttaagc gaaatggagg agttacatat gtgcactgca ctgctggaat   1920
gggaagggct cctgctgttg cggtatgtta cagaaacctg ttactaagct cttctctttt   1980
tccccctttt ctttccagta ttgaaaaaat gtaagactgt tgcaaacagt agttgtctta   2040
attttgtgct tatttggttg actcatgaag gtatgaacaa gttttcacat tttgctgact   2100
gatactgaga agggatatta aatttcatttt cagttgacat acatgttctg ggtgcaaggc   2160
tataagctta tggaagctca taaattactt atgataagat actaatttac ttgtggttta   2220
tgttctctat atgtgtttct ttatacttat attaagtaac caacatgtta atcatgttt    2280 actagtgtta ctgcctgtta tattatgtga ggatgtttgg ggatttcctt cttctcctat   2340
gaaccgacaa ttatgataac tagaatcata gaccattggg tcaggggttt gtagtaaata   2400
tacactgaag atatagcact ttaaaagaca aaaatcttgg gttagttcat ccaaaatagt   2460
ctagcattag acattttag tttgatatct ctagatggct ggtgaaacat aaaggcacgc   2520
gtaaatttgg tttatataac atttctgaaa ttttcttgca gagcaaaagg tcgtgctttc   2580
cgaagctgga tgctatcaga aatgcaacaa ttgatattgt gagtcagcgt tcaactttca   2640
caatgcttcc tatgtttgaa aaacctcagt tccattgatt agcatgagtg cgcaacagtt   2700
acctggttcc ttgactcctg attattgttt ccgggtgtat atggataaaa gcttacagga   2760
ctcaagagga agactgttac tctgacactg aaagataagg ggttctccag agtagaaatt   2820
tctggccttg acattggatg gggacaggta aatatatttt atcttaaacc aatttattta   2880
ttatgacacc ttgctcttaa atctatggtg tgccatataa gctttaaagc caggatgcac   2940
ttttgtcact gctattaaaa gaatggcctc tttgataaga agtggaagag atgagtgttg   3000
gatttctgaa aattattgtc ttatgattgt gcaaaactat ttggacgtat atatataaaa   3060
```

```
ggtaatgtat tctttagct cttttcgttt ttaccatttt tctctttatg tagaggatac    3120
ctctaacact ggacaaggga acaggattct ggatcctaaa gagagaactg cctgtgagtt    3180
ttcttcttaa ctgttaagca tagtgtctga tcattttcca acaaccacta caatttctga    3240
aatgcaggaa ggacagtttg aatataaata catcatagat ggtgaatgga cacacaatga    3300
ggccgaaccg tttataggac ctaacaaaga cggccatacc aacaattacg ctaaagtaaa    3360
aatgtctctg tctcttaaca tatagctgaa caagttttga tgaatgagtt aatgctgtaa    3420
tgttgttgtg tactaatgaa ttaggtagtg acgatccaa caagtgtgga tggtacaact     3480
cgggagagac tatcgagcga agaccctgag ctgttggagg aagaacgctc gaaactaatc    3540
cagttcttgg agacttgttc tgaggcagaa gtttga                              3576

<210> SEQ ID NO 14
<211> LENGTH: 5380
<212> TYPE: DNA
<213> ORGANISM: Arabidopsis thaliana

<400> SEQUENCE: 14
atggaggcca gtgccggctt ggttgctgga tcctaccgga gaaacgagct cgttcggatc      60
cgacatgaat ctgatggcgg ggtctgttca tcttcccttt ttcccatttt tttgttattg     120
tttttcgttc ttacaatttt tgatgtgtag atctcatcta gatttctctg tttctaaatc     180
tcgtctcttt tggatccata attggatcat tgaaactcag atttcgcttc ctttgactgt     240
gtagttagtt agtgtcagtt gatcaagtaa gtgtctgaaa atggaaactt ttctgctcca     300
attcttcaaa ttgttgtgat ctatatcaat taatgccgca tctgttttct taaaatctct     360 tatgaaagt gtcggtggat ttcagttcgt taacttttt aagctaaaat ctttgactct      420
taaagtttag ctttacttat tgagatttag ctcaactaga tctcgttagt tcccgccatg     480
ggatacagac tgtgactcgc cttaattcag atctgcattg attgttttga tttagatcct     540
tgctcatctc tttctgtagt ttctaatact caatgactaa caatgatgca atgttggtca     600
aagtgcagac caaacctttg aagaatatga atggccagat atgtcagatc tgtggtgatg     660
atgttggact cgctgaaact ggagatgtct ttgtcgcgtg taatgaatgt gccttccctg     720
tgtgtcggcc ttgctatgag tacgagagga aagatggaac tcagtgttgc cctcaatgca     780
agactagatt cagacgacac aggggtcagt tgtcttttc ttttgttgg caattgctat       840 atatggattt tctctttttg tttctttgct gttgtgttga acaatttttt ggaattttcc     900
agggagtcct cgtgttgaag gagatgaaga tgaggatgat gttgatgata tcgagaatga     960
gttcaattac gcccagggag ctaacaaggc gagacaccaa cgccatggcg aagagttttc    1020
ttcttcctct agacatgaat ctcaaccaat tcctcttctc acccatgcc atacggtagg     1080 gacctacatt ttccctttag actctagagt gatttgtatt actcaataaa tccctagagt    1140 ggtcattat tacttactat tcacgttaat gttatatgtg aacaaatctt aacagaattt     1200
ttttctgata gtacatggtc atccaaatta agaaataata atagatgttg ttagttgtgt    1260
ctgttttcaa tagattcatg acctttttct atacacaggt ttctggagag attcgcacgc    1320
ctgatacaca atctgtgcga actacatcag gtccttggg tccttctgac aggaatgcta     1380
tttcatctcc atatattgat ccacggcaac ctggtattca tatgttttc ccttgtgcac     1440 gtggtctttg ttaaatgtga ttcctattca tttttacaac atatatattt tgtgtaccgt    1500
aactgatagc tcccgctaaa aattgcagtc cctgtaagaa tcgtggaccc gtcaaaagac    1560
```

```
ttgaactctt atgggcttgg taatgttgac tggaaagaaa gagttgaagg ctggaagctg    1620
aagcaggaga aaaatatgtt acagatgact ggtaaatacc atgaagggaa aggaggagaa    1680
attgaaggga ctggttccaa tggcgaagaa ctccaaatgt aagtggaaat actagaccaa    1740
tatctttatt gtccaactca aacagctctt ggccgtgatg ctaataacca ctcttggttt    1800
cttattatgt attgatagac ataattaagt atctgctttg ttacatttgt ttccttccac    1860
tcaattatgt ttctcgtact tacagggctg atgatacacg tcttcctatg agtcgtgtgg    1920
tgcctatccc atcttctcgc ctaacccctt atcgggttgt gattattctc cggcttatca    1980
tcttgtgttt cttcttgcaa tatcgtacaa ctcaccctgt gaaaaatgca tatcctttgt    2040
ggttgacctc ggttatctgt gagatctggt ttgcattttc ttggcttctt gatcagtttc    2100
ccaaatggta ccccattaac agggagactt atcttgaccg tctcgctata aggttggtct    2160
ttaagtttat acatcccta ctctcatctc tcttttatgt attaacttga tatcttctat     2220
cacagttttc gatagttgac ttttccccc tgtaaattta atttaaattt agacaatggt     2280
gcatctgaat tttgattatg atatatctta agaagattat gattgtaaat cttgaaattt    2340
agtagaaaac catctgcaat ctactgacca tgtgaagttt ccgactagac tatgatagaa    2400
gcatgccaag tggagtgttt attaagatag agcttagcta ttatactgat tttatatgtg    2460
ttttgatttt ttggtttctt attgtagata tgatcgagac ggtgaaccat cacagctcgt    2520
tcctgttgat gtgtttgtta gtacagtgga cccattgaaa gagcctcccc ttgttacagc    2580
aaacacagtt ctctcgattc tttctgtgga ctacccggta gataaagtag cctgttatgt    2640
ttcagatgat ggttcagcta tgcttacctt tgaatcccctt tctgaaaccg ctgagtttgc    2700
aaagaaatgg gtaccatttt gcaagaaatt caacattgaa cctagggccc ctgaattcta    2760
ttttgcccag aagatagatt acttgaagga caagatccaa ccgtcttttg ttaaagagcg    2820
acgagctatg aaggtcattt gaaaagtcca cctgcttctc atccatacgg caaagagatt    2880
gactgacttt ttctttggtt tgtattgaca gagagagtat gaaagagttta aagtgaggat    2940 aaatgctctt gttgccaaag cacagaaaat ccctgaagaa ggctggacaa tgcaggatgg    3000
tactccctgg cctggtaaca acactagaga tcatcctgga atgatacagg tacagtgtgg    3060
caatcccttg attgtgacag agaggataac gtaaaggaaa catgtttaca tcgttttgtt    3120
tcaatttcag gtgttcttag gccatagtgg gggtctggat accgatgaa atgagctgcc    3180 tagactcatc tatgtttctc gtgaaaagcg gcctggattt caacaccaca aaaaggctgg    3240
agctatgaat gcattggttt gttaactttc agaatcctat tgtgtcctct attttattct    3300
cttgttcact gcctaagaaa cgttcttctt gtgtagccgt tgcttcacat tctttttttt    3360
ctaggctatg tgttctctcc taatttagta tctctttact ttgacagatc cgtgtatctg    3420
ctgttcttac caatggagca tatcttttga acgtggattg tgatcattac tttaataaca    3480
gtaaggctat taagaagct atgtgtttca tgatggaccc ggctattgga agaagtgct     3540 gctatgtcca gttccctcaa cgttttgacg gtattgattt gcacgatcga tatgccaaca    3600
ggaatatagt cttttcgat gtgagtatca cttccccatt gtcttttgtt tctcttttgt     3660
tcatattttg gttggattta ctcgtttctg ctatggcctg acttggatat ttgttctctt    3720
gggcagatta acatgaaggg gttggatggt atccagggtc cagtatatgt gggtactggt    3780
tgttgtttta ataggcaggc tctatatggg tatgatcctg ttttgacgga agaagattta    3840
gaaccaaata ttattgtcaa gagctgttgc gggtcaagga agaaaggtaa aagtagcaag    3900
aagtataact acgaaaagag gagaggcatc aacagaagtg actccaatgc tccacttttc    3960
```

-continued

```
aatatggagg acatcgatga gggttttgaa ggtttgattg agctgattgt gtaataacat    4020
cacttcttta tgtaatgatt tatgtgatgg tgaaatctta caatccttgt ttatgcaggt    4080
tatgatgatg agaggtctat tctaatgtcc cagaggagtg tagagaagcg ttttggtcag    4140
tcgccggtat ttattgcggc aaccttcatg aacaaggcg gcattccacc aacaaccaat     4200
cccgctactc ttctgaagga ggctattcat gttataagct gtggttacga agacaagact    4260
gaatggggca aagaggtcag ttttcaaatg cagctacaga atcttcttat gttctctttc    4320
ttacctgttt gatgacatct tatttggcac ttttgttaga ttggttggat ctatggttcc    4380
gtgacggaag atattcttac tgggttcaag atgcatgccc ggggttggat atcgatctac    4440
tgcaatcctc cacgccctgc gttcaaggga tctgcaccaa tcaatctttc tgatcgtttg    4500
aaccaagttc ttcgatgggc tttgggatct atcgagattc ttcttagcag acattgtcct    4560
atctggtatg gttaccatgg aaggttgaga cttttggaga ggatcgctta tatcaacacc    4620
atcgtctatc ctattacatc catccctctt attgcgtatt gtattcttcc cgcttttgt     4680 ctcatcaccg acagattcat catacccgag gtttgtaaaa ctgaccacac tgctatttac    4740
tatttgaatc ccatttttgtg aatgcatttt tttgtcatca tcattgttgc agataagcaa    4800
ctacgcgagt atttggttca ttctactctt catctcaatt gctgtgactg gaatcctgga    4860
gctgagatgg agcggtgtga gcattgagga ttggtggagg aacgagcagt tctgggtcat    4920
tggtggcaca tccgcccatc ttttgctgt cttccaaggt ctacttaagg ttcttgctgg     4980
tatcgacacc aacttcaccg ttacatctaa agccacagac gaagatgggg attttgcaga    5040
actctacatc ttcaaatgga cagctcttct cattccacca accaccgtcc tacttgtgaa    5100
cctcataggc attgtggctg gtgtctctta tgctgtaaac agtggctacc agtcgtgggg    5160
tccgcttttc aggaagctct tcttcgcctt atgggttatt gcccatctct acctttcctt    5220
gaaaggtctg ttgggaagac aaaaccgaac accaaccatc gtcattgtct ggtctgttct    5280
tctcgcctcc atcttctcgt tgctttgggt caggatcaat cccttttgtgg acgccaatcc   5340 caatgccaac aacttcaatg gcaaaggagg tgtctttttag                        5380
```

<210> SEQ ID NO 15
<211> LENGTH: 1081
<212> TYPE: PRT
<213> ORGANISM: Arabidopsis thaliana

<400> SEQUENCE: 15

```
Met Glu Ala Ser Ala Gly Leu Val Ala Gly Ser Tyr Arg Arg Asn Glu
1               5                   10                  15

Leu Val Arg Ile Arg His Glu Ser Asp Gly Gly Thr Lys Pro Leu Lys
            20                  25                  30

Asn Met Asn Gly Gln Ile Cys Gln Ile Cys Gly Asp Asp Val Gly Leu
        35                  40                  45

Ala Glu Thr Gly Asp Val Phe Val Ala Cys Asn Glu Cys Ala Phe Pro
    50                  55                  60

Val Cys Arg Pro Cys Tyr Glu Tyr Glu Arg Lys Asp Gly Thr Gln Cys
65                  70                  75                  80

Cys Pro Gln Cys Lys Thr Arg Phe Arg Arg His Arg Gly Ser Pro Arg
                85                  90                  95

Val Glu Gly Asp Glu Asp Glu Asp Val Asp Asp Ile Glu Asn Glu
            100                 105                 110

Phe Asn Tyr Ala Gln Gly Ala Asn Lys Ala Arg His Gln Arg His Gly
```

```
            115                 120                 125
Glu Glu Phe Ser Ser Ser Ser Arg His Glu Ser Gln Pro Ile Pro Leu
130                 135                 140

Leu Thr His Gly His Thr Val Ser Gly Glu Ile Arg Thr Pro Asp Thr
145                 150                 155                 160

Gln Ser Val Arg Thr Thr Ser Gly Pro Leu Gly Pro Ser Asp Arg Asn
                165                 170                 175

Ala Ile Ser Ser Pro Tyr Ile Asp Pro Arg Gln Pro Val Pro Val Arg
                180                 185                 190

Ile Val Asp Pro Ser Lys Asp Leu Asn Ser Tyr Gly Leu Gly Asn Val
                195                 200                 205

Asp Trp Lys Glu Arg Val Glu Gly Trp Lys Leu Lys Gln Glu Lys Asn
                210                 215                 220

Met Leu Gln Met Thr Gly Lys Tyr His Glu Gly Lys Gly Gly Glu Ile
225                 230                 235                 240

Glu Gly Thr Gly Ser Asn Gly Glu Glu Leu Gln Met Ala Asp Asp Thr
                245                 250                 255

Arg Leu Pro Met Ser Arg Val Val Pro Ile Pro Ser Ser Arg Leu Thr
                260                 265                 270

Pro Tyr Arg Val Val Ile Ile Leu Arg Leu Ile Ile Leu Cys Phe Phe
                275                 280                 285

Leu Gln Tyr Arg Thr Thr His Pro Val Lys Asn Ala Tyr Pro Leu Trp
290                 295                 300

Leu Thr Ser Val Ile Cys Glu Ile Trp Phe Ala Phe Ser Trp Leu Leu
305                 310                 315                 320

Asp Gln Phe Pro Lys Trp Tyr Pro Ile Asn Arg Glu Thr Tyr Leu Asp
                325                 330                 335

Arg Leu Ala Ile Arg Tyr Asp Arg Asp Gly Glu Pro Ser Gln Leu Val
                340                 345                 350

Pro Val Asp Val Phe Val Ser Thr Val Asp Pro Leu Lys Glu Pro Pro
                355                 360                 365

Leu Val Thr Ala Asn Thr Val Leu Ser Ile Leu Ser Val Asp Tyr Pro
                370                 375                 380

Val Asp Lys Val Ala Cys Tyr Val Ser Asp Asp Gly Ser Ala Met Leu
385                 390                 395                 400

Thr Phe Glu Ser Leu Ser Glu Thr Ala Glu Phe Ala Lys Lys Trp Val
                405                 410                 415

Pro Phe Cys Lys Lys Phe Asn Ile Glu Pro Arg Ala Pro Glu Phe Tyr
                420                 425                 430

Phe Ala Gln Lys Ile Asp Tyr Leu Lys Asp Lys Ile Gln Pro Ser Phe
                435                 440                 445

Val Lys Glu Arg Arg Ala Met Lys Arg Glu Tyr Glu Glu Phe Lys Val
                450                 455                 460

Arg Ile Asn Ala Leu Val Ala Lys Ala Gln Lys Ile Pro Glu Glu Gly
465                 470                 475                 480

Trp Thr Met Gln Asp Gly Thr Pro Trp Pro Gly Asn Asn Thr Arg Asp
                485                 490                 495

His Pro Gly Met Ile Gln Val Phe Leu Gly His Ser Gly Gly Leu Asp
                500                 505                 510

Thr Asp Gly Asn Glu Leu Pro Arg Leu Ile Tyr Val Ser Arg Glu Lys
                515                 520                 525

Arg Pro Gly Phe Gln His His Lys Lys Ala Gly Ala Met Asn Ala Leu
                530                 535                 540
```

```
Ile Arg Val Ser Ala Val Leu Thr Asn Gly Ala Tyr Leu Leu Asn Val
545                 550                 555                 560

Asp Cys Asp His Tyr Phe Asn Asn Ser Lys Ala Ile Lys Glu Ala Met
            565                 570                 575

Cys Phe Met Met Asp Pro Ala Ile Gly Lys Lys Cys Cys Tyr Val Gln
        580                 585                 590

Phe Pro Gln Arg Phe Asp Gly Ile Asp Leu His Asp Arg Tyr Ala Asn
    595                 600                 605

Arg Asn Ile Val Phe Phe Asp Ile Asn Met Lys Gly Leu Asp Gly Ile
610                 615                 620

Gln Gly Pro Val Tyr Val Gly Thr Gly Cys Cys Phe Asn Arg Gln Ala
625                 630                 635                 640

Leu Tyr Gly Tyr Asp Pro Val Leu Thr Glu Glu Asp Leu Glu Pro Asn
            645                 650                 655

Ile Ile Val Lys Ser Cys Cys Gly Ser Arg Lys Lys Gly Lys Ser Ser
            660                 665                 670

Lys Lys Tyr Asn Tyr Glu Lys Arg Gly Ile Asn Arg Ser Asp Ser
        675                 680                 685

Asn Ala Pro Leu Phe Asn Met Glu Asp Ile Asp Glu Gly Phe Glu Gly
        690                 695                 700

Tyr Asp Asp Glu Arg Ser Ile Leu Met Ser Gln Arg Ser Val Glu Lys
705                 710                 715                 720

Arg Phe Gly Gln Ser Pro Val Phe Ile Ala Ala Thr Phe Met Glu Gln
                725                 730                 735

Gly Gly Ile Pro Pro Thr Thr Asn Pro Ala Thr Leu Leu Lys Glu Ala
            740                 745                 750

Ile His Val Ile Ser Cys Gly Tyr Glu Asp Lys Thr Glu Trp Gly Lys
            755                 760                 765

Glu Ile Gly Trp Ile Tyr Gly Ser Val Thr Glu Asp Ile Leu Thr Gly
770                 775                 780

Phe Lys Met His Ala Arg Gly Trp Ile Ser Ile Tyr Cys Asn Pro Pro
785                 790                 795                 800

Arg Pro Ala Phe Lys Gly Ser Ala Pro Ile Asn Leu Ser Asp Arg Leu
                805                 810                 815

Asn Gln Val Leu Arg Trp Ala Leu Gly Ser Ile Glu Ile Leu Leu Ser
            820                 825                 830

Arg His Cys Pro Ile Trp Tyr Gly Tyr His Gly Arg Leu Arg Leu Leu
        835                 840                 845

Glu Arg Ile Ala Tyr Ile Asn Thr Ile Val Tyr Pro Ile Thr Ser Ile
        850                 855                 860

Pro Leu Ile Ala Tyr Cys Ile Leu Pro Ala Phe Cys Leu Ile Thr Asp
865                 870                 875                 880

Arg Phe Ile Ile Pro Glu Ile Ser Asn Tyr Ala Ser Ile Trp Phe Ile
            885                 890                 895

Leu Leu Phe Ile Ser Ile Ala Val Thr Gly Ile Leu Glu Leu Arg Trp
            900                 905                 910

Ser Gly Val Ser Ile Glu Asp Trp Trp Arg Asn Glu Gln Phe Trp Val
        915                 920                 925

Ile Gly Gly Thr Ser Ala His Leu Phe Ala Val Phe Gln Gly Leu Leu
        930                 935                 940

Lys Val Leu Ala Gly Ile Asp Thr Asn Phe Thr Val Thr Ser Lys Ala
945                 950                 955                 960
```

```
Thr Asp Glu Asp Gly Asp Phe Ala Glu Leu Tyr Ile Phe Lys Trp Thr
                965                 970                 975

Ala Leu Leu Ile Pro Pro Thr Thr Val Leu Leu Val Asn Leu Ile Gly
            980                 985                 990

Ile Val Ala Gly Val Ser Tyr Ala  Val Asn Ser Gly Tyr  Gln Ser Trp
            995                 1000                1005

Gly Pro  Leu Phe Arg Lys Leu  Phe Phe Ala Leu Trp  Val Ile Ala
    1010                1015                1020

His Leu  Tyr Pro Phe Leu Lys  Gly Leu Leu Gly Arg  Gln Asn Arg
    1025                1030                1035

Thr Pro  Thr Ile Val Ile Val  Trp Ser Val Leu Leu  Ala Ser Ile
    1040                1045                1050

Phe Ser  Leu Leu Trp Val Arg  Ile Asn Pro Phe Val  Asp Ala Asn
    1055                1060                1065

Pro Asn  Ala Asn Asn Phe Asn  Gly Lys Gly Gly Val  Phe
    1070                1075                1080
```

<210> SEQ ID NO 16
<211> LENGTH: 5380
<212> TYPE: DNA
<213> ORGANISM: Arabidopsis thaliana

<400> SEQUENCE: 16

```
atggaggcca gtgccggctt ggttgctgga tcctaccgga gaaacgagct cgttcggatc       60
cgacatgaat ctgatggcgg ggtctgttca tcttcccttt ttcccatttt tttgttattg      120
tttttcgttc ttacaatttt tgatgtgtag atctcatcta gatttctctg tttctaaatc      180
tcgtctcttt tggatccata attggatcat tgaaactcag atttcgcttc ctttgactgt      240
gtagttagtt agtgtcagtt gatcaagtaa gtgtctgaaa atggaaactt ttctgctcca      300
attcttcaaa ttgttgtgat ctatatcaat taatgccgca tctgttttct taaaatctct      360
tatgaaaagt gtcggtggat ttcagttcgt taactttttt aagctaaaat ctttgactct      420
taaagtttag ctttacttat tgagatttag ctcaactaga tctcgttagt tcccgccatg      480
ggatacagac tgtgactcgc cttaattcag atctgcattg attgttttga tttagatcct      540
tgctcatctc tttctgtagt ttctaatact caatgactaa caatgatgca atgttggtca      600
aagtgcagac caaaccttttg aagaatatga atggccagat atgtcagatc tgtggtgatg      660
atgttggact cgctgaaact ggagatgtct ttgtcgcgtg taatgaatgt gccttccctg      720
tgtgtcggcc ttgctatgag tacgagagga aagatggaac tcagtgttgc cctcaatgca      780
agactagatt cagacgacac agggtcagt tgtctttttc tttttgttgg caattgctat      840
atatggattt tctctttttg tttctttgct gttgtgttga acaattttt ggaattttcc      900
agggagtcct cgtgttgaag gagatgaaga tgaggatgat gttgatgata tcgagaatga      960
gttcaattac gcccagggag ctaacaaggc gagacaccaa cgccatggcg aagagttttc     1020
ttcttcctct agacatgaat ctcaaccaat tcctcttctc acccatggcc atacggtagg     1080
gacctacatt ttccctttag actctagagt gatttgtatt actcaataaa tccctagagt     1140
ggtcatttat tacttactat tcacgttaat gttatatgtg aacaaatctt aacagaattt     1200
ttttctgata gtacatggtc atccaaatta agaaataata atagatgttg ttagttgtgt     1260
ctgttttcaa tagattcatg accttttttct atacacaggt ttctggagag attcgcacgc     1320
ctgatacaca atctgtgcga actacatcag gtcctttggg tccttctgac aggaatgcta     1380
tttcatctcc atatattgat ccacggcaac ctggtattca tatgttttc ccttgtgcac     1440
```

```
gtggtctttg ttaaatgtga ttcctattca tttttacaac atatatattt tgtgtaccgt   1500
aactgatagc tcccgctaaa aattgcagtc cctgtaagaa tcgtggaccc gtcaaaagac   1560
ttgaactctt atgggcttgg taatgttgac tggaaagaaa gagttgaagg ctggaagctg   1620
aagcaggaga aaaatatgtt acagatgact ggtaaatacc atgaagggaa aggaggagaa   1680
attgaaggga ctggttccaa tggcgaagaa ctccaaatgt aagtggaaat actagaccaa   1740
tatctttatt gtccaactca aacagctctt ggccgtgatg ctaataacca ctcttggttt   1800
cttattatgt attgatagac ataattaagt atctgctttg ttacatttgt ttccttccac   1860
tcaattatgg ttctcgtact tacagggctg atgatacacg tcttcctatg agtcgtgtgg   1920
tgcctatccc atcttctcgc ctaaccccctt atcgggttgt gattattctc cggcttatca   1980
tcttgtgttt cttcttgcaa tatcgtacaa ctcaccctgt gaaaaatgca tatccttgt    2040 ggttgacctc ggttatctgt gagatctggt ttgcattttc ttggcttctt gatcagtttc   2100
ccaaatggta ccccattaac agggagactt atcttgaccg tctcgctata aggttggtct   2160
ttaagtttat acatccccta ctctcatctc tcttttatgt attaacttga tatcttctat   2220
cacagttttc gatagttgac ttttccccc tgtaaattta atttaaattt agacaatggt   2280
gcatctgaat tttgattatg atatatctta agaagattat gattgtaaat cttgaaattt   2340
agtagaaaac catctgcaat ctactgacca tgtgaagttt ccgactagac tatgatagaa   2400
gcatgccaag tggagtgttt attaagatag agcttagcta ttatactgat tttatatgtg   2460
ttttgatttt ttggtttctt attgtagata tgatcgagac ggtgaaccat cacagctcgt   2520
tcctgttgat gtgtttgtta gtacagtgga cccattgaaa gagcctcccc ttgttacagc   2580
aaacacagtt ctctcgattc tttctgtgga ctacccggta gataaagtag cctgttatgt   2640
ttcagatgat ggttcagcta tgcttacctt tgaatcccctt tctgaaaccg ctgagtttgc   2700
aaagaaatgg gtaccatttt gcaagaaatt caacattgaa cctagggccc ctgaattcta   2760
ttttgcccag aagatagatt acttgaagga caagatccaa ccgtcttttg ttaaagagcg   2820
acgagctatg aaggtcattt gaaaagtcca cctgcttctc atccatacgg caaagagatt   2880
gactgacttt ttctttggtt tgtattgaca gagagagtat gaagagttta aagtgaggat   2940
aaatgctctt gttgccaaag cacagaaaat ccctgaagaa ggctggacaa tgcaggatgg   3000
tactccctgg cctggtaaca acactagaga tcatcctgga atgatacagg tacagtgtgg   3060
caatcccttg attgtgacag agaggataac gtaaaggaaa catgtttaca tcgttttgtt   3120
tcaatttcag gtgttcttag gccatagtgg gggtctggat accgatggaa atgagctgcc   3180
tagactcatc tatgtttctc gtgaaaagcg gcctggattt caacaccaca aaaaggctgg   3240
agctatgaat gcattggttt gttaactttc agaatcctat tgtgtcctct attttattct   3300
cttgttcact gcctaagaaa cgttcttctt gtgtagccgt tgcttcacat tctttttttt   3360
ctaggctatg tgttctctcc taatttagta tctctttact ttgacagatc cgtgtatctg   3420
ctgttcttac caatggagca tatcttttga acgtggattg tgatcattac tttaataaca   3480
gtaaggctat taaagaagct atgtgtttca tgatggaccc ggctattgga aagaagtgct   3540
gctatgtcca gttccctcaa cgttttgacg gtattgattt gcacgatcga tatgccaaca   3600
ggaatatagt cttttttcgat gtgagtatca cttccccatt gtcttttgtt tctcttttgt   3660
tcatattttg gttggattta ctcgtttctg ctatggcctg acttggatat ttgttctctt   3720
gggcagatta acatgaaggg gttggatggt atccagggtc cagtatatgt gggtactggt   3780
```

-continued

| | |
|---|---|
| tgttgtttta ataggcaggc tctatatggg tatgatcctg ttttgacgga agaagattta | 3840 |
| gaaccaaata ttattgtcaa gagctgttgc gggtcaagga agaaaggtaa aagtagcaag | 3900 |
| aagtataact acgaaaagag gagaggcatc aacagaagtg actccaatgc tccacttttc | 3960 |
| aatatggagg acatcgatga gggttttgaa ggtttgattg agctgattgt gtaataacat | 4020 |
| cacttctttta tgtaatgatt tatgtgatgg tgaaatctta caatccttgt ttatgcaggt | 4080 |
| tatgatgatg agaggtctat tctaatgtcc cagaggagtg tagagaagcg ttttggtcag | 4140 |
| tcgccggtat ttattgcggc aaccttcatg gaacaaggcg gcattccacc aacaaccaat | 4200 |
| cccgctactc ttctgaagga ggctattcat gttataagct gtggttacga agacaagact | 4260 |
| gaatggggca agaggtcag ttttcaaatg cagctacaga atcttcttat gttctctttc | 4320 |
| ttacctgttt gatgacatct tatttggcac ttttgttaga ttggttggat ctatggttcc | 4380 |
| gtgacggaag atattcttac tgggttcaag atgcatgccc ggggttggat atcgatctac | 4440 |
| tgcaatcctc cacgccctgc gttcaaggga tctgcaccaa tcaatctttc tgatcgtttg | 4500 |
| aaccaagttc ttcgatgggc tttgggatct atcgagattc ttcttagcag acattgtcct | 4560 |
| atctggtatg gttaccatgg aaggttgaga cttttggaga ggatcgctta tcaacacc | 4620 |
| atcgtctatc ctattacatc catccctctt attgcgtatt gtattcttcc cgcttttgt | 4680 |
| ctcatcaccg acagattcat catacccgag gtttgtaaaa ctgaccacac tgctatttac | 4740 |
| tatttgaatc ccatttttgtg aatgcatttt tttgtcatca tcattgttgc agataagcaa | 4800 |
| ctacgcgagt atttggttca ttctactctt catctcaatt gctgtgactg gaatcctgga | 4860 |
| gctgagatgg agcggtgtga gcattgagga ttggtggagg aacgagcagt tctgggtcat | 4920 |
| tggtggcaca tccgcccatc ttttttgctgt cttccaaggt ctacttaagg ttcttgctgg | 4980 |
| tatcgacacc aacttcaccg ttacatctaa agccacagac gaagatgggg attttgcaga | 5040 |
| actctacatc ttcaaatgga cagctcttct cattccacca accaccgtcc tacttgtgaa | 5100 |
| cctcataggc attgtggctg gtgtctctta tgctgtaaac agtggctacc agtcgtgggg | 5160 |
| tctgcttttc gggaagctct tcttcgcctt atgggttatt gcccatctct acccttcttt | 5220 |
| gaaaggtctg ttgggaagac aaaaccgaac accaaccatc gtcattgtct ggtctgttct | 5280 |
| tctcgcctcc atcttctcgt tgctttgggt caggatcaat ccctttgtgg acgccaatcc | 5340 |
| caatgccaac aacttcaatg gcaaaggagg tgtcttttag | 5380 |

<210> SEQ ID NO 17
<211> LENGTH: 1081
<212> TYPE: PRT
<213> ORGANISM: Arabidopsis thaliana

<400> SEQUENCE: 17

Met Glu Ala Ser Ala Gly Leu Val Ala Gly Ser Tyr Arg Arg Asn Glu
1               5                   10                  15

Leu Val Arg Ile Arg His Glu Ser Asp Gly Gly Thr Lys Pro Leu Lys
            20                  25                  30

Asn Met Asn Gly Gln Ile Cys Gln Ile Cys Gly Asp Asp Val Gly Leu
        35                  40                  45

Ala Glu Thr Gly Asp Val Phe Val Ala Cys Asn Glu Cys Ala Phe Pro
    50                  55                  60

Val Cys Arg Pro Cys Tyr Glu Tyr Glu Arg Lys Asp Gly Thr Gln Cys
65                  70                  75                  80

Cys Pro Gln Cys Lys Thr Arg Phe Arg Arg His Arg Gly Ser Pro Arg
                85                  90                  95

```
Val Glu Gly Asp Glu Asp Asp Val Asp Asp Ile Glu Asn Glu
            100                 105                 110

Phe Asn Tyr Ala Gln Gly Ala Asn Lys Ala Arg His Gln Arg His Gly
            115                 120                 125

Glu Glu Phe Ser Ser Ser Arg His Glu Ser Gln Pro Ile Pro Leu
            130                 135                 140

Leu Thr His Gly His Thr Val Ser Gly Glu Ile Arg Thr Pro Asp Thr
145                 150                 155                 160

Gln Ser Val Arg Thr Thr Ser Gly Pro Leu Gly Pro Ser Asp Arg Asn
                165                 170                 175

Ala Ile Ser Ser Pro Tyr Ile Asp Pro Arg Gln Pro Val Pro Val Arg
                180                 185                 190

Ile Val Asp Pro Ser Lys Asp Leu Asn Ser Tyr Gly Leu Gly Asn Val
                195                 200                 205

Asp Trp Lys Glu Arg Val Glu Gly Trp Lys Leu Lys Gln Glu Lys Asn
            210                 215                 220

Met Leu Gln Met Thr Gly Lys Tyr His Glu Gly Lys Gly Gly Glu Ile
225                 230                 235                 240

Glu Gly Thr Gly Ser Asn Gly Glu Glu Leu Gln Met Ala Asp Asp Thr
                245                 250                 255

Arg Leu Pro Met Ser Arg Val Val Pro Ile Pro Ser Ser Arg Leu Thr
                260                 265                 270

Pro Tyr Arg Val Val Ile Ile Leu Arg Leu Ile Ile Leu Cys Phe Phe
            275                 280                 285

Leu Gln Tyr Arg Thr Thr His Pro Val Lys Asn Ala Tyr Pro Leu Trp
            290                 295                 300

Leu Thr Ser Val Ile Cys Glu Ile Trp Phe Ala Phe Ser Trp Leu Leu
305                 310                 315                 320

Asp Gln Phe Pro Lys Trp Tyr Pro Ile Asn Arg Glu Thr Tyr Leu Asp
                325                 330                 335

Arg Leu Ala Ile Arg Tyr Asp Arg Asp Gly Glu Pro Ser Gln Leu Val
                340                 345                 350

Pro Val Asp Val Phe Val Ser Thr Val Asp Pro Leu Lys Glu Pro Pro
                355                 360                 365

Leu Val Thr Ala Asn Thr Val Leu Ser Ile Leu Ser Val Asp Tyr Pro
            370                 375                 380

Val Asp Lys Val Ala Cys Tyr Val Ser Asp Asp Gly Ser Ala Met Leu
385                 390                 395                 400

Thr Phe Glu Ser Leu Ser Glu Thr Ala Glu Phe Ala Lys Lys Trp Val
                405                 410                 415

Pro Phe Cys Lys Lys Phe Asn Ile Glu Pro Arg Ala Pro Glu Phe Tyr
            420                 425                 430

Phe Ala Gln Lys Ile Asp Tyr Leu Lys Asp Lys Ile Gln Pro Ser Phe
            435                 440                 445

Val Lys Glu Arg Arg Ala Met Lys Arg Glu Tyr Glu Glu Phe Lys Val
            450                 455                 460

Arg Ile Asn Ala Leu Val Ala Lys Ala Gln Lys Ile Pro Glu Glu Gly
465                 470                 475                 480

Trp Thr Met Gln Asp Gly Thr Pro Trp Pro Gly Asn Asn Thr Arg Asp
                485                 490                 495

His Pro Gly Met Ile Gln Val Phe Leu Gly His Ser Gly Gly Leu Asp
            500                 505                 510
```

```
Thr Asp Gly Asn Glu Leu Pro Arg Leu Ile Tyr Val Ser Arg Glu Lys
            515                 520                 525

Arg Pro Gly Phe Gln His His Lys Lys Ala Gly Ala Met Asn Ala Leu
        530                 535                 540

Ile Arg Val Ser Ala Val Leu Thr Asn Gly Ala Tyr Leu Leu Asn Val
545                 550                 555                 560

Asp Cys Asp His Tyr Phe Asn Asn Ser Lys Ala Ile Lys Glu Ala Met
                565                 570                 575

Cys Phe Met Met Asp Pro Ala Ile Gly Lys Lys Cys Cys Tyr Val Gln
            580                 585                 590

Phe Pro Gln Arg Phe Asp Gly Ile Asp Leu His Asp Arg Tyr Ala Asn
        595                 600                 605

Arg Asn Ile Val Phe Phe Asp Ile Asn Met Lys Gly Leu Asp Gly Ile
    610                 615                 620

Gln Gly Pro Val Tyr Val Gly Thr Gly Cys Cys Phe Asn Arg Gln Ala
625                 630                 635                 640

Leu Tyr Gly Tyr Asp Pro Val Leu Thr Glu Glu Asp Leu Glu Pro Asn
                645                 650                 655

Ile Ile Val Lys Ser Cys Cys Gly Ser Arg Lys Lys Gly Lys Ser Ser
            660                 665                 670

Lys Lys Tyr Asn Tyr Glu Lys Arg Arg Gly Ile Asn Arg Ser Asp Ser
        675                 680                 685

Asn Ala Pro Leu Phe Asn Met Glu Asp Ile Asp Glu Gly Phe Glu Gly
    690                 695                 700

Tyr Asp Asp Glu Arg Ser Ile Leu Met Ser Gln Arg Ser Val Glu Lys
705                 710                 715                 720

Arg Phe Gly Gln Ser Pro Val Phe Ile Ala Ala Thr Phe Met Glu Gln
                725                 730                 735

Gly Gly Ile Pro Pro Thr Thr Asn Pro Ala Thr Leu Leu Lys Glu Ala
            740                 745                 750

Ile His Val Ile Ser Cys Gly Tyr Glu Asp Lys Thr Glu Trp Gly Lys
        755                 760                 765

Glu Ile Gly Trp Ile Tyr Gly Ser Val Thr Glu Asp Ile Leu Thr Gly
    770                 775                 780

Phe Lys Met His Ala Arg Gly Trp Ile Ser Ile Tyr Cys Asn Pro Pro
785                 790                 795                 800

Arg Pro Ala Phe Lys Gly Ser Ala Pro Ile Asn Leu Ser Asp Arg Leu
                805                 810                 815

Asn Gln Val Leu Arg Trp Ala Leu Gly Ser Ile Glu Ile Leu Leu Ser
            820                 825                 830

Arg His Cys Pro Ile Trp Tyr Gly Tyr His Gly Arg Leu Arg Leu Leu
        835                 840                 845

Glu Arg Ile Ala Tyr Ile Asn Thr Ile Val Tyr Pro Ile Thr Ser Ile
    850                 855                 860

Pro Leu Ile Ala Tyr Cys Ile Leu Pro Ala Phe Cys Leu Ile Thr Asp
865                 870                 875                 880

Arg Phe Ile Ile Pro Glu Ile Ser Asn Tyr Ala Ser Ile Trp Phe Ile
                885                 890                 895

Leu Leu Phe Ile Ser Ile Ala Val Thr Gly Ile Leu Glu Leu Arg Trp
            900                 905                 910

Ser Gly Val Ser Ile Glu Asp Trp Trp Arg Asn Glu Gln Phe Trp Val
        915                 920                 925

Ile Gly Gly Thr Ser Ala His Leu Phe Ala Val Phe Gln Gly Leu Leu
```

```
            930              935              940
Lys Val Leu Ala Gly Ile Asp Thr Asn Phe Thr Val Thr Ser Lys Ala
945              950              955              960

Thr Asp Glu Asp Gly Asp Phe Ala Glu Leu Tyr Ile Phe Lys Trp Thr
                965              970              975

Ala Leu Leu Ile Pro Pro Thr Thr Val Leu Leu Val Asn Leu Ile Gly
            980              985              990

Ile Val Ala Gly Val Ser Tyr Ala  Val Asn Ser Gly Tyr Gln Ser Trp
            995              1000              1005

Gly Leu Leu Phe Gly Lys Leu  Phe Phe Ala Leu Trp  Val Ile Ala
    1010              1015              1020

His Leu Tyr Pro Phe Leu Lys  Gly Leu Leu Gly Arg  Gln Asn Arg
    1025              1030              1035

Thr Pro Thr Ile Val Ile Val  Trp Ser Val Leu Leu  Ala Ser Ile
    1040              1045              1050

Phe Ser Leu Leu Trp Val Arg  Ile Asn Pro Phe Val  Asp Ala Asn
    1055              1060              1065

Pro Asn Ala Asn Asn Phe Asn  Gly Lys Gly Gly Val  Phe
    1070              1075              1080

<210> SEQ ID NO 18
<211> LENGTH: 5380
<212> TYPE: DNA
<213> ORGANISM: Arabidopsis thaliana

<400> SEQUENCE: 18
atggaggcca gtgccggctt ggttgctgga tcctaccgga gaaacgagct cgttcggatc      60
cgacatgaat ctgatggcgg ggtctgttca tcttcccttt ttcccatttt tttgttattg     120
tttttcgttc ttacaatttt tgatgtgtag atctcatcta gatttctctg tttctaaatc     180
tcgtctcttt tggatccata attggatcat tgaaactcag atttcgcttc ctttgactgt     240
gtagttagtt agtgtcagtt gatcaagtaa gtgtctgaaa atggaaactt ttctgctcca     300
attcttcaaa ttgttgtgat ctatatcaat taatgccgca tctgttttct taaaatctct     360
tatggaaagt gtcggtggat ttcagttcgt taactttttt aagctaaaat ctttgactct     420
taaagtttag ctttacttat tgagatttag ctcaactaga tctcgttagt tcccgccatg     480
ggatacagac tgtgactcgc cttaattcag atctgcattg attgttttga tttagatcct     540
tgctcatctc tttctgtagt ttctaatact caatgactaa caatgatgca atgttggtca     600
aagtgcagac caaaccttg aagaatatga atggccagat atgtcagatc tgtggtgatg      660
atgttggact cgctgaaact ggagatgtct tgtcgcgtg taatgaatgt gccttccctg      720
tgtgtcggcc ttgctatgag tacgagagga aagatggaac tcagtgttgc cctcaatgca     780
agactagatt cagacgacac aggggtcagt tgtcttttc ttttgttgg caattgctat       840 atatggattt tctcttttg tttctttgct gttgtgttga caatttttt ggaatttcc        900 agggagtcct cgtgttgaag gagatgaaga tgaggatgat gttgatgata tcgagaatga     960
gttcaattac gcccaggag ctaacaaggc gagacaccaa cgccatggcg aagagttttc     1020
ttcttcctct agacatgaat ctcaaccaat tcctcttctc acccatggcc atacggtagg    1080
gacctacatt ttccctttag actctagagt gatttgtatt actcaataaa tccctagagt    1140
ggtcatttat tacttactat tcacgttaat gttatatgtg aacaaatctt aacagaattt    1200
ttttctgata gtacatggtc atccaaatta agaaataata atagatgttg ttagttgtgt    1260
```

```
ctgttttcaa tagattcatg acctttttct atacacaggt ttctggagag attcgcacgc   1320
ctgatacaca atctgtgcga actacatcag gtcctttggg tccttctgac aggaatgcta   1380
tttcatctcc atatattgat ccacggcaac ctggtattca tatgttttc ccttgtgcac    1440 gtggtctttg ttaaatgtga ttcctattca tttttacaac atatatattt tgtgtaccgt   1500
aactgatagc tcccgctaaa aattgcagtc cctgtaagaa tcgtggaccc gtcaaaagac   1560
ttgaactctt atgggcttgg taatgttgac tggaaagaaa gagttgaagg ctggaagctg   1620
aagcaggaga aaaatatgtt acagatgact ggtaaatacc atgaagggaa aggaggagaa   1680
attgaaggga ctggttccaa tggcgaagaa ctccaaatgt aagtggaaat actagaccaa   1740
tatctttatt gtccaactca aacagctctt ggccgtgatg ctaataacca ctcttggttt   1800
cttattatgt attgatagac ataattaagt atctgctttg ttacatttgt ttccttccac   1860
tcaattatgg ttctcgtact tacagggctg atgatacacg tcttcctatg agtcgtgtgg   1920
tgcctatccc atcttctcgc ctaaccccctt atcgggttgt gattattctc cggcttatca   1980
tcttgtgttt cttcttgcaa tatcgtacaa ctcaccctgt gaaaaatgca tatcctttgt   2040
ggttgacctc ggttatctgt gagatctggt ttgcattttc ttggcttctt gatcagtttc   2100
ccaaatggta ccccattaac agggagactt atcttgaccg tctcgctata aggttggtct   2160
ttaagtttat acatccccta ctctcatctc tcttttatgt attaacttga tatcttctat   2220
cacagttttc gatagttgac tttttccccc tgtaaattta atttaaattt agacaatggt   2280
gcatctgaat tttgattatg atatatctta agaagattat gattgtaaat cttgaaattt   2340
agtagaaaac catctgcaat ctactgacca tgtgaagttt ccgactagac tatgatagaa   2400
gcatgccaag tggagtgttt attaagatag agcttagcta ttatactgat tttatatgtg   2460
ttttgatttt ttggtttctt attgtagata tgatcgagac ggtgaaccat cacagctcgt   2520
tcctgttgat gtgtttgtta gtacagtgga cccattgaaa gagcctcccc ttgttacagc   2580
aaacacagtt ctctcgattc tttctgtgga ctacccggta gataaagtag cctgttatgt   2640
ttcagatgat ggttcagcta tgcttacctt tgaatccctt tctgaaaccg ctgagtttgc   2700
aaagaaatgg gtaccatttt gcaagaaatt caacattgaa cctagggccc ctgaattcta   2760
ttttgcccag aagatagatt acttgaagga caagatccaa ccgtcttttg ttaaagagcg   2820
acgagctatg aaggtcattt gaaaagtcca cctgcttctc atccatacgg caaagagatt   2880
gactgacttt ttctttggtt tgtattgaca gagagagtat gaagagttta aagtgaggat   2940
aaatgctctt gttgccaaag cacagaaaat ccctgaagaa ggctggacaa tgcaggatgg   3000
tactccctgg cctggtaaca acactagaga tcatcctgga atgatacagg tacagtgtgg   3060
caatcccttg attgtgacag agaggataac gtaaaggaaa catgtttaca tcgttttgtt   3120
tcaatttcag gtgttcttag gccatagtgg gggtctggat accgatggaa atgagctgcc   3180
tagactcatc tatgtttctc gtgaaaagcg gcctggattt caacaccaca aaaaggctgg   3240
agctatgaat gcattggttt gttaactttc agaatcctat tgtgtcctct attttattct   3300
cttgttcact gcctaagaaa cgttcttctt gtgtagccgt tgcttcacat tctttttttt   3360
ctaggctatg tgttctctcc taatttagta tctctttact ttgacagatc cgtgtatctg   3420
ctgttcttac caatggagca tatcttttga acgtggattg tgatcattac tttaataaca   3480
gtaaggctat taagaagct atgtgtttca tgatggaccc ggctattgga aagaagtgct   3540
gctatgtcca gttccctcaa cgttttgacg gtattgattt gcacgatcga tatgccaaca   3600
ggaatatagt cttttttcgat gtgagtatca cttccccatt gtcttttgtt tctcttttgt   3660
```

```
tcatattttg gttggattta ctcgtttctg ctatggcctg acttggatat ttgttctctt    3720
gggcagatta acatgaaggg gttggatggt atccagggtc cagtatatgt gggtactggt    3780
tgttgtttta ataggcaggc tctatatggg tatgatcctg ttttgacgga agaagattta    3840
gaaccaaata ttattgtcaa gagctgttgc gggtcaagga agaaaggtaa aagtagcaag    3900
aagtataact acgaaaagag gagaggcatc aacagaagtg actccaatgc tccactttc    3960 aatatggagg acatcgatga gggttttgaa ggtttgattg agctgattgt gtaataacat    4020
cacttcttta tgtaatgatt tatgtgatgg tgaaatctta caatccttgt ttatgcaggt    4080
tatgatgatg agaggtctat tctaatgtcc cagaggagtg tagagaagcg ttttggtcag    4140
tcgccggtat ttattgcggc aaccttcatg gaacaaggcg gcattccacc aacaaccaat    4200
cccgctactc ttctgaagga ggctattcat gttataagct gtggttacga agacaagact    4260
gaatggggca agaggtcag ttttcaaatg cagctacaga atcttcttat gttctctttc    4320
ttacctgttt gatgacatct tatttggcac ttttgttaga ttggttggat ctatggttcc    4380
gtgacggaag atattcttac tgggttcaag atgcatgccc ggggttggat atcgatctac    4440
tgcaatcctc cacgccctgc gttcaaggga tctgcaccaa tcaatctttc tgatcgtttg    4500
aaccaagttc ttcgatgggc tttgggatct atcgagattc ttcttagcag acattgtcct    4560
atctggtatg gttaccatgg aaggttgaga cttttggaga ggatcgctta tatcaacacc    4620
atcgtctatc ctattacatc catccctctt attgcgtatt gtattcttcc cgcttttgt    4680 ctcatcaccg acagattcat catacccgag gtttgtaaaa ctgaccacac tgctattac    4740 tatttgaatc ccatttttgtg aatgcatttt tttgtcatca tcattgttgc agataagcaa    4800
ctacgcgagt atttggttca ttctactctt catctcaatt gctgtgactg gaatcctgga    4860
gctgagatgg agcggtgtga gcattgagga ttggtggagg aacgagcagt tctgggtcat    4920
tggtggcaca tccgcccatc ttttttgctgt cttccaaggt ctacttaagg ttcttgctgg    4980
tatcgacacc aacttcaccg ttacatctaa agccacagac gaagatgggg attttgcaga    5040
actctacatc ttcaaatgga cagctcttct cattccacca accaccgtcc tacttgtgaa    5100
cctcataggc attgtggctg gtgtctctta tgctgtaaac agtggctacc agtcgtggga    5160
tccgcttttc gggaagctct tcttcgcctt atgggttatt gcccatctct acctttctt     5220 gaaaggtctg ttgggaagac aaaaccgaac accaaccatc gtcattgtct ggtctgttct    5280
tctcgcctcc atcttctcgt tgctttgggt caggatcaat ccctttgtgg acgccaatcc    5340
caatgccaac aacttcaatg gcaaaggagg tgtcttttag                         5380
```

<210> SEQ ID NO 19
<211> LENGTH: 1081
<212> TYPE: PRT
<213> ORGANISM: Arabidopsis thaliana

<400> SEQUENCE: 19

Met Glu Ala Ser Ala Gly Leu Val Ala Gly Ser Tyr Arg Arg Asn Glu
1               5                   10                  15

Leu Val Arg Ile Arg His Glu Ser Asp Gly Gly Thr Lys Pro Leu Lys
            20                  25                  30

Asn Met Asn Gly Gln Ile Cys Gln Ile Cys Gly Asp Asp Val Gly Leu
        35                  40                  45

Ala Glu Thr Gly Asp Val Phe Val Ala Cys Asn Glu Cys Ala Phe Pro
    50                  55                  60

-continued

Val Cys Arg Pro Cys Tyr Glu Tyr Glu Arg Lys Asp Gly Thr Gln Cys
 65                  70                  75                  80

Cys Pro Gln Cys Lys Thr Arg Phe Arg Arg His Arg Gly Ser Pro Arg
                 85                  90                  95

Val Glu Gly Asp Glu Asp Asp Val Asp Ile Glu Asn Glu
            100                 105                 110

Phe Asn Tyr Ala Gln Gly Ala Asn Lys Ala Arg His Gln Arg His Gly
            115                 120                 125

Glu Glu Phe Ser Ser Ser Arg His Glu Ser Gln Pro Ile Pro Leu
            130                 135                 140

Leu Thr His Gly His Thr Val Ser Gly Glu Ile Arg Thr Pro Asp Thr
145                 150                 155                 160

Gln Ser Val Arg Thr Thr Ser Gly Pro Leu Gly Pro Ser Asp Arg Asn
                165                 170                 175

Ala Ile Ser Ser Pro Tyr Ile Asp Pro Arg Gln Pro Val Pro Val Arg
                180                 185                 190

Ile Val Asp Pro Ser Lys Asp Leu Asn Ser Tyr Gly Leu Gly Asn Val
            195                 200                 205

Asp Trp Lys Glu Arg Val Glu Gly Trp Lys Leu Lys Gln Glu Lys Asn
            210                 215                 220

Met Leu Gln Met Thr Gly Lys Tyr His Glu Gly Lys Gly Glu Ile
225                 230                 235                 240

Glu Gly Thr Gly Ser Asn Gly Glu Glu Leu Gln Met Ala Asp Asp Thr
                245                 250                 255

Arg Leu Pro Met Ser Arg Val Val Pro Ile Pro Ser Ser Arg Leu Thr
                260                 265                 270

Pro Tyr Arg Val Val Ile Ile Leu Arg Leu Ile Ile Leu Cys Phe Phe
            275                 280                 285

Leu Gln Tyr Arg Thr Thr His Pro Val Lys Asn Ala Tyr Pro Leu Trp
            290                 295                 300

Leu Thr Ser Val Ile Cys Glu Ile Trp Phe Ala Phe Ser Trp Leu Leu
305                 310                 315                 320

Asp Gln Phe Pro Lys Trp Tyr Pro Ile Asn Arg Glu Thr Tyr Leu Asp
                325                 330                 335

Arg Leu Ala Ile Arg Tyr Asp Arg Asp Gly Glu Pro Ser Gln Leu Val
                340                 345                 350

Pro Val Asp Val Phe Val Ser Thr Val Asp Pro Leu Lys Glu Pro Pro
            355                 360                 365

Leu Val Thr Ala Asn Thr Val Leu Ser Ile Leu Ser Val Asp Tyr Pro
370                 375                 380

Val Asp Lys Val Ala Cys Tyr Val Ser Asp Asp Gly Ser Ala Met Leu
385                 390                 395                 400

Thr Phe Glu Ser Leu Ser Glu Thr Ala Glu Phe Ala Lys Lys Trp Val
                405                 410                 415

Pro Phe Cys Lys Lys Phe Asn Ile Glu Pro Arg Ala Pro Glu Phe Tyr
                420                 425                 430

Phe Ala Gln Lys Ile Asp Tyr Leu Lys Asp Lys Ile Gln Pro Ser Phe
            435                 440                 445

Val Lys Glu Arg Arg Ala Met Lys Arg Glu Tyr Glu Glu Phe Lys Val
            450                 455                 460

Arg Ile Asn Ala Leu Val Ala Lys Ala Gln Lys Ile Pro Glu Glu Gly
465                 470                 475                 480

Trp Thr Met Gln Asp Gly Thr Pro Trp Pro Gly Asn Asn Thr Arg Asp

```
                  485                 490                 495
His Pro Gly Met Ile Gln Val Phe Leu Gly His Ser Gly Gly Leu Asp
                500                 505                 510

Thr Asp Gly Asn Glu Leu Pro Arg Leu Ile Tyr Val Ser Arg Glu Lys
                515                 520                 525

Arg Pro Gly Phe Gln His His Lys Lys Ala Gly Ala Met Asn Ala Leu
            530                 535                 540

Ile Arg Val Ser Ala Val Leu Thr Asn Gly Ala Tyr Leu Leu Asn Val
545                 550                 555                 560

Asp Cys Asp His Tyr Phe Asn Asn Ser Lys Ala Ile Lys Glu Ala Met
                565                 570                 575

Cys Phe Met Met Asp Pro Ala Ile Gly Lys Lys Cys Cys Tyr Val Gln
            580                 585                 590

Phe Pro Gln Arg Phe Asp Gly Ile Asp Leu His Asp Arg Tyr Ala Asn
            595                 600                 605

Arg Asn Ile Val Phe Phe Asp Ile Asn Met Lys Gly Leu Asp Gly Ile
610                 615                 620

Gln Gly Pro Val Tyr Val Gly Thr Gly Cys Cys Phe Asn Arg Gln Ala
625                 630                 635                 640

Leu Tyr Gly Tyr Asp Pro Val Leu Thr Glu Glu Asp Leu Glu Pro Asn
                645                 650                 655

Ile Ile Val Lys Ser Cys Cys Gly Ser Arg Lys Lys Gly Lys Ser Ser
                660                 665                 670

Lys Lys Tyr Asn Tyr Glu Lys Arg Arg Gly Ile Asn Arg Ser Asp Ser
            675                 680                 685

Asn Ala Pro Leu Phe Asn Met Glu Asp Ile Asp Glu Gly Phe Glu Gly
690                 695                 700

Tyr Asp Asp Glu Arg Ser Ile Leu Met Ser Gln Arg Ser Val Glu Lys
705                 710                 715                 720

Arg Phe Gly Gln Ser Pro Val Phe Ile Ala Ala Thr Phe Met Glu Gln
                725                 730                 735

Gly Gly Ile Pro Pro Thr Thr Asn Pro Ala Thr Leu Leu Lys Glu Ala
                740                 745                 750

Ile His Val Ile Ser Cys Gly Tyr Glu Asp Lys Thr Glu Trp Gly Lys
            755                 760                 765

Glu Ile Gly Trp Ile Tyr Gly Ser Val Thr Glu Asp Ile Leu Thr Gly
            770                 775                 780

Phe Lys Met His Ala Arg Gly Trp Ile Ser Ile Tyr Cys Asn Pro Pro
785                 790                 795                 800

Arg Pro Ala Phe Lys Gly Ser Ala Pro Ile Asn Leu Ser Asp Arg Leu
                805                 810                 815

Asn Gln Val Leu Arg Trp Ala Leu Gly Ser Ile Glu Ile Leu Leu Ser
                820                 825                 830

Arg His Cys Pro Ile Trp Tyr Gly Tyr His Gly Arg Leu Arg Leu Leu
            835                 840                 845

Glu Arg Ile Ala Tyr Ile Asn Thr Ile Val Tyr Pro Ile Thr Ser Ile
850                 855                 860

Pro Leu Ile Ala Tyr Cys Ile Leu Pro Ala Phe Cys Leu Ile Thr Asp
865                 870                 875                 880

Arg Phe Ile Ile Pro Glu Ile Ser Asn Tyr Ala Ser Ile Trp Phe Ile
                885                 890                 895

Leu Leu Phe Ile Ser Ile Ala Val Thr Gly Ile Leu Glu Leu Arg Trp
                900                 905                 910
```

```
Ser Gly Val Ser Ile Glu Asp Trp Trp Arg Asn Glu Gln Phe Trp Val
        915                 920                 925

Ile Gly Gly Thr Ser Ala His Leu Phe Ala Val Phe Gln Gly Leu Leu
        930                 935                 940

Lys Val Leu Ala Gly Ile Asp Thr Asn Phe Thr Val Thr Ser Lys Ala
945                 950                 955                 960

Thr Asp Glu Asp Gly Asp Phe Ala Glu Leu Tyr Ile Phe Lys Trp Thr
                965                 970                 975

Ala Leu Leu Ile Pro Pro Thr Thr Val Leu Leu Val Asn Leu Ile Gly
            980                 985                 990

Ile Val Ala Gly Val Ser Tyr Ala Val Asn Ser Gly Tyr Gln Ser Trp
        995                 1000                1005

Asp Pro Leu Phe Gly Lys Leu Phe Phe Ala Leu Trp Val Ile Ala
    1010                1015                1020

His Leu Tyr Pro Phe Leu Lys Gly Leu Leu Gly Arg Gln Asn Arg
    1025                1030                1035

Thr Pro Thr Ile Val Ile Val Trp Ser Val Leu Leu Ala Ser Ile
    1040                1045                1050

Phe Ser Leu Leu Trp Val Arg Ile Asn Pro Phe Val Asp Ala Asn
    1055                1060                1065

Pro Asn Ala Asn Asn Phe Asn Gly Lys Gly Gly Val Phe
    1070                1075                1080

<210> SEQ ID NO 20
<211> LENGTH: 4690
<212> TYPE: DNA
<213> ORGANISM: Arabidopsis thaliana

<400> SEQUENCE: 20
atggaatccg aaggagaaac cgcggtatgc ttttttgact cttgcttcat cattatactt      60
acctttatcg aaatcaggaa ttatatgtac tgaaattgat tgatttgggt gttgaattgt     120
gtattggaga gatctgattt caaattttct gttgaggttt ctaattttgg cttcattgat     180
tcgacttgat tgtagggaa agccgatgaa gaacattgtt ccgcagactt gccagatctg     240
tagtgacaat gttggcaaga ctgttgatgg agatcgtttt gtggcttgtg atatttgttc     300
attcccagtt tgtcggcctt gctacgagta tgagaggaaa gatgggaatc aatcttgtcc     360
tcagtgcaaa accagataca agaggctcaa aggttctctt tgatccttc tgaagtatac     420 tgtcttcatt gttcatcgat agtttatcag tatgttttga attttggatc agattggtat     480
ttatagcaat ttgctaattt ctgattctag gtagtcctgc tattcctggt gataaagacg     540
aggatggctt agctgatgaa ggtactgttg agttcaacta ccctcagaag gagaaaattt     600
cagagcggat gcttggttgg catcttactc gtgggaaggg agaggaaatg ggggaacccc     660
agtatgataa agaggtctct cacaatcatc ttcctcgtct cacgagcaga caagatgtaa     720
ggcattgctg ttcattcttc cctcttaagc attcgcatcc tcacgcaatt tagttttgga     780
atctgatttt gtcatttgct tatttacaga cttcaggaga ttttctgct gcctcacctg     840 aacgcctctc tgtatcttct actatcgctg ggggaaagcg ccttcctat tcatcagatg     900 tcaatcaatc acgtaaatat cctttatttc taactctctc gccaacacat atatttgtac     960
ctaggcttct cttttatgtc aaaactctaa acaataaaat ctgttgttgt cattcacgct    1020
gcagcaaata gaaggattgt ggatcctgtt ggactcggga tgtagcttg aaggagaga    1080 gttgatggct ggaaaatgaa gcaagagaag aatactggtc ctgtcagcac gcaggctgct    1140
```

```
tctgaaagag gtggagtaga tattgatgcc agcacagata tcctagcaga tgaggctctg    1200
ctgtgagttc ttgttttgta atcttgtttg ttctgtcgtg gtgtaccgag cgttttttcct   1260 attaagcaat gtcctgatac tcatttttcca attctttatt tattgtacag gaatgacgaa   1320
gcgaggcagc ctctgtcaag gaaagtttca attccttcat cacggatcaa tccttacaga   1380
atggttatta tgctgcggct tgttatcctt tgtctcttct tgcattaccg tataacaaac    1440
ccagtgccaa atgcctttgc tctatggctg gtctctgtga tatgtgagat ctggtttgcc    1500
ttatcctgga ttttggatca gtttcccaag tggtttcctg tgaaccgtga aacctacctc    1560
gacaggcttg ctttaaggta agttctattt ccccattctt ctgaagcaat tactcaaagg    1620
attgtttgcc tatactgttt cccattttaa tttgatcatg gtcattttt gggacagata     1680 tgatcgtgaa ggtgagccat cacagttagc tgctgttgac attttcgtga gtactgttga    1740 cccctttgaag gagccacccc ttgtgacagc caacacagtg ctctctattc tggctgttga   1800
ctacccagtt gacaaggtgt cctgttatgt ttctgatgat ggtgctgcta tgttatcatt    1860
tgaatcactt gcagaaacat cagagtttgc tcgtaaatgg gtaccatttt gcaagaaata    1920
tagcatagag cctcgtgcac cagaatggta ctttgctgcg aaaatagatt acttgaagga    1980
taaagttcag acatcatttg tcaaagatcg tagagctatg aaggtaagtt tgtagtttta    2040
gtcatctagt caccctcact ttgatttttag tgtatgctat attgaccttt tatttttcttt  2100 cagagggaat atgaggaatt taaaatccga atcaatgcac ttgtttccaa agccctaaaa    2160
tgtcctgaag aagggtgggt tatgcaagat ggcacaccgt ggcctggaaa taatacaagg    2220
gaccatccag gaatgatcca ggtaagaaat tggttttaac tatggaatcg agaatgctct    2280
ctctttctct ctagaagttc attattgaag taccatttgc tgaatgcagg tcttcttagg    2340
gcaaaatggt ggacttgatg cagagggcaa tgagctcccg cgtttggtat atgtttctcg    2400
agaaaagcga ccaggattcc agcaccacaa aaaggctggt gctatgaatg cactggtaag    2460
tttctgatct tggatttttg acttcttcat tctgaccaat ttgttagtct aatctgggta    2520
cttttcaaat gaataggtga gagtttcagc agttcttacc aatggacctt tcatcttgaa    2580
tcttgattgt gatcattaca taaataacag caaagcctta agagaagcaa tgtgcttcct   2640
gatggaccca aacctcggga agcaagtttg ttatgttcag ttcccacaaa gatttgatgg   2700
tatcgataag aacgatagat atgctaatcg taataccgtg ttctttgatg taagtcacac   2760
ttacctatac ttgcgtctaa ttttcttgtt ctttcaaatt gcttttagac acgaatatac   2820
attaaactca cagtttcttg agtttgtcgt aattttttcca tgatatgttt tccagattaa  2880
cttgagaggt ttagatggga ttcaaggacc tgtatatgtc ggaactggat gtgttttcaa   2940
cagaacagca ttatacggtt atgaacctcc aataaaagta aaacacaaga agccaagtct   3000
tttatctaag ctctgtggtg gatcaagaaa gaagaattcc aaagctaaga aagagtcgga   3060
caaaaagaaa tcaggcaggc atactgactc aactgttcct gtattcaacc tcgatgacat   3120
agaagaggga gttgaaggta caactgtttt tatttcttct ttggtttccg ttatacccat   3180
atgttgctgt ttgaaatatt gatccagggg aggggattat ttatagttga cagttgtcta   3240
aatagtttcc atactaggta tctcatcatg tcttaactat ttggcatttg tgaaacttag   3300
gtgctggttt tgatgatgaa aaggcgctct taatgtcgca aatgagcctg gagaagcgat   3360
ttggacagtc tgctgttttt gttgcttcta ccctaatgga aaatggtggt gttcctcctt   3420
cagcaactcc agaaaacctt ctcaaagagg ctatccatgt cattagttgt ggttatgagg   3480
```

-continued

```
ataagtcaga ttggggaatg gaggtataat ctcatttgaa ctcctacatg aatctgcatt    3540
gttctgacat atccactttg gcattcactt tgtttatatt ttccgctgtc tttcttcaga    3600
ttggatggat ctatggttct gtgacagaag atattctgac tgggttcaaa atgcatgccc    3660
gtggatggcg atccatttac tgcatgccta agcttccagc tttcaagggt tctgctccta    3720
tcaatctttc agatcgtctg aaccaagtgc tgaggtgggc tttaggttca gttgagattc    3780
tcttcagtcg gcattgtcct atatggtatg gttacaatgg gaggctaaaa ttcttgaga    3840 ggtttgcgta tgtgaacacc accatctacc ctatcacctc cattcctctt ctcatgtatt    3900
gtacattgcc agccgtttgt ctcttcacca accagtttat tattcctcag gtttgacacc    3960
tctctctgtc tatctatctc tatctctatc tctatctcta gaacaaacct taattacgtt    4020
ctgtttaact gaaaccatgt tgtgtttgtc atctatttac ggttccaaat cctgatcagc    4080
tggttctatt gttcctcttt tgcagattag taacattgca agtatatggt ttctgtctct    4140
ctttctctcc attttcgcca cgggtatact agaaatgagg tggagtggcg taggcataga    4200
cgaatggtgg agaaacgagc agttttgggt cattggtgga gtatccgctc atttattcgc    4260
tgtgtttcaa ggtatcctca aagtccttgc cggtattgac acaaacttca cagttacctc    4320
aaaagcttca gatgaagacg gagactttgc tgagctctac ttgttcaaat ggacaacact    4380
tctgattccg ccaacgacgc tgctcattgt aaacttagtg ggagttgttg caggagtctc    4440
ttatgctatc aacagtggat accaatcatg gggaccactc tttggtaagt tgttctttgc    4500
cttctgggtg attgttcact tgtacccttt cctcaagggt ttgatgggtc gacagaaccg    4560
gactcctacc attgttgtgg tctggtctgt tctcttggct tctatcttct tgttgttgtg    4620
ggttaggatt gatcccttca ctagccgagt cactggcccg gacattctgg aatgtggaat    4680
caactgttga                                                           4690
```

<210> SEQ ID NO 21
<211> LENGTH: 1065
<212> TYPE: PRT
<213> ORGANISM: Arabidopsis thaliana

<400> SEQUENCE: 21

```
Met Glu Ser Glu Gly Glu Thr Ala Gly Lys Pro Met Lys Asn Ile Val
1               5                   10                  15

Pro Gln Thr Cys Gln Ile Cys Ser Asp Asn Val Gly Lys Thr Val Asp
            20                  25                  30

Gly Asp Arg Phe Val Ala Cys Asp Ile Cys Ser Phe Pro Val Cys Arg
        35                  40                  45

Pro Cys Tyr Glu Tyr Glu Arg Lys Asp Gly Asn Gln Ser Cys Pro Gln
    50                  55                  60

Cys Lys Thr Arg Tyr Lys Arg Leu Lys Gly Ser Pro Ala Ile Pro Gly
65                  70                  75                  80

Asp Lys Asp Glu Asp Gly Leu Ala Asp Glu Gly Thr Val Glu Phe Asn
                85                  90                  95

Tyr Pro Gln Lys Glu Lys Ile Ser Glu Arg Met Leu Gly Trp His Leu
            100                 105                 110

Thr Arg Gly Lys Gly Glu Glu Met Gly Glu Pro Gln Tyr Asp Lys Glu
        115                 120                 125

Val Ser His Asn His Leu Pro Arg Leu Thr Ser Arg Gln Asp Thr Ser
    130                 135                 140

Gly Glu Phe Ser Ala Ala Ser Pro Glu Arg Leu Ser Val Ser Ser Thr
145                 150                 155                 160
```

```
Ile Ala Gly Gly Lys Arg Leu Pro Tyr Ser Ser Asp Val Asn Gln Ser
                165                 170                 175

Pro Asn Arg Arg Ile Val Asp Pro Val Gly Leu Gly Asn Val Ala Trp
            180                 185                 190

Lys Glu Arg Val Asp Gly Trp Lys Met Lys Gln Glu Lys Asn Thr Gly
        195                 200                 205

Pro Val Ser Thr Gln Ala Ala Ser Glu Arg Gly Gly Val Asp Ile Asp
    210                 215                 220

Ala Ser Thr Asp Ile Leu Ala Asp Glu Ala Leu Leu Asn Asp Glu Ala
225                 230                 235                 240

Arg Gln Pro Leu Ser Arg Lys Val Ser Ile Pro Ser Ser Arg Ile Asn
                245                 250                 255

Pro Tyr Arg Met Val Ile Met Leu Arg Leu Val Ile Leu Cys Leu Phe
            260                 265                 270

Leu His Tyr Arg Ile Thr Asn Pro Val Pro Asn Ala Phe Ala Leu Trp
        275                 280                 285

Leu Val Ser Val Ile Cys Glu Ile Trp Phe Ala Leu Ser Trp Ile Leu
    290                 295                 300

Asp Gln Phe Pro Lys Trp Phe Pro Val Asn Arg Glu Thr Tyr Leu Asp
305                 310                 315                 320

Arg Leu Ala Leu Arg Tyr Asp Arg Glu Gly Glu Pro Ser Gln Leu Ala
                325                 330                 335

Ala Val Asp Ile Phe Val Ser Thr Val Asp Pro Leu Lys Glu Pro Pro
            340                 345                 350

Leu Val Thr Ala Asn Thr Val Leu Ser Ile Leu Ala Val Asp Tyr Pro
        355                 360                 365

Val Asp Lys Val Ser Cys Tyr Val Ser Asp Asp Gly Ala Ala Met Leu
    370                 375                 380

Ser Phe Glu Ser Leu Ala Glu Thr Ser Glu Phe Ala Arg Lys Trp Val
385                 390                 395                 400

Pro Phe Cys Lys Lys Tyr Ser Ile Glu Pro Arg Ala Pro Glu Trp Tyr
                405                 410                 415

Phe Ala Ala Lys Ile Asp Tyr Leu Lys Asp Lys Val Gln Thr Ser Phe
            420                 425                 430

Val Lys Asp Arg Arg Ala Met Lys Arg Glu Tyr Glu Glu Phe Lys Ile
        435                 440                 445

Arg Ile Asn Ala Leu Val Ser Lys Ala Leu Lys Cys Pro Glu Glu Gly
    450                 455                 460

Trp Val Met Gln Asp Gly Thr Pro Trp Pro Gly Asn Asn Thr Arg Asp
465                 470                 475                 480

His Pro Gly Met Ile Gln Val Phe Leu Gly Gln Asn Gly Gly Leu Asp
                485                 490                 495

Ala Glu Gly Asn Glu Leu Pro Arg Leu Val Tyr Val Ser Arg Glu Lys
            500                 505                 510

Arg Pro Gly Phe Gln His His Lys Lys Ala Gly Ala Met Asn Ala Leu
        515                 520                 525

Val Arg Val Ser Ala Val Leu Thr Asn Gly Pro Phe Ile Leu Asn Leu
    530                 535                 540

Asp Cys Asp His Tyr Ile Asn Asn Ser Lys Ala Leu Arg Glu Ala Met
545                 550                 555                 560

Cys Phe Leu Met Asp Pro Asn Leu Gly Lys Gln Val Cys Tyr Val Gln
                565                 570                 575
```

-continued

```
Phe Pro Gln Arg Phe Asp Gly Ile Asp Lys Asn Asp Arg Tyr Ala Asn
            580                 585                 590
Arg Asn Thr Val Phe Phe Asp Ile Asn Leu Arg Gly Leu Asp Gly Ile
        595                 600                 605
Gln Gly Pro Val Tyr Val Gly Thr Gly Cys Val Phe Asn Arg Thr Ala
    610                 615                 620
Leu Tyr Gly Tyr Glu Pro Pro Ile Lys Val Lys His Lys Lys Pro Ser
625                 630                 635                 640
Leu Leu Ser Lys Leu Cys Gly Gly Ser Arg Lys Lys Asn Ser Lys Ala
            645                 650                 655
Lys Lys Glu Ser Asp Lys Lys Lys Ser Gly Arg His Thr Asp Ser Thr
        660                 665                 670
Val Pro Val Phe Asn Leu Asp Asp Ile Glu Glu Gly Val Glu Gly Ala
    675                 680                 685
Gly Phe Asp Asp Glu Lys Ala Leu Leu Met Ser Gln Met Ser Leu Glu
690                 695                 700
Lys Arg Phe Gly Gln Ser Ala Val Phe Val Ala Ser Thr Leu Met Glu
705                 710                 715                 720
Asn Gly Gly Val Pro Pro Ser Ala Thr Pro Glu Asn Leu Leu Lys Glu
            725                 730                 735
Ala Ile His Val Ile Ser Cys Gly Tyr Glu Asp Lys Ser Asp Trp Gly
        740                 745                 750
Met Glu Ile Gly Trp Ile Tyr Gly Ser Val Thr Glu Asp Ile Leu Thr
    755                 760                 765
Gly Phe Lys Met His Ala Arg Gly Trp Arg Ser Ile Tyr Cys Met Pro
770                 775                 780
Lys Leu Pro Ala Phe Lys Gly Ser Ala Pro Ile Asn Leu Ser Asp Arg
785                 790                 795                 800
Leu Asn Gln Val Leu Arg Trp Ala Leu Gly Ser Val Glu Ile Leu Phe
            805                 810                 815
Ser Arg His Cys Pro Ile Trp Tyr Gly Tyr Asn Gly Arg Leu Lys Phe
        820                 825                 830
Leu Glu Arg Phe Ala Tyr Val Asn Thr Thr Ile Tyr Pro Ile Thr Ser
    835                 840                 845
Ile Pro Leu Leu Met Tyr Cys Thr Leu Pro Ala Val Cys Leu Phe Thr
850                 855                 860
Asn Gln Phe Ile Ile Pro Gln Ile Ser Asn Ile Ala Ser Ile Trp Phe
865                 870                 875                 880
Leu Ser Leu Phe Leu Ser Ile Phe Ala Thr Gly Ile Leu Glu Met Arg
            885                 890                 895
Trp Ser Gly Val Gly Ile Asp Glu Trp Trp Arg Asn Glu Gln Phe Trp
        900                 905                 910
Val Ile Gly Gly Val Ser Ala His Leu Phe Ala Val Phe Gln Gly Ile
    915                 920                 925
Leu Lys Val Leu Ala Gly Ile Asp Thr Asn Phe Thr Val Thr Ser Lys
930                 935                 940
Ala Ser Asp Glu Asp Gly Asp Phe Ala Glu Leu Tyr Leu Phe Lys Trp
945                 950                 955                 960
Thr Thr Leu Leu Ile Pro Pro Thr Thr Leu Ile Val Asn Leu Val
            965                 970                 975
Gly Val Val Ala Gly Val Ser Tyr Ala Ile Asn Ser Gly Tyr Gln Ser
        980                 985                 990
Trp Gly Pro Leu Phe Gly Lys Leu  Phe Phe Ala Phe Trp  Val Ile Val
```

```
                995                 1000                1005
His Leu Tyr Pro Phe Leu Lys Gly Leu Met Gly Arg Gln Asn Arg
    1010            1015            1020

Thr Pro Thr Ile Val Val Val Trp Ser Val Leu Leu Ala Ser Ile
    1025            1030            1035

Phe Leu Leu Leu Trp Val Arg Ile Asp Pro Phe Thr Ser Arg Val
    1040            1045            1050

Thr Gly Pro Asp Ile Leu Glu Cys Gly Ile Asn Cys
    1055            1060            1065

<210> SEQ ID NO 22
<211> LENGTH: 4690
<212> TYPE: DNA
<213> ORGANISM: Arabidopsis thaliana

<400> SEQUENCE: 22
atggaatccg aaggagaaac cgcggtatgc ttttttgact cttgcttcat cattatactt      60
acctttatcg aaatcaggaa ttatatgtac tgaaattgat tgatttgggt gttgaattgt     120
gtattggaga gatctgattt caaattttct gttgaggttt ctaattttgg cttcattgat     180
tcgacttgat ttgtagggaa agccgatgaa gaacattgtt ccgcagactt gccagatctg     240
tagtgacaat gttggcaaga ctgttgatgg agatcgtttt gtggcttgtg atatttgttc     300
attcccagtt tgtcggcctt gctacgagta tgagaggaaa gatgggaatc aatcttgtcc     360
tcagtgcaaa accagataca agaggctcaa aggttctctt tgatccttc tgaagtatac      420 tgtcttcatt gttcatcgat agtttatcag tatgttttga attttggatc agattggtat     480
ttatagcaat ttgctaattt ctgattctag gtagtcctgc tattcctggt gataaagacg     540
aggatggctt agctgatgaa ggtactgttg agttcaacta ccctcagaag gagaaaattt     600
cagagcggat gcttggttgg catcttactc gtgggaaggg agaggaaatg ggggaacccc     660
agtatgataa agaggtctct cacaatcatc ttcctcgtct cacgagcaga caagatgtaa     720
ggcattgctg ttcattcttc cctcttaagc attcgcatcc tcacgcaatt tagttttgga     780 atctgattt gtcatttgct tatttacaga cttcaggaga gttttctgct gcctcacctg      840
aacgcctctc tgtatcttct actatcgctg ggggaaagcg ccttccctat tcatcagatg     900
tcaatcaatc acgtaaatat cctttatttc taactctctc gccaacacat atatttgtac     960
ctaggcttct cttttatgtc aaaactctaa acaataaaat ctgttgttgt cattcacgct    1020
gcagcaaata gaaggattgt ggatcctgtt ggactcggga atgtagcttg aaggagaga    1080 gttgatggct ggaaaatgaa gcaagagaag aatactggtc ctgtcagcac gcaggctgct    1140
tctgaaagag gtggagtaga tattgatgcc agcacagata tcctagcaga tgaggctctg    1200
ctgtgagttc ttgttttgta atcttgtttg ttctgtcgtg gtgtaccgag cgttttcct     1260 attaagcaat gtcctgatac tcattttcca attctttatt tattgtacag gaatgacgaa    1320
gcgaggcagc ctctgtcaag gaaagtttca attccttcat cacggatcaa tccttacaga    1380
atggttatta tgctgcggct tgttatcctt tgtctcttct tgcattaccg tataacaaac    1440
ccagtgccaa atgcctttgc tctatggctg gtctctgtga tatgtgagat ctggtttgcc    1500
ttatcctgga ttttggatca gtttcccaag tggtttcctg tgaaccgtga aacctacctc    1560
gacaggcttg ctttaaggta agttctattt ccccattctt ctgaagcaat tactcaaagg    1620
attgtttgcc tatactgttt cccatttttaa tttgatcatg tcaatttttt gggacagata    1680
tgatcgtgaa ggtgagccat cacagttagc tgctgttgac attttcgtga gtactgttga    1740
```

```
ccccttgaag gagccacccc ttgtgacagc aacacagtg ctctctattc tggctgttga      1800
ctacccagtt gacaaggtgt cctgttatgt ttctgatgat ggtgctgcta tgttatcatt      1860
tgaatcactt gcagaaacat cagagtttgc tcgtaaatgg gtaccatttt gcaagaaata      1920
tagcatagag cctcgtgcac cagaatggta ctttgctgcg aaaatagatt acttgaagga      1980
taaagttcag acatcatttg tcaaagatcg tagagctatg aaggtaagtt tgtagtttta      2040
gtcatctagt caccctcact ttgattttag tgtatgctat attgaccttt tattttcttt      2100
cagagggaat atgaggaatt taaaatccga atcaatgcac ttgtttccaa agccctaaaa      2160
tgtcctgaag aagggtgggt tatgcaagat ggcacaccgt ggcctggaaa taatacaagg      2220
gaccatccag gaatgatcca ggtaagaaat tggttttaac tatggaatcg agaatgctct      2280
ctctttctct ctagaagttc attattgaag taccatttgc tgaatgcagg tcttcttagg      2340
gcaaaatggt ggacttgatg cagagggcaa tgagctcccg cgtttggtat atgtttctcg      2400
agaaaagcga ccaggattcc agcaccacaa aaaggctggt gctatgaatg cactggtaag      2460
tttctgatct tggattttg acttcttcat tctgaccaat ttgttagtct aatctgggta      2520
cttttcaaat gaataggtga gagtttcagc agttcttacc aatggacctt tcatcttgaa      2580
tcttgattgt gatcattaca taaataacag caaagcctta agagaagcaa tgtgcttcct      2640
gatggaccca aacctcggga agcaagtttg ttatgttcag ttcccacaaa gatttgatgg      2700
tatcgataag aacgatagat atgctaatcg taataccgtg ttctttgatg taagtcacac      2760
ttacctatac ttgcgtctaa ttttcttgtt ctttcaaatt gcttttagac acgaatatac      2820
attaaactca cagtttcttg agtttgtcgt aatttttcca tgatatgttt tccagattaa      2880
cttgagaggt ttagatggga ttcaaggacc tgtatatgtc ggaactggat gtgttttcaa      2940
cagaacagca ttatacggtt atgaacctcc aataaaagta aaacacaaga agccaagtct      3000
tttatctaag ctctgtggtg gatcaagaaa gaagaattcc aaagctaaga aagagtcgga      3060 caaaagaaa tcaggcaggc atactgactc aactgttcct gtattcaacc tcgatgacat      3120
agaagaggga gttgaaggta caactgtttt tatttcttct ttggtttccg ttatacccat      3180
atgttgctgt ttgaaatatt gatccagggg aggggattat ttatagttga cagttgtcta      3240 aatagttttcc atactaggta tctcatcatg tcttaactat ttggcatttg tgaaacttag      3300
gtgctggttt tgatgatgaa aaggcgctct taatgtcgca aatgagcctg gagaagcgat      3360
ttggacagtc tgctgttttt gttgcttcta ccctaatgga aaatggtggt gttcctcctt      3420
cagcaactcc agaaaacctt ctcaaagagg ctatccatgt cattagttgt ggttatgagg      3480
ataagtcaga ttggggaatg gaggtataat ctcatttgaa ctcctacatg aatctgcatt      3540
gttctgacat atccactttg gcattcactt tgtttatatt ttccgctgtc tttcttcaga      3600
ttggatggat ctatggttct gtgacagaag atattctgac tgggttcaaa atgcatgccc      3660
gtggatggcg atccatttac tgcatgccta agcttccagc tttcaagggt tctgctccta      3720
tcaatctttc agatcgtctg aaccaagtgc tgaggtgggc tttaggttca gttgagattc      3780
tcttcagtcg gcattgtcct atatggtatg ttacaatgg gaggctaaaa tttcttgaga      3840
ggtttgcgta tgtgaacacc accatctacc ctatcacctc cattcctctt ctcatgtatt      3900
gtacattgcc agccgtttgt ctcttcacca accagtttat tattcctcag gtttgacacc      3960
tctctctgtc tatctatctc tatctctatc tctatctcta gaacaaacct taattacgtt      4020
ctgtttaact gaaaccatgt tgtgtttgtc atctatttac ggttccaaat cctgatcagc      4080
```

-continued

```
tggttctatt gttcctcttt tgcagattag taacattgca agtatatggt ttctgtctct    4140
ctttctctcc atttcgcca cgggtatact agaaatgagg tggagtggcg taggcataga    4200
cgaatggtgg agaaacgagc agttttgggt cattggtgga gtatccgctc atttattcgc    4260
tgtgtttcaa ggtatcctca agtccttgc cggtattgac acaaacttca cagttacctc    4320
aaaagcttca gatgaagacg gagactttgc tgagctctac ttgttcaaat ggacaacact    4380
tctgattccg ccaacgacgc tgctcattgt aaacttagtg ggagttgttg caggagtctc    4440
ttatgctatc aacagtggat accaatcatg gggaccactc tttggtaagt tgttctttgc    4500
cttctgggtg attgttcact tgtacccttt cctcaagggt ttgatgggtc gacagaaccg    4560
gactcctacc attgttgtgg tctggtctgt tctcttggct tttatcttct cgttgttgtg    4620
ggttaggatt gatcccttca ctagccgagt cactggcccg acattctgg aatgtggaat    4680 caactgttga                                                           4690
```

<210> SEQ ID NO 23
<211> LENGTH: 1065
<212> TYPE: PRT
<213> ORGANISM: Arabidopsis thaliana

<400> SEQUENCE: 23

```
Met Glu Ser Glu Gly Glu Thr Ala Gly Lys Pro Met Lys Asn Ile Val
1               5                   10                  15

Pro Gln Thr Cys Gln Ile Cys Ser Asp Asn Val Gly Lys Thr Val Asp
            20                  25                  30

Gly Asp Arg Phe Val Ala Cys Asp Ile Cys Ser Phe Pro Val Cys Arg
        35                  40                  45

Pro Cys Tyr Glu Tyr Glu Arg Lys Asp Gly Asn Gln Ser Cys Pro Gln
    50                  55                  60

Cys Lys Thr Arg Tyr Lys Arg Leu Lys Gly Ser Pro Ala Ile Pro Gly
65                  70                  75                  80

Asp Lys Asp Glu Asp Gly Leu Ala Asp Glu Gly Thr Val Glu Phe Asn
                85                  90                  95

Tyr Pro Gln Lys Glu Lys Ile Ser Glu Arg Met Leu Gly Trp His Leu
            100                 105                 110

Thr Arg Gly Lys Gly Glu Glu Met Gly Glu Pro Gln Tyr Asp Lys Glu
        115                 120                 125

Val Ser His Asn His Leu Pro Arg Leu Thr Ser Arg Gln Asp Thr Ser
    130                 135                 140

Gly Glu Phe Ser Ala Ala Ser Pro Glu Arg Leu Ser Val Ser Ser Thr
145                 150                 155                 160

Ile Ala Gly Gly Lys Arg Leu Pro Tyr Ser Ser Asp Val Asn Gln Ser
                165                 170                 175

Pro Asn Arg Arg Ile Val Asp Pro Val Gly Leu Gly Asn Val Ala Trp
            180                 185                 190

Lys Glu Arg Val Asp Gly Trp Lys Met Lys Gln Glu Lys Asn Thr Gly
        195                 200                 205

Pro Val Ser Thr Gln Ala Ala Ser Glu Arg Gly Gly Val Asp Ile Asp
    210                 215                 220

Ala Ser Thr Asp Ile Leu Ala Asp Glu Ala Leu Asn Asp Glu Ala
225                 230                 235                 240

Arg Gln Pro Leu Ser Arg Lys Val Ser Ile Pro Ser Ser Arg Ile Asn
                245                 250                 255

Pro Tyr Arg Met Val Ile Met Leu Arg Leu Val Ile Leu Cys Leu Phe
```

```
                260                 265                 270
Leu His Tyr Arg Ile Thr Asn Pro Val Pro Asn Ala Phe Ala Leu Trp
                275                 280                 285
Leu Val Ser Val Ile Cys Glu Ile Trp Phe Ala Leu Ser Trp Ile Leu
                290                 295                 300
Asp Gln Phe Pro Lys Trp Phe Pro Val Asn Arg Glu Thr Tyr Leu Asp
305                 310                 315                 320
Arg Leu Ala Leu Arg Tyr Asp Arg Glu Gly Glu Pro Ser Gln Leu Ala
                325                 330                 335
Ala Val Asp Ile Phe Val Ser Thr Val Asp Pro Leu Lys Glu Pro Pro
                340                 345                 350
Leu Val Thr Ala Asn Thr Val Leu Ser Ile Leu Ala Val Asp Tyr Pro
                355                 360                 365
Val Asp Lys Val Ser Cys Tyr Val Ser Asp Asp Gly Ala Ala Met Leu
                370                 375                 380
Ser Phe Glu Ser Leu Ala Glu Thr Ser Glu Phe Ala Arg Lys Trp Val
385                 390                 395                 400
Pro Phe Cys Lys Lys Tyr Ser Ile Glu Pro Arg Ala Pro Glu Trp Tyr
                405                 410                 415
Phe Ala Ala Lys Ile Asp Tyr Leu Lys Asp Lys Val Gln Thr Ser Phe
                420                 425                 430
Val Lys Asp Arg Arg Ala Met Lys Arg Glu Tyr Glu Glu Phe Lys Ile
                435                 440                 445
Arg Ile Asn Ala Leu Val Ser Lys Ala Leu Lys Cys Pro Glu Glu Gly
                450                 455                 460
Trp Val Met Gln Asp Gly Thr Pro Trp Pro Gly Asn Asn Thr Arg Asp
465                 470                 475                 480
His Pro Gly Met Ile Gln Val Phe Leu Gly Gln Asn Gly Gly Leu Asp
                485                 490                 495
Ala Glu Gly Asn Glu Leu Pro Arg Leu Val Tyr Val Ser Arg Glu Lys
                500                 505                 510
Arg Pro Gly Phe Gln His His Lys Lys Ala Gly Ala Met Asn Ala Leu
                515                 520                 525
Val Arg Val Ser Ala Val Leu Thr Asn Gly Pro Phe Ile Leu Asn Leu
                530                 535                 540
Asp Cys Asp His Tyr Ile Asn Asn Ser Lys Ala Leu Arg Glu Ala Met
545                 550                 555                 560
Cys Phe Leu Met Asp Pro Asn Leu Gly Lys Gln Val Cys Tyr Val Gln
                565                 570                 575
Phe Pro Gln Arg Phe Asp Gly Ile Asp Lys Asn Asp Arg Tyr Ala Asn
                580                 585                 590
Arg Asn Thr Val Phe Phe Asp Ile Asn Leu Arg Gly Leu Asp Gly Ile
                595                 600                 605
Gln Gly Pro Val Tyr Val Gly Thr Gly Cys Val Phe Asn Arg Thr Ala
                610                 615                 620
Leu Tyr Gly Tyr Glu Pro Pro Ile Lys Val Lys His Lys Lys Pro Ser
625                 630                 635                 640
Leu Leu Ser Lys Leu Cys Gly Gly Ser Arg Lys Lys Asn Ser Lys Ala
                645                 650                 655
Lys Lys Glu Ser Asp Lys Lys Ser Gly Arg His Thr Asp Ser Thr
                660                 665                 670
Val Pro Val Phe Asn Leu Asp Asp Ile Glu Glu Gly Val Glu Gly Ala
                675                 680                 685
```

-continued

Gly Phe Asp Asp Glu Lys Ala Leu Leu Met Ser Gln Met Ser Leu Glu
690                 695                 700

Lys Arg Phe Gly Gln Ser Ala Val Phe Val Ala Ser Thr Leu Met Glu
705                 710                 715                 720

Asn Gly Gly Val Pro Pro Ser Ala Thr Pro Glu Asn Leu Leu Lys Glu
            725                 730                 735

Ala Ile His Val Ile Ser Cys Gly Tyr Glu Asp Lys Ser Asp Trp Gly
            740                 745                 750

Met Glu Ile Gly Trp Ile Tyr Gly Ser Val Thr Glu Asp Ile Leu Thr
        755                 760                 765

Gly Phe Lys Met His Ala Arg Gly Trp Arg Ser Ile Tyr Cys Met Pro
770                 775                 780

Lys Leu Pro Ala Phe Lys Gly Ser Ala Pro Ile Asn Leu Ser Asp Arg
785                 790                 795                 800

Leu Asn Gln Val Leu Arg Trp Ala Leu Gly Ser Val Glu Ile Leu Phe
            805                 810                 815

Ser Arg His Cys Pro Ile Trp Tyr Gly Tyr Asn Gly Arg Leu Lys Phe
            820                 825                 830

Leu Glu Arg Phe Ala Tyr Val Asn Thr Thr Ile Tyr Pro Ile Thr Ser
        835                 840                 845

Ile Pro Leu Leu Met Tyr Cys Thr Leu Pro Ala Val Cys Leu Phe Thr
850                 855                 860

Asn Gln Phe Ile Ile Pro Gln Ile Ser Asn Ile Ala Ser Ile Trp Phe
865                 870                 875                 880

Leu Ser Leu Phe Leu Ser Ile Phe Ala Thr Gly Ile Leu Glu Met Arg
            885                 890                 895

Trp Ser Gly Val Gly Ile Asp Glu Trp Trp Arg Asn Glu Gln Phe Trp
            900                 905                 910

Val Ile Gly Gly Val Ser Ala His Leu Phe Ala Val Phe Gln Gly Ile
        915                 920                 925

Leu Lys Val Leu Ala Gly Ile Asp Thr Asn Phe Thr Val Thr Ser Lys
930                 935                 940

Ala Ser Asp Glu Asp Gly Asp Phe Ala Glu Leu Tyr Leu Phe Lys Trp
945                 950                 955                 960

Thr Thr Leu Leu Ile Pro Pro Thr Thr Leu Leu Ile Val Asn Leu Val
            965                 970                 975

Gly Val Val Ala Gly Val Ser Tyr Ala Ile Asn Ser Gly Tyr Gln Ser
            980                 985                 990

Trp Gly Pro Leu Phe Gly Lys Leu Phe Phe Ala Phe Trp Val Ile Val
        995                 1000                1005

His Leu Tyr Pro Phe Leu Lys Gly Leu Met Gly Arg Gln Asn Arg
    1010                1015                1020

Thr Pro Thr Ile Val Val Val Trp Ser Val Leu Leu Ala Phe Ile
    1025                1030                1035

Phe Ser Leu Leu Trp Val Arg Ile Asp Pro Phe Thr Ser Arg Val
    1040                1045                1050

Thr Gly Pro Asp Ile Leu Glu Cys Gly Ile Asn Cys
    1055                1060                1065

<210> SEQ ID NO 24
<211> LENGTH: 4690
<212> TYPE: DNA
<213> ORGANISM: Arabidopsis thaliana

<400> SEQUENCE: 24

```
atggaatccg aaggagaaac cgcggtatgc ttttttgact cttgcttcat cattatactt      60
acctttatcg aaatcaggaa ttatatgtac tgaaattgat tgatttgggt gttgaattgt     120
gtattggaga gatctgattt caaattttct gttgaggttt ctaattttgg cttcattgat     180
tcgacttgat ttgtagggaa agccgatgaa gaacattgtt ccgcagactt gccagatctg     240
tagtgacaat gttggcaaga ctgttgatgg agatcgtttt gtggcttgtg atatttgttc     300
attcccagtt tgtcggcctt gctacgagta tgagaggaaa gatgggaatc aatcttgtcc     360
tcagtgcaaa accagataca agaggctcaa aggttctctt tgatccttc tgaagtatac      420
tgtcttcatt gttcatcgat agtttatcag tatgttttga attttggatc agattggtat     480
ttatagcaat ttgctaattt ctgattctag gtagtcctgc tattcctggt gataaagacg     540
aggatggctt agctgatgaa ggtactgttg agttcaacta ccctcagaag gagaaaattt     600
cagagcggat gcttggttgg catcttactc gtgggaaggg agaggaaatg ggggaacccc     660
agtatgataa agaggtctct cacaatcatc ttcctcgtct cacgagcaga caagatgtaa     720
ggcattgctg ttcattcttc cctcttaagc attcgcatcc tcacgcaatt tagttttgga     780
atctgatttt gtcattgct tatttacaga cttcaggaga gttttctgct gcctcacctg      840
aacgcctctc tgtatcttct actatcgctg ggggaaagcg ccttccctat tcatcagatg     900
tcaatcaatc acgtaaatat cctttatttc taactctctc gccaacacat atatttgtac     960
ctaggcttct ctttatgtc aaaactctaa acaataaaat ctgttgttgt cattcacgct     1020
gcagcaaata gaaggattgt ggatcctgtt ggactcggga atgtagcttg aaggagaga    1080
gttgatggct ggaaaatgaa gcaagagaag aatactggtc ctgtcagcac gcaggctgct    1140
tctgaaagag gtggagtaga tattgatgcc agcacagata tcctagcaga tgaggctctg    1200
ctgtgagttc ttgttttgta atcttgtttg ttctgtcgtg gtgtaccgag cgttttcct    1260
attaagcaat gtcctgatac tcatttccca attctttatt tattgtacag gaatgacgaa    1320
gcgaggcagc ctctgtcaag gaaagtttca attccttcat cacggatcaa tccttacaga    1380
atggttatta tgctgcggct tgttatcctt tgtctcttct tgcattaccg tataacaaac    1440
ccagtgccaa atgcctttgc tctatggctg gtctctgtga tatgtgagat ctggtttgcc    1500
ttatcctgga ttttggatca gttccccaag tggtttcctg tgaaccgtga aacctacctc    1560
gacaggcttg ctttaaggta agttctattt ccccattctt ctgaagcaat tactcaaagg    1620
attgtttgcc tatactgttt cccatttta tttgatcatg gtcaatttt gggacagata    1680
tgatcgtgaa ggtgagccat cacagttagc tgctgttgac attttcgtga gtactgttga    1740
ccccttgaag gagccacccc ttgtgacagc caacacagtg ctctctattc tggctgttga    1800
ctacccagtt gacaaggtgt cctgttatgt ttctgatgat ggtgctgcta tgttatcatt    1860
tgaatcactt gcagaaacat cagagttgc tcgtaaatgg gtaccatttt gcaagaaata    1920
tagcatagag cctcgtgcac cagaatggta ctttgctgcg aaaatagatt acttgaagga    1980
taaagttcag acatcatttg tcaaagatcg tagagctatg aaggtaagtt tgtagtttta    2040
gtcatctagt caccctcact ttgattttag tgtatgctat attgaccttt tatttctttt    2100
cagagggaat atgaggaatt taaaatccga atcaatgcac ttgtttccaa agccctaaaa    2160
tgtcctgaag aagggtgggt tatgcaagat ggcacaccgt ggcctggaaa taatacaagg    2220
gaccatccag gaatgatcca ggtaagaaat tggtttttaac tatggaatcg agaatgctct    2280
ctcttctct ctagaagttc attattgaag taccatttgc tgaatgcagg tcttcttagg    2340
```

```
gcaaaatggt ggacttgatg cagagggcaa tgagctcccg cgtttggtat atgtttctcg    2400
agaaaagcga ccaggattcc agcaccacaa aaaggctggt gctatgaatg cactggtaag    2460
tttctgatct tggattttg acttcttcat tctgaccaat tgttagtct aatctgggta      2520 cttttcaaat gaataggtga gagtttcagc agttcttacc aatggacctt tcatcttgaa    2580
tcttgattgt gatcattaca taaataacag caaagcctta agagaagcaa tgtgcttcct    2640
gatggaccca aacctcggga agcaagtttg ttatgttcag ttcccacaaa gatttgatgg    2700
tatcgataag aacgatagat atgctaatcg taataccgtg ttctttgatg taagtcacac    2760
ttacctatac ttgcgtctaa ttttcttgtt ctttcaaatt gcttttagac acgaatatac    2820
attaaactca cagtttcttg agtttgtcgt aattttttcca tgatatgttt tccagattaa    2880
cttgagaggt ttagatggga ttcaaggacc tgtatatgtc ggaactggat gtgttttcaa    2940
cagaacagca ttatacggtt atgaacctcc aataaaagta aaacacaaga agccaagtct    3000
tttatctaag ctctgtggtg gatcaagaaa gaagaattcc aaagctaaga aagagtcgga    3060
caaaaagaaa tcaggcaggc atactgactc aactgttcct gtattcaacc tcgatgacat    3120
agaagaggga gttgaaggta caactgtttt tatttcttct ttggtttccg ttatacccat    3180
atgttgctgt ttgaaatatt gatccagggg aggggattat ttatagttga cagttgtcta    3240
aatagtttcc atactaggta tctcatcatg tcttaactat ttggcatttg tgaaacttag    3300
gtgctggttt tgatgatgaa aaggcgctct taatgtcgca aatgagcctg agaagcgat     3360 ttggacagtc tgctgttttt gttgcttcta ccctaatgga aaatggtggt gttcctcctt    3420
cagcaactcc agaaaacctt ctcaaagagg ctatccatgt cattagttgt ggttatgagg    3480
ataagtcaga ttggggaatg gaggtataat ctcatttgaa ctcctacatg aatctgcatt    3540
gttctgacat atccactttg gcattcactt tgtttatatt ttccgctgtc tttcttcaga    3600
ttggatggat ctatggttct gtgacagaag atattctgac tgggttcaaa atgcatgccc    3660
gtggatggcg atccatttac tgcatgccta agcttccagc tttcaagggt tctgctccta    3720
tcaatctttc agatcgtctg aaccaagtgc tgaggtgggc tttaggttca gttgagattc    3780
tcttcagtcg gcattgtcct atatggtatg gttacaatgg gaggctaaaa tttcttgaga    3840
ggtttgcgta tgtgaacacc accatctacc ctatcacctc cattcctctt ctcatgtatt    3900
gtacattgcc agccgtttgt ctcttcacca accagtttat tattcctcag gtttgacacc    3960
tctctctgtc tatctatctc tatctctatc tctatctcta gaacaaacct taattacgtt    4020
ctgtttaact gaaaccatgt tgtgtttgtc atctatttac ggttccaaat cctgatcagc    4080
tggttctatt gttcctcttt tgcagattag taacattgca agtatatggt ttctgtctct    4140 cttttctctcc attttcgcca cgggtatact agaaatgagg tggagtggcg taggcataga    4200
cgaatggtgg agaaacgagc agttttgggt cattggtgga gtatccgctc atttattcgc    4260
tgtgtttcaa ggtatcctca aagtccttgc cggtattgac acaaacttca cagttacctc    4320
aaaagcttca gatgaagacg gagactttgc tgagctctac ttgttcaaat ggacaacact    4380
tctgattccg ccaacgacgc tgctcattgt aaacttagtg ggagttgttg caggagtctt    4440
ttatgctatc aacagtggat accaatcatg gggaccactc tttggtaagt tgttctttgc    4500
cttctgggtg attgttcact tgtacccttt cctcaagggt ttgatgggtc gacagaaccg    4560
gactcctacc attgttgtgg tctggtctgt tctcttggct tctatcttct cgttgttgtg    4620
ggttaggatt gatcccttca ctagccgagt cactggcccg gacattctgg aatgtggaat    4680
```
caactgttga                                                              4690

<210> SEQ ID NO 25
<211> LENGTH: 1065
<212> TYPE: PRT
<213> ORGANISM: Arabidopsis thaliana

<400> SEQUENCE: 25

Met Glu Ser Glu Gly Glu Thr Ala Gly Lys Pro Met Lys Asn Ile Val
1               5                   10                  15

Pro Gln Thr Cys Gln Ile Cys Ser Asp Asn Val Gly Lys Thr Val Asp
            20                  25                  30

Gly Asp Arg Phe Val Ala Cys Asp Ile Cys Ser Phe Pro Val Cys Arg
        35                  40                  45

Pro Cys Tyr Glu Tyr Glu Arg Lys Asp Gly Asn Gln Ser Cys Pro Gln
    50                  55                  60

Cys Lys Thr Arg Tyr Lys Arg Leu Lys Gly Ser Pro Ala Ile Pro Gly
65                  70                  75                  80

Asp Lys Asp Glu Asp Gly Leu Ala Asp Glu Gly Thr Val Glu Phe Asn
                85                  90                  95

Tyr Pro Gln Lys Glu Lys Ile Ser Glu Arg Met Leu Gly Trp His Leu
            100                 105                 110

Thr Arg Gly Lys Gly Glu Glu Met Gly Glu Pro Gln Tyr Asp Lys Glu
        115                 120                 125

Val Ser His Asn His Leu Pro Arg Leu Thr Ser Arg Gln Asp Thr Ser
    130                 135                 140

Gly Glu Phe Ser Ala Ala Ser Pro Glu Arg Leu Ser Val Ser Ser Thr
145                 150                 155                 160

Ile Ala Gly Gly Lys Arg Leu Pro Tyr Ser Ser Asp Val Asn Gln Ser
                165                 170                 175

Pro Asn Arg Arg Ile Val Asp Pro Val Gly Leu Gly Asn Val Ala Trp
            180                 185                 190

Lys Glu Arg Val Asp Gly Trp Lys Met Lys Gln Glu Lys Asn Thr Gly
        195                 200                 205

Pro Val Ser Thr Gln Ala Ala Ser Glu Arg Gly Gly Val Asp Ile Asp
    210                 215                 220

Ala Ser Thr Asp Ile Leu Ala Asp Glu Ala Leu Leu Asn Asp Glu Ala
225                 230                 235                 240

Arg Gln Pro Leu Ser Arg Lys Val Ser Ile Pro Ser Ser Arg Ile Asn
                245                 250                 255

Pro Tyr Arg Met Val Ile Met Leu Arg Leu Val Ile Leu Cys Leu Phe
            260                 265                 270

Leu His Tyr Arg Ile Thr Asn Pro Val Pro Asn Ala Phe Ala Leu Trp
        275                 280                 285

Leu Val Ser Val Ile Cys Glu Ile Trp Phe Ala Leu Ser Trp Ile Leu
    290                 295                 300

Asp Gln Phe Pro Lys Trp Phe Pro Val Asn Arg Glu Thr Tyr Leu Asp
305                 310                 315                 320

Arg Leu Ala Leu Arg Tyr Asp Arg Glu Gly Glu Pro Ser Gln Leu Ala
                325                 330                 335

Ala Val Asp Ile Phe Val Ser Thr Val Asp Pro Leu Lys Glu Pro Pro
            340                 345                 350

Leu Val Thr Ala Asn Thr Val Leu Ser Ile Leu Ala Val Asp Tyr Pro
        355                 360                 365

-continued

Val Asp Lys Val Ser Cys Tyr Val Ser Asp Asp Gly Ala Ala Met Leu
370             375                 380

Ser Phe Glu Ser Leu Ala Glu Thr Ser Glu Phe Ala Arg Lys Trp Val
385             390                 395                 400

Pro Phe Cys Lys Lys Tyr Ser Ile Glu Pro Arg Ala Pro Glu Trp Tyr
                405                 410                 415

Phe Ala Ala Lys Ile Asp Tyr Leu Lys Asp Lys Val Gln Thr Ser Phe
            420                 425                 430

Val Lys Asp Arg Arg Ala Met Lys Arg Glu Tyr Glu Glu Phe Lys Ile
        435                 440                 445

Arg Ile Asn Ala Leu Val Ser Lys Ala Leu Lys Cys Pro Glu Glu Gly
    450                 455                 460

Trp Val Met Gln Asp Gly Thr Pro Trp Pro Gly Asn Asn Thr Arg Asp
465                 470                 475                 480

His Pro Gly Met Ile Gln Val Phe Leu Gly Gln Asn Gly Gly Leu Asp
                485                 490                 495

Ala Glu Gly Asn Glu Leu Pro Arg Leu Val Tyr Val Ser Arg Glu Lys
                500                 505                 510

Arg Pro Gly Phe Gln His His Lys Lys Ala Gly Ala Met Asn Ala Leu
            515                 520                 525

Val Arg Val Ser Ala Val Leu Thr Asn Gly Pro Phe Ile Leu Asn Leu
        530                 535                 540

Asp Cys Asp His Tyr Ile Asn Asn Ser Lys Ala Leu Arg Glu Ala Met
545                 550                 555                 560

Cys Phe Leu Met Asp Pro Asn Leu Gly Lys Gln Val Cys Tyr Val Gln
                565                 570                 575

Phe Pro Gln Arg Phe Asp Gly Ile Asp Lys Asn Asp Arg Tyr Ala Asn
            580                 585                 590

Arg Asn Thr Val Phe Phe Asp Ile Asn Leu Arg Gly Leu Asp Gly Ile
        595                 600                 605

Gln Gly Pro Val Tyr Val Gly Thr Gly Cys Val Phe Asn Arg Thr Ala
    610                 615                 620

Leu Tyr Gly Tyr Glu Pro Pro Ile Lys Val Lys His Lys Lys Pro Ser
625                 630                 635                 640

Leu Leu Ser Lys Leu Cys Gly Gly Ser Arg Lys Lys Asn Ser Lys Ala
                645                 650                 655

Lys Lys Glu Ser Asp Lys Lys Ser Gly Arg His Thr Asp Ser Thr
            660                 665                 670

Val Pro Val Phe Asn Leu Asp Asp Ile Glu Glu Gly Val Glu Gly Ala
        675                 680                 685

Gly Phe Asp Asp Glu Lys Ala Leu Leu Met Ser Gln Met Ser Leu Glu
    690                 695                 700

Lys Arg Phe Gly Gln Ser Ala Val Phe Val Ala Ser Thr Leu Met Glu
705                 710                 715                 720

Asn Gly Gly Val Pro Pro Ser Ala Thr Pro Glu Asn Leu Leu Lys Glu
                725                 730                 735

Ala Ile His Val Ile Ser Cys Gly Tyr Glu Asp Lys Ser Asp Trp Gly
            740                 745                 750

Met Glu Ile Gly Trp Ile Tyr Gly Ser Val Thr Glu Asp Ile Leu Thr
        755                 760                 765

Gly Phe Lys Met His Ala Arg Gly Trp Arg Ser Ile Tyr Cys Met Pro
    770                 775                 780

Lys Leu Pro Ala Phe Lys Gly Ser Ala Pro Ile Asn Leu Ser Asp Arg

```
                785                 790                 795                 800
Leu Asn Gln Val Leu Arg Trp Ala Leu Gly Ser Val Glu Ile Leu Phe
                805                 810                 815

Ser Arg His Cys Pro Ile Trp Tyr Gly Tyr Asn Gly Arg Leu Lys Phe
                820                 825                 830

Leu Glu Arg Phe Ala Tyr Val Asn Thr Thr Ile Tyr Pro Ile Thr Ser
                835                 840                 845

Ile Pro Leu Leu Met Tyr Cys Thr Leu Pro Ala Val Cys Leu Phe Thr
            850                 855                 860

Asn Gln Phe Ile Ile Pro Gln Ile Ser Asn Ile Ala Ser Ile Trp Phe
865                 870                 875                 880

Leu Ser Leu Phe Leu Ser Ile Phe Ala Thr Gly Ile Leu Glu Met Arg
                885                 890                 895

Trp Ser Gly Val Gly Ile Asp Glu Trp Trp Arg Asn Glu Gln Phe Trp
                900                 905                 910

Val Ile Gly Gly Val Ser Ala His Leu Phe Ala Val Phe Gln Gly Ile
                915                 920                 925

Leu Lys Val Leu Ala Gly Ile Asp Thr Asn Phe Thr Val Thr Ser Lys
                930                 935                 940

Ala Ser Asp Glu Asp Gly Asp Phe Ala Glu Leu Tyr Leu Phe Lys Trp
945                 950                 955                 960

Thr Thr Leu Leu Ile Pro Pro Thr Thr Leu Leu Ile Val Asn Leu Val
                965                 970                 975

Gly Val Val Ala Gly Val Phe Tyr Ala Ile Asn Ser Gly Tyr Gln Ser
                980                 985                 990

Trp Gly Pro Leu Phe Gly Lys Leu Phe Phe Ala Phe Trp Val Ile Val
                995                 1000                1005

His Leu Tyr Pro Phe Leu Lys Gly Leu Met Gly Arg Gln Asn Arg
                1010                1015                1020

Thr Pro Thr Ile Val Val Val Trp Ser Val Leu Leu Ala Ser Ile
                1025                1030                1035

Phe Ser Leu Leu Trp Val Arg Ile Asp Pro Phe Thr Ser Arg Val
                1040                1045                1050

Thr Gly Pro Asp Ile Leu Glu Cys Gly Ile Asn Cys
                1055                1060                1065

<210> SEQ ID NO 26
<211> LENGTH: 4690
<212> TYPE: DNA
<213> ORGANISM: Arabidopsis thaliana

<400> SEQUENCE: 26
atggaatccg aaggagaaac cgcggtatgc ttttttgact cttgcttcat cattatactt      60
acctttatcg aaatcaggaa ttatatgtac tgaaattgat tgatttgggt gttgaattgt     120
gtattggaga gatctgattt caaattttct gttgaggttt ctaattttgg cttcattgat     180
tcgacttgat ttgtagggaa agccgatgaa gaacattgtt ccgcagactt gccagatctg     240
tagtgacaat gttggcaaga ctgttgatgg agatcgtttt gtggcttgtg atatttgttc     300
attcccagtt tgtcggcctt gctacgagta tgagaggaaa gatgggaatc aatcttgtcc     360
tcagtgcaaa accagataca agaggctcaa aggttctctt tgatccttc tgaagtatac      420 tgtcttcatt gttcatcgat agtttatcag tatgttttga attttggatc agattggtat     480
ttatagcaat ttgctaattt ctgattctag gtagtcctgc tattcctggt gataaagacg     540
```

```
aggatggctt agctgatgaa ggtactgttg agttcaacta ccctcagaag gagaaaattt     600
cagagcggat gcttggttgg catcttactc gtgggaaggg agaggaaatg ggggaacccc     660
agtatgataa agaggtctct cacaatcatc ttcctcgtct cacgagcaga caagatgtaa     720
ggcattgctg ttcattcttc cctcttaagc attcgcatcc tcacgcaatt tagttttgga     780
atctgatttt gtcatttgct tatttacaga cttcaggaga gttttctgct gcctcacctg     840
aacgcctctc tgtatcttct actatcgctg ggggaaagcg ccttccctat tcatcagatg     900
tcaatcaatc acgtaaatat cctttatttc taactctctc gccaacacat atatttgtac     960
ctaggcttct cttttatgtc aaaactctaa acaataaaat ctgttgttgt cattcacgct    1020
gcagcaaata gaaggattgt ggatcctgtt ggactcggga atgtagcttg aaggagaga    1080
gttgatggct ggaaaatgaa gcaagagaag aatactggtc ctgtcagcac gcaggctgct    1140
tctgaaagag gtggagtaga tattgatgcc agcacagata tcctagcaga tgaggctctg    1200
ctgtgagttc ttgttttgta atcttgtttg ttctgtcgtg gtgtaccgag cgttttttcct    1260
attaagcaat gtcctgatac tcattttcca attctttatt tattgtacag gaatgacgaa    1320
gcgaggcagc ctctgtcaag gaaagtttca attccttcat cacggatcaa tccttacaga    1380
atggttatta tgctgcggct tgttatcctt tgtctcttct tgcattaccg tataacaaac    1440
ccagtgccaa atgcctttgc tctatggctg gtctctgtga tatgtgagat ctggtttgcc    1500
ttatcctgga ttttggatca gtttcccaag tggtttcctg tgaaccgtga aacctacctc    1560
gacaggcttg ctttaaggta agttctattt ccccattctt ctgaagcaat tactcaaagg    1620
attgtttgcc tatactgttt cccatttaa tttgatcatg gtcaatttt gggacagata    1680
tgatcgtgaa ggtgagccat cacagttagc tgctgttgac attttcgtga gtactgttga    1740
cccttgaag gagccacccc ttgtgacagc caacacagtg ctctctattc tggctgttga    1800
ctacccagtt gacaaggtgt cctgttatgt ttctgatgat ggtgctgcta tgttatcatt    1860
tgaatcactt gcagaaacat cagagttgc tcgtaaatgg gtaccatttt gcaagaaata    1920
tagcatagag cctcgtgcac cagaatggta ctttgctgcg aaaatagatt acttgaagga    1980
taaagttcag acatcatttg tcaaagatcg tagagctatg aaggtaagtt tgtagtttta    2040
gtcatctagt caccctcact ttgattttag tgtatgctat attgaccttt tattttcttt    2100
cagagggaat atgaggaatt taaaatccga atcaatgcac ttgtttccaa agccctaaaa    2160
tgtcctgaag aagggtgggt tatgcaagat ggcacaccgt ggcctggaaa taatacaagg    2220
gaccatccag gaatgatcca ggtaagaaat tggttttaac tatggaatcg agaatgctct    2280
ctctttctct ctagaagttc attattgaag taccatttgc tgaatgcagg tcttcttagg    2340
gcaaaatggt ggacttgatg cagagggcaa tgagctcccg cgtttggtat atgtttctcg    2400
agaaaagcga ccaggattcc agcaccacaa aaaggctggt gctatgaatg cactggtaag    2460
tttctgatct tggattttg acttcttcat tctgaccaat ttgttagtct aatctgggta    2520
cttttcaaat gaataggtga gagtttcagc agttcttacc aatggacctt tcatcttgaa    2580
tcttgattgt gatcattaca taaataacag caaagcctta agagaagcaa tgtgcttcct    2640
gatggaccca aacctcggga agcaagtttg ttatgttcag ttcccacaaa gatttgatgg    2700
tatcgataag aacgatagat atgctaatcg taataccgtg ttctttgatg taagtcacac    2760
ttacctatac ttgcgtctaa ttttcttgtt ctttcaaatt gctttagac acgaatatac    2820
attaaactca cagtttcttg agtttgtcgt aattttccca tgatatgttt tccagattaa    2880
cttgagaggt ttagatggga ttcaaggacc tgtatatgtc ggaactggat gtgttttcaa    2940
```

-continued

```
cagaacagca ttatacggtt atgaacctcc aataaaagta aaacacaaga agccaagtct     3000
tttatctaag ctctgtggtg gatcaagaaa gaagaattcc aaagctaaga aagagtcgga     3060
caaaaagaaa tcaggcaggc atactgactc aactgttcct gtattcaacc tcgatgacat     3120
agaagaggga gttgaaggta caactgtttt tatttcttct ttggtttccg ttatacccat     3180
atgttgctgt ttgaaatatt gatccagggg aggggattat ttatagttga cagttgtcta     3240
aatagtttcc atactaggta tctcatcatg tcttaactat ttggcatttg tgaaacttag     3300
gtgctggttt tgatgatgaa aaggcgctct taatgtcgca aatgagcctg gagaagcgat     3360
ttggacagtc tgctgttttt gttgcttcta ccctaatgga aaatggtggt gttcctcctt     3420
cagcaactcc agaaaacctt ctcaaagagg ctatccatgt cattagttgt ggttatgagg     3480
ataagtcaga ttggggaatg gaggtataat ctcatttgaa ctcctacatg aatctgcatt     3540
gttctgacat atccactttg gcattcactt tgtttatatt ttccgctgtc tttcttcaga     3600
ttggatggat ctatggttct gtgacagaag atattctgac tgggttcaaa atgcatgccc     3660
gtggatggcg atccatttac tgcatgccta agcttccagc tttcaagggt tctgctccta     3720
tcaatctttc agatcgtctg aaccaagtgc tgaggtgggc tttaggttca gttgagattc     3780
tcttcagtcg gcattgtcct atatggtatg gttacaatgg gaggctaaaa tttcttgaga     3840
ggtttgcgta tgtgaacacc accatctacc ctatcacctc cattcctctt ctcatgtatt     3900
gtacattgcc agccgtttgt ctcttcacca accagtttat tattcctcag gtttgacacc     3960
tctctctgtc tatctatctc tatctctatc tctatctcta gaacaaacct taattacgtt     4020
ctgtttaact gaaaccatgt tgtgtttgtc atctatttac ggttccaaat cctgatcagc     4080
tggttctatt gttcctcttt tgcagattag taacattgca agtatatggt ttctgtctct     4140 cttctctcc attttcgcca cgggtatact agaaatgagg tggagtggcg taggcataga     4200
cgaatggtgg agaaacgagc agttttgggt cattggtgga gtatccgctc atttattcgc     4260
tgtgtttcaa ggtatcctca aagtccttgc cggtattgac acaaacttca cagttacctc     4320
aaaagcttca gatgaagacg gagactttgc tgagctctac ttgttcaaat ggacaacact     4380
tctgattccg ccaacgacgc tgctcattgt aaacttagtg ggagttgttg caggagtctc     4440
ttatgctatc aacagtggat accaatcatg gggaccactc tttagtaagt tgttctttgc     4500
cttctgggtg attgttcact tgtaccctt cctcaagggt ttgatgggtc gacagaaccg     4560
gactcctacc attgttgtgg tctggtctgt tctcttggct tctatcttct cgttgttgtg     4620
ggttaggatt gatcccttca ctagccgagt cactggcccg gacattctgg aatgtggaat     4680
caactgttga                                                            4690
```

<210> SEQ ID NO 27
<211> LENGTH: 1065
<212> TYPE: PRT
<213> ORGANISM: Arabidopsis thaliana

<400> SEQUENCE: 27

Met Glu Ser Glu Gly Glu Thr Ala Gly Lys Pro Met Lys Asn Ile Val
1               5                   10                  15

Pro Gln Thr Cys Gln Ile Cys Ser Asp Asn Val Gly Lys Thr Val Asp
            20                  25                  30

Gly Asp Arg Phe Val Ala Cys Asp Ile Cys Ser Phe Pro Val Cys Arg
        35                  40                  45

Pro Cys Tyr Glu Tyr Glu Arg Lys Asp Gly Asn Gln Ser Cys Pro Gln

-continued

```
                50                  55                  60
Cys Lys Thr Arg Tyr Lys Arg Leu Lys Gly Ser Pro Ala Ile Pro Gly
 65                  70                  75                  80

Asp Lys Asp Glu Asp Gly Leu Ala Asp Glu Gly Thr Val Glu Phe Asn
                 85                  90                  95

Tyr Pro Gln Lys Glu Lys Ile Ser Glu Arg Met Leu Gly Trp His Leu
                100                 105                 110

Thr Arg Gly Lys Gly Glu Glu Met Gly Glu Pro Gln Tyr Asp Lys Glu
                115                 120                 125

Val Ser His Asn His Leu Pro Arg Leu Thr Ser Arg Gln Asp Thr Ser
130                 135                 140

Gly Glu Phe Ser Ala Ala Ser Pro Glu Arg Leu Ser Val Ser Ser Thr
145                 150                 155                 160

Ile Ala Gly Gly Lys Arg Leu Pro Tyr Ser Ser Asp Val Asn Gln Ser
                165                 170                 175

Pro Asn Arg Arg Ile Val Asp Pro Val Gly Leu Gly Asn Val Ala Trp
                180                 185                 190

Lys Glu Arg Val Asp Gly Trp Lys Met Lys Gln Glu Lys Asn Thr Gly
                195                 200                 205

Pro Val Ser Thr Gln Ala Ala Ser Glu Arg Gly Gly Val Asp Ile Asp
210                 215                 220

Ala Ser Thr Asp Ile Leu Ala Asp Glu Ala Leu Leu Asn Asp Glu Ala
225                 230                 235                 240

Arg Gln Pro Leu Ser Arg Lys Val Ser Ile Pro Ser Arg Ile Asn
                245                 250                 255

Pro Tyr Arg Met Val Ile Met Leu Arg Leu Val Ile Leu Cys Leu Phe
                260                 265                 270

Leu His Tyr Arg Ile Thr Asn Pro Val Pro Asn Ala Phe Ala Leu Trp
                275                 280                 285

Leu Val Ser Val Ile Cys Glu Ile Trp Phe Ala Leu Ser Trp Ile Leu
                290                 295                 300

Asp Gln Phe Pro Lys Trp Phe Pro Val Asn Arg Glu Thr Tyr Leu Asp
305                 310                 315                 320

Arg Leu Ala Leu Arg Tyr Asp Arg Glu Gly Glu Pro Ser Gln Leu Ala
                325                 330                 335

Ala Val Asp Ile Phe Val Ser Thr Val Asp Pro Leu Lys Glu Pro Pro
                340                 345                 350

Leu Val Thr Ala Asn Thr Val Leu Ser Ile Leu Ala Val Asp Tyr Pro
                355                 360                 365

Val Asp Lys Val Ser Cys Tyr Val Ser Asp Asp Gly Ala Ala Met Leu
370                 375                 380

Ser Phe Glu Ser Leu Ala Glu Thr Ser Glu Phe Ala Arg Lys Trp Val
385                 390                 395                 400

Pro Phe Cys Lys Lys Tyr Ser Ile Glu Pro Arg Ala Pro Glu Trp Tyr
                405                 410                 415

Phe Ala Ala Lys Ile Asp Tyr Leu Lys Asp Lys Val Gln Thr Ser Phe
                420                 425                 430

Val Lys Asp Arg Arg Ala Met Lys Arg Glu Tyr Glu Glu Phe Lys Ile
                435                 440                 445

Arg Ile Asn Ala Leu Val Ser Lys Ala Leu Lys Cys Pro Glu Glu Gly
                450                 455                 460

Trp Val Met Gln Asp Gly Thr Pro Trp Pro Gly Asn Asn Thr Arg Asp
465                 470                 475                 480
```

-continued

His Pro Gly Met Ile Gln Val Phe Leu Gly Gln Asn Gly Gly Leu Asp
              485                 490                 495

Ala Glu Gly Asn Glu Leu Pro Arg Leu Val Tyr Val Ser Arg Glu Lys
          500                 505                 510

Arg Pro Gly Phe Gln His His Lys Lys Ala Gly Ala Met Asn Ala Leu
      515                 520                 525

Val Arg Val Ser Ala Val Leu Thr Asn Gly Pro Phe Ile Leu Asn Leu
  530                 535                 540

Asp Cys Asp His Tyr Ile Asn Asn Ser Lys Ala Leu Arg Glu Ala Met
545                 550                 555                 560

Cys Phe Leu Met Asp Pro Asn Leu Gly Lys Gln Val Cys Tyr Val Gln
              565                 570                 575

Phe Pro Gln Arg Phe Asp Gly Ile Asp Lys Asn Asp Arg Tyr Ala Asn
          580                 585                 590

Arg Asn Thr Val Phe Phe Asp Ile Asn Leu Arg Gly Leu Asp Gly Ile
      595                 600                 605

Gln Gly Pro Val Tyr Val Gly Thr Gly Cys Val Phe Asn Arg Thr Ala
  610                 615                 620

Leu Tyr Gly Tyr Glu Pro Pro Ile Lys Val Lys His Lys Lys Pro Ser
625                 630                 635                 640

Leu Leu Ser Lys Leu Cys Gly Gly Ser Arg Lys Lys Asn Ser Lys Ala
              645                 650                 655

Lys Lys Glu Ser Asp Lys Lys Ser Gly Arg His Thr Asp Ser Thr
          660                 665                 670

Val Pro Val Phe Asn Leu Asp Asp Ile Glu Glu Gly Val Glu Gly Ala
      675                 680                 685

Gly Phe Asp Asp Glu Lys Ala Leu Leu Met Ser Gln Met Ser Leu Glu
  690                 695                 700

Lys Arg Phe Gly Gln Ser Ala Val Phe Val Ala Ser Thr Leu Met Glu
705                 710                 715                 720

Asn Gly Gly Val Pro Pro Ser Ala Thr Pro Glu Asn Leu Leu Lys Glu
              725                 730                 735

Ala Ile His Val Ile Ser Cys Gly Tyr Glu Asp Lys Ser Asp Trp Gly
          740                 745                 750

Met Glu Ile Gly Trp Ile Tyr Gly Ser Val Thr Glu Asp Ile Leu Thr
      755                 760                 765

Gly Phe Lys Met His Ala Arg Gly Trp Arg Ser Ile Tyr Cys Met Pro
  770                 775                 780

Lys Leu Pro Ala Phe Lys Gly Ser Ala Pro Ile Asn Leu Ser Asp Arg
785                 790                 795                 800

Leu Asn Gln Val Leu Arg Trp Ala Leu Gly Ser Val Glu Ile Leu Phe
              805                 810                 815

Ser Arg His Cys Pro Ile Trp Tyr Gly Tyr Asn Gly Arg Leu Lys Phe
          820                 825                 830

Leu Glu Arg Phe Ala Tyr Val Asn Thr Thr Ile Tyr Pro Ile Thr Ser
      835                 840                 845

Ile Pro Leu Leu Met Tyr Cys Thr Leu Pro Ala Val Cys Leu Phe Thr
850                 855                 860

Asn Gln Phe Ile Ile Pro Gln Ile Ser Asn Ile Ala Ser Ile Trp Phe
              870                 875                 880

Leu Ser Leu Phe Leu Ser Ile Phe Ala Thr Gly Ile Leu Glu Met Arg
          885                 890                 895

```
Trp Ser Gly Val Gly Ile Asp Glu Trp Trp Arg Asn Glu Gln Phe Trp
            900                 905                 910

Val Ile Gly Gly Val Ser Ala His Leu Phe Ala Val Phe Gln Gly Ile
        915                 920                 925

Leu Lys Val Leu Ala Gly Ile Asp Thr Asn Phe Thr Val Thr Ser Lys
    930                 935                 940

Ala Ser Asp Glu Asp Gly Asp Phe Ala Glu Leu Tyr Leu Phe Lys Trp
945                 950                 955                 960

Thr Thr Leu Leu Ile Pro Pro Thr Thr Leu Leu Ile Val Asn Leu Val
                965                 970                 975

Gly Val Val Ala Gly Val Ser Tyr Ala Ile Asn Ser Gly Tyr Gln Ser
            980                 985                 990

Trp Gly Pro Leu Phe Ser Lys Leu Phe Phe Ala Phe Trp Val Ile Val
        995                 1000                1005

His Leu Tyr Pro Phe Leu Lys Gly Leu Met Gly Arg Gln Asn Arg
    1010                1015                1020

Thr Pro Thr Ile Val Val Val Trp Ser Val Leu Leu Ala Ser Ile
    1025                1030                1035

Phe Ser Leu Leu Trp Val Arg Ile Asp Pro Phe Thr Ser Arg Val
    1040                1045                1050

Thr Gly Pro Asp Ile Leu Glu Cys Gly Ile Asn Cys
    1055                1060                1065

<210> SEQ ID NO 28
<211> LENGTH: 4690
<212> TYPE: DNA
<213> ORGANISM: Arabidopsis thaliana

<400> SEQUENCE: 28
atggaatccg aaggagaaac cgcggtatgc ttttttgact cttgcttcat cattatactt    60
acctttatcg aaatcaggaa ttatatgtac tgaaattgat tgatttgggt gttgaattgt   120
gtattggaga gatctgattt caaatttttct gttgaggttt ctaattttgg cttcattgat   180
tcgacttgat ttgtagggaa agccgatgaa gaacattgtt ccgcagactt gccagatctg   240
tagtgacaat gttggcaaga ctgttgatgg agatcgtttt gtggcttgtg atatttgttc   300
attcccagtt tgtcggcctt gctacgagta tgagaggaaa gatgggaatc aatcttgtcc   360
tcagtgcaaa accagataca agaggctcaa aggttctctt tgatccttc tgaagtatac    420 tgtcttcatt gttcatcgat agtttatcag tatgttttga attttggatc agattggtat   480
ttatagcaat ttgctaattt ctgattctag gtagtcctgc tattcctggt gataaagacg   540
aggatggctt agctgatgaa ggtactgttg agttcaacta ccctcagaag gagaaaattt   600
cagagcggat gcttggttgg catcttactc gtgggaaggg agaggaaatg ggggaacccc   660
agtatgataa agaggtctct cacaatcatc ttcctcgtct cacgagcaga caagatgtaa   720
ggcattgctt tcattcttc cctcttaagc attcgcatcc tcacgcaatt tagttttgga    780
atctgatttt gtcatttgct tatttacaga cttcaggaga gttttctgct gcctcacctg   840
aacgcctctc tgtatcttct actatcgctg ggggaaagcg ccttccctat tcatcagatg   900
tcaatcaatc acgtaaatat cctttatttc taactctctc gccaacacat atatttgtac   960
ctaggcttct ctttatgtc aaaactctaa acaataaaat ctgttgttgt cattcacgct   1020
gcagcaaata gaaggattgt ggatcctgtt ggactcggga atgtagcttg aaggagaga   1080 gttgatggct ggaaaatgaa gcaagagaag aatactggtc ctgtcagcac gcaggctgct  1140
```

```
tctgaaagag gtggagtaga tattgatgcc agcacagata tcctagcaga tgaggctctg    1200
ctgtgagttc ttgttttgta atcttgtttg ttctgtcgtg gtgtaccgag cgttttcct     1260 attaagcaat gtcctgatac tcattttcca attctttatt tattgtacag gaatgacgaa    1320
gcgaggcagc ctcgtcaag gaaagtttca attccttcat cacggatcaa tccttacaga     1380
atggttatta tgctgcggct tgttatcctt tgtctcttct tgcattaccg tataacaaac    1440
ccagtgccaa atgcctttgc tctatggctg gtctctgtga tatgtgagat ctggtttgcc    1500
ttatcctgga ttttggatca gtttcccaag tggtttcctg tgaaccgtga aacctacctc    1560
gacaggcttg ctttaaggta agttctattt ccccattctt ctgaagcaat tactcaaagg    1620
attgtttgcc tatactgttt cccattttaa tttgatcatg gtcaattttt gggacagata    1680
tgatcgtgaa ggtgagccat cacagttagc tgctgttgac attttcgtga gtactgttga    1740 cccccttgaag gagccacccc ttgtgacagc caacacagtg ctctctattc tggctgttga    1800
ctacccagtt gacaaggtgt cctgttatgt ttctgatgat ggtgctgcta tgttatcatt    1860
tgaatcactt gcagaaacat cagagtttgc tcgtaaatgg gtaccatttt gcaagaaata    1920
tagcatagag cctcgtgcac cagaatggta ctttgctgcg aaaatagatt acttgaagga    1980
taaagttcag acatcatttg tcaaagatcg tagagctatg aaggtaagtt tgtagtttta    2040
gtcatctagt caccctcact ttgatttttag tgtatgctat attgaccttt tattttcttt    2100
cagagggaat atgaggaatt taaaatccga atcaatgcac ttgtttccaa agccctaaaa    2160
tgtcctgaag aagggtgggt tatgcaagat ggcacaccgt ggcctggaaa taatacaagg    2220
gaccatccag gaatgatcca ggtaagaaat tggttttaac tatggaatcg agaatgctct    2280
ctctttctct ctagaagttc attattgaag taccatttgc tgaatgcagg tcttcttagg    2340
gcaaaatggt ggacttgatg cagagggcaa tgagctcccg cgtttggtat atgtttctcg    2400
agaaaagcga ccaggattcc agcaccacaa aaaggctggt gctatgaatg cactggtaag    2460
tttctgatct tggattttgg acttcttcat tctgaccaat tgttagtct aatctgggta     2520 cttttcaaat gaataggtga gagtttcagc agttcttacc aatggacctt tcatcttgaa    2580
tcttgattgt gatcattaca taaataacag caaagcctta agagaagcaa tgtgcttcct    2640
gatggaccca aacctcggga agcaagtttg ttatgttcag ttcccacaaa gatttgatgg    2700
tatcgataag aacgatagat atgctaatcg taataccgtg ttctttgatg taagtcacac    2760
ttacctatac ttgcgtctaa ttttcttgtt ctttcaaatt gcttttagac acgaatatac    2820
attaaactca cagtttcttg agtttgtcgt aattttttcca tgtatatgttt tccagattaa    2880 cttgagaggt ttagatggga ttcaaggacc tgtatatgtc ggaactggat gtgttttcaa    2940
cagaacagca ttatacggtt atgaacctcc aataaaagta aaacacaaga agccaagtct    3000
tttatctaag ctctgtggtg gatcaagaaa gaagaattcc aaagctaaga aagagtcgga    3060
caaaaagaaa tcaggcaggc atactgactc aactgttcct gtattcaacc tcgatgacat    3120
agaagaggga gttgaaggta caactgttttt tatttcttct ttggtttccg ttataccat     3180 atgttgctgt ttgaaatatt gatccagggg aggggattat ttatagttga cagttgtcta    3240
aatagtttcc atactaggta tctcatcatg tcttaactat ttggcatttg tgaaacttag    3300
gtgctggttt tgatgatgaa aaggcgctct taatgtcgca aatgagcctg gagaagcgat    3360
ttggacagtc tgctgttttt gttgcttcta ccctaatgga aaatggtggt gttcctcctt    3420
cagcaactcc agaaaacctt ctcaaagagg ctatccatgt cattagttgt ggttatgagg    3480
ataagtcaga ttggggaatg gaggtataat ctcatttgaa ctcctacatg aatctgcatt    3540
```

-continued

```
gttctgacat atccactttg gcattcactt tgtttatatt ttccgctgtc tttcttcaga    3600
ttggatggat ctatggttct gtgacagaag atattctgac tgggttcaaa atgcatgccc    3660
gtggatggcg atccatttac tgcatgccta agcttccagc tttcaagggt tctgctccta    3720
tcaatctttc agatcgtctg aaccaagtgc tgaagtgggc tttaggttca gttgagattc    3780
tcttcagtcg gcattgtcct atatggtatg gttacaatgg gaggctaaaa tttcttgaga    3840
ggtttgcgta tgtgaacacc accatctacc ctatcacctc cattcctctt ctcatgtatt    3900
gtacattgcc agccgtttgt ctcttcacca accagtttat tattcctcag gtttgacacc    3960
tctctctgtc tatctatctc tatctctatc tctatctcta gaacaaacct taattacgtt    4020
ctgtttaact gaaaccatgt tgtgtttgtc atctatttac ggttccaaat cctgatcagc    4080
tggttctatt gttcctcttt tgcagattag taacattgca agtatatggt ttctgtctct    4140
ctttctctcc attttcgcca cgggtatact agaaatgagg tggagtggcg taggcataga    4200
cgaatggtgg agaaacgagc agttttgggt cattggtgga gtatccgctc atttattcgc    4260
tgtgtttcaa ggtatcctca aagtccttgc cggtattgac acaaacttca cagttacctc    4320
aaaagcttca gatgaagacg gagactttgc tgagctctac ttgttcaaat ggacaacact    4380
tctgattccg ccaacgacgc tgctcattgt aaacttagtg ggagttgttg caggagtctc    4440
ttatgctatc aacagtggat accaatcatg gggaccactc tttggtaagt tgttctttgc    4500
cttctgggtg attgttcact gtacccttt cctcaagggt ttgatgggtc gacagaaccg    4560
gactcctacc attgttgtgg tctggtctgt tctcttggct tctatcttct cgttgttgtg    4620
ggttaggatt gatcccttca ctagccgagt cactggcccg gacattctgg aatgtggaat    4680
caactgttga                                                           4690
```

```
<210> SEQ ID NO 29
<211> LENGTH: 1065
<212> TYPE: PRT
<213> ORGANISM: Arabidopsis thaliana

<400> SEQUENCE: 29

Met Glu Ser Glu Gly Glu Thr Ala Gly Lys Pro Met Lys Asn Ile Val
1               5                   10                  15

Pro Gln Thr Cys Gln Ile Cys Ser Asp Asn Val Gly Lys Thr Val Asp
            20                  25                  30

Gly Asp Arg Phe Val Ala Cys Asp Ile Cys Ser Phe Pro Val Cys Arg
        35                  40                  45

Pro Cys Tyr Glu Tyr Glu Arg Lys Asp Gly Asn Gln Ser Cys Pro Gln
    50                  55                  60

Cys Lys Thr Arg Tyr Lys Arg Leu Lys Gly Ser Pro Ala Ile Pro Gly
65                  70                  75                  80

Asp Lys Asp Glu Asp Gly Leu Ala Asp Glu Gly Thr Val Glu Phe Asn
                85                  90                  95

Tyr Pro Gln Lys Glu Lys Ile Ser Glu Arg Met Leu Gly Trp His Leu
            100                 105                 110

Thr Arg Gly Lys Gly Glu Glu Met Gly Glu Pro Gln Tyr Asp Lys Glu
        115                 120                 125

Val Ser His Asn His Leu Pro Arg Leu Thr Ser Arg Gln Asp Thr Ser
    130                 135                 140

Gly Glu Phe Ser Ala Ala Ser Pro Glu Arg Leu Ser Val Ser Ser Thr
145                 150                 155                 160
```

```
Ile Ala Gly Gly Lys Arg Leu Pro Tyr Ser Ser Asp Val Asn Gln Ser
                165                 170                 175

Pro Asn Arg Arg Ile Val Asp Pro Val Gly Leu Gly Asn Val Ala Trp
            180                 185                 190

Lys Glu Arg Val Asp Gly Trp Lys Met Lys Gln Glu Lys Asn Thr Gly
        195                 200                 205

Pro Val Ser Thr Gln Ala Ala Ser Glu Arg Gly Gly Val Asp Ile Asp
    210                 215                 220

Ala Ser Thr Asp Ile Leu Ala Asp Glu Ala Leu Leu Asn Asp Glu Ala
225                 230                 235                 240

Arg Gln Pro Leu Ser Arg Lys Val Ser Ile Pro Ser Ser Arg Ile Asn
                245                 250                 255

Pro Tyr Arg Met Val Ile Met Leu Arg Leu Val Ile Leu Cys Leu Phe
            260                 265                 270

Leu His Tyr Arg Ile Thr Asn Pro Val Pro Asn Ala Phe Ala Leu Trp
        275                 280                 285

Leu Val Ser Val Ile Cys Glu Ile Trp Phe Ala Leu Ser Trp Ile Leu
    290                 295                 300

Asp Gln Phe Pro Lys Trp Phe Pro Val Asn Arg Glu Thr Tyr Leu Asp
305                 310                 315                 320

Arg Leu Ala Leu Arg Tyr Asp Arg Glu Gly Glu Pro Ser Gln Leu Ala
                325                 330                 335

Ala Val Asp Ile Phe Val Ser Thr Val Asp Pro Leu Lys Glu Pro Pro
            340                 345                 350

Leu Val Thr Ala Asn Thr Val Leu Ser Ile Leu Ala Val Asp Tyr Pro
        355                 360                 365

Val Asp Lys Val Ser Cys Tyr Val Ser Asp Asp Gly Ala Ala Met Leu
    370                 375                 380

Ser Phe Glu Ser Leu Ala Glu Thr Ser Glu Phe Ala Arg Lys Trp Val
385                 390                 395                 400

Pro Phe Cys Lys Lys Tyr Ser Ile Glu Pro Arg Ala Pro Glu Trp Tyr
                405                 410                 415

Phe Ala Ala Lys Ile Asp Tyr Leu Lys Asp Lys Val Gln Thr Ser Phe
            420                 425                 430

Val Lys Asp Arg Arg Ala Met Lys Arg Glu Tyr Glu Glu Phe Lys Ile
        435                 440                 445

Arg Ile Asn Ala Leu Val Ser Lys Ala Leu Lys Cys Pro Glu Glu Gly
    450                 455                 460

Trp Val Met Gln Asp Gly Thr Pro Trp Pro Gly Asn Asn Thr Arg Asp
465                 470                 475                 480

His Pro Gly Met Ile Gln Val Phe Leu Gly Gln Asn Gly Gly Leu Asp
                485                 490                 495

Ala Glu Gly Asn Glu Leu Pro Arg Leu Val Tyr Val Ser Arg Glu Lys
            500                 505                 510

Arg Pro Gly Phe Gln His His Lys Lys Ala Gly Ala Met Asn Ala Leu
        515                 520                 525

Val Arg Val Ser Ala Val Leu Thr Asn Gly Pro Phe Ile Leu Asn Leu
    530                 535                 540

Asp Cys Asp His Tyr Ile Asn Asn Ser Lys Ala Leu Arg Glu Ala Met
545                 550                 555                 560

Cys Phe Leu Met Asp Pro Asn Leu Gly Lys Gln Val Cys Tyr Val Gln
                565                 570                 575

Phe Pro Gln Arg Phe Asp Gly Ile Asp Lys Asn Asp Arg Tyr Ala Asn
```

```
            580             585             590
Arg Asn Thr Val Phe Asp Ile Asn Leu Arg Gly Leu Asp Gly Ile
            595             600             605

Gln Gly Pro Val Tyr Val Gly Thr Gly Cys Val Phe Asn Arg Thr Ala
610             615             620

Leu Tyr Gly Tyr Glu Pro Pro Ile Lys Val Lys His Lys Lys Pro Ser
625             630             635             640

Leu Leu Ser Lys Leu Cys Gly Gly Ser Arg Lys Lys Asn Ser Lys Ala
            645             650             655

Lys Lys Glu Ser Asp Lys Lys Ser Gly Arg His Thr Asp Ser Thr
            660             665             670

Val Pro Val Phe Asn Leu Asp Asp Ile Glu Glu Gly Val Glu Gly Ala
            675             680             685

Gly Phe Asp Asp Glu Lys Ala Leu Leu Met Ser Gln Met Ser Leu Glu
            690             695             700

Lys Arg Phe Gly Gln Ser Ala Val Phe Val Ala Ser Thr Leu Met Glu
705             710             715             720

Asn Gly Gly Val Pro Pro Ser Ala Thr Pro Glu Asn Leu Leu Lys Glu
            725             730             735

Ala Ile His Val Ile Ser Cys Gly Tyr Glu Asp Lys Ser Asp Trp Gly
            740             745             750

Met Glu Ile Gly Trp Ile Tyr Gly Ser Val Thr Glu Asp Ile Leu Thr
            755             760             765

Gly Phe Lys Met His Ala Arg Gly Trp Arg Ser Ile Tyr Cys Met Pro
            770             775             780

Lys Leu Pro Ala Phe Lys Gly Ser Ala Pro Ile Asn Leu Ser Asp Arg
785             790             795             800

Leu Asn Gln Val Leu Lys Trp Ala Leu Gly Ser Val Glu Ile Leu Phe
            805             810             815

Ser Arg His Cys Pro Ile Trp Tyr Gly Tyr Asn Gly Arg Leu Lys Phe
            820             825             830

Leu Glu Arg Phe Ala Tyr Val Asn Thr Thr Ile Tyr Pro Ile Thr Ser
            835             840             845

Ile Pro Leu Leu Met Tyr Cys Thr Leu Pro Ala Val Cys Leu Phe Thr
850             855             860

Asn Gln Phe Ile Ile Pro Gln Ile Ser Asn Ile Ala Ser Ile Trp Phe
865             870             875             880

Leu Ser Leu Phe Leu Ser Ile Phe Ala Thr Gly Ile Leu Glu Met Arg
            885             890             895

Trp Ser Gly Val Gly Ile Asp Glu Trp Trp Arg Asn Glu Gln Phe Trp
            900             905             910

Val Ile Gly Gly Val Ser Ala His Leu Phe Ala Val Phe Gln Gly Ile
            915             920             925

Leu Lys Val Leu Ala Gly Ile Asp Thr Asn Phe Thr Val Thr Ser Lys
            930             935             940

Ala Ser Asp Glu Asp Gly Asp Phe Ala Glu Leu Tyr Leu Phe Lys Trp
945             950             955             960

Thr Thr Leu Leu Ile Pro Pro Thr Thr Leu Leu Ile Val Asn Leu Val
            965             970             975

Gly Val Val Ala Gly Val Ser Tyr Ala Ile Asn Ser Gly Tyr Gln Ser
            980             985             990

Trp Gly Pro Leu Phe Gly Lys Leu  Phe Phe Ala Phe Trp  Val Ile Val
            995             1000            1005
```

| His | Leu | Tyr | Pro | Phe | Leu | Lys | Gly | Leu | Met | Gly | Arg | Gln | Asn | Arg |
| | 1010 | | | | 1015 | | | | 1020 | | | | | |

| Thr | Pro | Thr | Ile | Val | Val | Val | Trp | Ser | Val | Leu | Leu | Ala | Ser | Ile |
| | 1025 | | | | 1030 | | | | 1035 | | | | | |

| Phe | Ser | Leu | Leu | Trp | Val | Arg | Ile | Asp | Pro | Phe | Thr | Ser | Arg | Val |
| | 1040 | | | | 1045 | | | | 1050 | | | | | |

| Thr | Gly | Pro | Asp | Ile | Leu | Glu | Cys | Gly | Ile | Asn | Cys |
| | 1055 | | | | 1060 | | | | 1065 | | |

<210> SEQ ID NO 30
<211> LENGTH: 4690
<212> TYPE: DNA
<213> ORGANISM: Arabidopsis thaliana

<400> SEQUENCE: 30

| | |
|---|---|
| atggaatccg aaggagaaac cgcggtatgc tttttttgact cttgcttcat cattatactt | 60 |
| acctttatcg aaatcaggaa ttatatgtac tgaaattgat tgatttgggt gttgaattgt | 120 |
| gtattggaga gatctgattt caaattttct gttgaggttt ctaattttgg cttcattgat | 180 |
| tcgacttgat ttgtagggaa agccgatgaa gaacattgtt ccgcagactt gccagatctg | 240 |
| tagtgacaat gttggcaaga ctgttgatgg agatcgtttt gtggcttgtg atatttgttc | 300 |
| attcccagtt tgtcggcctt gctacgagta tgagaggaaa gatgggaatc aatcttgtcc | 360 |
| tcagtgcaaa accagataca agaggctcaa aggttctctt tgatccttc tgaagtatac | 420 |
| tgtcttcatt gttcatcgat agtttatcag tatgttttga attttggatc agattggtat | 480 |
| ttatagcaat ttgctaattt ctgattctag gtagtcctgc tattcctggt gataaagacg | 540 |
| aggatggctt agctgatgaa ggtactgttg agttcaacta ccctcagaag gagaaaattt | 600 |
| cagagcggat gcttggttgg catcttactc gtgggaaggg agaggaaatg ggggaacccc | 660 |
| agtatgataa agaggtctct cacaatcatc ttcctcgtct cacgagcaga caagatgtaa | 720 |
| ggcattgctg ttcattcttc cctcttaagc attcgcatcc tcacgcaatt tagttttgga | 780 |
| atctgatttt gtcatttgct tatttacaga cttcaggaga gttttctgct gcctcacctg | 840 |
| aacgcctctc tgtatcttct actatcgctg ggggaaagcg ccttccctat tcatcagatg | 900 |
| tcaatcaatc acgtaaatat cctttatttc taactctctc gccaacacat atatttgtac | 960 |
| ctaggcttct cttttatgtc aaaactctaa acaataaaat ctgttgttgt cattcacgct | 1020 |
| gcagcaaata gaaggattgt ggatcctgtt ggactcggga atgtagcttg aaggagaga | 1080 |
| gttgatggct ggaaaatgaa gcaagagaag aatactggtc ctgtcagcac gcaggctgct | 1140 |
| tctgaaagag gtggagtaga tattgatgcc agcacagata tcctagcaga tgaggctctg | 1200 |
| ctgtgagttc ttgttttgta atcttgtttg ttctgtcgtg gtgtaccgag cgttttttcct | 1260 |
| attaagcaat gtcctgatac tcattttcca attctttatt tattgtacag gaatgacgaa | 1320 |
| gcgaggcagc ctctgtcaag gaaagtttca attccttcat cacggatcaa tccttacaga | 1380 |
| atggttatta tgctgcggct tgttatcctt tgtctcttct tgcattaccg tataacaaac | 1440 |
| ccagtgccaa atgcctttgc tctatggctg gtctctgtga tatgtgagat ctggtttgcc | 1500 |
| ttatcctgga ttttgatca gtttcccaag tggtttcctg tgaaccgtga aacctaccctc | 1560 |
| gacaggcttg ctttaaggta agttctattt ccccattctt ctgaagcaat tactcaaagg | 1620 |
| attgtttgcc tatactgttt cccatttaa tttgatcatg tcaatttttt gggacagata | 1680 |
| tgatcgtgaa ggtgagccat cacagttagc tgctgttgac attttcgtga gtactgttga | 1740 |

```
ccccttgaag gagccacccc ttgtgacagc aacacagtg ctctctattc tggctgttga      1800
ctacccagtt gacaaggtgt cctgttatgt ttctgatgat ggtgctgcta tgttatcatt      1860
tgaatcactt gcagaaacat cagagtttgc tcgtaaatgg gtaccatttt gcaagaaata     1920
tagcatagag cctcgtgcac cagaatggta ctttgctgcg aaaatagatt acttgaagga      1980
taaagttcag acatcatttg tcaaagatcg tagagctatg aaggtaagtt tgtagtttta      2040
gtcatctagt caccctcact ttgattttag tgtatgctat attgaccttt tatttttctt      2100
cagagggaat atgaggaatt taaaatccga atcaatgcac ttgtttccaa agccctaaaa     2160
tgtcctgaag aagggtgggt tatgcaagat ggcacaccgt ggcctggaaa taatacaagg      2220
gaccatccag gaatgatcca ggtaagaaat tggttttaac tatggaatcg agaatgctct      2280
ctctttctct ctagaagttc attattgaag taccatttgc tgaatgcagg tcttcttagg      2340
gcaaaatggt ggacttgatg cagagggcaa tgagctcccg cgtttggtat atgtttctcg      2400
agaaaagcga ccaggattcc agcaccacaa aaaggctggt gctatgaatg cactggtaag      2460
tttctgatct tggatttttg acttcttcat tctgaccaat ttgttagtct aatctgggta      2520
cttttcaaat gaataggtga gagtttcagc agttcttacc aatggaccttt tcatcttgaa     2580
tcttgattgt gatcattaca taaataacag caaagcctta agagaagcaa tgtgcttcct      2640
gatggaccca aacctcggga agcaagtttg ttatgttcag ttcccacaaa gatttgatgg      2700
tatcgataag aacgatagat atgctaatcg taataccgtg ttctttgatg taagtcacac      2760
ttacctatac ttgcgtctaa ttttcttgtt ctttcaaatt gcttttagac acgaatatac      2820
attaaactca cagtttcttg agtttgtcgt aattttttcca tgatatgttt tccagattaa      2880
cttgagaggt ttagatggga ttcaaggacc tgtatatgtc ggaactggat gtgttttcaa      2940
cagaacagca ttatacggtt atgaacctcc aataaaagta aaacacaaga agccaagtct      3000
tttatctaag ctctgtggtg gatcaagaaa gaagaattcc aaagctaaga aagagtcgga      3060
caaaaagaaa tcaggcaggc atactgactc aactgttcct gtattcaacc tcgatgacat      3120
agaagaggga gttgaaggta caactgtttt tatttcttct ttggtttccg ttatacccat      3180
atgttgctgt ttgaaatatt gatccagggg agggggattat ttatagttga cagttgtcta      3240
aatagtttcc atactaggta tctcatcatg tcttaactat ttggcatttg tgaaacttag      3300
gtgctggttt tgatgatgaa aaggcgctct taatgtcgca aatgagcctg gagaagcgat      3360
ttggacagtc tgctgttttt gttgcttcta ccctaatgga aaatggtggt gttcctcctt      3420
cagcaactcc agaaaacctt ctcaaagagg ctatccatgt cattagttgt ggttatgagg      3480
ataagtcaga ttggggaatg gaggtataat ctcatttgaa ctcctacatg aatctgcatt      3540
gttctgacat atccactttg gcattcactt tgtttatatt ttccgctgtc tttcttcaga      3600
ttggatggat ctatggttct gtgacagaag atattctgac tgggttcaaa atgcatgccc      3660
gtggatggcg atccatttac tgcatgccta agcttccagc tttcaagggt tctgctccta      3720
tcaattttc agatcgtctg aaccaagtgc tgaggtgggc tttaggttca gttgagattc      3780
tcttcagtcg gcattgtcct atatggtatg ttacaatgg gaggctaaaa tttcttgaga      3840
ggtttgcgta tgtgaacacc accatctacc ctatcacctc cattcctctt ctcatgtatt      3900
gtacattgcc agccgtttgt ctcttcacca accagtttat tattcctcag gtttgacacc      3960
tctctctgtc tatctatctc tatctctatc tctatctcta gaacaaacct taattacgtt      4020
ctgtttaact gaaaccatgt tgtgtttgtc atctatttac ggttccaaat cctgatcagc      4080
tggttctatt gttcctcttt tgcagattag taacattgca agtatatggt ttctgtctct      4140
```

```
ctttctctcc attttcgcca cgggtatact agaaatgagg tggagtggcg taggcataga    4200
cgaatggtgg agaaacgagc agttttgggt cattggtgga gtatccgctc atttattcgc    4260
tgtgtttcaa ggtatcctca aagtccttgc cggtattgac acaaacttca cagttacctc    4320
aaaagcttca gatgaagacg gagactttgc tgagctctac ttgttcaaat ggacaacact    4380
tctgattccg ccaacgacgc tgctcattgt aaacttagtg ggagttgttg caggagtctc    4440
ttatgctatc aacagtggat accaatcatg gggaccactc tttggtaagt tgttctttgc    4500
cttctgggtg attgttcact tgtacccttt cctcaagggt ttgatgggtc gacagaaccg    4560
gactcctacc attgttgtgg tctggtctgt tctcttggct tctatcttct cgttgttgtg    4620
ggttaggatt gatcccttca ctagccgagt cactggcccg gacattctgg aatgtggaat    4680
caactgttga                                                           4690
```

<210> SEQ ID NO 31
<211> LENGTH: 1065
<212> TYPE: PRT
<213> ORGANISM: Arabidopsis thaliana

<400> SEQUENCE: 31

```
Met Glu Ser Glu Gly Glu Thr Ala Gly Lys Pro Met Lys Asn Ile Val
1               5                   10                  15

Pro Gln Thr Cys Gln Ile Cys Ser Asp Asn Val Gly Lys Thr Val Asp
            20                  25                  30

Gly Asp Arg Phe Val Ala Cys Asp Ile Cys Ser Phe Pro Val Cys Arg
        35                  40                  45

Pro Cys Tyr Glu Tyr Glu Arg Lys Asp Gly Asn Gln Ser Cys Pro Gln
    50                  55                  60

Cys Lys Thr Arg Tyr Lys Arg Leu Lys Gly Ser Pro Ala Ile Pro Gly
65                  70                  75                  80

Asp Lys Asp Glu Asp Gly Leu Ala Asp Glu Gly Thr Val Glu Phe Asn
                85                  90                  95

Tyr Pro Gln Lys Glu Lys Ile Ser Glu Arg Met Leu Gly Trp His Leu
            100                 105                 110

Thr Arg Gly Lys Gly Glu Glu Met Gly Glu Pro Gln Tyr Asp Lys Glu
        115                 120                 125

Val Ser His Asn His Leu Pro Arg Leu Thr Ser Arg Gln Asp Thr Ser
    130                 135                 140

Gly Glu Phe Ser Ala Ala Ser Pro Glu Arg Leu Ser Val Ser Ser Thr
145                 150                 155                 160

Ile Ala Gly Gly Lys Arg Leu Pro Tyr Ser Ser Asp Val Asn Gln Ser
                165                 170                 175

Pro Asn Arg Arg Ile Val Asp Pro Val Gly Leu Gly Asn Val Ala Trp
            180                 185                 190

Lys Glu Arg Val Asp Gly Trp Lys Met Lys Gln Glu Lys Asn Thr Gly
        195                 200                 205

Pro Val Ser Thr Gln Ala Ala Ser Glu Arg Gly Gly Val Asp Ile Asp
    210                 215                 220

Ala Ser Thr Asp Ile Leu Ala Asp Glu Ala Leu Leu Asn Asp Glu Ala
225                 230                 235                 240

Arg Gln Pro Leu Ser Arg Lys Val Ser Ile Pro Ser Ser Arg Ile Asn
                245                 250                 255

Pro Tyr Arg Met Val Ile Met Leu Arg Leu Val Ile Leu Cys Leu Phe
            260                 265                 270
```

```
Leu His Tyr Arg Ile Thr Asn Pro Val Pro Asn Ala Phe Ala Leu Trp
            275                 280                 285

Leu Val Ser Val Ile Cys Glu Ile Trp Phe Ala Leu Ser Trp Ile Leu
    290                 295                 300

Asp Gln Phe Pro Lys Trp Phe Pro Val Asn Arg Glu Thr Tyr Leu Asp
305                 310                 315                 320

Arg Leu Ala Leu Arg Tyr Asp Arg Glu Gly Glu Pro Ser Gln Leu Ala
                325                 330                 335

Ala Val Asp Ile Phe Val Ser Thr Val Asp Pro Leu Lys Glu Pro Pro
                340                 345                 350

Leu Val Thr Ala Asn Thr Val Leu Ser Ile Leu Ala Val Asp Tyr Pro
                355                 360                 365

Val Asp Lys Val Ser Cys Tyr Val Ser Asp Asp Gly Ala Ala Met Leu
                370                 375                 380

Ser Phe Glu Ser Leu Ala Glu Thr Ser Glu Phe Ala Arg Lys Trp Val
385                 390                 395                 400

Pro Phe Cys Lys Lys Tyr Ser Ile Glu Pro Arg Ala Pro Glu Trp Tyr
                405                 410                 415

Phe Ala Ala Lys Ile Asp Tyr Leu Lys Asp Lys Val Gln Thr Ser Phe
                420                 425                 430

Val Lys Asp Arg Arg Ala Met Lys Arg Glu Tyr Glu Glu Phe Lys Ile
                435                 440                 445

Arg Ile Asn Ala Leu Val Ser Lys Ala Leu Lys Cys Pro Glu Glu Gly
                450                 455                 460

Trp Val Met Gln Asp Gly Thr Pro Trp Pro Gly Asn Asn Thr Arg Asp
465                 470                 475                 480

His Pro Gly Met Ile Gln Val Phe Leu Gly Gln Asn Gly Gly Leu Asp
                485                 490                 495

Ala Glu Gly Asn Glu Leu Pro Arg Leu Val Tyr Val Ser Arg Glu Lys
                500                 505                 510

Arg Pro Gly Phe Gln His His Lys Lys Ala Gly Ala Met Asn Ala Leu
                515                 520                 525

Val Arg Val Ser Ala Val Leu Thr Asn Gly Pro Phe Ile Leu Asn Leu
                530                 535                 540

Asp Cys Asp His Tyr Ile Asn Asn Ser Lys Ala Leu Arg Glu Ala Met
545                 550                 555                 560

Cys Phe Leu Met Asp Pro Asn Leu Gly Lys Gln Val Cys Tyr Val Gln
                565                 570                 575

Phe Pro Gln Arg Phe Asp Gly Ile Asp Lys Asn Asp Arg Tyr Ala Asn
                580                 585                 590

Arg Asn Thr Val Phe Phe Asp Ile Asn Leu Arg Gly Leu Asp Gly Ile
                595                 600                 605

Gln Gly Pro Val Tyr Val Gly Thr Gly Cys Val Phe Asn Arg Thr Ala
                610                 615                 620

Leu Tyr Gly Tyr Glu Pro Pro Ile Lys Val Lys His Lys Lys Pro Ser
625                 630                 635                 640

Leu Leu Ser Lys Leu Cys Gly Gly Ser Arg Lys Lys Asn Ser Lys Ala
                645                 650                 655

Lys Lys Glu Ser Asp Lys Lys Lys Ser Gly Arg His Thr Asp Ser Thr
                660                 665                 670

Val Pro Val Phe Asn Leu Asp Asp Ile Glu Glu Gly Val Glu Gly Ala
                675                 680                 685
```

-continued

Gly Phe Asp Asp Glu Lys Ala Leu Leu Met Ser Gln Met Ser Leu Glu
690                 695                 700

Lys Arg Phe Gly Gln Ser Ala Val Phe Val Ala Ser Thr Leu Met Glu
705                 710                 715                 720

Asn Gly Gly Val Pro Pro Ser Ala Thr Pro Glu Asn Leu Leu Lys Glu
            725                 730                 735

Ala Ile His Val Ile Ser Cys Gly Tyr Glu Asp Lys Ser Asp Trp Gly
        740                 745                 750

Met Glu Ile Gly Trp Ile Tyr Gly Ser Val Thr Glu Asp Ile Leu Thr
    755                 760                 765

Gly Phe Lys Met His Ala Arg Gly Trp Arg Ser Ile Tyr Cys Met Pro
770                 775                 780

Lys Leu Pro Ala Phe Lys Gly Ser Ala Pro Ile Asn Phe Ser Asp Arg
785                 790                 795                 800

Leu Asn Gln Val Leu Arg Trp Ala Leu Gly Ser Val Glu Ile Leu Phe
            805                 810                 815

Ser Arg His Cys Pro Ile Trp Tyr Gly Tyr Asn Gly Arg Leu Lys Phe
        820                 825                 830

Leu Glu Arg Phe Ala Tyr Val Asn Thr Thr Ile Tyr Pro Ile Thr Ser
    835                 840                 845

Ile Pro Leu Leu Met Tyr Cys Thr Leu Pro Ala Val Cys Leu Phe Thr
850                 855                 860

Asn Gln Phe Ile Ile Pro Gln Ile Ser Asn Ile Ala Ser Ile Trp Phe
865                 870                 875                 880

Leu Ser Leu Phe Leu Ser Ile Phe Ala Thr Gly Ile Leu Glu Met Arg
            885                 890                 895

Trp Ser Gly Val Gly Ile Asp Glu Trp Trp Arg Asn Glu Gln Phe Trp
        900                 905                 910

Val Ile Gly Gly Val Ser Ala His Leu Phe Ala Val Phe Gln Gly Ile
    915                 920                 925

Leu Lys Val Leu Ala Gly Ile Asp Thr Asn Phe Thr Val Thr Ser Lys
930                 935                 940

Ala Ser Asp Glu Asp Gly Asp Phe Ala Glu Leu Tyr Leu Phe Lys Trp
945                 950                 955                 960

Thr Thr Leu Leu Ile Pro Pro Thr Thr Leu Leu Ile Val Asn Leu Val
            965                 970                 975

Gly Val Val Ala Gly Val Ser Tyr Ala Ile Asn Ser Gly Tyr Gln Ser
        980                 985                 990

Trp Gly Pro Leu Phe Gly Lys Leu Phe Phe Ala Phe Trp Val Ile Val
    995                 1000                1005

His Leu Tyr Pro Phe Leu Lys Gly Leu Met Gly Arg Gln Asn Arg
    1010                1015                1020

Thr Pro Thr Ile Val Val Val Trp Ser Val Leu Leu Ala Ser Ile
    1025                1030                1035

Phe Ser Leu Leu Trp Val Arg Ile Asp Pro Phe Thr Ser Arg Val
    1040                1045                1050

Thr Gly Pro Asp Ile Leu Glu Cys Gly Ile Asn Cys
    1055                1060                1065

<210> SEQ ID NO 32
<211> LENGTH: 4690
<212> TYPE: DNA
<213> ORGANISM: Arabidopsis thaliana

<400> SEQUENCE: 32

-continued

```
atggaatccg aaggagaaac cgcggtatgc tttttttgact cttgcttcat cattatactt     60
acctttatcg aaatcaggaa ttatatgtac tgaaattgat tgatttgggt gttgaattgt    120
gtattggaga gatctgattt caaattttct gttgaggttt ctaattttgg cttcattgat    180
tcgacttgat ttgtagggaa agccgatgaa gaacattgtt ccgcagactt gccagatctg    240
tagtgacaat gttggcaaga ctgttgatgg agatcgtttt gtggcttgtg atatttgttc    300
attcccagtt tgtcggcctt gctacgagta tgagaggaaa gatgggaatc aatcttgtcc    360
tcagtgcaaa accagataca agaggctcaa aggttctctt tgatccttc  tgaagtatac    420
tgtcttcatt gttcatcgat agtttatcag tatgttttga attttggatc agattggtat    480
ttatagcaat ttgctaattt ctgattctag gtagtcctgc tattcctggt gataaagacg    540
aggatggctt agctgatgaa ggtactgttg agttcaacta ccctcagaag gagaaaattt    600
cagagcggat gcttggttgg catcttactc gtgggaaggg agaggaaatg ggggaacccc    660
agtatgataa agaggtctct cacaatcatc ttcctcgtct cacgagcaga caagatgtaa    720
ggcattgctg ttcattcttc cctcttaagc attcgcatcc tcacgcaatt tagttttgga    780
atctgatttt gtcatttgct tatttacaga cttcaggaga gttttctgct gcctcacctg    840
aacgcctctc tgtatcttct actatcgctg ggggaaagcg ccttccctat tcatcagatg    900
tcaatcaatc acgtaaatat cctttatttc taactctctc gccaacacat atatttgtac    960
ctaggcttct cttttatgtc aaaactctaa acaataaaat ctgttgttgt cattcacgct   1020
gcagcaaata aaggattgt ggatcctgtt ggactcggga atgtagcttg aaggagaga    1080
gttgatggct ggaaaatgaa gcaagagaag aatactggtc ctgtcagcac gcaggctgct   1140
tctgaaagag gtggagtaga tattgatgcc agcacagata tcctagcaga tgaggctctg   1200
ctgtgagttc ttgttttgta atcttgtttg ttctgtcgtg gtgtaccgag cgttttttcct   1260
attaagcaat gtcctgatac tcattttcca attctttatt tattgtacag gaatgacgaa   1320
gcgaggcagc ctctgtcaag gaaagtttca attccttcat cacggatcaa tccttacaga   1380
atggttatta tgctgcggct tgttatcctt tgtctcttct tgcattaccg tataacaaac   1440
ccagtgccaa atgcctttgc tctatggctg gtctctgtga tatgtgagat ctggtttgcc   1500
ttatcctgga ttttggatca gtttcccaag tggtttcctg tgaaccgtga aacctacctc   1560
gacaggcttg ctttaaggta agttctattt ccccattctt ctgaagcaat tactcaaagg   1620
attgtttgcc tatactgttt cccatttta  tttgatcatg gtcaattttt gggacagata   1680
tgatcgtgaa ggtgagccat cacagttagc tgctgttgac atttttcgtga gtactgttga   1740
ccccttgaag gagccacccc ttgtgacagc caacacagtg ctctctattc tggctgttga   1800
ctacccagtt gacaaggtgt cctgttatgt ttttgatgat ggtgctgcta tgttatcatt   1860
tgaatcactt gcagaaacat cagagtttgc tcgtaaatgg gtaccatttt gcaagaaata   1920
tagcatagag cctcgtgcac cagaatggta ctttgctgcg aaaatagatt acttgaagga   1980
taaagttcag acatcatttg tcaaagatcg tagagctatg aaggtaagtt tgtagttta    2040
gtcatctagt caccctcact ttgattttag tgtatgctat attgaccttt tattttcttt   2100
cagagggaat atgaggaatt taaaatccga atcaatgcac ttgtttccaa agccctaaaa   2160
tgtcctgaag aagggtgggt tatgcaagat ggcacaccgt ggcctggaaa taatacaagg   2220
gaccatccag gaatgatcca ggtaagaaat tggttttaac tatggaatcg agaatgctct   2280
ctctttctct ctagaagttc attattgaag taccattttgc tgaatgcagg tcttcttagg   2340
```

```
gcaaaatggt ggacttgatg cagagggcaa tgagctcccg cgtttggtat atgtttctcg    2400
agaaaagcga ccaggattcc agcaccacaa aaaggctggt gctatgaatg cactggtaag    2460
tttctgatct tggattttg acttcttcat tctgaccaat ttgttagtct aatctgggta     2520
cttttcaaat gaataggtga gagtttcagc agttcttacc aatggacctt tcatcttgaa    2580
tcttgattgt gatcattaca taaataacag caaagcctta agagaagcaa tgtgcttcct    2640
gatggaccca aacctcggga agcaagtttg ttatgttcag ttcccacaaa gatttgatgg    2700
tatcgataag aacgatagat atgctaatcg taataccgtg ttctttgatg taagtcacac    2760
ttacctatac ttgcgtctaa ttttcttgtt ctttcaaatt gcttttagac acgaatatac    2820
attaaactca cagtttcttg agtttgtcgt aatttttcca tgatatgttt tccagattaa    2880
cttgagaggt ttagatggga ttcaaggacc tgtatatgtc ggaactggat gtgttttcaa    2940
cagaacagca ttatacggtt atgaacctcc aataaaagta aaacacaaga agccaagtct    3000
tttatctaag ctctgtggtg gatcaagaaa gaagaattcc aaagctaaga aagagtcgga    3060
caaaaagaaa tcaggcaggc atactgactc aactgttcct gtattcaacc tcgatgacat    3120
agaagaggga gttgaaggta caactgtttt tatttcttct ttggtttccg ttatacccat    3180
atgttgctgt ttgaaatatt gatccagggg aggggattat ttatagttga cagttgtcta    3240
aatagtttcc atactaggta tctcatcatg tcttaactat ttggcatttg tgaaacttag    3300
gtgctggttt tgatgatgaa aaggcgctct taatgtcgca aatgagcctg agaagcgat     3360
ttggacagtc tgctgttttt gttgcttcta ccctaatgga aaatggtggt gttcctcctt    3420
cagcaactcc agaaaacctt ctcaaagagg ctatccatgt cattagttgt ggttatgagg    3480
ataagtcaga ttggggaatg gaggtataat ctcatttgaa ctcctacatg aatctgcatt    3540
gttctgacat atccactttg gcattcactt tgtttatatt ttccgctgtc tttcttcaga    3600
ttggatggat ctatggttct gtgacagaag atattctgac tgggttcaaa atgcatgccc    3660
gtggatggcg atccatttac tgcatgccta agcttccagc tttcaagggt tctgctccta    3720
tcaatctttc agatcgtctg aaccaagtgc tgaggtgggc tttaggttca gttgagattc    3780
tcttcagtcg gcattgtcct atatggtatg gttacaatgg gaggctaaaa tttcttgaga    3840
ggtttgcgta tgtgaacacc accatctacc ctatcacctc cattcctctt ctcatgtatt    3900
gtacattgcc agccgtttgt ctcttcacca accagtttat tattcctcag gtttgacacc    3960
tctctctgtc tatctatctc tatctctatc tctatctcta gaacaaacct taattacgtt    4020
ctgtttaact gaaaccatgt tgtgtttgtc atctatttac ggttccaaat cctgatcagc    4080
tggttctatt gttcctcttt tgcagattag taacattgca agtatatggt ttctgtctct    4140
ctttctctcc attttcgcca cgggtatact agaaatgagg tggagtggcg taggcataga    4200
cgaatggtgg agaaacgagc agttttgggt cattggtgga gtatccgctc atttattcgc    4260
tgtgtttcaa ggtatcctca agtccttgc cggtattgac acaaacttca cagttacctc     4320
aaaagcttca gatgaagacg gagactttgc tgagctctac ttgttcaaat ggacaacact    4380
tctgattccg ccaacgacgc tgctcattgt aaacttagtg ggagttgttg caggagtctc    4440
ttatgctatc aacagtggat accaatcatg gggaccactc tttggtaagt tgttctttgc    4500
cttctgggtg attgttcact tgtaccctt cctcaagggt ttgatgggtc gacagaaccg     4560
gactcctacc attgttgtgg tctggtctgt tctcttggct tctatcttct cgttgttgtg    4620
ggttaggatt gatcccttca ctagccgagt cactggcccg gacattctgg aatgtggaat    4680
caactgttga                                                            4690
```

<210> SEQ ID NO 33
<211> LENGTH: 1065
<212> TYPE: PRT
<213> ORGANISM: Arabidopsis thaliana

<400> SEQUENCE: 33

```
Met Glu Ser Glu Gly Glu Thr Ala Gly Lys Pro Met Lys Asn Ile Val
1               5                   10                  15

Pro Gln Thr Cys Gln Ile Cys Ser Asp Asn Val Gly Lys Thr Val Asp
            20                  25                  30

Gly Asp Arg Phe Val Ala Cys Asp Ile Cys Ser Phe Pro Val Cys Arg
        35                  40                  45

Pro Cys Tyr Glu Tyr Glu Arg Lys Asp Gly Asn Gln Ser Cys Pro Gln
    50                  55                  60

Cys Lys Thr Arg Tyr Lys Arg Leu Lys Gly Ser Pro Ala Ile Pro Gly
65                  70                  75                  80

Asp Lys Asp Glu Asp Gly Leu Ala Asp Glu Gly Thr Val Glu Phe Asn
                85                  90                  95

Tyr Pro Gln Lys Glu Lys Ile Ser Glu Arg Met Leu Gly Trp His Leu
            100                 105                 110

Thr Arg Gly Lys Gly Glu Glu Met Gly Glu Pro Gln Tyr Asp Lys Glu
        115                 120                 125

Val Ser His Asn His Leu Pro Arg Leu Thr Ser Arg Gln Asp Thr Ser
    130                 135                 140

Gly Glu Phe Ser Ala Ala Ser Pro Glu Arg Leu Ser Val Ser Ser Thr
145                 150                 155                 160

Ile Ala Gly Gly Lys Arg Leu Pro Tyr Ser Ser Asp Val Asn Gln Ser
                165                 170                 175

Pro Asn Arg Arg Ile Val Asp Pro Val Gly Leu Gly Asn Val Ala Trp
            180                 185                 190

Lys Glu Arg Val Asp Gly Trp Lys Met Lys Gln Glu Lys Asn Thr Gly
        195                 200                 205

Pro Val Ser Thr Gln Ala Ala Ser Glu Arg Gly Gly Val Asp Ile Asp
    210                 215                 220

Ala Ser Thr Asp Ile Leu Ala Asp Glu Ala Leu Leu Asn Asp Glu Ala
225                 230                 235                 240

Arg Gln Pro Leu Ser Arg Lys Val Ser Ile Pro Ser Ser Arg Ile Asn
                245                 250                 255

Pro Tyr Arg Met Val Ile Met Leu Arg Leu Val Ile Leu Cys Leu Phe
            260                 265                 270

Leu His Tyr Arg Ile Thr Asn Pro Val Pro Asn Ala Phe Ala Leu Trp
        275                 280                 285

Leu Val Ser Val Ile Cys Glu Ile Trp Phe Ala Leu Ser Trp Ile Leu
    290                 295                 300

Asp Gln Phe Pro Lys Trp Phe Pro Val Asn Arg Glu Thr Tyr Leu Asp
305                 310                 315                 320

Arg Leu Ala Leu Arg Tyr Asp Arg Glu Gly Glu Pro Ser Gln Leu Ala
                325                 330                 335

Ala Val Asp Ile Phe Val Ser Thr Val Asp Pro Leu Lys Glu Pro Pro
            340                 345                 350

Leu Val Thr Ala Asn Thr Val Leu Ser Ile Leu Ala Val Asp Tyr Pro
        355                 360                 365

Val Asp Lys Val Ser Cys Tyr Val Phe Asp Asp Gly Ala Ala Met Leu
```

```
                370                 375                 380
Ser Phe Glu Ser Leu Ala Glu Thr Ser Glu Phe Ala Arg Lys Trp Val
385                 390                 395                 400

Pro Phe Cys Lys Lys Tyr Ser Ile Glu Pro Arg Ala Pro Glu Trp Tyr
                405                 410                 415

Phe Ala Ala Lys Ile Asp Tyr Leu Lys Asp Lys Val Gln Thr Ser Phe
                420                 425                 430

Val Lys Asp Arg Arg Ala Met Lys Arg Glu Tyr Glu Glu Phe Lys Ile
            435                 440                 445

Arg Ile Asn Ala Leu Val Ser Lys Ala Leu Lys Cys Pro Glu Glu Gly
            450                 455                 460

Trp Val Met Gln Asp Gly Thr Pro Trp Pro Gly Asn Asn Thr Arg Asp
465                 470                 475                 480

His Pro Gly Met Ile Gln Val Phe Leu Gly Asn Gly Gly Leu Asp
                485                 490                 495

Ala Glu Gly Asn Glu Leu Pro Arg Leu Val Tyr Val Ser Arg Glu Lys
                500                 505                 510

Arg Pro Gly Phe Gln His His Lys Lys Ala Gly Ala Met Asn Ala Leu
            515                 520                 525

Val Arg Val Ser Ala Val Leu Thr Asn Gly Pro Phe Ile Leu Asn Leu
            530                 535                 540

Asp Cys Asp His Tyr Ile Asn Asn Ser Lys Ala Leu Arg Glu Ala Met
545                 550                 555                 560

Cys Phe Leu Met Asp Pro Asn Leu Gly Lys Gln Val Cys Tyr Val Gln
                565                 570                 575

Phe Pro Gln Arg Phe Asp Gly Ile Asp Lys Asn Asp Arg Tyr Ala Asn
                580                 585                 590

Arg Asn Thr Val Phe Phe Asp Ile Asn Leu Arg Gly Leu Asp Gly Ile
            595                 600                 605

Gln Gly Pro Val Tyr Val Gly Thr Gly Cys Val Phe Asn Arg Thr Ala
            610                 615                 620

Leu Tyr Gly Tyr Glu Pro Pro Ile Lys Val Lys His Lys Lys Pro Ser
625                 630                 635                 640

Leu Leu Ser Lys Leu Cys Gly Gly Ser Arg Lys Lys Asn Ser Lys Ala
                645                 650                 655

Lys Lys Glu Ser Asp Lys Lys Lys Ser Gly Arg His Thr Asp Ser Thr
                660                 665                 670

Val Pro Val Phe Asn Leu Asp Asp Ile Glu Glu Gly Val Glu Gly Ala
            675                 680                 685

Gly Phe Asp Asp Glu Lys Ala Leu Leu Met Ser Gln Met Ser Leu Glu
690                 695                 700

Lys Arg Phe Gly Gln Ser Ala Val Phe Val Ala Ser Thr Leu Met Glu
705                 710                 715                 720

Asn Gly Gly Val Pro Pro Ser Ala Thr Pro Glu Asn Leu Leu Lys Glu
                725                 730                 735

Ala Ile His Val Ile Ser Cys Gly Tyr Glu Asp Lys Ser Asp Trp Gly
                740                 745                 750

Met Glu Ile Gly Trp Ile Tyr Gly Ser Val Thr Glu Asp Ile Leu Thr
            755                 760                 765

Gly Phe Lys Met His Ala Arg Gly Trp Arg Ser Ile Tyr Cys Met Pro
            770                 775                 780

Lys Leu Pro Ala Phe Lys Gly Ser Ala Pro Ile Asn Leu Ser Asp Arg
785                 790                 795                 800
```

Leu Asn Gln Val Leu Arg Trp Ala Leu Gly Ser Val Glu Ile Leu Phe
              805                 810                 815

Ser Arg His Cys Pro Ile Trp Tyr Gly Tyr Asn Gly Arg Leu Lys Phe
              820                 825                 830

Leu Glu Arg Phe Ala Tyr Val Asn Thr Thr Ile Tyr Pro Ile Thr Ser
              835                 840                 845

Ile Pro Leu Leu Met Tyr Cys Thr Leu Pro Ala Val Cys Leu Phe Thr
              850                 855                 860

Asn Gln Phe Ile Ile Pro Gln Ile Ser Asn Ile Ala Ser Ile Trp Phe
865                 870                 875                 880

Leu Ser Leu Phe Leu Ser Ile Phe Ala Thr Gly Ile Leu Glu Met Arg
              885                 890                 895

Trp Ser Gly Val Gly Ile Asp Glu Trp Trp Arg Asn Glu Gln Phe Trp
              900                 905                 910

Val Ile Gly Gly Val Ser Ala His Leu Phe Ala Val Phe Gln Gly Ile
              915                 920                 925

Leu Lys Val Leu Ala Gly Ile Asp Thr Asn Phe Thr Val Thr Ser Lys
              930                 935                 940

Ala Ser Asp Glu Asp Gly Asp Phe Ala Glu Leu Tyr Leu Phe Lys Trp
945                 950                 955                 960

Thr Thr Leu Leu Ile Pro Pro Thr Thr Leu Leu Ile Val Asn Leu Val
              965                 970                 975

Gly Val Val Ala Gly Val Ser Tyr Ala Ile Asn Ser Gly Tyr Gln Ser
              980                 985                 990

Trp Gly Pro Leu Phe Gly Lys Leu Phe Phe Ala Phe Trp Val Ile Val
              995                1000                1005

His Leu Tyr Pro Phe Leu Lys Gly Leu Met Gly Arg Gln Asn Arg
              1010                1015                1020

Thr Pro Thr Ile Val Val Val Trp Ser Val Leu Leu Ala Ser Ile
              1025                1030                1035

Phe Ser Leu Leu Trp Val Arg Ile Asp Pro Phe Thr Ser Arg Val
              1040                1045                1050

Thr Gly Pro Asp Ile Leu Glu Cys Gly Ile Asn Cys
              1055                1060                1065

<210> SEQ ID NO 34
<211> LENGTH: 4690
<212> TYPE: DNA
<213> ORGANISM: Arabidopsis thaliana

<400> SEQUENCE: 34
atggaatccg aaggagaaac cgcggtatgc ttttttgact cttgcttcat cattatactt    60
acctttatcg aaatcaggaa ttatatgtac tgaaattgat tgatttgggt gttgaattgt   120
gtattggaga gatctgattt caaattttct gttgaggttt ctaattttgg cttcattgat   180
tcgacttgat ttgtagggaa agccgatgaa gaacattgtt ccgcagactt gccagatctg   240
tagtgacaat gttggcaaga ctgttgatgg agatcgtttt gtggcttgtg atatttgttc   300
attcccagtt gtcggcctt gctacgagta tgagaggaaa gatgggaatc aatcttgtcc   360
tcagtgcaaa accagataca agaggctcaa aggttctctt tgatccttc tgaagtatac   420 tgtcttcatt gttcatcgat agtttatcag tatgttttga attttggatc agattggtat   480
ttatagcaat ttgctaattt ctgattctag gtagtcctgc tattcctggt gataagacg    540 aggatggctt agctgatgaa ggtactgttg agttcaacta ccctcagaag gagaaaattt   600

```
cagagcggat gcttggttgg catcttactc gtgggaaggg agaggaaatg ggggaacccc      660
agtatgataa agaggtctct cacaatcatc ttcctcgtct cacgagcaga caagatgtaa      720
ggcattgctg ttcattcttc cctcttaagc attcgcatcc tcacgcaatt tagttttgga      780
atctgatttt gtcatttgct tatttacaga cttcaggaga gttttctgct gcctcacctg      840
aacgcctctc tgtatcttct actatcgctg ggggaaagcg ccttccctat tcatcagatg      900
tcaatcaatc acgtaaatat cctttatttc taactctctc gccaacacat atatttgtac      960
ctaggcttct cttttatgtc aaaactctaa acaataaaat ctgttgttgt cattcacgct     1020
gcagcaaata aaggattgt ggatcctgtt ggactcggga atgtagcttg aaggagaga      1080 gttgatggct ggaaaatgaa gcaagagaag aatactggtc ctgtcagcac gcaggctgct     1140
tctgaaagag gtggagtaga tattgatgcc agcacagata tcctagcaga tgaggctctg     1200
ctgtgagttc ttgttttgta atcttgtttg ttctgtcgtg gtgtaccgag cgttttcct     1260 attaagcaat gtcctgatac tcattttcca attctttatt tattgtacag gaatgacgaa     1320
gcgaggcagc ctctgtcaag gaaagtttca attccttcat cacggatcaa tccttacaga     1380
atggttatta tgctgcggct tgttatcctt tgtctcttct tgcattacca tataacaaac     1440
ccagtgccaa atgcctttgc tctatggctg gtctctgtga tatgtgagat ctggtttgcc     1500
ttatcctgga ttttggatca gtttcccaag tggtttcctg tgaaccgtga aacctacctc     1560
gacaggcttg ctttaaggta agttctattt ccccattctt ctgaagcaat tactcaaagg     1620
attgtttgcc tatactgttt cccatttaa tttgatcatg gtcaatttt gggacagata      1680 tgatcgtgaa ggtgagccat cacagttagc tgctgttgac attttcgtga gtactgttga     1740 cccttgaag gagccacccc ttgtgacagc caacacagtg ctctctattc tggctgttga      1800
ctacccagtt gacaaggtgt cctgttatgt ttctgatgat ggtgctgcta tgttatcatt     1860
tgaatcactt gcagaaacat cagagtttgc tcgtaaatgg gtaccatttt gcaagaaata     1920
tagcatagag cctcgtgcac cagaatggta ctttgctgcg aaaatagatt acttgaagga     1980
taaagttcag acatcatttg tcaaagatcg tagagctatg aaggtaagtt tgtagtttta     2040
gtcatctagt caccctcact ttgattttag tgtatgctat attgaccttt tattttcttt     2100
cagagggaat atgaggaatt taaaatccga atcaatgcac ttgtttccaa agccctaaaa     2160
tgtcctgaag aagggtgggt tatgcaagat ggcacaccgt ggcctggaaa taatacaagg     2220
gaccatccag gaatgatcca ggtaagaaat tggttttaac tatggaatcg agaatgctct     2280
ctctttctct ctagaagttc attattgaag taccatttgc tgaatgcagg tcttcttagg     2340
gcaaaatggt ggacttgatg cagagggcaa tgagctcccg cgtttggtat atgtttctcg     2400
agaaaagcga ccaggattcc agcaccacaa aaaggctggt gctatgaatg cactggtaag     2460
tttctgatct tggattttg acttcttcat tctgaccaat ttgttagtct aatctgggta     2520
cttttcaaat gaataggtga gagtttcagc agttcttacc aatggacctt tcatcttgaa     2580
tcttgattgt gatcattaca taaataacag caaagcctta agagaagcaa tgtgcttcct     2640
gatggaccca aacctcggga agcaagtttg ttatgttcag ttcccacaaa gatttgatgg     2700
tatcgataag aacgatagat atgctaatcg taataccgtg ttctttgatg taagtcacac     2760
ttacctatac ttgcgtctaa ttttcttgtt ctttcaaatt gctttagac acgaatatac      2820 attaaactca cagtttcttg agtttgtcgt aattttccca tgtatatgttt tccagattaa     2880 cttgagaggt ttagatggga ttcaaggacc tgtatatgtc ggaactggat gtgttttcaa     2940
```

-continued

| | |
|---|---|
| cagaacagca ttatacggtt atgaacctcc aataaaagta aaacacaaga agccaagtct | 3000 |
| tttatctaag ctctgtggtg gatcaagaaa gaagaattcc aaagctaaga aagagtcgga | 3060 |
| caaaaagaaa tcaggcaggc atactgactc aactgttcct gtattcaacc tcgatgacat | 3120 |
| agaagaggga gttgaaggta caactgtttt tatttcttct ttggtttccg ttatacccat | 3180 |
| atgttgctgt ttgaaatatt gatccagggg aggggattat ttatagttga cagttgtcta | 3240 |
| aatagtttcc atactaggta tctcatcatg tcttaactat ttggcatttg tgaaacttag | 3300 |
| gtgctggttt tgatgatgaa aaggcgctct taatgtcgca aatgagcctg gagaagcgat | 3360 |
| ttggacagtc tgctgttttt gttgcttcta ccctaatgga aaatggtggt gttcctcctt | 3420 |
| cagcaactcc agaaaacctt ctcaaagagg ctatccatgt cattagttgt ggttatgagg | 3480 |
| ataagtcaga ttggggaatg gaggtataat ctcatttgaa ctcctacatg aatctgcatt | 3540 |
| gttctgacat atccactttg gcattcactt tgtttatatt ttccgctgtc tttcttcaga | 3600 |
| ttggatggat ctatggttct gtgacagaag atattctgac tgggttcaaa atgcatgccc | 3660 |
| gtggatggcg atccatttac tgcatgccta agcttccagc tttcaagggt tctgctccta | 3720 |
| tcaatctttc agatcgtctg aaccaagtgc tgaggtgggc tttaggttca gttgagattc | 3780 |
| tcttcagtcg gcattgtcct atatggtatg gttacaatgg gaggctaaaa tttcttgaga | 3840 |
| ggtttgcgta tgtgaacacc accatctacc ctatcacctc cattcctctt ctcatgtatt | 3900 |
| gtacattgcc agccgtttgt ctcttcacca accagtttat tattcctcag gtttgacacc | 3960 |
| tctctctgtc tatctatctc tatctctatc tctatctcta gaacaaacct taattacgtt | 4020 |
| ctgtttaact gaaaccatgt tgtgtttgtc atctatttac ggttccaaat cctgatcagc | 4080 |
| tggttctatt gttcctcttt tgcagattag taacattgca agtatatggt ttctgtctct | 4140 |
| ctttctctcc attttcgcca cgggtatact agaaatgagg tggagtggcg taggcataga | 4200 |
| cgaatggtgg agaaacgagc agttttgggt cattggtgga gtatccgctc atttattcgc | 4260 |
| tgtgtttcaa ggtatcctca aagtccttgc cggtattgac acaaacttca cagttacctc | 4320 |
| aaaagcttca gatgaagacg gagactttgc tgagctctac ttgttcaaat ggacaacact | 4380 |
| tctgattccg ccaacgacgc tgctcattgt aaacttagtg ggagttgttg caggagtctc | 4440 |
| ttatgctatc aacagtggat accaatcatg gggaccactc tttggtaagt tgttctttgc | 4500 |
| cttctgggtg attgttcact tgtacccttt cctcaagggt ttgatgggtc gacagaaccg | 4560 |
| gactcctacc attgttgtgg tctggtctgt tctcttggct tctatcttct cgttgttgtg | 4620 |
| ggttaggatt gatcccttca ctagccgagt cactggcccg gacattctgg aatgtggaat | 4680 |
| caactgttga | 4690 |

<210> SEQ ID NO 35
<211> LENGTH: 1065
<212> TYPE: PRT
<213> ORGANISM: Arabidopsis thaliana

<400> SEQUENCE: 35

Met Glu Ser Glu Gly Glu Thr Ala Gly Lys Pro Met Lys Asn Ile Val
1               5                   10                  15

Pro Gln Thr Cys Gln Ile Cys Ser Asp Asn Val Gly Lys Thr Val Asp
            20                  25                  30

Gly Asp Arg Phe Val Ala Cys Asp Ile Cys Ser Phe Pro Val Cys Arg
        35                  40                  45

Pro Cys Tyr Glu Tyr Glu Arg Lys Asp Gly Asn Gln Ser Cys Pro Gln
    50                  55                  60

```
Cys Lys Thr Arg Tyr Lys Arg Leu Lys Gly Ser Pro Ala Ile Pro Gly
 65                  70                  75                  80

Asp Lys Asp Glu Asp Gly Leu Ala Asp Glu Gly Thr Val Glu Phe Asn
                 85                  90                  95

Tyr Pro Gln Lys Glu Lys Ile Ser Glu Arg Met Leu Gly Trp His Leu
            100                 105                 110

Thr Arg Gly Lys Gly Glu Glu Met Gly Glu Pro Gln Tyr Asp Lys Glu
        115                 120                 125

Val Ser His Asn His Leu Pro Arg Leu Thr Ser Arg Gln Asp Thr Ser
    130                 135                 140

Gly Glu Phe Ser Ala Ala Ser Pro Glu Arg Leu Ser Val Ser Ser Thr
145                 150                 155                 160

Ile Ala Gly Gly Lys Arg Leu Pro Tyr Ser Ser Asp Val Asn Gln Ser
                165                 170                 175

Pro Asn Arg Arg Ile Val Asp Pro Val Gly Leu Gly Asn Val Ala Trp
            180                 185                 190

Lys Glu Arg Val Asp Gly Trp Lys Met Lys Gln Glu Lys Asn Thr Gly
        195                 200                 205

Pro Val Ser Thr Gln Ala Ala Ser Glu Arg Gly Gly Val Asp Ile Asp
    210                 215                 220

Ala Ser Thr Asp Ile Leu Ala Asp Glu Ala Leu Leu Asn Asp Glu Ala
225                 230                 235                 240

Arg Gln Pro Leu Ser Arg Lys Val Ser Ile Pro Ser Ser Arg Ile Asn
                245                 250                 255

Pro Tyr Arg Met Val Ile Met Leu Arg Leu Val Ile Leu Cys Leu Phe
            260                 265                 270

Leu His Tyr His Ile Thr Asn Pro Val Pro Asn Ala Phe Ala Leu Trp
        275                 280                 285

Leu Val Ser Val Ile Cys Glu Ile Trp Phe Ala Leu Ser Trp Ile Leu
    290                 295                 300

Asp Gln Phe Pro Lys Trp Phe Pro Val Asn Arg Glu Thr Tyr Leu Asp
305                 310                 315                 320

Arg Leu Ala Leu Arg Tyr Asp Arg Glu Gly Glu Pro Ser Gln Leu Ala
                325                 330                 335

Ala Val Asp Ile Phe Val Ser Thr Val Asp Pro Leu Lys Glu Pro Pro
            340                 345                 350

Leu Val Thr Ala Asn Thr Val Leu Ser Ile Leu Ala Val Asp Tyr Pro
        355                 360                 365

Val Asp Lys Val Ser Cys Tyr Val Ser Asp Asp Gly Ala Ala Met Leu
    370                 375                 380

Ser Phe Glu Ser Leu Ala Glu Thr Ser Glu Phe Ala Arg Lys Trp Val
385                 390                 395                 400

Pro Phe Cys Lys Lys Tyr Ser Ile Glu Pro Arg Ala Pro Glu Trp Tyr
                405                 410                 415

Phe Ala Ala Lys Ile Asp Tyr Leu Lys Asp Lys Val Gln Thr Ser Phe
            420                 425                 430

Val Lys Asp Arg Arg Ala Met Lys Arg Glu Tyr Glu Glu Phe Lys Ile
        435                 440                 445

Arg Ile Asn Ala Leu Val Ser Lys Ala Leu Lys Cys Pro Glu Glu Gly
    450                 455                 460

Trp Val Met Gln Asp Gly Thr Pro Trp Pro Gly Asn Asn Thr Arg Asp
465                 470                 475                 480
```

-continued

```
His Pro Gly Met Ile Gln Val Phe Leu Gly Gln Asn Gly Gly Leu Asp
                485                 490                 495

Ala Glu Gly Asn Glu Leu Pro Arg Leu Val Tyr Val Ser Arg Glu Lys
            500                 505                 510

Arg Pro Gly Phe Gln His His Lys Lys Ala Gly Ala Met Asn Ala Leu
            515                 520                 525

Val Arg Val Ser Ala Val Leu Thr Asn Gly Pro Phe Ile Leu Asn Leu
        530                 535                 540

Asp Cys Asp His Tyr Ile Asn Asn Ser Lys Ala Leu Arg Glu Ala Met
545                 550                 555                 560

Cys Phe Leu Met Asp Pro Asn Leu Gly Lys Gln Val Cys Tyr Val Gln
                565                 570                 575

Phe Pro Gln Arg Phe Asp Gly Ile Asp Lys Asn Asp Arg Tyr Ala Asn
            580                 585                 590

Arg Asn Thr Val Phe Phe Asp Ile Asn Leu Arg Gly Leu Asp Gly Ile
        595                 600                 605

Gln Gly Pro Val Tyr Val Gly Thr Gly Cys Val Phe Asn Arg Thr Ala
    610                 615                 620

Leu Tyr Gly Tyr Glu Pro Pro Ile Lys Val Lys His Lys Lys Pro Ser
625                 630                 635                 640

Leu Leu Ser Lys Leu Cys Gly Gly Ser Arg Lys Lys Asn Ser Lys Ala
                645                 650                 655

Lys Lys Glu Ser Asp Lys Lys Ser Gly Arg His Thr Asp Ser Thr
            660                 665                 670

Val Pro Val Phe Asn Leu Asp Asp Ile Glu Glu Gly Val Glu Gly Ala
        675                 680                 685

Gly Phe Asp Asp Glu Lys Ala Leu Leu Met Ser Gln Met Ser Leu Glu
    690                 695                 700

Lys Arg Phe Gly Gln Ser Ala Val Phe Val Ala Ser Thr Leu Met Glu
705                 710                 715                 720

Asn Gly Gly Val Pro Pro Ser Ala Thr Pro Glu Asn Leu Leu Lys Glu
                725                 730                 735

Ala Ile His Val Ile Ser Cys Gly Tyr Glu Asp Lys Ser Asp Trp Gly
            740                 745                 750

Met Glu Ile Gly Trp Ile Tyr Gly Ser Val Thr Glu Asp Ile Leu Thr
        755                 760                 765

Gly Phe Lys Met His Ala Arg Gly Trp Arg Ser Ile Tyr Cys Met Pro
    770                 775                 780

Lys Leu Pro Ala Phe Lys Gly Ser Ala Pro Ile Asn Leu Ser Asp Arg
785                 790                 795                 800

Leu Asn Gln Val Leu Arg Trp Ala Leu Gly Ser Val Glu Ile Leu Phe
                805                 810                 815

Ser Arg His Cys Pro Ile Trp Tyr Gly Tyr Asn Gly Arg Leu Lys Phe
            820                 825                 830

Leu Glu Arg Phe Ala Tyr Val Asn Thr Thr Ile Tyr Pro Ile Thr Ser
        835                 840                 845

Ile Pro Leu Leu Met Tyr Cys Thr Leu Pro Ala Val Cys Leu Phe Thr
    850                 855                 860

Asn Gln Phe Ile Ile Pro Gln Ile Ser Asn Ile Ala Ser Ile Trp Phe
865                 870                 875                 880

Leu Ser Leu Phe Leu Ser Ile Phe Ala Thr Gly Ile Leu Glu Met Arg
                885                 890                 895

Trp Ser Gly Val Gly Ile Asp Glu Trp Trp Arg Asn Glu Gln Phe Trp
```

```
                900              905                910
Val Ile Gly Gly Val Ser Ala His Leu Phe Ala Val Phe Gln Gly Ile
            915                920                925

Leu Lys Val Leu Ala Gly Ile Asp Thr Asn Phe Thr Val Thr Ser Lys
        930                935                940

Ala Ser Asp Glu Asp Gly Asp Phe Ala Glu Leu Tyr Leu Phe Lys Trp
945                950                955                960

Thr Thr Leu Leu Ile Pro Pro Thr Thr Leu Leu Ile Val Asn Leu Val
                965                970                975

Gly Val Val Ala Gly Val Ser Tyr Ala Ile Asn Ser Gly Tyr Gln Ser
            980                985                990

Trp Gly Pro Leu Phe Gly Lys Leu  Phe Phe Ala Phe Trp  Val Ile Val
        995                1000                1005

His Leu Tyr Pro Phe Leu Lys  Gly Leu Met Gly Arg  Gln Asn Arg
    1010                1015                1020

Thr Pro Thr Ile Val Val Val  Trp Ser Val Leu Leu  Ala Ser Ile
    1025                1030                1035

Phe Ser Leu Leu Trp Val Arg  Ile Asp Pro Phe Thr  Ser Arg Val
    1040                1045                1050

Thr Gly  Pro Asp Ile Leu Glu  Cys Gly Ile Asn Cys
    1055                1060                1065

<210> SEQ ID NO 36
<211> LENGTH: 4779
<212> TYPE: DNA
<213> ORGANISM: Arabidopsis thaliana

<400> SEQUENCE: 36
atgaacaccg gtggtcggtt aatcgccggt tctcacaaca ggaatgagtt tgtcctcatt    60
aatgccgatg agaatgcccg agtatgtttc tcctcttctt ttgtttccaa ttctctgtct   120
tttgatctgt gtttctctat ctctgttcaa aagtctctga ctttttttac ttttcttgtg   180
gatctggctc ttaccactgc aaatcaatta agatttaggg ttttttagtac tagtattaag   240 attacgtacc cttgtagcta attttatcaa gaattgattg tgtcggtggg atggattttt   300
ccggatttga cttgtcttaa ttctccaatt taagagattt cttcaattgc aattatgaat   360
ctatcaatgt gaagagtaat aattatgtta ttgggttact tgatctggt gtgagatcca    420 gtctgatagt gtcactacta tgatctgatg tatttaactc tactgttttg tgcagataag   480
atcagtccaa gagctgagtg gacagacatg tcaaatctgc agagatgaga tcgaattgac   540
tgttgatgga gaaccgtttg tggcatgtaa cgaatgtgca ttccctgtgt gtagaccttg   600
ctatgagtac gaaagacgag aaggcaatca agcttgtcca cagtgcaaaa cccgtttcaa   660
acgtcttaaa ggttcgttgt tgttagacc aaatttcttt ggttttttgt gaatgtagaa    720
gattttctga tttgttcggc ctatgttgtt gtttgttagg aagtccaaga gttgaaggtg   780
atgaagagga agatgacatt gatgatttag acaatgagtt tgagtatgga aataatggga   840
ttggatttga tcaggtttct gaaggtatgt caatctctcg tcgcaactcc ggtttcccac   900
aatctgattt ggattcagct ccacctggct ctcagattcc attgctgact acggcgacg    960 aggtaaaaat ctcagaatgt atccacattg tataacccat cttcagtaat tggctcactc   1020
agatttctct tttgtttat tacaggacgt tgagatttct tctgatagac atgctcttat    1080
tgttcctcct tcacttggtg gtcatggcaa tagagttcat cctgtttctc tttctgaccc   1140
gaccgtggct gcacatccaa ggcctatggt acctcagaaa gatcttgcgg tttatggtta   1200
```

```
tggaagtgtc gcttggaaag atcggatgga ggaatggaag agaaagcaga atgagaaact   1260
tcaggttgtt aggcatgaag gagatcctga ttttgaagat ggtgatgatg ctgattttcc   1320
aatgtaaggc aaagaatata atttttttg  ttgatgtctt gttccgttgc agtgatattt   1380
atcaagcctt ttttttccat tttaggatgg atgagggaag gcagccattg tctaggaaga   1440
taccaatcaa atcgagcaag ataaatcctt accggatgtt aattgtgcta cgtcttgtga   1500
ttcttggtct cttcttcac  taccgtattc ttcaccccgt caaagatgca tatgctttgt   1560
ggcttatttc tgttatatgt gagatatggt ttgctgtttc atgggttctt gatcagttcc   1620
ctaaatggta ccctatcgag cgagaaacgt acttggaccg actctcatta aggtacttac   1680
atcttgtggg ttattacact tggaaatgtt aaaactttgt ttggggata  taatccttat   1740
ttttttttgtt tgcagatatg agaaagaagg gaaaccgtcg ggactatccc ctgtggatgt   1800
atttgttagt acagtggatc cattgaaaga gcctccgctt attactgcaa atactgtctt   1860
gtctattctt gctgttgatt atcctgtcga taaggttgct tgttacgtat ctgatgatgg   1920
tgctgctatg cttactttcg aagctctttc tgagaccgct gaattcgcaa ggaaatgggt   1980
tccttttctgc aagaaatatt gtattgagcc tcgtgctccc gaatggtatt tctgccataa   2040
aatggactac ttgaagaata aagttcatcc cgcatttgtt agggagcggc gagccatgaa   2100
ggttactagt tcttactttt ttataaattt gatttgatga gaaagttttt ggtctaattg   2160
attcttgctt tagaaaaaaa aaattcatga gaaagttat  caatcttttg ttatatgggc   2220
tcttatgaaa gaagatggtg gctttgaaaa ttgatttgaa agattgtgtg ttttactggt   2280
tttgacagag agattatgaa gaattcaaag taaagatcaa tgctttagta gcaacagcac   2340
agaaagtgcc tgaggatggt tggactatgc aagacggtac accttggccc ggtaatagtg   2400
tgcgagatca tcctggcatg attcaggtga gtttcaaatg cttcttattt ctgaaaagcc   2460
ttcttatgtg ttgtccttca aaatttaatt atactttgtt ttcttgttaa aggtcttcct   2520
tggaagtgac ggtgttcgtg atgtcgaaaa caacgagttg cctcgattag tttacgtttc   2580
tcgtgagaag agacccggat tgatcacca  taagaaggct ggagctatga attccctggt   2640
aaatgatata cttttttaaag ctctaaacct tcttctttgt aaattcgtc  ttgccattta   2700
ttgaaatggt tcctgactct tgatttcatc tacaaaactt tgttgaaga  tacgagtctc   2760
tggggttcta tcaaatgctc cttaccttct gaatgtcgat tgtgatcact acatcaacaa   2820
tagcaaagct cttagagaag caatgtgttt catgatggat cctcagtcag gaaagaaaat   2880
ctgttatgtt cagttccctc aaaggttcga tgggattgat aggcacgatc gatactcaaa   2940
tcgcaatgtt gtgttctttg atgtaagtac agccaccact ttcctattgt atccctttt   3000
cttgagattt ctgtagaata ccaactaatg aatctttatt tacagatcaa tatgaaaggt   3060
ttggatgggc tacaagggcc tatatacgtc ggtacaggtt gtgttttcag gaggcaagcg   3120
ctttacggat ttgatgcacc gaagaagaag aagggcccac gtaagacatg caattgctgg   3180
ccaaaatggt gtctcctatg ttttggttca agaaagaatc gtaaagcaaa gacagtggct   3240
gcggataaga agaagaagaa tagggaagcg tcaaagcaga tccacgcatt agaaaatatc   3300
gaagagggcc gcgtcactaa aggtatcata caaatcctgt ttgttgttaa actctttcgt   3360
tagtcggtgc attttactaa aaaaataaaa tttaaaaaac attctaggtt ctaacgtaga   3420
acagtcaacc gaggcaatgc aaatgaagtt ggagaagaaa tttgggcagt ctcctgtatt   3480
tgttgcatct gcgcgtatgg agaatggtgg gatggctaga aacgcaagcc cggcttgtct   3540
```

| | | |
|---|---|---|
| gcttaaagaa gccatccaag tcattagttg cggatatgaa gataaaactg aatggggaaa | 3600 |
| agaggtaagc agccggtttt aaacctttgt tgtgtttatt caatcaattc ttgattttga | 3660 |
| tgatgacctt gtgaaaaaaa tctcagattg ggtggatcta tggttctgtt accgaagata | 3720 |
| ttcttacggg ttttaagatg cattctcatg gttggagatc tgtttattgt acaccaaagt | 3780 |
| tagcggcttt caaaggatca gctccaatca atctttcgga tcgtctccat caagttcttc | 3840 |
| gatgggcgct tgggtcggtt gagattttct tgagtaggca ttgtcctatt tggtatggtt | 3900 |
| atggaggtgg gttgaaatgg cttgagcggt tgtcctacat taactctgtg gtttacccgt | 3960 |
| ggacctctct accgctcatc gtttactgtt ctctccctgc catctgtctt ctcactggaa | 4020 |
| aattcatcgt tcccgaggta aacaatcat cttgagttct caaaatatga atctttattt | 4080 |
| cacgttttgt gcttattcat tttccttgcc actgggggtt aaaagtatca tatgaatctt | 4140 |
| tattccaagt tgtgtgtttt aagaccggaa aacgattctt gttccttctt tttccagatt | 4200 |
| agcaactatg cgagtatcct cttcatggcg ctcttctcgt cgattgcaat aacgggtatt | 4260 |
| ctcgagatgc aatgggcaa agttgggatc gatgattggt ggagaaacga acagttttgg | 4320 |
| gtcattggag gtgtttctgc gcatctgttt gctctcttcc aaggtctcct caaggttctt | 4380 |
| gctggtgtcg acactaactt cacagtcaca tcaaaagcag ctgatgatgg agagttctct | 4440 |
| gacctttacc tcttcaaatg gacttcactt ctcatccctc caatgactct actcatcata | 4500 |
| aacgtcattg gagtcatagt cggagtcttt gatgccatca gcaatggata cgactcgtgg | 4560 |
| ggaccgcttt tcggaagact gttctttgca ctttgggtca tcattcatct ttacccgttc | 4620 |
| cttaaaggtt tgcttgggaa acaagataga atgccaacca ttattgtcgt ctggtccatc | 4680 |
| ctcctggcct cgattcttac acttctttgg gtccgggtta atccgtttgt ggcgaaaggc | 4740 |
| ggtcctattc tcgagatctg tggtttagac tgcttgtga | 4779 |

<210> SEQ ID NO 37
<211> LENGTH: 1084
<212> TYPE: PRT
<213> ORGANISM: Arabidopsis thaliana

<400> SEQUENCE: 37

Met Asn Thr Gly Gly Arg Leu Ile Ala Gly Ser His Asn Arg Asn Glu
1               5                   10                  15

Phe Val Leu Ile Asn Ala Asp Glu Asn Ala Arg Ile Arg Ser Val Gln
            20                  25                  30

Glu Leu Ser Gly Gln Thr Cys Gln Ile Cys Arg Asp Glu Ile Glu Leu
        35                  40                  45

Thr Val Asp Gly Glu Pro Phe Val Ala Cys Asn Glu Cys Ala Phe Pro
    50                  55                  60

Val Cys Arg Pro Cys Tyr Glu Tyr Glu Arg Arg Glu Gly Asn Gln Ala
65                  70                  75                  80

Cys Pro Gln Cys Lys Thr Arg Phe Lys Arg Leu Lys Gly Ser Pro Arg
                85                  90                  95

Val Glu Gly Asp Glu Glu Asp Asp Ile Asp Asp Leu Asp Asn Glu
            100                 105                 110

Phe Glu Tyr Gly Asn Asn Gly Ile Gly Phe Asp Gln Val Ser Glu Gly
        115                 120                 125

Met Ser Ile Ser Arg Arg Asn Ser Gly Phe Pro Gln Ser Asp Leu Asp
    130                 135                 140

Ser Ala Pro Pro Gly Ser Gln Ile Pro Leu Leu Thr Tyr Gly Asp Glu
145                 150                 155                 160

-continued

```
Asp Val Glu Ile Ser Ser Asp Arg His Ala Leu Ile Val Pro Pro Ser
                165                 170                 175

Leu Gly Gly His Gly Asn Arg Val His Pro Val Ser Leu Ser Asp Pro
            180                 185                 190

Thr Val Ala Ala His Pro Arg Pro Met Val Pro Gln Lys Asp Leu Ala
        195                 200                 205

Val Tyr Gly Tyr Gly Ser Val Ala Trp Lys Asp Arg Met Glu Glu Trp
    210                 215                 220

Lys Arg Lys Gln Asn Glu Lys Leu Gln Val Val Arg His Glu Gly Asp
225                 230                 235                 240

Pro Asp Phe Glu Asp Gly Asp Ala Asp Phe Pro Met Met Asp Glu
                245                 250                 255

Gly Arg Gln Pro Leu Ser Arg Lys Ile Pro Ile Lys Ser Ser Lys Ile
                260                 265                 270

Asn Pro Tyr Arg Met Leu Ile Val Leu Arg Leu Val Ile Leu Gly Leu
            275                 280                 285

Phe Phe His Tyr Arg Ile Leu His Pro Val Lys Asp Ala Tyr Ala Leu
        290                 295                 300

Trp Leu Ile Ser Val Ile Cys Glu Ile Trp Phe Ala Val Ser Trp Val
305                 310                 315                 320

Leu Asp Gln Phe Pro Lys Trp Tyr Pro Ile Glu Arg Glu Thr Tyr Leu
                325                 330                 335

Asp Arg Leu Ser Leu Arg Tyr Glu Lys Glu Gly Lys Pro Ser Gly Leu
            340                 345                 350

Ser Pro Val Asp Val Phe Val Ser Thr Val Asp Pro Leu Lys Glu Pro
        355                 360                 365

Pro Leu Ile Thr Ala Asn Thr Val Leu Ser Ile Leu Ala Val Asp Tyr
    370                 375                 380

Pro Val Asp Lys Val Ala Cys Tyr Val Ser Asp Gly Ala Ala Met
385                 390                 395                 400

Leu Thr Phe Glu Ala Leu Ser Glu Thr Ala Glu Phe Ala Arg Lys Trp
                405                 410                 415

Val Pro Phe Cys Lys Lys Tyr Cys Ile Glu Pro Arg Ala Pro Glu Trp
            420                 425                 430

Tyr Phe Cys His Lys Met Asp Tyr Leu Lys Asn Lys Val His Pro Ala
        435                 440                 445

Phe Val Arg Glu Arg Arg Ala Met Lys Arg Asp Tyr Glu Glu Phe Lys
    450                 455                 460

Val Lys Ile Asn Ala Leu Val Ala Thr Ala Gln Lys Val Pro Glu Asp
465                 470                 475                 480

Gly Trp Thr Met Gln Asp Gly Thr Pro Trp Pro Gly Asn Ser Val Arg
                485                 490                 495

Asp His Pro Gly Met Ile Gln Val Phe Leu Gly Ser Asp Gly Val Arg
            500                 505                 510

Asp Val Glu Asn Asn Glu Leu Pro Arg Leu Val Tyr Val Ser Arg Glu
        515                 520                 525

Lys Arg Pro Gly Phe Asp His His Lys Lys Ala Gly Ala Met Asn Ser
    530                 535                 540

Leu Ile Arg Val Ser Gly Val Leu Ser Asn Ala Pro Tyr Leu Leu Asn
545                 550                 555                 560

Val Asp Cys Asp His Tyr Ile Asn Asn Ser Lys Ala Leu Arg Glu Ala
                565                 570                 575
```

```
Met Cys Phe Met Met Asp Pro Gln Ser Gly Lys Lys Ile Cys Tyr Val
                580                 585                 590

Gln Phe Pro Gln Arg Phe Asp Gly Ile Asp Arg His Asp Arg Tyr Ser
        595                 600                 605

Asn Arg Asn Val Val Phe Phe Asp Ile Asn Met Lys Gly Leu Asp Gly
        610                 615                 620

Leu Gln Gly Pro Ile Tyr Val Gly Thr Gly Cys Val Phe Arg Arg Gln
625                 630                 635                 640

Ala Leu Tyr Gly Phe Asp Ala Pro Lys Lys Lys Gly Pro Arg Lys
                645                 650                 655

Thr Cys Asn Cys Trp Pro Lys Trp Cys Leu Leu Cys Phe Gly Ser Arg
                660                 665                 670

Lys Asn Arg Lys Ala Lys Thr Val Ala Ala Asp Lys Lys Lys Lys Asn
            675                 680                 685

Arg Glu Ala Ser Lys Gln Ile His Ala Leu Glu Asn Ile Glu Glu Gly
                690                 695                 700

Arg Val Thr Lys Gly Ser Asn Val Glu Gln Ser Thr Glu Ala Met Gln
705                 710                 715                 720

Met Lys Leu Glu Lys Lys Phe Gly Gln Ser Pro Val Phe Val Ala Ser
                725                 730                 735

Ala Arg Met Glu Asn Gly Gly Met Ala Arg Asn Ala Ser Pro Ala Cys
                740                 745                 750

Leu Leu Lys Glu Ala Ile Gln Val Ile Ser Cys Gly Tyr Glu Asp Lys
                755                 760                 765

Thr Glu Trp Gly Lys Glu Ile Gly Trp Ile Tyr Gly Ser Val Thr Glu
        770                 775                 780

Asp Ile Leu Thr Gly Phe Lys Met His Ser His Gly Trp Arg Ser Val
785                 790                 795                 800

Tyr Cys Thr Pro Lys Leu Ala Ala Phe Lys Gly Ser Ala Pro Ile Asn
                805                 810                 815

Leu Ser Asp Arg Leu His Gln Val Leu Arg Trp Ala Leu Gly Ser Val
                820                 825                 830

Glu Ile Phe Leu Ser Arg His Cys Pro Ile Trp Tyr Gly Tyr Gly Gly
                835                 840                 845

Gly Leu Lys Trp Leu Glu Arg Leu Ser Tyr Ile Asn Ser Val Val Tyr
850                 855                 860

Pro Trp Thr Ser Leu Pro Leu Ile Val Tyr Cys Ser Leu Pro Ala Ile
865                 870                 875                 880

Cys Leu Leu Thr Gly Lys Phe Ile Val Pro Glu Ile Ser Asn Tyr Ala
                885                 890                 895

Ser Ile Leu Phe Met Ala Leu Phe Ser Ser Ile Ala Ile Thr Gly Ile
                900                 905                 910

Leu Glu Met Gln Trp Gly Lys Val Gly Ile Asp Asp Trp Arg Asn
                915                 920                 925

Glu Gln Phe Trp Val Ile Gly Gly Val Ser Ala His Leu Phe Ala Leu
        930                 935                 940

Phe Gln Gly Leu Leu Lys Val Leu Ala Gly Val Asp Thr Asn Phe Thr
945                 950                 955                 960

Val Thr Ser Lys Ala Ala Asp Asp Gly Glu Phe Ser Asp Leu Tyr Leu
                965                 970                 975

Phe Lys Trp Thr Ser Leu Leu Ile Pro Pro Met Thr Leu Leu Ile Ile
                980                 985                 990

Asn Val Ile Gly Val Ile Val Gly  Val Phe Asp Ala Ile  Ser Asn Gly
```

-continued

```
                995                  1000                    1005
Tyr Asp Ser Trp Gly Pro Leu Phe Gly Arg Leu Phe Phe Ala Leu
        1010                1015                1020

Trp Val Ile Ile His Leu Tyr Pro Phe Leu Lys Gly Leu Leu Gly
        1025                1030                1035

Lys Gln Asp Arg Met Pro Thr Ile Ile Val Val Trp Ser Ile Leu
        1040                1045                1050

Leu Ala Ser Ile Leu Thr Leu Leu Trp Val Arg Val Asn Pro Phe
        1055                1060                1065

Val Ala Lys Gly Gly Pro Ile Leu Glu Ile Cys Gly Leu Asp Cys
        1070                1075                1080

Leu
```